(12) United States Patent
Aslanian et al.

(10) Patent No.: US 6,720,328 B2
(45) Date of Patent: Apr. 13, 2004

(54) NON-IMIDAZOLE COMPOUNDS

(75) Inventors: Robert G. Aslanian, Rockaway, NJ (US); Neng-Yang Shih, North Caldwell, NJ (US); Pauline C. Ting, New Providence, NJ (US); Michael Y. Berlin, Flemington, NJ (US); Stuart B. Rosenblum, West Orange, NJ (US); Kevin D. McCormick, Edison, NJ (US); Wing C. Tom, Cedar Grove, NJ (US); Christopher W. Boyce, Flemington, NJ (US); Pietro Mangiaracina, Monsey, NY (US); Mwangi W. Mutahi, Fords, NJ (US); John J. Piwinski, Clinton Township, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/978,267

(22) Filed: Oct. 15, 2001

(65) Prior Publication Data

US 2003/0045519 A1 Mar. 6, 2003

Related U.S. Application Data

(60) Provisional application No. 60/240,901, filed on Oct. 17, 2000.

(51) Int. Cl.[7] .................. C07D 401/14; A61K 31/4985; A61K 31/4523; A61K 31/506; A61P 3/04
(52) U.S. Cl. ................. 514/275; 546/187; 514/318; 514/321; 544/331; 544/353
(58) Field of Search ........................... 546/187; 514/318, 514/321, 275; 544/331, 353

(56) References Cited

U.S. PATENT DOCUMENTS

| | | | |
|---|---|---|---|
| 5,463,074 A | 10/1995 | Shih et al. | 548/314.7 |
| 5,578,616 A | 11/1996 | Aslanian et al. | 514/341 |
| 5,633,250 A | 5/1997 | Shih | 514/218 |
| 5,807,872 A | 9/1998 | Shih et al. | 514/326 |
| 5,869,479 A | 2/1999 | Kreutner et al. | 514/212 |
| 5,990,147 A | 11/1999 | Aslanian | 514/400 |
| 6,034,251 A | 3/2000 | Aslanian et al. | 548/338.1 |
| 6,100,279 A | 8/2000 | Vaccaro et al. | 514/326 |

FOREIGN PATENT DOCUMENTS

| | | |
|---|---|---|
| EP | 0 407 217 A1 | 6/1990 |
| WO | WO 95/14007 | 5/1995 |
| WO | WO 97/19074 | 5/1997 |
| WO | WO 98/06394 | 2/1998 |
| WO | WO 99/24405 | 5/1999 |

OTHER PUBLICATIONS

Fox et al. (Behavioural Brain Research 131 (2002) 151–161).*
Leurs et al. (Therapeutic potential of histamine H3 receptor agonists and antagonists: TiPS–May 1998 (vol. 19), 177–183).*
Bakker et al. Clin Allergy Immuno 2002; 17:27–64.*
European Journal of Pharmacology vol. 294 (1995) 329–335.
The Journal of Organic Chemistry, vol. 33, No. 6, Jun. 1968, pp. 2388–2392.
Journal of Medicinal Chemistry, vol. 19, 1976, pp. 360–365.
J. Heterocyclic Chem., 3 (1960) pp. 252–256.
Journal of Medicinal Chemistry, 37(16), (1994), pp. 2537–2551.
T. Zsuzsanna, Hung. Magy. Kem Foly. 74(3) (1968) pp. 116–119.
Journal of Medicinal Chemistry, 43(12), (2000), pp. 2362–2370.
Arch. Pharm. Pharm. Med. Chem. 332 (1999), pp. 389–398.
Arch. Pharm. Pharm. Med. Chem. 331 (1998), pp. 395–404.
US application 10/095,134.

* cited by examiner

Primary Examiner—Mark L Berch
Assistant Examiner—Kahsay Habte
(74) Attorney, Agent, or Firm—Anita W. Magatti

(57) ABSTRACT

Disclosed are novel compounds of the formula (I)

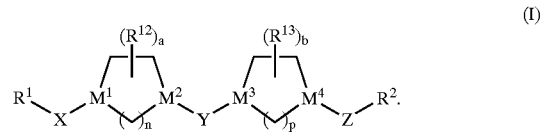

In Formula I, $M^1$ is carbon, $M^2$, $M^3$ and $M^4$ are carbon or nitrogen and the remaining variables are as defined in the specification. Also disclosed are pharmaceutical compositions comprising the compounds of Formula I.

Also disclosed are methods of treating various diseases or conditions, such as, for example, allergy, allergy-induced airway responses, and congestion (e.g., nasal congestion) using the compounds of Formula I.

Also disclosed are methods of treating various diseases or conditions, such as, for example, allergy, allergy-induced airway responses, and congestion (e.g., nasal congestion) using the compounds of Formula I in combination with a $H_1$ receptor antagonist.

43 Claims, No Drawings

NON-IMIDAZOLE COMPOUNDS

REFERENCE TO RELATED APPLICATIONS

This application claims the benefit of U.S. Provisional Application Serial No. 60/240,901 filed Oct. 17, 2000.

BACKGROUND OF THE INVENTION

WO 95/14007 published May 26, 1995 discloses $H_3$ receptor antagonists of the imidazole type.

WO99/24405 published May 20, 1999 discloses $H_3$ receptor ligands of the imidazole type.

U.S. Pat. No. 5,869,479 issued Feb. 9, 1999 discloses compositions for the treatment of the symptoms of allergic rhinitis using a combination of at least one histamine $H_1$ receptor antagonist and at least one histamine $H_3$ receptor antagonist.

In view of the art's interest in compounds which affect $H_3$ receptors, novel compounds that are antagonists of $H_3$ receptors would be a welcome contribution to the art. This invention provides just such a contribution.

SUMMARY OF THE INVENTION

The present invention provides novel compounds of structure I.

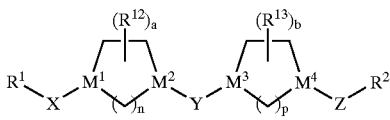

or a pharmaceutically acceptable salt or solvate thereof, wherein:

(1) $R^1$ is is selected from:
  (a) aryl;
  (b) heteroaryl;
  (c) heterocycloalkyl
  (d) alkyl;
  (e) cycloalkyl; or
  (f) alkylaryl;

wherein said $R^1$ groups are optionally substituted with 1 to 4 substituents independently selected from:
  (1) halogen (e.g., Br, F, or Cl, preferably F or Cl);
  (2) hydroxyl (i.e., —OH);
  (3) lower alkoxy (e.g., $C_1$ to $C_6$ alkoxy, preferably $C_1$ to $C_4$ alkoxy, most preferably $C_1$ to $C_2$ alkoxy, more preferably methoxy);
  (4) —$CF_3$;
  (5) $CF_3O$—;
  (6) —$NR^4R^5$;
  (7) phenyl;
  (8) —$NO_2$,
  (9) —$CO_2R^4$;
  (10) —$CON(R^4)_2$ wherein each $R^4$ is the same or different;
  (11) —$S(O)_mN(R^{20})_2$ wherein each $R^{20}$ is the same or different H or alkyl group, preferably $C_1$ to $C_4$ alkyl, most preferably $C_1$–$C_2$ alkyl, and more preferably methyl;
  (12) —CN; or
  (13) alkyl; or (2) $R^1$ and X taken together form a group selected from:

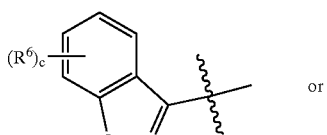

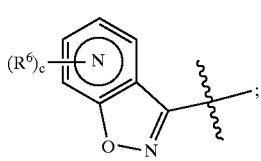

(3) X is selected from: =C(O), =C($NOR^3$), =C($NNR^4R^5$),

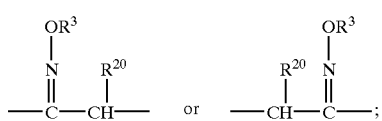

(4) $M^1$ is carbon;
(5) $M^2$ is selected from C or N;
(6) $M^3$ and $M^4$ are independently selected from C or N;
(7) Y is selected from: is —$CH_2$—, =C(O), =C($NOR^{20}$) (wherein $R^{20}$ is as defined above), or =C(S);
(8) Z is a $C_1$–$C_6$ alkyl group;
(9) $R^2$ is a five or six-membered heteroaryl ring, said six-membered heteroaryl ring comprising 1 or 2 nitrogen atoms with the remaining ring atoms being carbon, and said five-membered heteroaryl ring containing 1 or 2 heteroatoms selected from: nitrogen, oxygen, or sulfur with the remaining ring atoms being carbon; said five or six membered heteroaryl rings being optionally substituted with 1 to 3 substituents independently selected from: halogen, hydroxyl, lower alkyl, lower alkoxy, —$CF_3$, $CF_3O$—, —$NR^4R^5$, phenyl, —$NO_2$, —$CO_2R^4$, —$CON(R^4)_2$ wherein each $R^4$ is the same or different, —$CH_2NR^4R^5$, —(N)C($NR^4R^5$)$_2$, or —CN;

(10) $R^3$ is selected from:
  (a) hydrogen;
  (b) $C_1$–$C_6$ alkyl;
  (c) aryl;
  (d) heteroaryl;
  (e) heterocycloalkyl;
  (f) arylalkyl (e.g., aryl($C_1$ to $C_4$)alkyl, e.g., —$(CH_2)_w$aryl wherein w is 1 to 4, preferably 1 or 2, and most preferably 1, such as, for example —$CH_2$phenyl or —$CH_2$substituted phenyl);
  (g) —$(CH_2)_e$—C(O)N($R^4$)$_2$ wherein each $R^4$ is the same or different,
  (h) —$(CH_2)_e$—C(O)$OR^4$;
  (i) —$(CH_2)_e$—C(O)$R^{30}$ wherein $R^{30}$ is a heterocycloalkyl group, such as, for example, morpholinyl, piperidinyl, piperazinyl or pyrrolidinyl, including

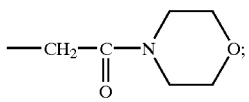

(j) —CF$_3$; or (k) —CH$_2$CF$_3$;

wherein said aryl, heteroaryl, heterocycloalkyl, and the aryl portion of said arylalkyl are optionally substituted with 1 to 3 (preferably 1) substituents selected from: halogen (e.g., F or Cl), —OH, —OCF$_3$, —CF$_3$, —CN, —N(R$^{45}$)$_2$, —CO$_2$R$^{45}$, or —C(O)N (R$^{45}$)$_2$, wherein each R$^{45}$ is independently selected from: H, alkyl, alkylaryl, or alkylaryl wherein said aryl moiety is substituted with 1 to 3 substituents independently selected from —CF$_3$, —OH, halogen, alkyl, —NO$_2$, or —CN;

(11) R$^4$ is selected from: hydrogen, C$_1$-C$_6$ alkyl, aryl, alkylaryl, said aryl and alkylaryl groups being optionally substituted with 1 to 3 substituents selected from: halogen, —CF$_3$, —OCF$_3$, —OH, —N(R$^{45}$)$_2$, —CO$_2$R$^{45}$, —C(O)N (R$^{45}$)$_2$, or —CN; wherein R$^{45}$ is as defined above;

(12) R$^5$ is selected from: hydrogen, C$_1$-C$_6$ alkyl, —C(O) R$^4$, —C(O)$_2$R$^4$, or —C(O)N(R$^4$)$_2$ wherein each R$^4$ is independently selected, and R$^4$ is as defined above;

(13) or R$^4$ and R$^5$ taken together with the nitrogen atom to which they are bound forms a five or six membered heterocycloalkyl ring (e.g., morpholine);

(14) R$^6$ is selected from: alkyl, aryl, alkylaryl, halogen, hydroxyl, lower alkoxy, —CF$_3$, CF$_3$O—, —NR$^4$R$^5$, phenyl, —NO$_2$, —CO$_2$R$^4$, —CON(R$^4$)$_2$ wherein each R$^4$ is the same or different, or —CN;

(15) R$^{12}$ is selected from: alkyl, hydroxyl, alkoxy, or fluoro;

(16) R$^{13}$ is selected from: alkyl, hydroxyl, alkoxy, or fluoro;

(17) a (subscript for R$^{12}$) is 0 to 2;

(18) b (subscript for R$^{13}$) is 0 to 2;

(19) c (subscript for R$^6$) is 0 to 2;

(20) e is 0 to 5;

(21) m is 1 or 2;

(22) n is 1, 2 or 3; and

(23) p is 1, 2 or 3, with the proviso that when M$^3$ and M$^4$ are both nitrogen, then p is 2 or 3 (i.e., p is not 1 when M$^3$ and M$^2$ are both nitrogen).

This invention also provides a pharmaceutical composition comprising an effective amount of compound of Formula I, and a pharmaceutically acceptable carrier.

This invention further provides a method of treating: allergy, allergy-induced airway (e.g., upper airway) responses, congestion (e.g., nasal congestion), hypotension, cardiovascular disease, diseases of the GI tract, hyper and hypo motility and acidic secretion of the gastrointestinal tract, obesity, sleeping disorders (e.g., hypersomnia, somnolence, and narcolepsy), disturbances of the central nervous system, attention deficit hyperactivity disorder ADHD), hypo and hyperactivity of the central nervous system (for example, agitation and depression), and other CNS disorders (such as Alzheimer's, schizophrenia, and migraine) comprising administering to a patient in need of such treatment (e.g., a mammal, such as a human being) an effective amount of a compound of Formula I.

This invention further provides a method of treating: allergy comprising administering to a patient in need of such treatment (e.g., a mammal, such as a human being) an effective amount of a compound of Formula I.

This invention further provides a method of treating: allergy-induced airway (e.g., upper airway) responses comprising administering to a patient in need of such treatment (e.g., a mammal, such as a human being) an effective amount of a compound of Formula I.

This invention further provides a method of treating: congestion (e.g., nasal congestion) comprising administering to a patient in need of such treatment (e.g., a mammal, such as a human being) an effective amount of a compound of Formula I.

This invention further provides a pharmaceutical composition comprising an effective amount of a compound of Formula I, and an effective amount of a H$_1$ receptor antagonist in combination with a pharmaceutically acceptable carrier.

This invention further provides a method of treating: allergy, allergy-induced airway (e.g., upper airway) responses, and congestion (e.g., nasal congestion) comprising administering to a patient in need of such treatment (e.g., a mammal, such as a human being) an effective amount of a compound of Formula I in combination with an effective amount of an H$_1$ receptor antagonist.

This invention further provides a method of treating: allergy comprising administering to a patient in need of such treatment (e.g., a mammal, such as a human being) an effective amount of a compound of Formula I in combination with an effective amount of an H$_1$ receptor antagonist.

This invention further provides a method of treating: allergy-induced airway (e.g., upper airway) responses comprising administering to a patient in need of such treatment (e.g., a mammal, such as a human being) an effective amount of a compound of Formula I in combination with an effective amount of an H$_1$ receptor antagonist.

This invention further provides a method of treating: congestion (e.g., nasal congestion) comprising administering to a patient in need of such treatment (e.g., a mammal, such as a human being) an effective amount of a compound of Formula I in combination with an effective amount of an H$_1$ receptor antagonist.

DETAILED DESCRIPTION OF THE INVENTION

As used herein, the following terms have the following meanings, unless indicated otherwise:

alkyl-(including the alkyl portions of alkoxy and alkylaryl)-represents straight and branched carbon chains and contains from one to twenty carbon atoms, preferably one to six carbon atoms;

alkylaryl-represents an alkyl group, as defined above, bound to an aryl group, as defined below, wherein said aryl group is bound to the rest of the molecule;

aryl (including the aryl portion of alkylaryl)-represents a carbocyclic group containing from 6 to 15 carbon atoms and having at least one aromatic ring (e.g., aryl is a phenyl ring), with all available substitutable carbon atoms of the carbocyclic group being intended as possible points of attachment;

arylalkyl-represents an aryl group, as defined above, bound to an alkyl group, as defined above, wherein said alkyl group is bound to the rest of the molecule;

cycloalkyl-represents saturated carbocyclic rings of from 3 to 20 carbon atoms, preferably 3 to 7 carbon atoms;

halo (halogen)-represents fluoro, chloro, bromo and iodo;

heteroaryl-represents cyclic groups, having at least one heteroatom selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms; examples include but are not limited to isothiazolyl, isoxazolyl, furazanyl, triazolyl, thiazolyl, thienyl, furanyl (furyl), pyrrolyl, pyrazolyl, pyranyl, pyrimidinyl, pyrazinyl, pyridazinyl, pyridyl (e.g., 2-, 3-, or 4-pyridyl), pyridyl N-oxide (e.g., 2-, 3-, or 4-pyridyl N-oxide), triazinyl, pteridinyl, indolyl (benzopyrrolyl), pyridopyrazinyl, isoqinolinyl, quinolinyl, quinoxolinyl, naphthyridinyl, wherein said pyridyl N-oxide can be represented as:

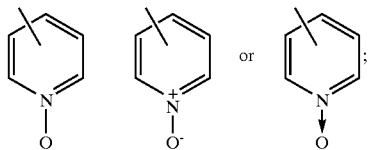

heterocycloalkyl-represents a saturated, carbocylic ring containing from 3 to 15 carbon atoms, preferably from 4 to 6 carbon atoms, which carbocyclic ring is interrupted by 1 to 3 hetero groups selected from —O—, —S— or —NR$^{40}$— wherein R$^{40}$ represents C$_1$ to C$_6$ alkyl, arylalkyl, —C(O)R$^4$, —C(O)OR$^4$, or —C(O)N(R$^{45}$)$_2$ (wherein R$^{45}$ is as defined above, and each R$^{45}$ is independently selected); examples include but are not limited to 2- or 3-tetrahydrofuranyl, 2- or 3-tetrahydrothienyl, 2-, 3- or 4-piperidinyl, 2- or 3-pyrrolidinyl, 2- or 3-piperizinyl, 2- or 4-dioxanyl, 1,3-dioxolanyl, 1,3,5-trithianyl, pentamethylene sulfide, perhydroisoquinolinyl, decahydroquinolinyl, trimethylene oxide, azetidinyl, 1-azacycloheptanyl, 1,3-dithianyl, 1,3,5-trioxanyl, morpholinyl, thiomorpholinyl, 1,4-thioxanyl, and 1,3,5-hexahydrotriazinyl, thiazolidinyl, tetrahydropyranyl;

lower alkyl-represents an alkyl group, as defined above, that comprises 1 to 6 carbon atoms, preferably 1–4 carbon atoms;

lower alkoxy-represents an alkoxy group whose alkyl moiety comprises 1 to 6 carbon atoms, preferably 1–4 carbon atoms;

=C(O)-represents

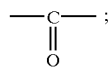

=C(NOR$^3$)-represents

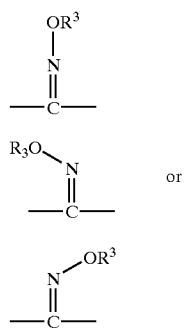

wherein (1) represents a mixture of oxime isomers; (2) represents one geometric isomer of the oxime wherein the —OR$^3$ group is on the same side of the double bond as the group to the left of the carbon atom; (3) represents one geometric isomer of the oxime wherein the —OR$^3$ group is on the same side of the double bond as the group to the right of the carbon atom; and (1) can also be represented as:

=C(NNR$^4$R$^5$) represents

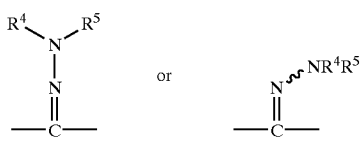

and represents a mixture of the isomers

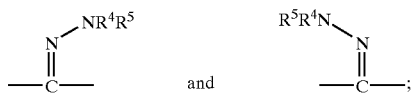

—(N)C(NR$^4$R$^5$)$_2$ represents

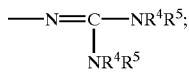

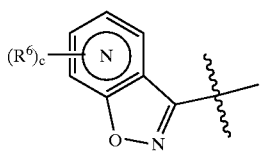 in the structure

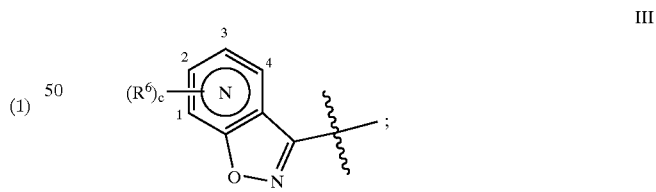

represents a nitrogen atom that is located at one of the 4 non-fused positions of the ring, i.e., positions 1, 2, 3 or 4 indicated below:

III (R$^6$)$_c$— [structure with positions 1,2,3,4 labeled]

AcOH-represents acetic acid;
t-BOC-represents t-butyloxycarbonyl;
Ci/mmol-represents curie/mmol (a measure of specific activity);
m-CPBA-represents m-chloroperbenzoic acid;
CSA-represents camphorsulfonic acid;
CBZ-represents carbonylbenzyloxy (—C(O)OCH$_2$C$_6$H$_5$);
DBU-represents 1,8-diazabicyclo[5.4.0]undec-7-ene;
DBN-represents 1,5-diazabicyclo[4.3.0]non-5-ene;
DCC-represents dicyclohexylcarbodiimide;

Dibal-H-represents diisobutylaluminum hydride;

DIDPEA-represents N,N-diisopropylethylamine;

DMAP-represents 4-(dimethylamino)pyridine;

DEC-represents 2-diethylaminoethyl chloride hydrochloride;

DMF-represents dimethylformamide;

EDCI-represents 1-(3-dimethylaminopropyl)-3-ethylcarbodiimide;

EtOAc-represents ethyl acetate;

EtOH-represents ethanol;

FMOC-represents 9-fluorenylmethoxycarbonyl;

HOBT-represents 1-hydroxybenzotriazole;

HPLC-represents high performance liquid chromatography;

HRMS-represents high resolution mass spectrometry;

Ki-represents inhibition constant for substrate/receptor complex;

LAH-lithium aluminum hydride;

LDA-represents lithium diisopropylamide;

LRMS-represents low resolution mass spectrometry;

MeOH-represents methanol;

NaBH(OAc)$_3$-represents sodium triacetoxyborohydride;

NaBH$_4$-represents sodium borohydride;

NaBH$_3$CN-represents sodium cyanoborohydride;

NaHMDS-represents sodium hexamethyl disilylazide;

nM-represents nanomolar;

pA$_2$-represents-log EC$_{50}$, as defined by J. Hey, Eur. J. Pharmacol., (1995), Vol. 294, 329–335;

PCC-represents pyridinium chlorochromate;

PyBOP-represents benzotriazole-1-yl-oxy-trispyrrolidino-phosphonium hexaflurophosphate;

TEMPO-represents 2,2,6,6-tetramethyl-1-piperidinyloxy, free radical;

TFA-represents trifluoroacetic acid;

TMAD-represents N,N,N',N'-tetramethylazodicarboxamide;

TMEDA-represents tetramethylethylenediamine;

Tr-represents triphenylmethyl;

Tris-represents tris(hydroxymethyl)aminomethane;and p-TsOH-represents p-toluenesulfonic acid.

Also, as used herein, "upper airway" usually means the upper respiratory system—i.e., the nose, throat, and associated structures.

Also, as used herein, "effective amount" generally means a therapeutically effective amount.

Lines drawn into the rings indicate that the indicated bond may be attached to any of the substitutable ring carbon atoms.

Certain compounds of the invention may exist in different isomeric (e.g., enantiomers, diastereoisomers and geometric) forms. The invention contemplates all such isomers both in pure form and in admixture, including racemic mixtures. Enol forms are also included.

The compounds of this invention are ligands for the histamine H$_3$ receptor. The compounds of this invention can also be described as antagonists of the H$_3$ receptor, or as H$_3$ antagonists.

The compounds of the invention are basic and form pharmaceutically acceptable salts with organic and inorganic acids. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their corresponding salt forms somewhat in certain physical properties, such as solubility in polar solvents, but the salts are otherwise equivalent to their corresponding free base forms for purposes of this invention.

The compounds of Formula I can exist in unsolvated as well as solvated forms, including hydrated forms, e.g., hemi-hydrate. In general, the solvated forms, with pharmaceutically acceptable solvents such as water, ethanol and the like are equivalent to the unsolvated forms for purposes of the invention.

The compounds of this invention can be combined with an H$_1$ receptor antagonist (i.e., the compounds of this invention can be combined with an H$_1$ receptor antagonist in a pharmaceutical composition, or the compounds of this invention can be administered with H$_1$ receptor antagonist).

Numerous chemical substances are known to have histamine H$_1$ receptor antagonist activity. Many useful compounds can be classified as ethanolamines, ethylenediamines, alkylamines, phenothiazines or piperidines. Representative H$_1$ receptor antagonists include, without limitation: astemizole, azatadine, azelastine, acrivastine, brompheniramine, cetirizine, chlorpheniramine, clemastine, cyclizine, carebastine, cyproheptadine, carbinoxamine, descarboethoxyloratadine (also known as SCH-34117), diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine and triprolidine. Other compounds can readily be evaluated to determine activity at H$_1$ receptors by known methods, including specific blockade of the contractile response to histamine of isolated guinea pig ileum. See for example, WO98/06394 published Feb. 19, 1998.

Thus, in the methods of this invention wherein a compound of Formula I is combined with an effective amount of an H$_1$ receptor antagonist, said H$_1$ receptor antagonist is selected from: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine or triprolidine.

Also, in the methods of this invention wherein a compound of Formula I is combined with an effective amount of an H$_1$ receptor antagonist, said H$_1$ receptor antagonist is selected from: astemizole, azatadine, azelastine, brompheniramine, cetirizine, chlorpheniramine, clemastine, carebastine, descarboethoxyloratadine, diphenhydramine, doxylamine, ebastine, fexofenadine, loratadine, levocabastine, mizolastine, norastemizole, or terfenadine.

Also, in the methods of this invention wherein a compound of Formula I is combined with an effective amount of an H₁ receptor antagonist, said H₁ receptor antagonist is selected from: azatadine, brompheniramine, cetirizine, chlorpheniramine, carebastine, descarboethoxyloratadine (also known as SCH-34117), diphenhydramine, ebastine, fexofenadine, loratadine, or norastemizole.

Also, in the methods of this invention wherein a compound of Formula I is combined with an effective amount of an H₁ receptor antagonist, said H₁ receptor antagonist is loratadine.

Also, in the methods of this invention wherein a compound of Formula I is combined with an effective amount of an H₁ receptor antagonist, said H₁ receptor antagonist is descarboethoxyloratadine.

Also, in the methods of this invention wherein a compound of Formula I is combined with an effective amount of an H₁ receptor antagonist, said H₁ receptor antagonist is fexofenadine.

Also, in the methods of this invention wherein a compound of Formula I is combined with an effective amount of an H₁ receptor antagonist, said H₁ receptor antagonist is cetirizine.

Preferably, in the above methods, allergy-induced airway responses are treated.

Also, preferably, in the above methods, allergy is treated.

Also, preferably, in the above methods, nasal congestion is treated.

Preferably, in the above methods using a combination of a compound of Formula I (H₃ antagonist) and an H₁ antagonist, the H₁ antagonist is selected from: loratadine, descarboethoxyloratadine, fexofenadine or cetirizine. Most preferably the H₁ antagonist is loratadine or descarboethoxyloratadine.

In the methods of this invention wherein a combination of an H₃ antagonist of this invention (compound of Formula I) is administered with a H₁ antagonist, the antagonists can be administered simultaneously, consecutively (one after the other within a relatively short period of time), or sequentially (first one and then the other over a period of time). In general, when the antagonists are administered consecutively or sequentially, the H₃ antagonist of this invention (compound of Formula I) is administered first.

Thus, one emodiment of this invention is directed to a pharmaceutical composition comprising an effective amount of Compound 32 and a pharmaceutically acceptable carrier.

Another emodiment of this invention is directed to a pharmaceutical composition comprising an effective amount of Compound 54 and a pharmaceutically acceptable carrier.

Another emodiment of this invention is directed to a pharmaceutical composition comprising an effective amount of Compound 55 and a pharmaceutically acceptable carrier.

Another emodiment of this invention is directed to a pharmaceutical composition comprising an effective amount of Compound 253A and a pharmaceutically acceptable carrier.

Another emodiment of this invention is directed to a pharmaceutical composition comprising an effective amount of Compound 287 and a pharmaceutically acceptable carrier.

Another emodiment of this invention is directed to a pharmaceutical composition comprising an effective amount of Compound 320 and a pharmaceutically acceptable carrier.

Another embodiment of this invention is directed to a method of treating: allergy, allergy-induced airway responses, congestion, hypotension, cardiovascular disease, hypotension, diseases of the GI tract, hyper and hypo motility and acidic secretion of the gastrointestinal tract, obesity, sleeping disorders, disturbances of the central nervous system, attention deficit hyperactivity disorder, hypo and hyperactivity of the central nervous system, Alzheimer's disease, schizophrenia, and migraine comprising administering to a patient in need of such treatment an effective amount of Compound 32.

Another embodiment of this invention is directed to a method of treating: allergy, allergy-induced airway responses, congestion, hypotension, cardiovascular disease, hypotension, diseases of the GI tract, hyper and hypo motility and acidic secretion of the gastrointestinal tract, obesity, sleeping disorders, disturbances of the central nervous system, attention deficit hyperactivity disorder, hypo and hyperactivity of the central nervous system, Alzheimer's disease, schizophrenia, and migraine comprising administering to a patient in need of such treatment an effective amount of Compound 54.

Another embodiment of this invention is directed to a method of treating: allergy, allergy-induced airway responses, congestion, hypotension, cardiovascular disease, hypotension, diseases of the GI tract, hyper and hypo motility and acidic secretion of the gastrointestinal tract, obesity, sleeping disorders, disturbances of the central nervous system, attention deficit hyperactivity disorder, hypo and hyperactivity of the central nervous system, Alzheimer's disease, schizophrenia, and migraine comprising administering to a patient in need of such treatment an effective amount of Compound 55.

Another embodiment of this invention is directed to a method of treating: allergy, allergy-induced airway responses, congestion, hypotension, cardiovascular disease, hypotension, diseases of the GI tract, hyper and hypo motility and acidic as secretion of the gastro-intestinal tract, obesity, sleeping disorders, disturbances of the central nervous system, attention deficit hyperactivity disorder, hypo and hyperactivity of the central nervous system, Alzheimer's disease, schizophrenia, and migraine comprising administering to a patient in need of such treatment an effective amount of Compound 253A.

Another embodiment of this invention is directed to a method of treating: allergy, allergy-induced airway responses, congestion, hypotension, cardiovascular disease, hypotension, diseases of the GI tract, hyper and hypo motility and acidic secretion of the gastro-intestinal tract, obesity, sleeping disorders, disturbances of the central nervous system, attention deficit hyperactivity disorder, hypo and hyperactivity of the central nervous system, Alzheimer's disease, schizophrenia, and migraine comprising administering to a patient in need of such treatment an effective amount of Compound 287.

Another embodiment of this invention is directed to a method of treating: allergy, allergy-induced airway responses, congestion, hypotension, cardiovascular disease, hypotension, diseases of the GI tract, hyper and hypo motility and acidic secretion of the gastro-intestinal tract, obesity, sleeping disorders, disturbances of the central nervous system, attention deficit hyperactivity disorder, hypo and hyperactivity of the central nervous system, Alzheimer's disease, schizophrenia, and migraine comprising administering to a patient in need of such treatment an effective amount of Compound 320.

Another embodiment of this invention is directed to a method of treating allergy-induced airway responses comprising administering to a patient in need of such treatment an effective amount of Compound 32.

Another embodiment of this invention is directed to a method of treating allergy-induced airway responses comprising administering to a patient in need of such treatment an effective amount of Compound 54.

Another embodiment of this invention is directed to a method of treating allergy-induced airway responses comprising administering to a patient in need of such treatment an effective amount of Compound 55.

Another embodiment of this invention is directed to a method of treating allergy-induced airway responses comprising administering to a patient in need of such treatment an effective amount of Compound 253A.

Another embodiment of this invention is directed to a method of treating allergy-induced airway responses comprising administering to a patient in need of such treatment an effective amount of Compound 287.

Another embodiment of this invention is directed to a method of treating allergy-induced airway responses comprising administering to a patient in need of such treatment an effective amount of Compound 320.

Another embodiment of this invention is directed to a method of treating allergy or nasal congestion comprising administering to a patient in need of such treatment an effective amount of Compound 32.

Another embodiment of this invention is directed to a method of treating allergy or nasal congestion comprising administering to a patient in need of such treatment an effective amount of Compound 54.

Another embodiment of this invention is directed to a method of treating allergy or nasal congestion comprising administering to a patient in need of such treatment an effective amount of Compound 55.

Another embodiment of this invention is directed to a method of treating allergy or nasal congestion comprising administering to a patient in need of such treatment an effective amount of Compound 253A.

Another embodiment of this invention is directed to a method of treating allergy or nasal congestion comprising administering to a patient in need of such treatment an effective amount of Compound 287.

Another embodiment of this invention is directed to a method of treating allergy or nasal congestion comprising administering to a patient in need of such treatment an effective amount of Compound 320.

Another embodiment of this invention is directed to a pharmaceutical composition comprising an effective amount of Compound 32, and an effective amount of $H_1$ receptor antagonist, and a pharmaceutically effective carrier.

Another embodiment of this invention is directed to a pharmaceutical composition comprising an effective amount of Compound 54, and an effective amount of $H_1$ receptor antagonist, and a pharmaceutically effective carrier.Another embodiment of this invention is directed to a pharmaceutical composition comprising an effective amount of Compound 55, and an effective amount of $H_1$ receptor antagonist, and a pharmaceutically effective carrier.

Another embodiment of this invention is directed to a pharmaceutical composition comprising an effective amount of Compound 253A, and an effective amount of $H_1$ receptor antagonist, and a pharmaceutically effective carrier.

Another embodiment of this invention is directed to a pharmaceutical composition comprising an effective amount of Compound 287, and an effective amount of $H_1$ receptor antagonist, and a pharmaceutically effective carrier.Another embodiment of this invention is directed to a pharmaceutical composition comprising an effective amount of Compound 320, and an effective amount of $H_1$ receptor antagonist, and a pharmaceutically effective carrier.

Another embodiment of this invention is directed to a method of treating: allergy, allergy-induced airway responses, and congestion comprising administering to a patient in need of such treatment an effective amount of Compound 32 in combination with an effective amount of an $H_1$ receptor antagonist.

Another embodiment of this invention is directed to a method of treating: allergy, allergy-induced airway responses, and congestion comprising administering to a patient in need of such treatment an effective amount of Compound 54 in combination with an effective amount of an $H_1$ receptor antagonist.

Another embodiment of this invention is directed to a method of treating: allergy, allergy-induced airway responses, and congestion comprising administering to a patient in need of such treatment an effective amount of a Compound 55 in combination with an effective amount of an $H_1$ receptor antagonist.Another embodiment of this invention is directed to a method of treating: allergy, allergy-induced airway responses, and congestion comprising administering to a patient in need of such treatment an effective amount of Compound 253A in combination with an effective amount of an $H_1$ receptor antagonist.

Another embodiment of this invention is directed to a method of treating: allergy, allergy-induced airway responses, and congestion comprising administering to a patient in need of such treatment an effective amount of Compound 287 in combination with an effective amount of an $H_1$ receptor antagonist.

Another embodiment of this invention is directed to a method of treating: allergy, allergy-induced airway responses, and congestion comprising administering to a patient in need of such treatment an effective amount of Compound 320 in combination with an effective amount of an $H_1$ receptor antagonist.

Another embodiment of this invention is directed to a method of treating: allergy, allergy-induced airway responses, and congestion comprising administering to a patient in need of such treatment an effective amount of Compound 32 in combination with an effective amount of an $H_1$ receptor antagonist selected from: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine or triprolidine.

Another embodiment of this invention is directed to a method of treating: allergy, allergy-induced airway responses, and congestion comprising administering to a patient in need of such treatment an effective amount of Compound 54 in combination with an effective amount of an $H_1$ receptor antagonist selected from: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine or triprolidine.

Another embodiment of this invention is directed to a method of treating: allergy, allergy-induced airway responses, and congestion comprising administering to a patient in need of such treatment an effective amount of Compound 55 in combination with an effective amount of an H₁ receptor antagonist selected from: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine or triprolidine.

Another embodiment of this invention is directed to a method of treating: allergy, allergy-induced airway responses, and congestion comprising administering to a patient in need of such treatment an effective amount of Compound 253A in combination with an effective amount of an H₁ receptor antagonist selected from: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine or triprolidine.

Another embodiment of this invention is directed to a method of treating: allergy, allergy-induced airway responses, and congestion comprising administering to a patient in need of such treatment an effective amount of Compound 287 in combination with an effective amount of an H₁ receptor antagonist selected from: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine or triprolidine.

Another embodiment of this invention is directed to a method of treating: allergy, allergy-induced airway responses, and congestion comprising administering to a patient in need of such treatment an effective amount of Compound 320 in combination with an effective amount of an H₁ receptor antagonist selected from: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine or triprolidine.

Another embodiment of this invention is directed to a method of treating: allergy, allergy-induced airway responses, and congestion comprising administering to a patient in need of such treatment an effective amount of Compound 32 in combination with an effective amount of an H₁ receptor antagonist selected from: loratadine, descarboethoxyloratadine, fexofenadine or cetirizine.

Another embodiment of this invention is directed to a method of treating: allergy, allergy-induced airway responses, and congestion comprising administering to a patient in need of such treatment an effective amount of Compound 54 in combination with an effective amount of an H₁ receptor antagonist selected from: loratadine, descarboethoxyloratadine, fexofenadine or cetirizine.

Another embodiment of this invention is directed to a method of treating: allergy, allergy-induced airway responses, and congestion comprising administering to a patient in need of such treatment an effective amount of Compound 55 in combination with an effective amount of an H₁ receptor antagonist selected from: loratadine, descarboethoxyloratadine, fexofenadine or cetirizine.

Another embodiment of this invention is directed to a method of treating: allergy, allergy-induced airway responses, and congestion comprising administering to a patient in need of such treatment an effective amount of Compound 253A in combination with an effective amount of an H₁ receptor antagonist selected from: loratadine, descarboethoxyloratadine, fexofenadine or cetirizine.

Another embodiment of this invention is directed to a method of treating: allergy, allergy-induced airway responses, and congestion comprising administering to a patient in need of such treatment an effective amount of Compound 287 in combination with an effective amount of an H₁ receptor antagonist selected from: loratadine, descarboethoxyloratadine, fexofenadine or cetirizine.

Another embodiment of this invention is directed to a method of treating: allergy, allergy-induced airway responses, and congestion comprising administering to a patient in need of such treatment an effective amount of Compound 320 in combination with an effective amount of an H₁ receptor antagonist selected from: loratadine, descarboethoxyloratadine, fexofenadine or cetirizine.

Another embodiment of this invention is directed to a method of treating: allergy, allergy-induced airway responses, and congestion comprising administering to a patient in need of such treatment an effective amount of Compound 32 in combination with an effective amount of an H₁ receptor antagonist selected from: loratadine or descarboethoxyloratadine.

Another embodiment of this invention is directed to a method of treating: allergy, allergy-induced airway responses, and congestion comprising administering to a patient in need of such treatment an effective amount of Compound 54 in combination with an effective amount of an H₁ receptor antagonist selected from: loratadine or descarboethoxyloratadine.

Another embodiment of this invention is directed to a method of treating: allergy, allergy-induced airway responses, and congestion comprising administering to a patient in need of such treatment an effective amount of Compound 55 in combination with an effective amount of an H₁ receptor antagonist selected from: loratadine or descarboethoxyloratadine.

Another embodiment of this invention is directed to a method of treating: allergy, allergy-induced airway responses, and congestion comprising administering to a patient in need of such treatment an effective amount of Compound 253A in combination with an effective amount of an H₁ receptor antagonist selected from: loratadine or descarboethoxyloratadine.

Another embodiment of this invention is directed to a method of treating: allergy, allergy-induced airway responses, and congestion comprising administering to a patient in need of such treatment an effective amount of Compound 287 in combination with an effective amount of an H₁ receptor antagonist selected from: loratadine or descarboethoxyloratadine.

Another embodiment of this invention is directed to a method of treating: allergy, allergy-induced airway responses, and congestion comprising administering to a patient in need of such treatment an effective amount of Compound 320 in combination with an effective amount of an $H_1$ receptor antagonist selected from: loratadine or descarboethoxyloratadine.

$R^1$ is preferably selected from:

(A) aryl (most preferably phenyl);

(B) substituted aryl (e.g., substituted phenyl), wherein the substituents on said substitued aryl are most preferably selected from: (1) halo (e.g., monohalo or dihalo), more preferably chloro or fluoro, even more preferably monochloro, dichloro, monofluoro or difluoro; or (2) alkyl, more preferably unbranched (i.e., straight chain, e.g., methyl) alkyl, even more preferably substituted alkyl, still more preferably alkyl substituted with halo (e.g., 1, 2 or 3 halo atoms, such as Cl or F), even still more preferably alkyl substituted with fluoro atoms, yet still more preferably trifluromethyl;

(C) heteroaryl, most preferably a five or six membered heteroaryl ring, more preferably a six membered heteroaryl ring, and still more preferably pyridyl, examples of heteroaryl rings include pyridyl, thienyl, pyrimidinyl, thiazolyl or pyridyl N-Oxide, most preferred heteroaryl rings are exemplified by

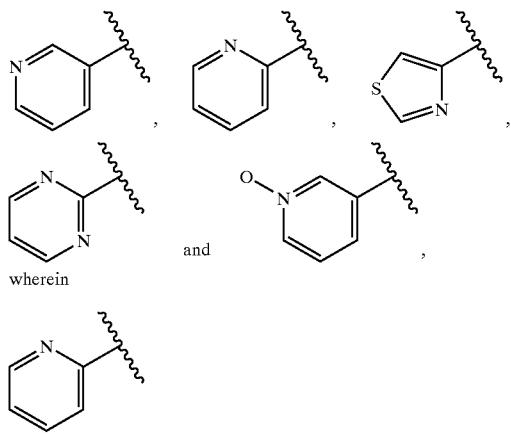

wherein is preferred more;

(D) substituted heteroaryl, most preferably halo or alkyl substituted heteroaryl (e.g., halopyridyl (e.g., fluoropyridyl) and alkylthiazolyl), more preferably substituted heteroaryl wherein the substituents are independently selected from the same or different alkyl groups (even more preferably one straight chain alkyl group, e.g., methyl), still more preferably alkyl substituted thiazolyl, and even more preferably

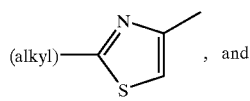, and yet even more preferably

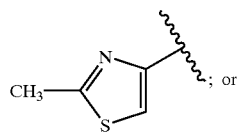; or (E) when $R^1$ is taken together with X, then the moiety is

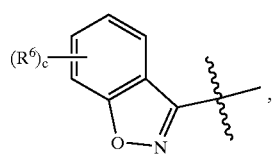

II wherein c is most preferably 0 or 1, and when c is 1 then $R^6$ is most preferably halo, and when c is 1 then $R^6$ is more preferably fluoro.

X is preferably $=C(NOR^3)$ wherein $R^3$ is preferably selected from H, alkyl or halo substituted alkyl (e.g., fluoro substituted alkyl, such as $—CH_2CF_3$), most preferably alkyl, more preferably methyl or ethyl, and still more preferably methyl.

Preferably $M^2$ is nitrogen.

n is preferably 2.

a is preferably 0 or 1, and most preferably 0.

b is preferably 0 or 1, and most preferably 0.

c is preferably 0 or 1, and most preferably 0, and when c is 1 then $R^6$ is preferably halo, and when c is 1 $R^6$ is most preferably fluoro.

e is preferably 1–5.

Y is preferably $=C(O)$ (i.e., $=C=O$).

$M^3$ and $M^4$ are preferably selected such that: (1) one is carbon and the other is nitrogen, or (2) both are nitrogen, with $M^3$ most preferably being carbon.

p is preferably 2.

Z is preferably $C_1$ to $C_3$ alkyl, and most preferably

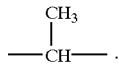

$R^2$ is preferably a six membered heteroaryl ring, most preferably pyridyl, substituted pyridyl, pyrimidinyl or substituted pyrimidinyl, more preferably pyridyl, pyridyl substituted with $—NR^4R^5$, pyrimidinyl or pyrimidinyl substituted with $—NR^4R^5$, still more preferably pyridyl, pyridyl substituted with $—NH_2$ (i.e., $R^4$ and $R^5$ are H), pyrimidinyl or pyrimidinyl substituted with $—NH_2$ (i.e., $R^4$ and $R^5$ are H), and even more preferably

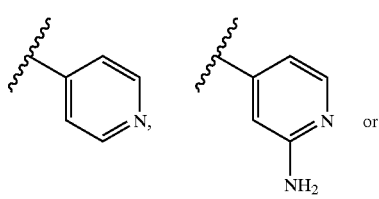

-continued

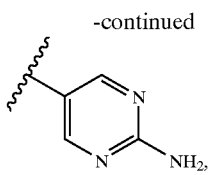

and still even more preferably

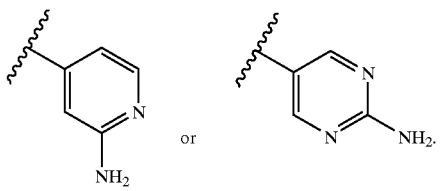

$R^3$ is preferably H or alkyl, most preferably H or methyl.

$R^4$ is preferably H or lower alkyl, most preferably H or methyl, and more preferably H.

$R^5$ is preferably H, $C_1$ to $C_6$alkyl or —C(O)$R^4$, most preferably H or methyl, and more preferably H.

$R^{12}$ is preferably alkyl, hydroxyl or fluoro, and most preferably H.

$R^{13}$ is preferably alkyl, hydroxyl or fluoro, and most preferably H.

Representative compounds of this invention include, but are not limited to: Compounds 23, 30, 31, 32, 33, 41, 44, 45, 49, 50, 52, 53, 54, 55, 56, 57A, 59, 65, 75, 76, 80, 82, 83, 88, 92, 99, 104, 105, 110, 111, 117, 121, 123, 127, 128, 200–241, 244–273, 275, and 278–282, 287, 296, 301–439 and 446.

Thus, representative compounds of this invention include, but are not limited to: Compounds 23, 30, 31, 32, 33, 44, 45, 49, 50, 53, 54, 55, 59, 75, 76, 83, 88, 92, 99, 104, 110, 117, 128, 200, 201, 203–215, 217–241, 244–246, 246A, 247–253, 253A, 254–273, 275, 278, and 280–282, 317, 334 and 403.

Preferred compounds of this invention are selected from: Compound 23, 30, 31, 32, 33, 50, 53, 54, 55, 56, 57A, 59, 92, 212, 215, 218, 219, 220, 224, 225, 226, 227, 229, 233, 235, 237, 238, 246, 246A, 247, 248, 251, 253, 253A, 268–273, 275, 278–281, 287, 296, 301, 304–307, 309, 312, 314–318, 320–356, or 358–376.

Most preferred compounds of this invention are selected from: Compound 30, 31, 32, 33, 54, 55, 56, 57A, 225, 237, 246A, 253A, 273, 280, 287, 296, 301, 304–307, 309, 312, 314–318, 320–348, 350–356, 359–372, and 374–376.

Thus, one embodiment of this invention is directed to Compound 32.

Another embodiment of this invention is directed to Compound 54.

Another embodiment of this invention is directed to Compound 55.

Another embodiment of this invention is directed to Compound 253A.

Another embodiment of this invention is directed to Compound 287.

Another embodiment of this invention is directed to Compound 320.

Structures for the above compounds are found in the Examples below, and in Tables 1 to 3 below.

The more preferred compound of this invention is the compound of the formula:

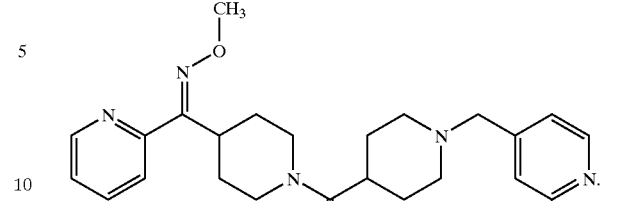

(32)

This invention also provides a compound of the formula:

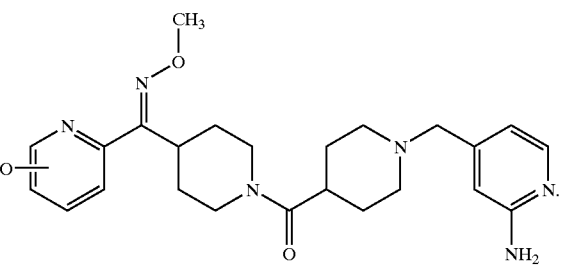

(32A)

This invention also provides a compound of the formula:

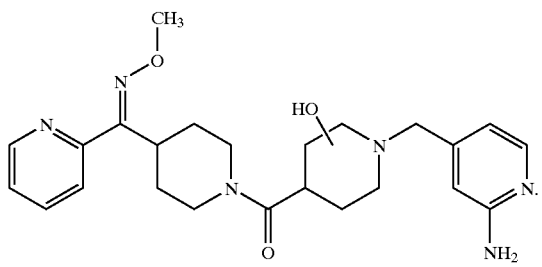

(32B)

Compounds 32A and 32B can also be used in the pharmaceutical compositions, and the methods of this invention.

The following processes may be employed to produce compounds of the invention.

One synthetic route involves a linear sequence of reactions to obtain the desired compounds, i.e., $$A+B \rightarrow AB+C \rightarrow ABC+D \rightarrow ABCD$$

This linear sequence of reactions to synthesize compounds of this invention is illustrated below. In the illustrated procedure $R^1$ is aryl, heteroaryl, or alkyl; X=a ketone, oxime or substituted oxime; $M^1=M^3$=carbon; $M^2=M^4$=nitrogen; Y is C=O; Z=CHR; $R^2$ is heteroaryl; and n and m=2 (n and m being 1 can also be prepared by this procedure).

Step: 1 Synthesis of Ketone 8

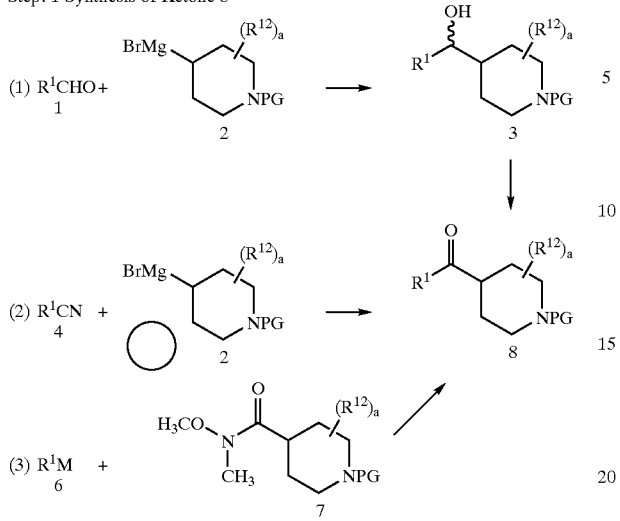

In the above equations PG represents a protecting group, and M represents Li or MgX$^1$ (wherein X$^1$ represents Cl, Br or I).

In equation 1 and 2, a Grignard reagent 2 is reacted with an electrophile such as the aldehyde 1 or the nitrile 4 in a suitable aprotic solvent such as THF or ether. PG represents a protecting group. Suitable protecting groups include, for example, methyl and benzyl. In the case of nitrile 4, acidic workup yields the ketone 8 directly. Alcohol 3 can be oxidized by a number of different reagents to give 8. Alternatively, the amide 7 can be reacted with an organometallic reagent to directly give the ketone 8. Suitable protecting groups for this step include carbamates or amides or the like. Thus, examples of protecting groups in equation 3 include t-BOC, CBZ and FMOC.

Step 2: Deprotection of 8

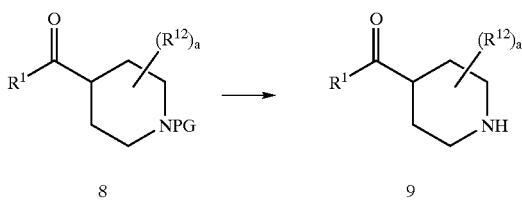

When the protecting group, PG, is a methyl group, said methyl group can be removed using a reagent such as a chloroformate; when PG is a carbamate, such as, a t-Boc group, it can be removed by dilute acid, such as, for example HCl.

Step 3: Synthesis of 11

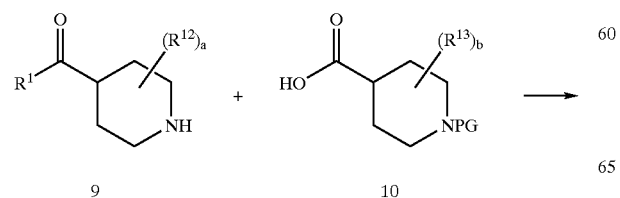

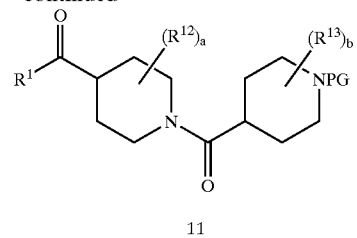

Amine 9 can be coupled to acid 10 using a number of methods well known in the art such as DCC or PyBOP. Alternatively, the acid 10 can be activated by conversion to the acid chloride or mixed anhydride and then reacted with the amine 9 to give 11. Suitable protecting groups for 10 include, for example, t-Boc.

Step 4: Synthesis of Amine 12

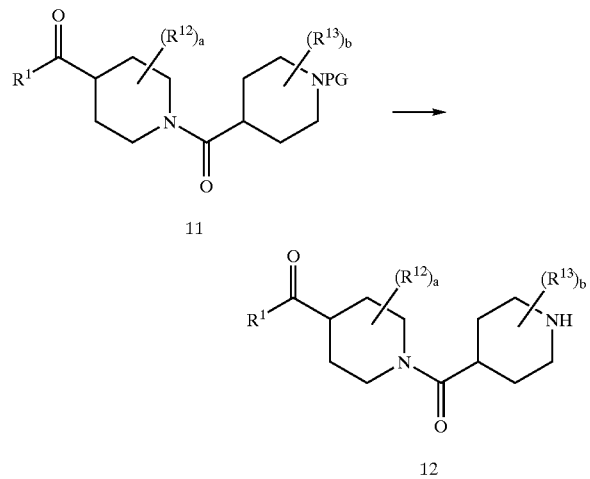

Compound 11 in which the protecting group is a t-Boc can be deprotected under acidic conditions such as HCl in dioxane or TFA in CH$_2$Cl$_2$ to give the amine 12.

Step 5: Synthesis of Compound 14

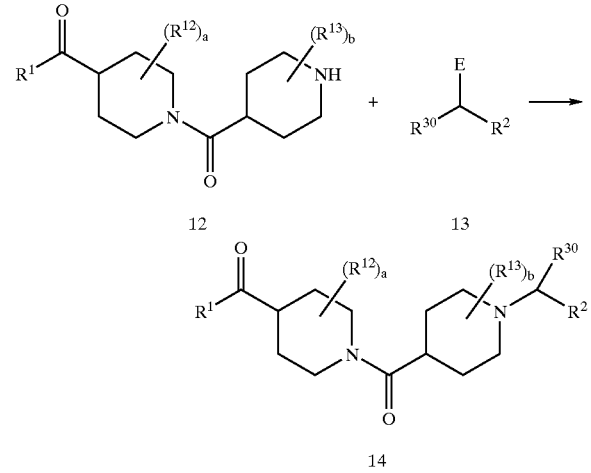

R$^{30}$ in 13 represents an alkyl group. E is a leaving group, halogen, or E is a carbonyl group.

Compound 14 can be prepared by reacting amine 12 with 13. When E represents a carbonyl group (C=O), 12 and 13 are combined in a solvent such as CH$_2$Cl$_2$ in the presence of molecular sieves. After the reaction is complete (e.g., 1 to 10 h), a reducing agent such as NaBH(OAc)$_3$ is added. Alternatively, when E is a halogen atom such as Cl or Br, 12 and 13 are combined in a solvent, such as DMF, in the presence of a tertiary amine base to give the product 14. Suitable protecting groups include, for example t-Boc, phthaloyl.

Step 6: Synthesis of Compound 16

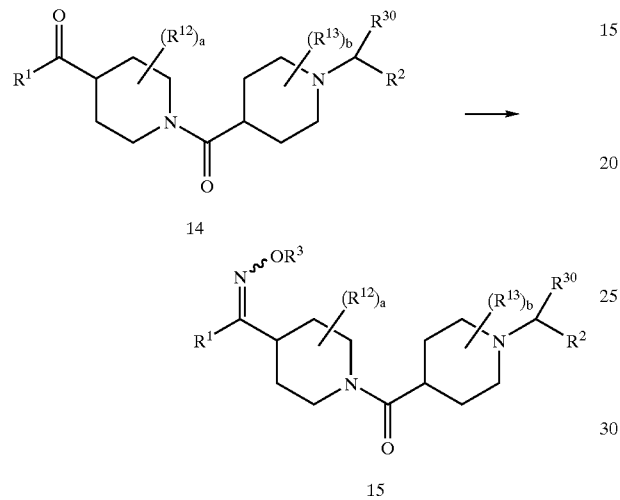

Compound 14 can be converted to the oxime 15 by combining 14 with H$_2$NOR$^3$.HCl in pyridine at a temperature of 40–60° C. Alternatively, 14 can be combined with H$_2$NOR$^3$.HCl in an alcoholic solvent in the presence of a base, such as, NaOAc, to give 15.

An alternate approach to the synthesis of compounds of Formula I involves the synthesis of the two halves of the molecule followed by coupling of the two pieces, i.e.,

In this case, the synthesis of the AB fragment is the same as that described above. The synthesis of the CD fragment is given below.

Step 1: Synthesis of Compound 17

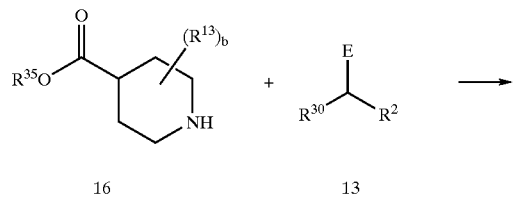

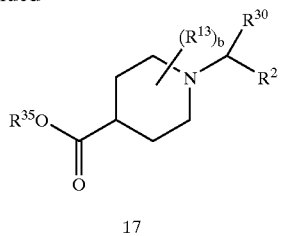

R$^{30}$ is as defined above (i.e., alkyl). R$^{35}$ is methyl or ethyl.

Compound 17 is synthesized in the same manner as that described for the synthesis of compound 14.

Step 2: Synthesis of Compound 18

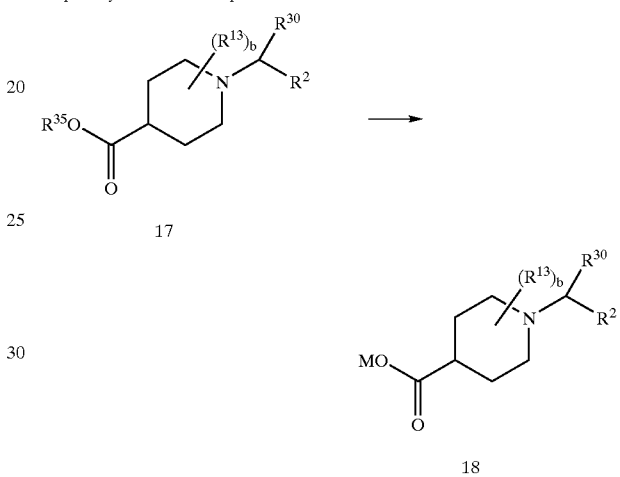

M represents Li, Na, or K.

Compound 17 is saponified in a mixed solvent, such as, for example: (1) EtOH or MeOH and water, or (2) THF, water, and MeOH, using an alkali metal base such as LiOH or NaOH at a temperature of from 50 to 100° C. to give the salt 18.

Compound 18 can be combined with compound 9, as described above, to give 14. The remaining steps are the same.

Compounds useful in this invention are exemplified by the following examples which should not be construed as limiting the scope of the disclosure. Alternative mechanistic pathways and analogous structures within the scope of the invention may be apparent to those skilled in the art.

EXAMPLE 1

Step 1

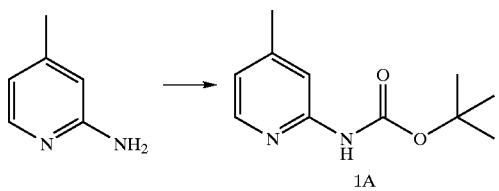

To a solution of 10.81 g (100 mmol) of 2-amino-4-methylpyridine in 250 ml of tert-butanol was added 26.19 g (120 mmol) of BOC anhydride. The reaction mixture was stirred at room temperature overnight, concentrated, loaded on silica gel and flash chromatographed (from 30% hexanes/CH$_2$Cl$_2$ to 0–2% acetone/CH$_2$Cl$_2$) to produce 15.25 g (73.32 mmol; 73%) of 1A as a white solid.

Step 2

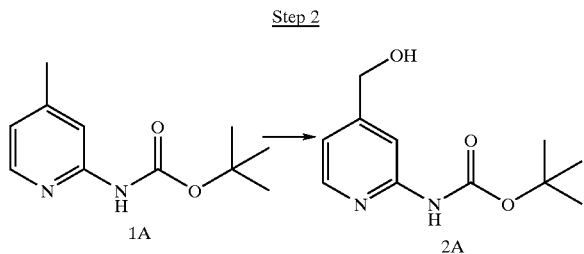

To a −78° C. solution of of 1A (35.96 g, 173 mmol) in THF (1.4 L) was added 1.4 M BuLi solution (272 ml, 381 mmol) in hexanes in portions over 30 min. Reaction mixture was then allowed to warm up and was stirred for 2 h at room temperature, which resulted in the formation of an orange precipitate. The mixture was cooled back to −78° C., and predried oxygen (passed through a Drierite column) was bubbled through the suspension for 6 h while the temperature was maintained at −78° C. Reaction mixture color changed to yellow during this time. It was then quenched at −78° C. with 51.4 ml (700 mmol) of Me$_2$S followed by 22 ml (384 mmol) of AcOH. Reaction mixture was allowed to warm up and was stirred for 48 h at room temperature. Dilution with water and extraction with EtOAc were followed by concentration and flash chromatography (0–15% acetone/CH$_2$Cl$_2$) to provide 20.15 g (90 mmol; 52%) of alcohol 2A as a pale yellow solid.

Step 3

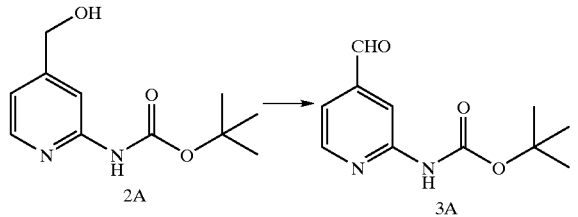

To a solution of 19.15 g (85.5 mmol) of alcohol 2A in 640 ml of CH$_2$Cl$_2$ was added saturated aqueous solution of 8.62 g (103 mmol) of NaHCO$_3$ and 444 mg (4.3 mmol) of NaBr. Reaction mixture was cooled to 0° C., and 140 mg (0.90 mmol) of TEMPO was introduced. Upon vigorous stirring 122 ml of 0.7 M (85.4 mmol) commercial bleach solution (5.25% in NaOCl) was added in portions over 40 min. After additional 20 min at 0° C. reaction mixture was quenched with saturated aqueous Na$_2$S$_2$O$_3$ and allowed to warm to room temperature. Dilution with water and extraction with CH$_2$Cl$_2$ were followed by concentration and flash chromatography (from 30% hexanes/CH$_2$Cl$_2$ to 0–2% acetone/CH$_2$Cl$_2$) to afford 15.97 g (71.9 mmol; 84%) of aldehyde 3A as an off-white solid.

Step 4

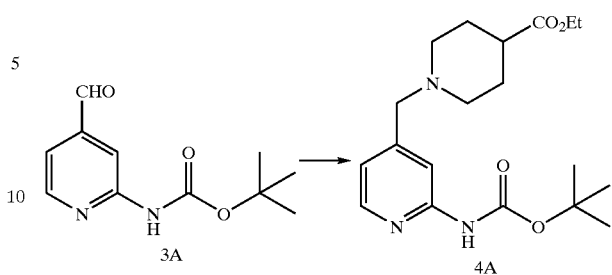

To a solution of 11.87 g (53.5 mmol) of aldehyde 3A in 370 ml of CH$_2$Cl$_2$ was added 9.07 ml (58.8 mmol) of ethyl isonipecotate followed by four drops of AcOH. Reaction mixture was then stirred for 40 min at room temperature after which 22.68 g (107 mmol) of NaBH(OAc)$_3$ was introduced. Reaction mixture was stirred overnight at room temperature, neutralized with saturated aqueous NaHCO$_3$, diluted with water and extracted with CH$_2$Cl$_2$. Concentration and flash chromatography (0–4% sat. NH$_3$ in MeOH/CH$_2$Cl$_2$) provided 19.09 mg (52.6 mmol; 98%) of 4A as an off-white solid.

Step 5

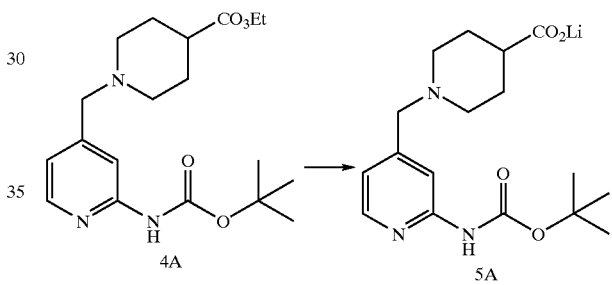

To a solution of 1.57 g (4.33 mmol) of ester 4A in 10 ml of a 3:1:1 mixture of THF—water—methanol was added 0.125 g (5.21 mmol) of LiOH. Reaction mixture was stirred overnight at room temperature, concentrated and exposed to high vacuum to obtain 1.59 g of crude acid 5A as a yellowish solid which was used without purification.

EXAMPLE 2

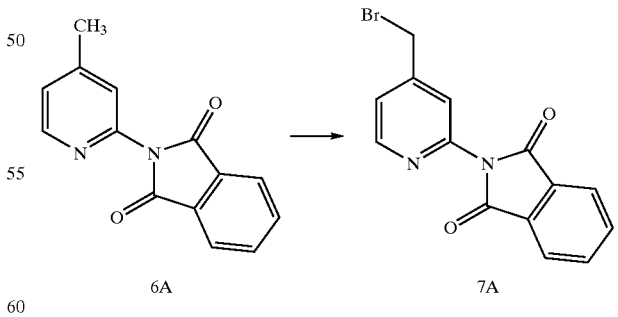

A solution of compound 6A (42 mmol), NBS (126 mmol) and Bz$_2$O$_2$ (4.2 mmol) in CCl$_4$ (400 ml) was refluxed at 80° C. for 5 h, cooled and stirred at room temperature overnight. The reaction was filtered and concentrated, and the residue was purified by flash column (30% EtOAc/Hexane) to obtain the desired compound 7A (3.1 g, 23%).

EXAMPLE 3

Step 1

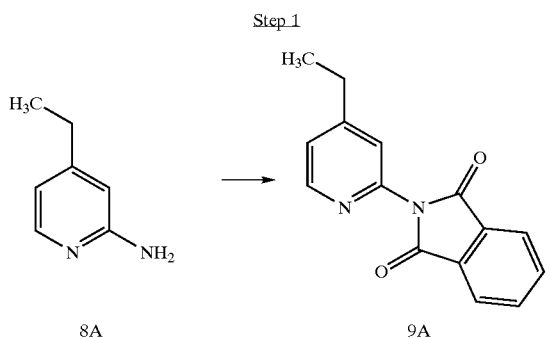

To a solution of 8A (10 g, 79.4 mmol) and DMAP (0.029 g, 0.24 mmol) in methylene chloride (150 mL) at 0° C. was added phthaloyl dichloride (16.1 g, 79.4 mmol) dropwise. The reaction mixture was stirred at room temperature overnight. After stirring overnight, the reaction was washed with saturated aqueous NaHCO$_3$, water, dried and concentrated to give compound 9A as a yellow solid (20 g, 99.8%) which was used without further purification.

Step 2

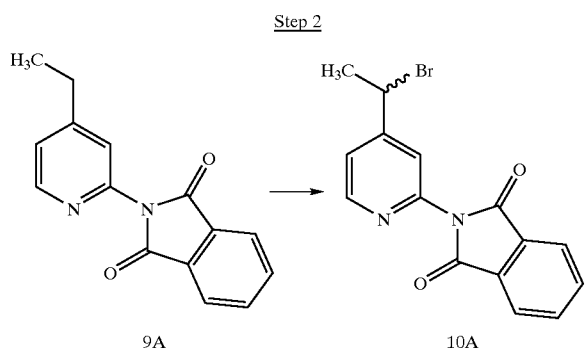

In a manner similar to that described in Example 2, compound 9A (20 g, 79.3 mmol) was converted to compound 10A.

Step 3

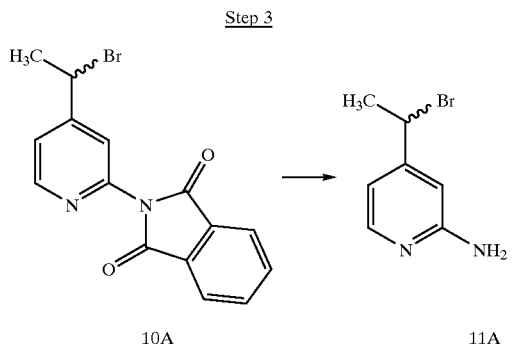

Compound 10A (0.5 g, 1.5 mmol) and hydrazine (0.5 M in ethanol, 5 mL, 2.5 mmol) were combined and stirred at room temperature overnight. The reaction was diluted with water and extracted with methylene chloride. The organic layer was dried, concentrated and the residue purified on a flash column (3% methanol in ethyl acetate) to give compound 11A (0.2 g, 66%).

EXAMPLE 4

Step 1

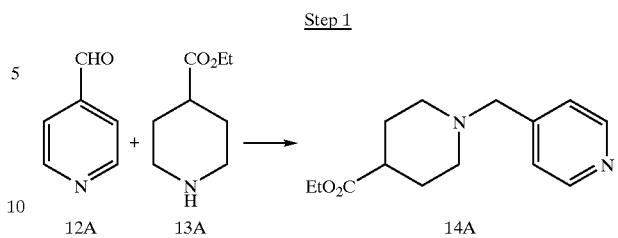

Compounds 12A (2 g, 18.3 mmol) and 13A (3.5 g, 22 mmol) were dissolved in methylene chloride and stirred at room temperature for 1 h. NaB(OAc)$_3$H (5.4 g, 25.6 mmol) was added and the mixture stirred at room temperature for 5 h. The reaction was washed with saturated aqueous NaHCO$_3$, dried and concentrated, and the residue purified by flash column (2% methanol in ethyl acetate). Compound 14A was obtained (4.5 g, 99%).

Step 2

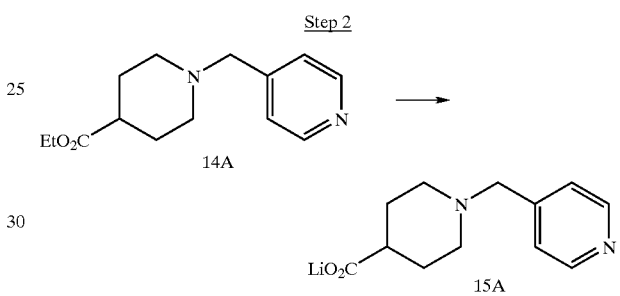

In a manner similar to that described in Example 1, Step 5, compound 14A (0.35 g, 1.4 mmol) was converted to compound 15A (0.31 g, 100%).

EXAMPLE 5

Step 1

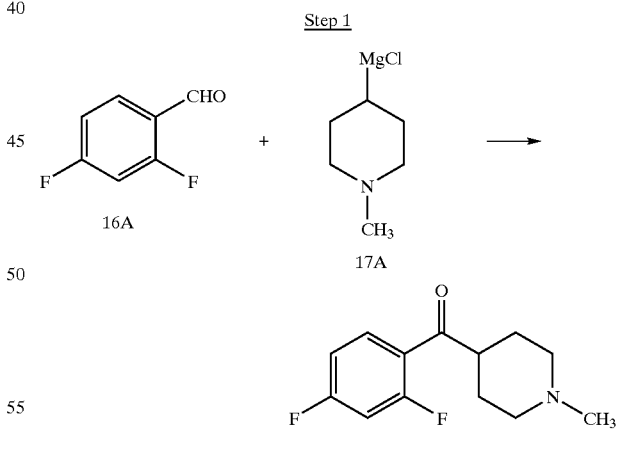

To the solution of 2,4-diflorobenzylaldehyde (16A, 28.1 mmol) in THF (10 ml) was added the Grignard reagent 17A (1.33M in THF, 30 ml), and the mixture was stirred at room temperature overnight. The reaction was quenched with saturated NH$_4$Cl (150 ml), extracted three times with EtOAc (100 ml), dried, filtered and concentrated. Flash chromatography (20% MeOH/EtOAc) yielded the desired compound 18A (1.8 g, 27%).

Step 2

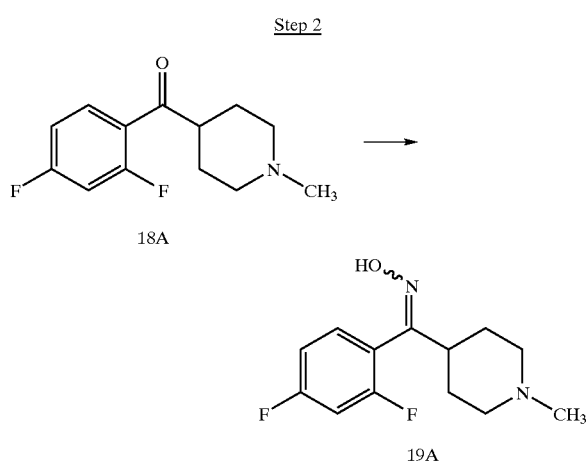

Compound 18A (1.6 g, 6.7 mmol), H$_2$NHOH·HCl (0.95 g, 6.7 mmol) and pyridine (10 mL) were combined and heated to 60° C. overnight. The pyridine was removed under vacuum and the residue treated with methylene chloride and saturated aqueous NaHCO$_3$. The organic layer was separated, dried, and concentrated, and the residue purified by flash chromatography to give compound 19A (1.4 g, 82%).

Step 3

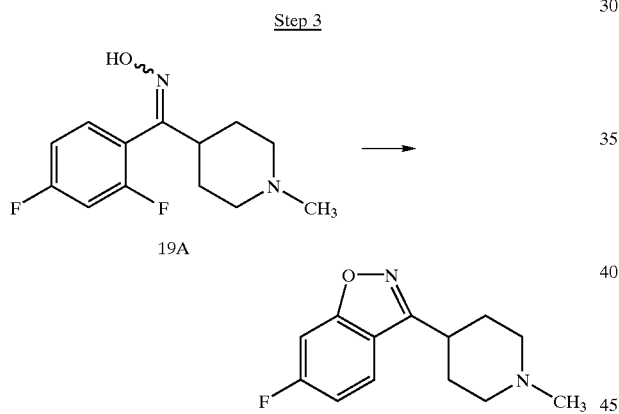

To the suspension of NaH (0.41 g, 10.2 mmol) in THF (10 ml) was slowly added a solution of 19A (1.3 g, 5.11 mmol) in DMF (5 mL) dropwise and the reaction stirred at 70–75° C. overnight. The mixture was extracted twice with EtOAc and three times with H$_2$O (30 mL), dried over MgSO$_4$ and concentrated to give crude 20A which was used without further purification (1.04 g, 87%).

Step 4

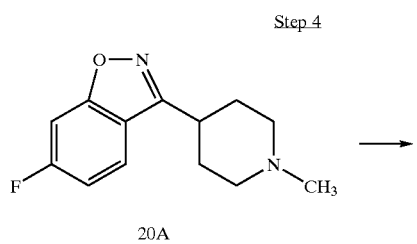

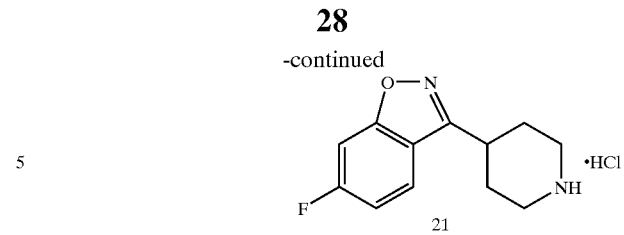

To the solution of compound 20A (4.3 mmol) in dichloroethane (20 ml) at 0° C. was added 2-chloroethyl chloroformate (6.2 mmol) and triethylamine (7.2 mmol) and the reaction was stirred at room temperature overnight. The solvent was evaporated, Et$_2$O was added to the residue, and the unreacted starting material was removed by filtration. The filtrate was concentrated and the residue redissolved in MeOH and refluxed for 30 min. Removal of the methanol gave the product 21 (0.3 g) which was used without further purification.

Step 5

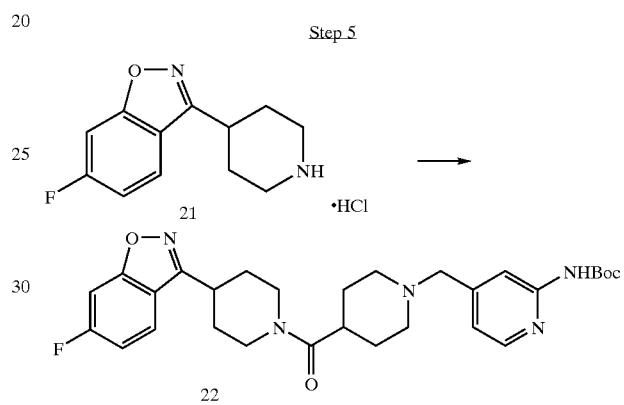

To a mixture of compound 21 (1.64 mmol), compound 5A (1.64 mmol) and PyBOP (1.64 mmol) was added DIPEA (4.92 mmol) and CH$_2$Cl$_2$ (10 ml), and the reaction was stirred over the weekend at room temperature. Saturated NaHCO$_3$ (100 ml) was added and the reaction was extracted and twice with CH$_2$Cl$_2$ (100 mL), dried over solid MgSO$_4$, concentrated and flash chromatographed (70% EtOAc/Hexane) to give compound 22 (1.04 mmol, 64%).

Step 6

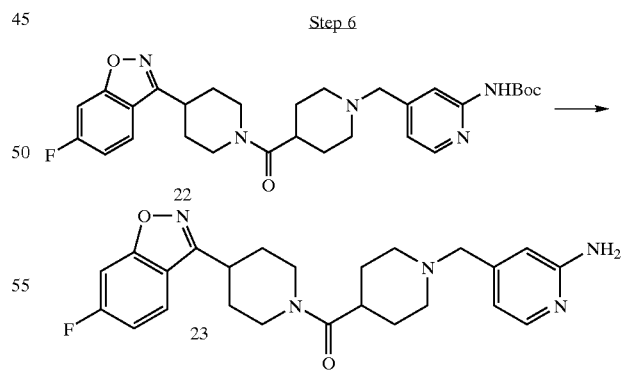

Compound 22 (0.2 g, 0.37 mmol) was dissolved in CF$_3$CO$_2$H (3 mL) and methylene chloride (3 mL) and stirred at room temperature overnight. The solvent was removed by evaporation, saturated aqueous NaHCO$_3$ was added and mixture extracted with methylene chloride. The organic layer was dried (MgSO$_4$), filtered and concentrated, and the residue purified by flash chromatography to give compound 23 (0.11 g, 68%).

EXAMPLE 6

Step 1

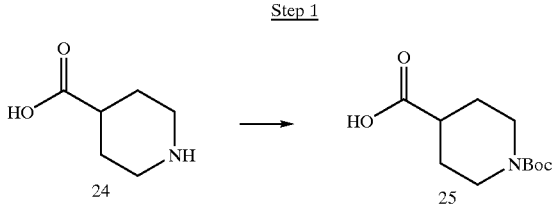

A solution of 24 (50 g, 387 mmol) and triethylamine (110 mL) in dioxane (400 mL) and water (400 mL) at 4° C. was treated with Boc₂O (93 g, 426 mmol). The cooling bath was removed and the solution allowed to warm to room temperature. After 21 h, the volume was reduced by two-thirds under vacuum. The residue was poured into ethyl acetate (250 mL) and water (250 mL). Saturated aqueous NaHCO₃ (250 mL) was added and the organic phase was separated and discarded. The aqueous phase was acidified with 10% HCl and extracted with ethyl acetate. The combined organic phases were washed with water, brine, and dried (Na₂SO₄), and concentrated to give 25 as a white powder (82 g, 94%).

Step 2

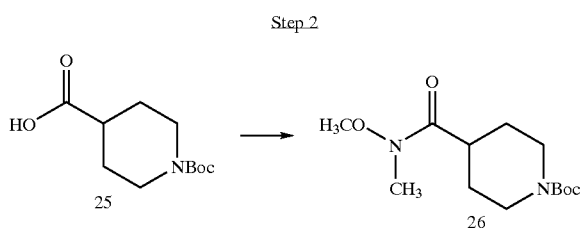

To a solution of compound 25 (40 g, 175 mmol) in DMF (250 mL) at 4° C. was added N,O-dimethylhydroxylamine, hydrochloride (34 g), EDCl (44 g, 0.228 mol), HOBT (2.4 g), and DIPEA (120 mL). The reaction was warmed to room temperature and stirred overnight. The reaction was then concentrated to half volume in vacuo and poured onto 1:1 ethyl acetate:water. The organic layer was separated and the aqueous layer extracted with additional ethyl acetate. The combined organic layers were washed with saturated aqueous NH₄Cl, saturated aqueous NaHCO₃, water, and brine, and dried. Concentration gave 26 as a light yellow oil (46.7 g, 99%)

Step 3

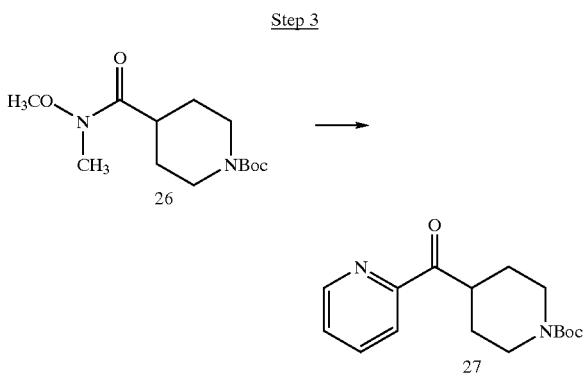

To a solution of 2-bromopyridine (17.6 mL, 0.184 mol) in THF (600 mL) at −78° C. was added n-BuLi (115 mL of a 1.6M solution in hexanes, 0.184 mol) dropwise over 15 min. After stirring for an additional 30 min at this temperature, a solution of 26 (25 g, 91.9 mmol) in THF (500 mL) was added dropwise over 15 min. The reaction was removed from the cold bath and placed in an oil bath and heated to 60° C. for 1.5 h. The reaction was then cooled to 4° C., diluted with ether (500 mL), and treated with saturated aqueous Na₂SO₄ (≈5 mL). The mixture was transferred to an Erlenmeyer flask and diluted with additional ether (700 mL). Additional saturated aqueous Na₂SO₄ was added followed by solid Na₂SO₄. The mixture was filtered through a plug of solid Na₂SO₄ and concentrated in vacuo. Flash column chromatography (0–20% ethyl acetate in hexanes) yielded compound 27 as a yellow oil (16.85 g, 63%).

Step 4

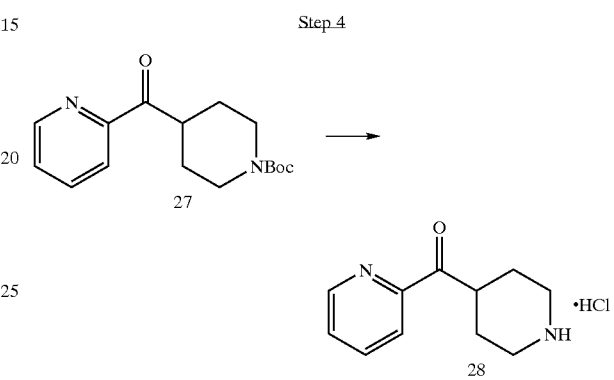

A solution of 27 (3.3 g, 11.4 mmol) in methanol (50 mL) was treated with 4M HCl in dioxane (50 mL) and stirred at room temperature for 1.5 h. Removal of the solvent in vacuo gave 28 as a tan powder (3 g, 100%).

Step 5

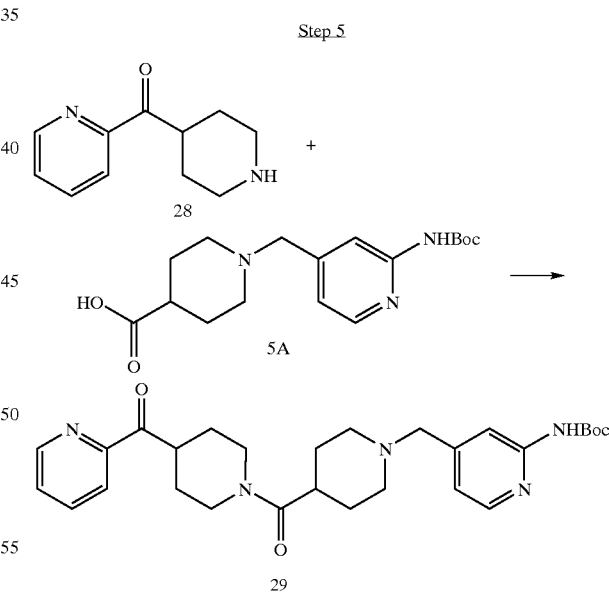

To a suspension of compound 5A (17.4 g, 50 mmol), compound 28 (11 g, 42 mmol), and diisopropylethylamine (34.6 mL, 199 mmol) in DMF (125 mL) was added HOBT (7.83 g, 58 mmol), EDC (18.54 g, 96.7 mmol), and 4A molecular sieves. The mixture was stirred for 40 h at room temperature, diluted with methylene chloride (600 mL) and 0.5 N NaOH (400 mL) and filtered. The precipitate was washed thoroughly with additional 0.5N NaOH and methylene chloride. The combined organic phases were concentrated and chromatographed twice on silica gel (1:1 hexane:methylene chloride to 6% saturated NH₃ in methanol in methylene chloride) to produce 29 as a tan solid (22.3 g) which was used as is in the next step.

Step 6

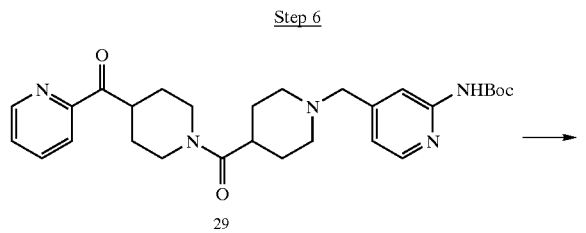

29

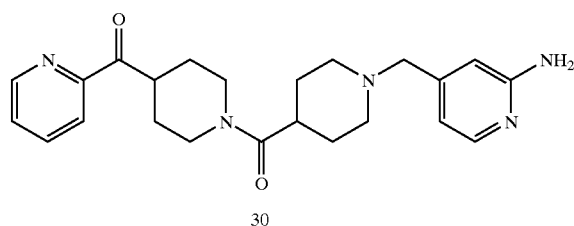

30

A solution of 29 (22.3 g, 44 mmol) in methylene chloride (120 mL) and trifluoroacetic acid (60 mL) was stirred for 7 h at room temperature. The reaction was concentrated, exposed to high vacuum for 3 h, dissolved in toluene and concentrated and then exposed again to high vacuum. The so-obtained crude brown oil was used in the next step without further purification.

Step 7

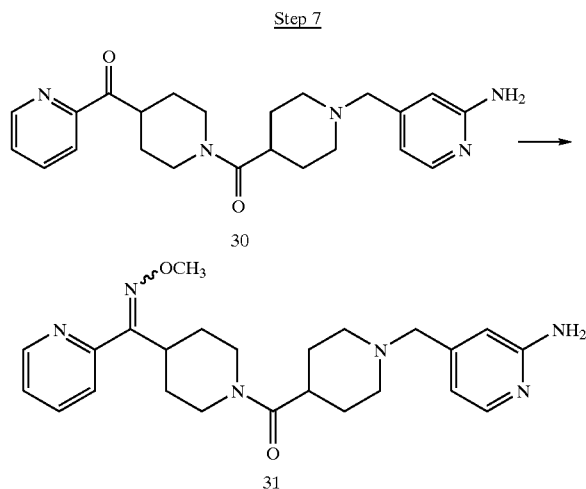

Compound 30 (≈17.9 g, 44 mmol) was dissolved in pyridine (420 mL), treated with H₂NOCH₃.HCl (21.78 g, 264 mmol) and heated to 90° C. for 14 h. The reaction was then concentrated and the residue taken up in a mixture of methylene chloride (500 mL) and 2N NaOH (500 mL). The organic phase was separated and the aqueous phase extracted with additional methylene chloride (300 mL). The organic phases were dried and concentrated, and the residue chromatographed on SiO₂ (0–13% NH₃/MeOH in CH₂Cl₂) to produce a yellow solid (9.26 g). The mixed fractions from the column were rechromatographed to give an additional 3.23 g of the desired material. Total yield 12.49 g (65% yield over the last two steps).

Step 8

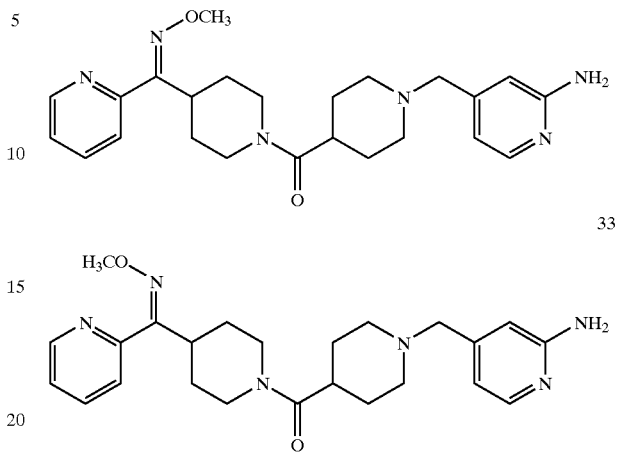

Compound 31 (1 g) in ethanol (15 mL) was separated into the pure isomers using a Chiralcel AD column (20 mm×500 mm) (eluent: 75:25 hexane: isopropanol plus 0.5% N,N-diethylamine; flow rate: 50 mL/min; UV detection at 254 nM) to give compound 32 (0.6 g) and compound 33 (0.4 g). [M+H]⁺437 for 32 and 33.

Alternatively, compound 32 can preferably be prepared from compound 5A in a manner similar to that described for compound 287 in Step 3 of Example 28.

EXAMPLE 7

Step 1

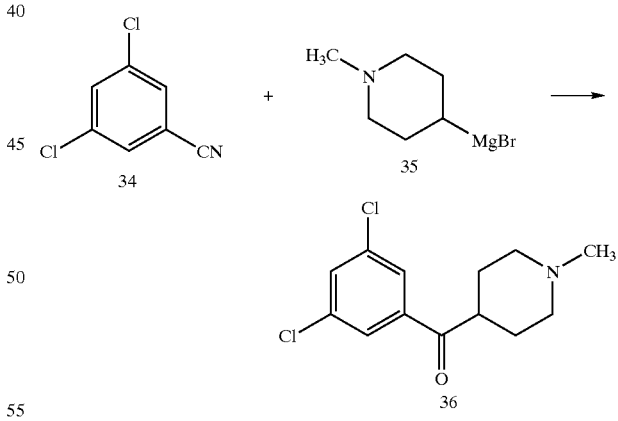

To a solution of 34 (2.4 g, 13.5 mmol) in THF (15 mL) was added compound 35 (26 mL of a 1.3M solution) and the reaction stirred overnight at room temperature. 2N HCl was then added till the pH<2 and the THF was removed under reduced pressure. The pH was neutralized by the addition of 1N NaOH and the aqueous phase extracted with 5% MeOH in EtOAc. The organic phase was dried, concentrated, and the residue chromatographed (20% MeOH in EtOAc) to give 36 (1.03 g, 28%).

Step 2

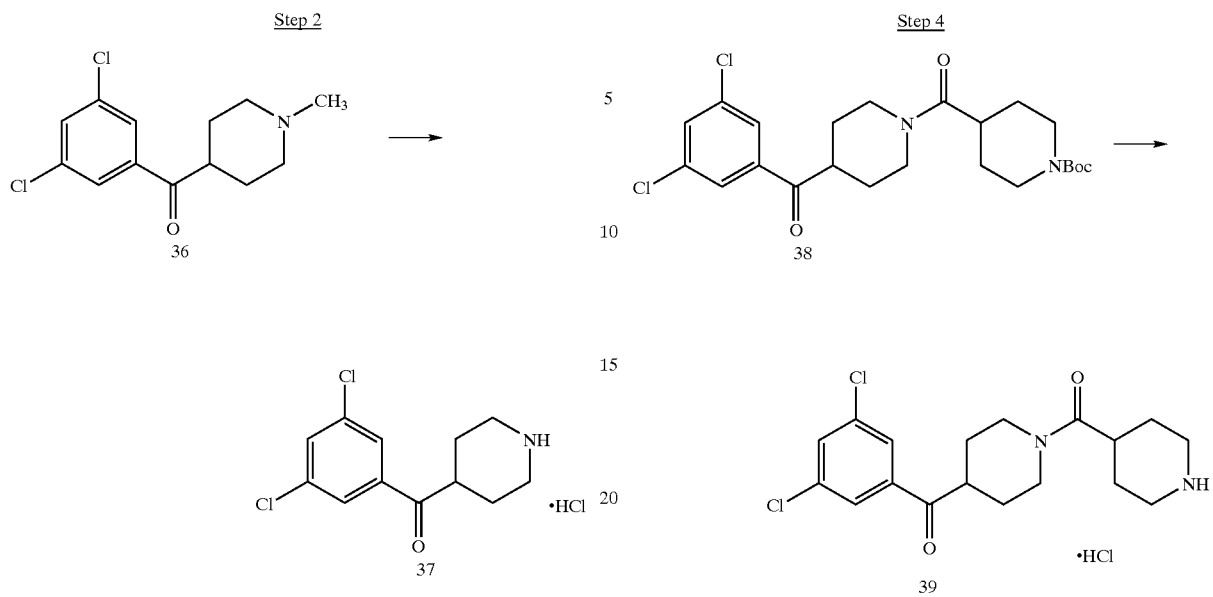

To a solution of 36 (1.03 g, 3.78 mmol) in 1,2-dichloroethane (30 mL) was added 1-chloroethylchloro formate (0.76 mL, 7.6 mmol) and the reaction stirred at room temperature overnight. The solvent was removed in vacuo and the residue washed with ether. Solid residue was removed by filtration and the ether removed by evaporation to give an oil which was dissolved in MeOH (15 mL) and heated to reflux for 2 h. Removal of the solvent gave 37 which was used in the next step without further purification (1.4 g).

Compound 37 (0.98 g, 3.78 mmol), N-Boc isonipocotic acid (0.87 g, 3.78 mmol), DEC (1.11 g, 5.7 mmol), HOBT (0.68 g, 4.91 mmol) and DIPEA (3 mL) were combined in CH$_2$Cl$_2$ (40 mL) and stirred overnight at room temperature. The reaction was then diluted with CH$_2$Cl$_2$ and washed with saturated aqueous NaHCO$_3$. The organic layer was dried, concentrated and the residue chromatographed (10% hexane in EtOAc) to give 38 (1.61 g, 91%).

Step 4

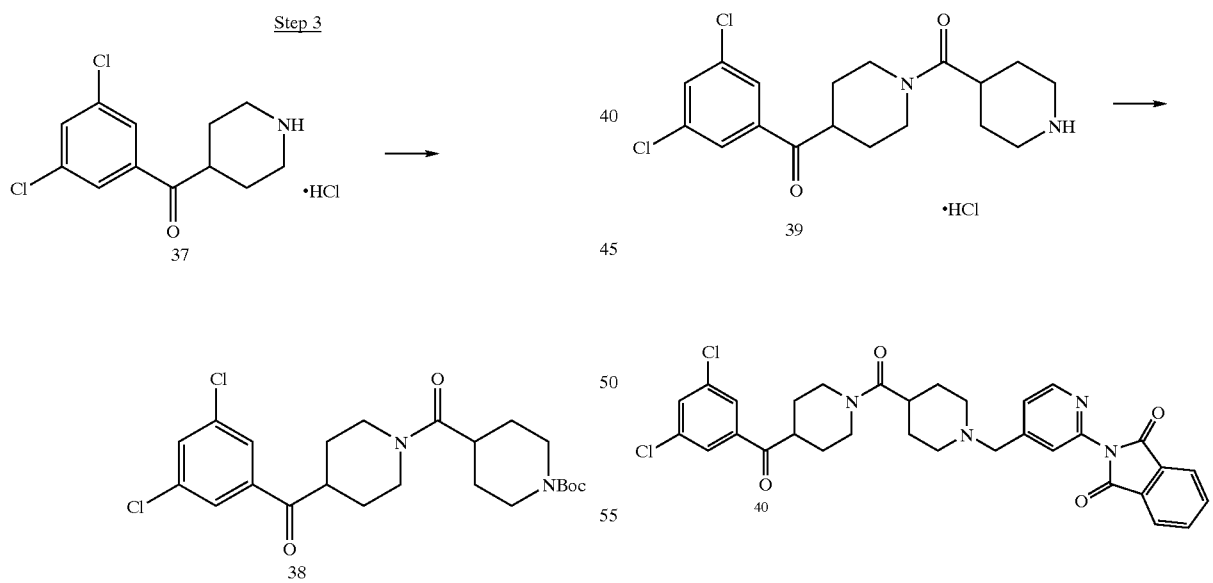

Compound 38 (1.61 g, 3.43 mmol) in CH$_2$Cl$_2$ (15 mL) was treated with 1N HCl in dioxane (5.2 mL) and stirred overnight at room temperature. The solvent was removed in vacuo to give 39 (1.65 g) which was used without further purification.

Compound 39 (1.65 g, 4.01 mmol), 7 (1.29 g, 4.07 mmol) and Et$_3$N (1.7 mL) were combined in DMF (40 mL) and stirred at room temperature overnight. The reaction was dissolved in EtOAc and washed 4 times with water. The organic layer was dried and concentrated, and the residue purified by chromatography (5% MeOH in EtOAc) to give 40 (0.6 g, 47%).

Step 6

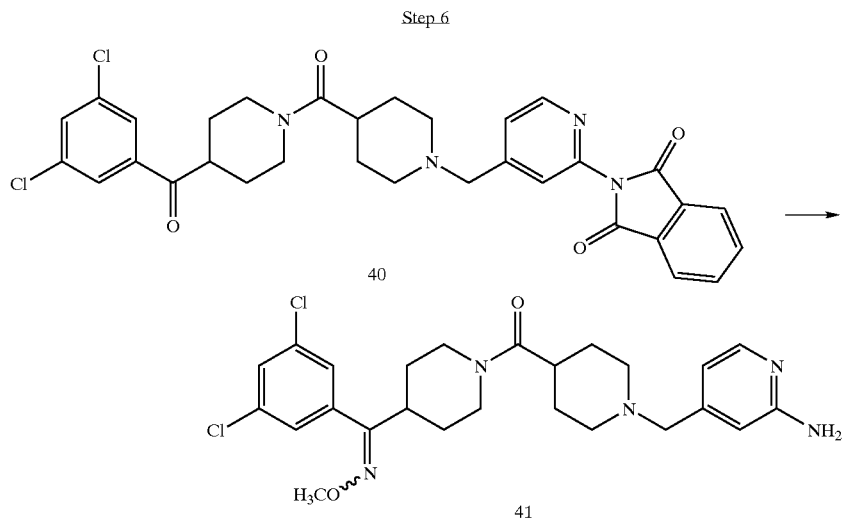

A solution of 40 (0.31 g, 0.51 mmol) in pyridine (5 mL) was treated with H$_2$NOMe.HCl (0.092 g, 1.08 mmol) and heated to 60° C. overnight. The reaction was diluted with 10% MeOH in CH$_2$Cl$_2$, washed with saturated aqueous NaHCO$_3$, dried, and concentrated, and the residue purified by chromatography (10–15% MeOH in EtOAc) to give 41 (0.09 g).

EXAMPLE 8

Step 1

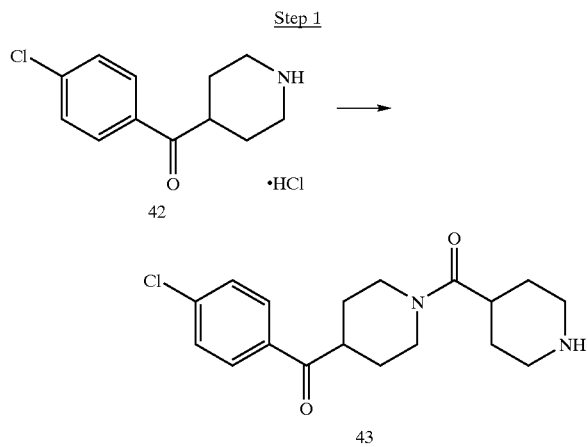

In a manner similar to that described in Example 7, Steps 3–4, compound 42 was converted to compound 43.

Step 2

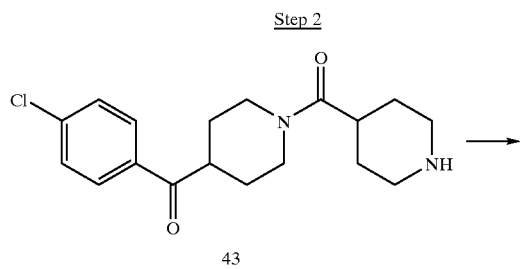

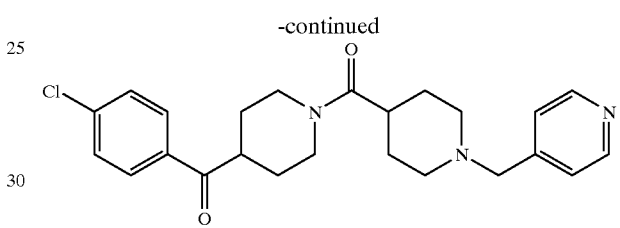

To a solution of 43 (2.3 g, 6.3 mmol) in CH$_2$Cl$_2$ (60 mL) was added 4 Å molecular sieves and 4-formylpyridine (0.68 mL, 6.9 mmol) and the mixture stirred for 3 h at room temperature. Na(OAc)$_3$BH (2.7 g, 12.7 mmol) was then added and the reaction stirred for 1 h. The reaction was quenched by the addition of NH$_4$Cl followed by the addition of saturated aqueous NaHCO$_3$. The reaction mixture was then extracted with EtOAc, and the combined organic layers were dried and concentrated to give a residue which was chromatographed (20% MeOH in EtOAc). Compound 44 was obtained (2.3 g, 87%).

Step 3

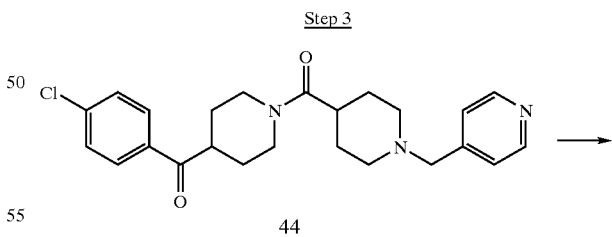

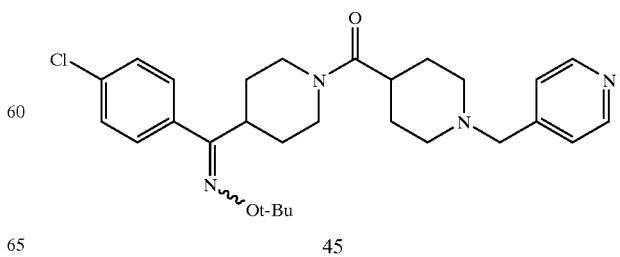

In a manner similar to that described in Example 7, Step 6, compound 44 was converted to compound 45.

EXAMPLE 9

Step 1

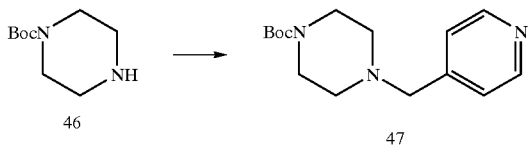

In a manner similar to that described in Example 8, Step 2, compound 46 (1.13 g, 6 mmol) was converted to compound 47 (1.7 g, 100%).

Step 2

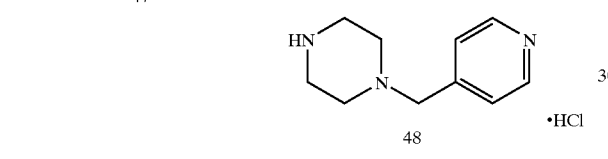

In a manner similar to that described in Example 7, Step 4, compound 47 (1.7 g, 6.13 mmol) was converted to compound 48 (1.9 g, 100%).

Step 3

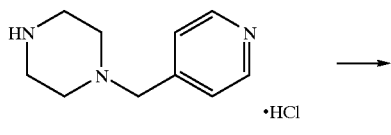

A mixture of compound 48 (0.57 g, 2 mmol) and compound 42 (0.52 g, 2 mmol) in CH$_2$Cl (20 mL) was added Et$_3$N (1.95 mL) and the reaction cooled to −40° C. Triphosgene (0.2 g) was added and the reaction stirred at −40° C. for 2 h and room temperature for 48 h. The reaction was then washed with 1N NaOH, brine, and the organic layer dried. Concentration gave a residue that was purified by column chromatography (10% MeOH in EtOAc) to give 49 (0.14 g, 55%).

Step 4

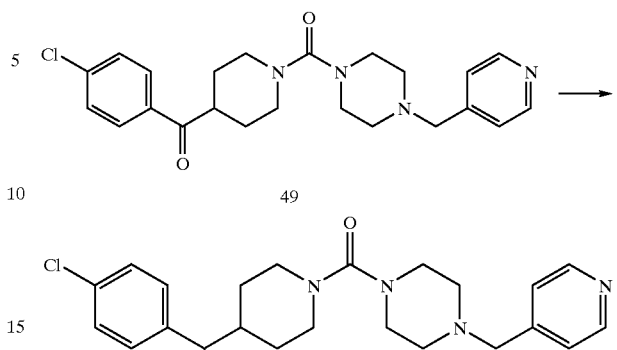

In a manner similar to that described in Example 7, Step 6, compound 49 (0.09 g, 0.21 mmol) was converted to compound 50.

EXAMPLE 10

Step 1

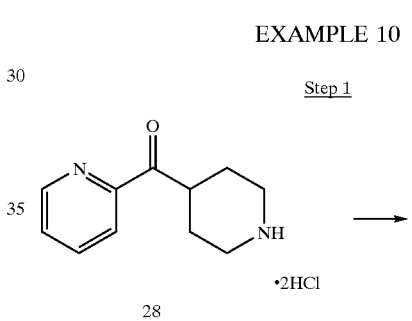

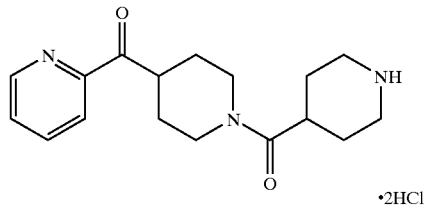

In a manner similar to that described in Example 7, Steps 3–4, compound 28 (2.6 g, 9.9 mmol) was converted to compound 51 (1.1 g).

Step 2

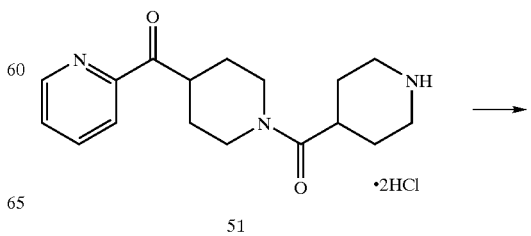

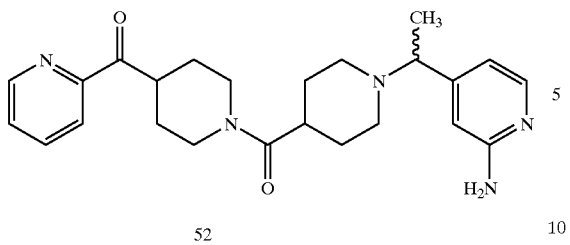

52

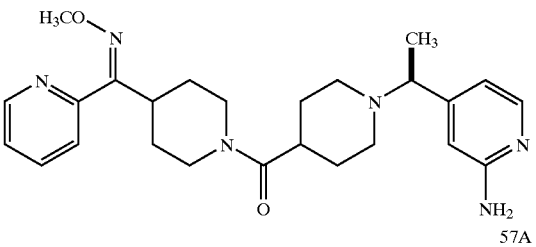

57A

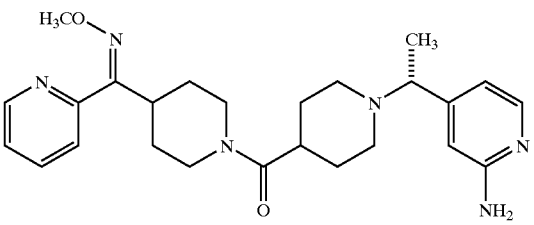

In a manner similar to that described in Example 7, Step 5, compound 51 (1.1 g, 2.94 mmol) was reacted with compound 11 (0.59 g, 2.94 mmol) to give compound 52 (0.53 g).

Step 3

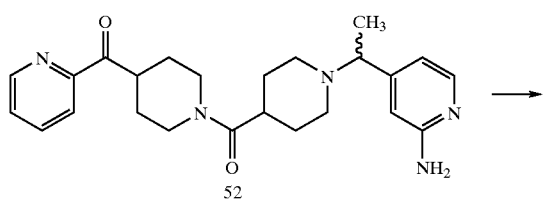

In a manner similar to that described in Example 6, Step 8, the 4 diastereomers of compound 53 could be obtained using a Chiralcel AD column (75:25 hexane:EtOAc plus 0.5% Et$_2$NH). The two faster eluting compounds (54 and 55) were the E-oxime isomers and the slower eluting compounds (56 and 57A) were the Z-oxime isomers.

| Isomer A | 54  | 0.12 g |
| Isomer B | 55  | 0.11 g |
| Isomer C | 56  | 0.08 g |
| Isomer D | 57A | 0.06 g |

EXAMPLE 11

Step 1

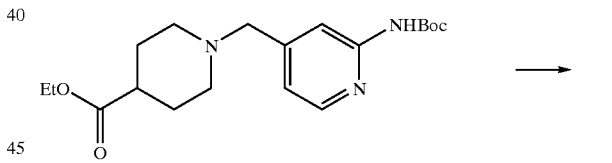

4A

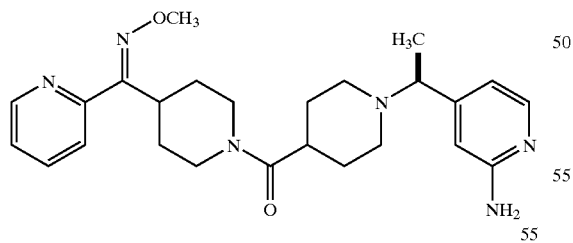

57

In a manner similar to that described in Example 6, Step 7, compound 52 (0.53 g, 1.26 mmol) was converted to compound 53 (0.48 g).

Step 4

54

55

A solution of n-BuLi (4.2 mL of a 1.6 M solution in hexane) in THF (25 mL) was treated at −25° C. with (i-Pr)$_2$NH (0.69 g, 6.8 mmol). The reaction was stirred for 1 h at 0° C. and then cooled to −70° C. Compound 4A (0.82 g, 2.26 mmol) in THF (5 mL) was added dropwise and the reaction stirred at −70° C. for 2 h and −50° C. for 2 h. The reaction was recooled to −70° C. and (1S)-(+)-(10-camphorsulfonyl)oxaziridine (1.04 g, 4.52 mmol) in THF (5 mL) was added. The reaction was stirred at −70° C. for 2 h and slowly warmed to room temperature overnight. The reaction was quenched by the addition of saturated aqueous NH$_4$Cl and extracted with EtOAc. The organic layer was dried and concentrated, and the residue purified by column chromatography (1:1 hexane:EtOAc) to give 57 (0.44 g, 51%).

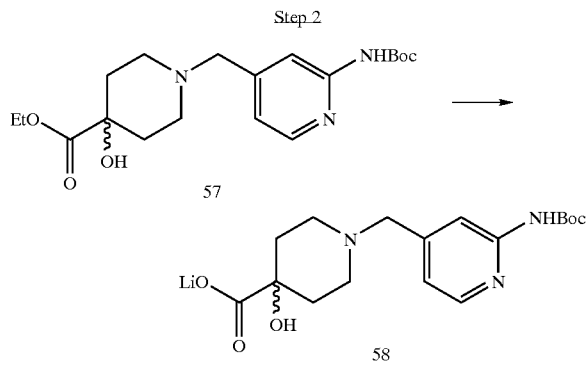

In a manner similar to that described in Example 1, Step 5, compound 57 (0.42 g, 1.1 mmol) was converted to compound 58 (0.4 g).

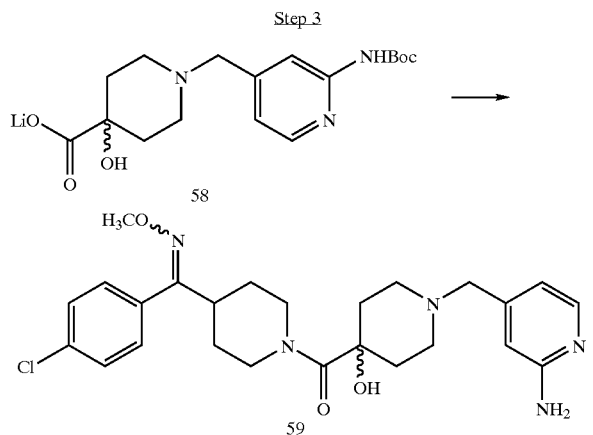

In a manner similar to that described in Example 6, Steps 5–8, compound 58 (0.25 g, 0.7 mmol) was converted to compound 59 (0.1 g).

EXAMPLE 12

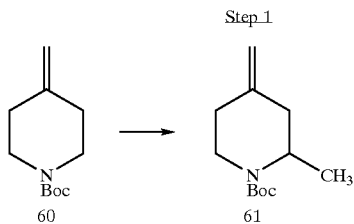

A solution of compound 60 (10 g, 50.7 mmol) in ether (150 mL) at −78° C. was treated sequentially with TMEDA (11.8 g, 101.4 mmol) and s-BuLi (58.5 mL of a 1.3M solution in hexanes, 76 mmol) and the reaction stirred at this temperature for 6 h. Neat $CH_3SO_4CH_3$ (12.8 g, 101.4 mmol) was then added and the reaction allowed to slowly warm to room temperature overnight. Saturated aqueous NaCl was added and the organic layer was separated. The aqueous layer was extracted three times with ether and the combined organic layers were dried and concentrated, and the residue chromatographed (5% EtOAc in hexane) to give 61 (8.0 g, 75%).

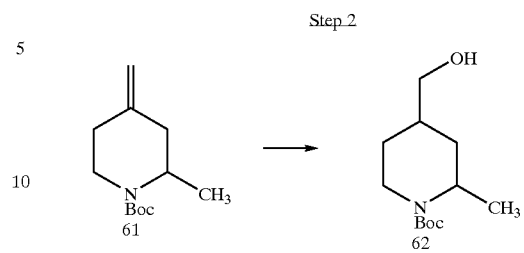

A solution of 61 (8 g, 37.9 mmol) in THF (40 mL) at 0° C. was treated dropwise with a solution of $BH_3 \cdot THF$ (45.4 mL of a 1.0M solution in THF, 45.4 mmol) and the reaction allowed to slowly warm to room temperature overnight. The reaction was recooled to 0° C., EtOH (13 mL), pH=7 buffer (25 mL) and $H_2O_2$ (25 mL) was added, and the reaction allowed to stir at room temperature overnight. The solvent was then removed in vacuo and the residue poured into water and $CH_2Cl_2$. 10% aqueous NaOH (10 mL) was added and the organic layer separated. The aqueous layer was extracted with additional $CH_2Cl_2$ and the combined organic layers were dried and concentrated. The residue was chromatographed (40% EtOAc in hexane) to give 62 (3 g).

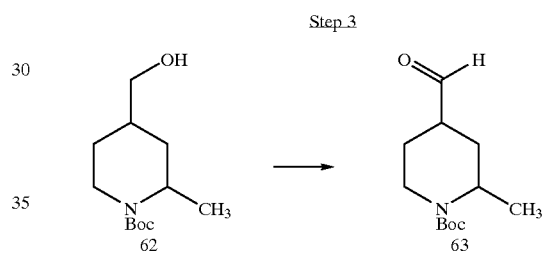

A solution of 62 (2.8 g, 12.2 mmol) in EtOAc (30 mL) and NaBr (1.26 g, 0.12 mmol) in saturated aqueous $NaHCO_3$ (30 mL) was cooled to 0° C. and treated with TEMPO (0.02 g, 0.12 mmol). After 15 min., NaOCl (17.44 mL) was added and the mixture stirred for 3 h. Saturated aqueous $Na_2S_2O_3$ was added and the pH adjusted to 5–6 by the addition of 1N HCl. The mixture was extracted with EtOAc and the organic layers were dried and concentrated. The residue was chromatographed (10–20% EtOAc in hexane) to give compound 63 (2.1 g, 76%).

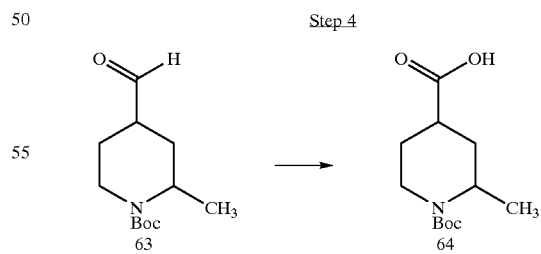

To a cooled (0° C.) suspension of PCC (0.95 g, 4.4 mmol) in $CH_2Cl_2$ (5 mL) was added dropwise a solution of 63 (0.5 g, 2.2 mmol). And the mixture stirred overnight at room temperature. Additional PCC (1 eq.) was added and the mixture was heated to reflux for 2 h. The reaction was cooled, filtered through celite, and concentrated to give crude 64 (1.5 g) which was used without further purification.

Step 5

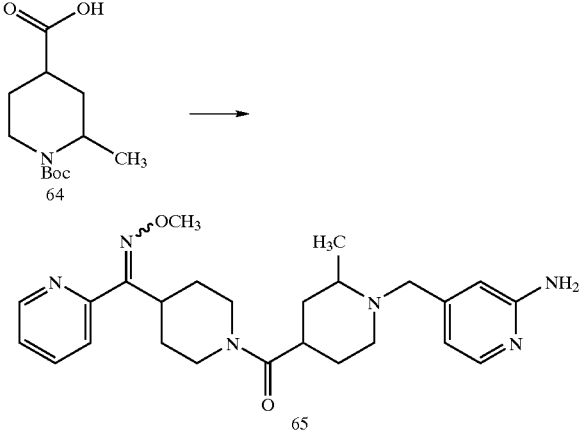

In a manner similar to that described in Example 5, Step 5, Example 7, Step 4, Example 1, Step 4, and Example 6, Steps 6 and 7, 64 (0.73 g, 3 mmol) was converted to 65 (0.1 g).

EXAMPLE 13

Step 1

HO₂C⟨⟩CO₂H  →

66

To a 0° C. solution of Vilsmeier salt, prepared by the dropwise addition of phosphorus oxychloride (150.0 mL; 1.61 mol) to DMF (310.4 mL; 4.01 mol) over 15 min. and subsequent cooling in an ice bath, was added malonic acid (40.1 g; 0.39 mol) in portions over 45 min. The reaction mixture was then heated to 100° C., and the stirring was continued for 48 h. The reaction mixture was then allowed to cool to room temperature and was quenched by slowly pouring it into a suspension of NaHCO₃ (808 g; 9.62 mol) in water. The solution was decanted off the excess of NaHCO₃ and concentrated to dryness under vacuum. After exposure to high vacuum for 2 days, the solid residue was washed repeatedly with CH₂Cl₂ until TLC indicated complete removal of product. Combined organic extracts were concentrated under vacuum to produce 41.0 g of dark brown oil, which was used directly in the next step.

Step 2

66 → 67

To a solution of 32.5 g (256 mmol) of crude malondialdehyde 66 in 650 ml of absolute ethanol was added 24.5 g (256 mmol) of guanidine hydrochloride and 17.4 g (256 mmol) of sodium ethoxide. The reaction mixture was refluxed for 4 h, cooled down to room temperature, concentrated and dry loaded on silica gel under vacuum. Flash chromatography (0–10% MeOH/20% acetone/CH₂Cl₂) afforded 11.0 g (89.4 mmol; 23% from malonic acid (2 steps)) of pyrimidine 67 as a light yellow solid.

Step 3

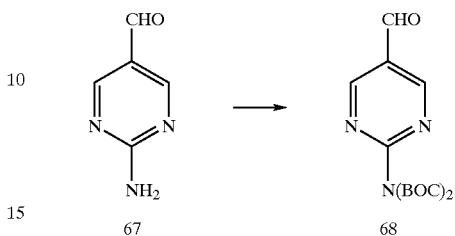

To a mixture of 166 mg (1.35 mmol) of aminopyrimidine 67, 17 mg (0.14 mmol) of DMAP and 418 μL (3.00 mmol) of Et₃N in 10 mL of THF was added 589 mg (2.7 mmol) of (BOC)₂O. The mixture was stirred at room temperature for 5 h, concentrated-dry loaded on silica gel and flash chromatographed (1–3% acetone/ CH₂Cl₂) to produce 117 mg (0.36 mmol; 27%) of 68 as a clear oil.

Step 4

68 → 69

To a solution of 117 mg (0.36 mmol) of aldehyde 68 in 7 mL of CH₂Cl₂ was added 67 μL (0.43 mmol) of ethyl isonipecotate and 5 μL of acetic acid. 30 min. later 153 mg (0.72 mmol) of NaBH(OAc)₃ was introduced. The mixture was stirred overnight at room temperature, diluted with CH₂Cl₂, washed with aqueous NaHCO₃, dried and concentrated, and crude residue was flash chromatographed (0–4% sat. NH₃ in MeOH/CH₂Cl₂) to produce 133 mg (0.29 mmol; 81%) of 69 as a white film.

Step 5

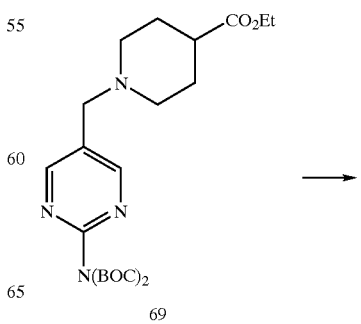

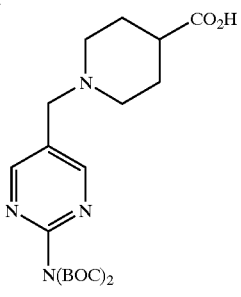

70

To a solution of ester 69 in 5 mL of a 3:1:1 mixture of THF—water—methanol was added 11 mg (0.44 mmol) of LiOH. Reaction mixture was stirred overnight at room temperature, concentrated to dryness and exposed to high vacuum to obtain 134 mg of crude acid 70 as a yellowish solid which was used without purification.

EXAMPLE 14

Step 1

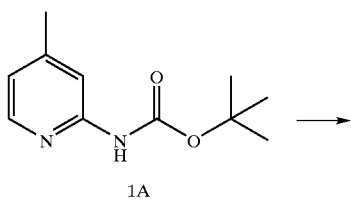

To a −78° C. solution of 2.36 g (11.4 mmol) of picoline 1A in 70 mL of THF was added 16.3 mL of 1.4 M BuLi solution (22.8 mmol) in hexanes in portions over 10 min. Reaction mixture was then allowed to warm up and was then stirred for 2 h at room temperature, which resulted in the formation of an orange precipiate. The mixture was cooled back to −78° C., and ethylene oxide was bubbled through the solution for 1 min. followed by stirring for 5 min. This two-step sequence was repeated eight times. The mixture was then allowed to warm to −50° C., stirred at that temperature for 40 min., quenched with 1.34 mL (23 mmol) of AcOH and allowed to warm to room temperature. Dilution with water was followed by extraction with EtOAc, concentration of the organic phase, and flash chromatography of the crude residue (10–15% acetone/$CH_2Cl_2$) to produce 1.50 g (5.95 mmol; 53%) of 71 as a white solid.

Step 2

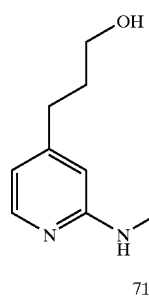

72

To a −60° C. solution of 628 μL (7.2 mmol) of oxalyl chloride in 20 mL of $CH_2Cl_2$ was added dropwise 1.03 mL (14.5 mmol) of DMSO. After stirring the mixture for 15 min. at −55° C., a solution of 1.50 g (5.95 mmol) of alcohol 71 in 20 mL of $CH_2Cl_2$ was introduced over the period of 15 min. After the addition was complete, the mixture was stirred for 30 min. at −55° C., followed by the addition of 4.18 mL (30.0 mmol) of $Et_3N$ and stirring for another 15 min. The reaction mixture was then warmed to room temperature and diluted with water. Extraction with $CH_2Cl_2$ was followed by concentration of the organic phase and flash chromatography (1–15% acetone/$CH_2Cl_2$) to produce 1.00 g (4.00 mmol; 67%) of 72 as an off-white solid.

Step 3

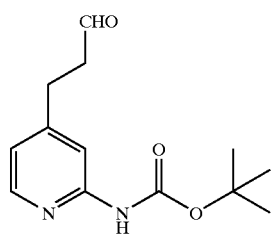

72

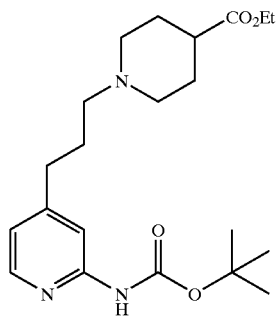

73

To a solution of 1.00 g (4.0 mmol) of aldehyde 72 in 25 mL of $CH_2Cl_2$ was added 617 μL (4.8 mmol) of ethyl isonipecotate followed by one drop of AcOH. Reaction mixture was then stirred for 40 min at room temperature after which 1.70 g (8.0 mmol) of NaBH(OAc)₃ was introduced. Reaction mixture was stirred overnight at room temperature, neutralized with saturated aqueous NaHCO₃, diluted with water and extracted with CH₂Cl₂. Concentration and flash chromatography (0–4% saturated NH₃ in MeOH/CH₂Cl₂) provided 1.41 g (3.6 mmol; 90%) of 73 as a white solid.

Step 4

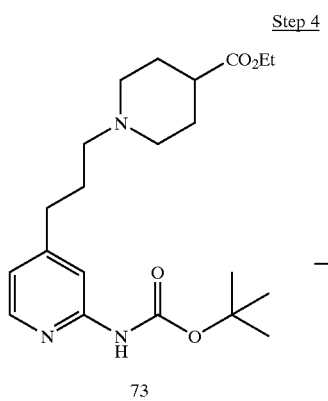

73

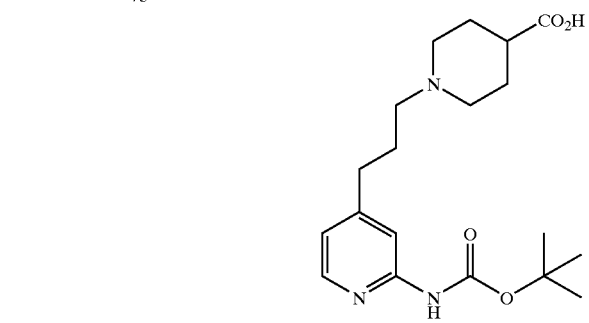

74

To a solution of 534 mg (1.47 mmol) of ester 73 in 4 mL of a 3:1:1 mixture of THF—water—methanol was added 60 mg (2.50 mmol) of LiOH. Reaction mixture was stirred overnight at room temperature, concentrated to dryness and exposed to high vacuum to obtain 540 mg of crude acid 74 as a white solid which was used without purification.

EXAMPLE 15

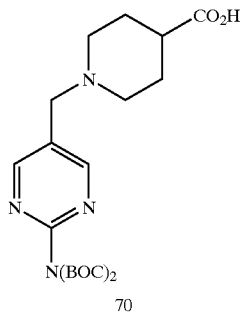

70

-continued

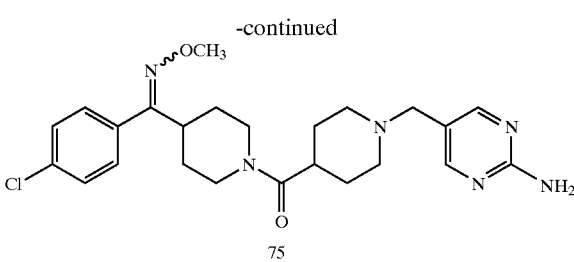

75

In a manner similar to that described in Example 6, steps 5, 6, and 7, 70 was converted to 75.

EXAMPLE 16

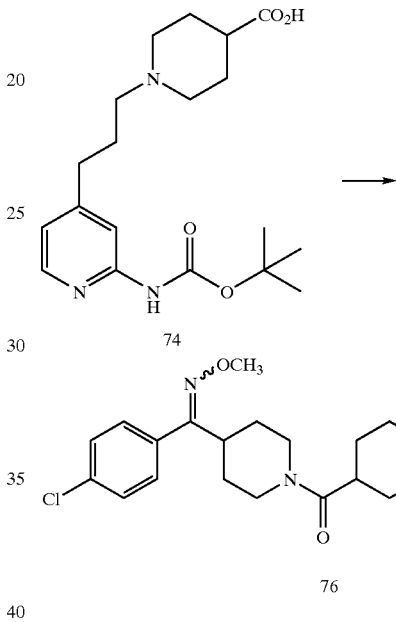

74

76

In a manner similar to that described in Example 6, steps 5, 6, and 7, 74 was converted to 76.

EXAMPLE 17

Step 1

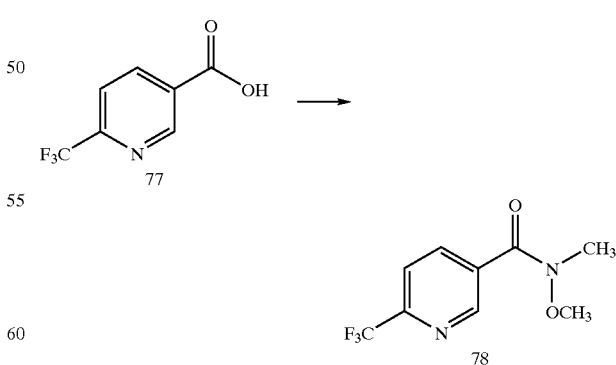

77

78

To a solution of 77 (0.73 g, 3.82 mmol) in CH₂Cl₂ (10 mL) was added (COCl)₂ (0.41 mL, 4.58 mmol) followed by DMF (0.1 mL) and the reaction was maintained at 40° C. for 3 h. The reaction was then concentrated to give a brown solid which was dissolved in CH₂Cl₂ (10 mL). N,O-dimethylhydroxylamine hydrochloride (0.56 g, 5.73 mmol) and DIPEA (1.33 mL) were added and the reaction was stirred at room temperature overnight. The reaction was quenched by the addition of saturated aqueous NaHCO₃ and extracted with EtOAc. The combined organic layers were dried and concentrated, and the residue purified by chromatography to give 78 (3.2 g, 84%).

Step 2

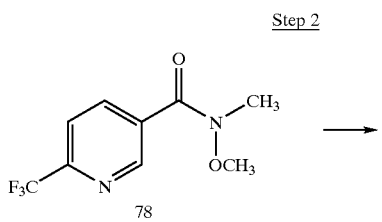
78

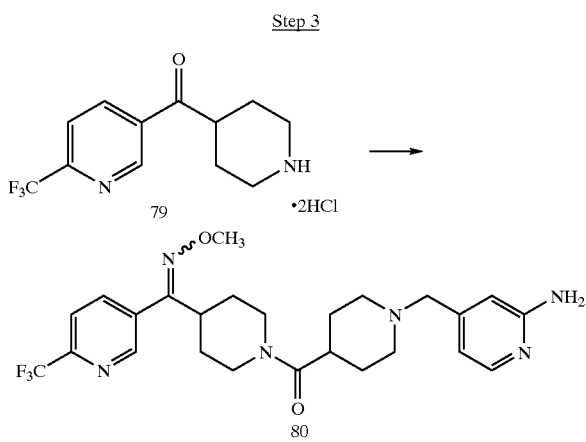

In a manner similar to that described in Example 5, steps 1 and 4, 78 (0.57 g, 2.41 mmol) was converted to 79 (0.59 g).

Step 3

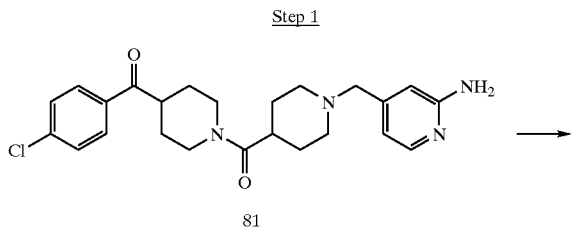

In a manner similar to that described in Example 6, steps 5, 6 and 7, 79 (0.38 g, 1.49 mmol) was converted to 80 (0.24 g).

EXAMPLE 18

Step 1

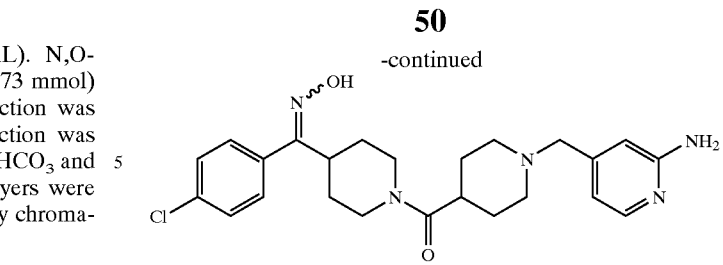
81

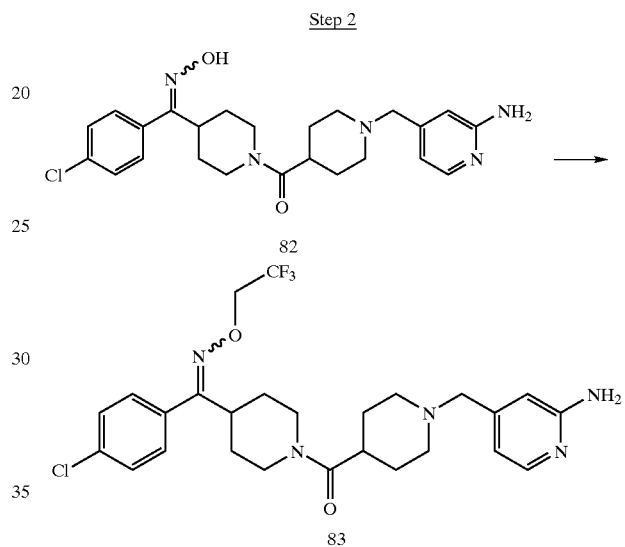

In a manner similar to that described in Example 6, step 7, 81 (0.36 g, 0.53 mmol; synthesized in the same manner as compound 30) was converted to 82 (0.34 g, 63%).

Step 2

To a solution of 82 (0.115 g, 0.25 mmol) in DMF (4 mL) was added NaH (60% dispersion in mineral oil, 0.03 g, 0.76 mmol). After 5 h at room temperature, CF₃CH₂OSO₂CF₃ (0.069 g, 0.3 mmol) was added and the reaction stirred at room temperature overnight. The reaction was diluted with EtOAc and extracted 3 times with water to remove the DMF. The organic layer was dried and concentrated to give a residue which was purified by chromatography (10% MeOH/NH₃ in EtOAc) to give 83 (0.08 g, 30%).

EXAMPLE 19

Step 1

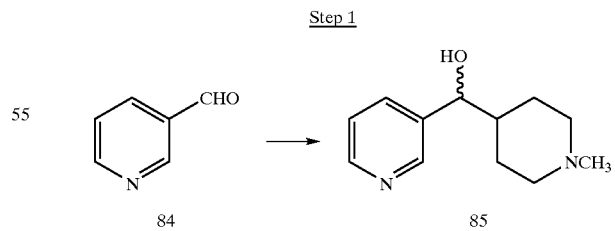

To a solution of 17 (0.21 mole, 100 ml THF, −10° C.) was added 84 (0.14 mole) over 5 min and the reaction mixture became very viscous. Additional THF (100 ml) was added and the yellow suspension was warmed from −10° C. to 10° C. over about 2.5 hr. The reaction was quenched by the addition of 100 ml saturated NH₄Cl and 100 ml H₂O.

Extracted once with EtOAc (300 ml) and eight times with CH$_2$Cl$_2$ (150 ml). Dried over solid MgSO$_4$ and filtered. Concentrated and flashed over silica gel chromatography (3 to 10% MeOH (NH$_3$)/CH$_2$Cl$_2$) to obtain 85 (11 g, yield: 38%).

Step 2

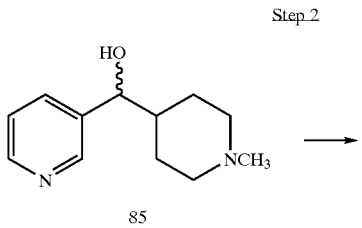

85

86

To the mixture of 85 (9.2 g) and MnO$_2$ (42 g) was added 200 ml CH$_2$Cl$_2$, and the mixture was stirred at room temperature overnight. Additional MnO$_2$ (20 g) was added and the reaction was stirred another 24 hrs. The MnO$_2$ was filtered off and the reaction was concentrated and flashed over silica gel(5% and 10% MeOH (NH$_3$)/CH$_2$Cl$_2$) to give 86 (3.1 g, yield: 33%).

Step 3

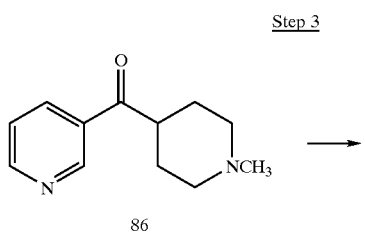

86

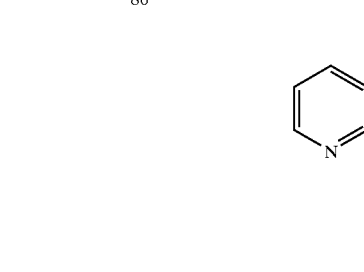

87

In a manner similar to that described in Example 7, step 2, 86 (3.1 g) was converted to 87 (2.0 g, yield: 68%).

Step 4

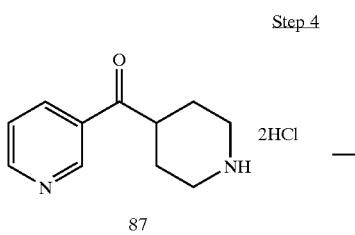

87

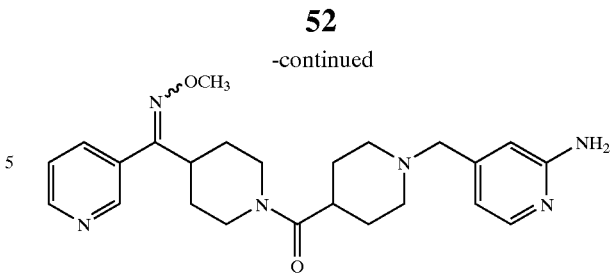

88

In a manner similar to that described in Example 7, step 3, 4, 5, and 6, 87 was converted to 88.

EXAMPLE 20

Step 1

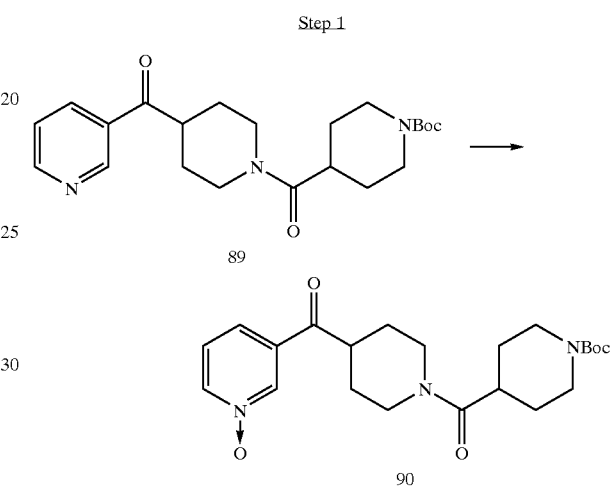

To the solution of compound 89 in CH$_2$Cl$_2$ (20 ml) at 0° C. was added m-CPBA (0.54 g) and the reaction was stirred at 0° C. for 25 min. and then at room temperature stirred for 2 hrs. 40% NH$_4$OH (12 ml) was added and the mixture was stirred for 30 min. Separated and extracted the aqueous layer with CH$_2$Cl$_2$ (10 ml). Dried (MgSO$_4$), filtered and concentrated in vacuo. Flash chromatography (5% MeOH(NH$_3$)/CH$_2$Cl$_2$) gave 90 (0.67 g, 80%).

Step 2

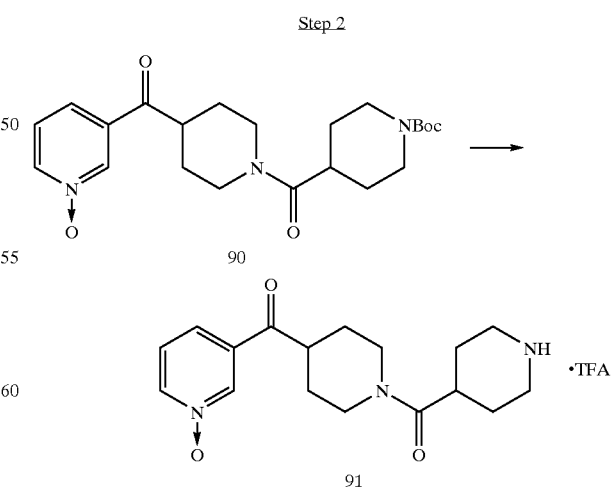

To the solution of 90 (0.65 g) in CH$_2$Cl$_2$ (6 ml) at −10° C. was added TFA (6 ml) and the reaction was stirred for 1 hr from −10° C. to 0° C. Concentrated down and azeotroped twice with toluene (20 ml), and concentrated to dryness to obtain 91 as a gummy oil which was used as is.

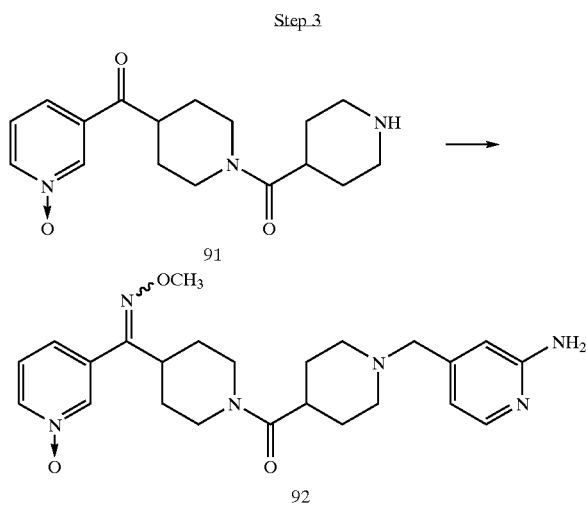

In a manner similar to that described in Example 7, steps 5 and 6, 91 was converted to 92.

EXAMPLE 21

Step 1

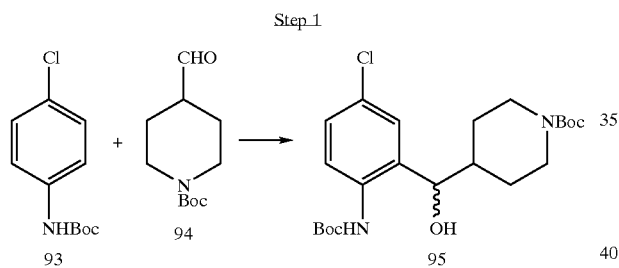

To a solution of 93 (5.17 g, 22.7 mmol) in THF (100 mL) at −50° C. was added s-BuLI (38.4 mL of a 1.3M solution in hexane, 49.9 mmol) dropwise. After 1.5 h at −40° C., the reaction was recooled to −50° C. and 95 (4.84 g, 22.7 mmol) in THF (20 mL) was added. After 2.75 h at −50° C., glacial acetic acid was added followed by saturated aqueous NH₄Cl. The mixture was warmed to room temperature and the layers were separated. The aqueous layer was extracted with EtOAc. The combined organic layers were dried (MgSO₄) filtered and concentrated to give a residue that was purified by flash column chromatography (1% to 3% MeOH/ NH₃ in CH₂Cl₂) to give 95 (6.35 g, 63%).

Step 2

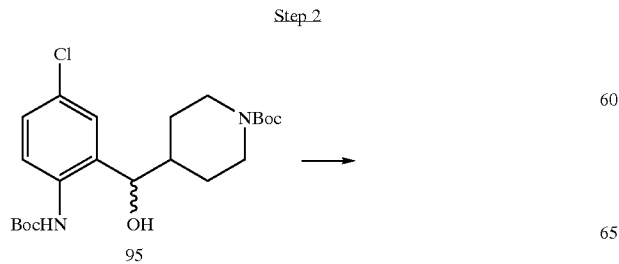

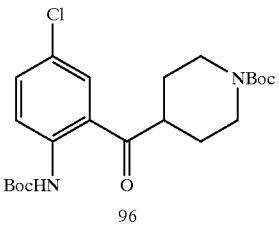

In a manner similar to that described in Example 12, step 3, 95 (5.34 g, 12.11 mmol) was converted to 96 (4.71 g, 75%).

Step 3

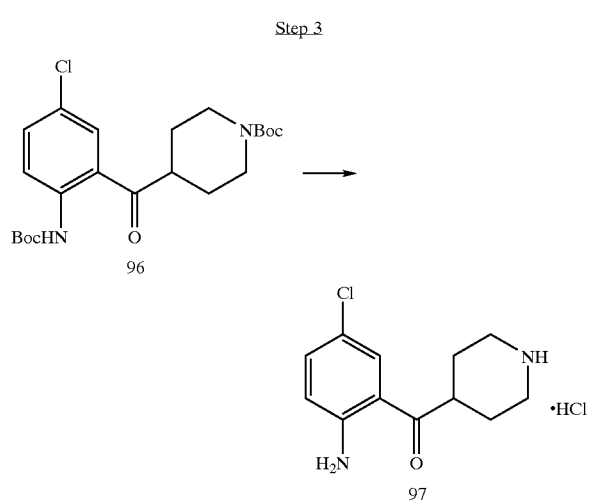

In a manner similar to that described in Example 6, step 4, 96 (3.7 g, 8.43 mmol) was converted to 97 (3.08 g, >100%) which was used as is in the next step.

Step 4

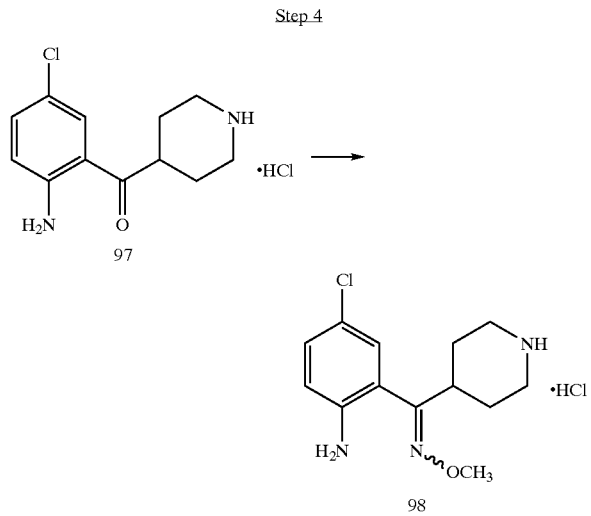

Compound 97 (0.7 g, 2.25 mmol), H₂NOCH₃.HCl (0.94 g, 11.23 mmol) and NaOAc (1.47 g, 17.97 mmol) were combined in 1-pentanol (20 mL) and water (2 mL) and heated to reflux for 2 days. The reaction was cooled to room temperature and 0.5 N NaOH was added. The EtOH was removed in vacuo, additional water (15 mL) was added, and the reaction extracted with 10% EtOH in CH₂Cl₂ (180 ML total volume). The combined organic extracts were dried and concentrated to give 98 (0.55 g, 92%).

Step 5

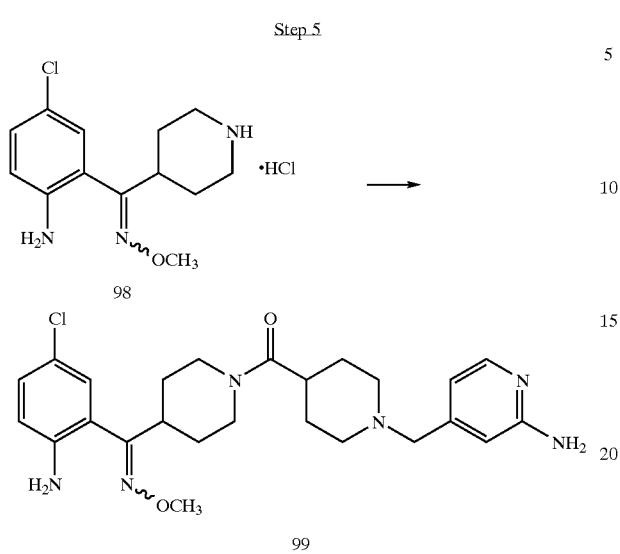

In a manner similar to that described in Example 6, steps 5, 6, and 7, 98 was converted to 99.

EXAMPLE 22

Step 1

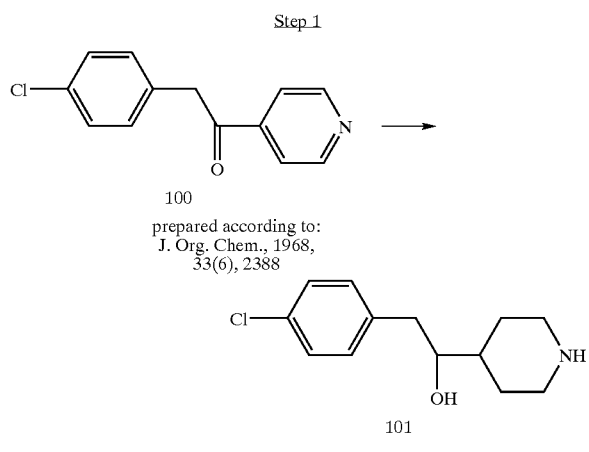

A solution of 2.2 g (9.5 mmol) of 100 in 75 mL of glacial acetic acid was hydrogenated in the presence of 0.5 g of 10% w/w platinum-on-charcoal for 5 h. The reaction mixture was filtered to remove the catalyst and the filtrate was concentrated by evaporation under reduced pressure to produce a solid residue which was basified with 0.5N NaOH and extracted with methylene chloride ($CH_2Cl_2$). Methylene chloride extracts were dried over anhydrous $MgSO_4$ and concentrated. The residue was purified by flash chromatography eluted with 10–30% of 7N $NH_3$-MeOH in $CH_2Cl_2$ to give 0.82 g of 101 (mp 158–163° C.). LCMS m/z 240 (MH+).

Step 2

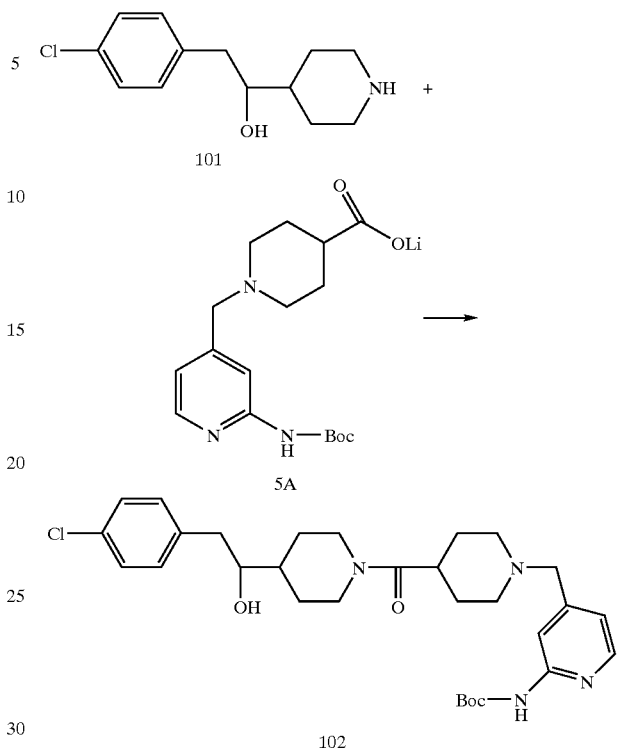

A mixture of 0.12 g (0.52 mmol) of 101, 0.2 g (0.52 mmol) of 5A, 0.67 g (0.5 mmol) of 1-hydroxybenzotriazole hydrate (HOBt), and 0.11 g (0.57 mmol) of 1-(3-dimethylaminopropyl)-3-ethylcarbodiimide hydrochloride (DEC) in 7 mL of anhydrous dimethylformamide (DMF) was stirred at ambient temperature for 18 h. The mixture was diluted with water and the resulting precipitate was filtered to produce 0.26 g of 102 as a white solid (mp 110–115° C.). LCMS m/z 557 (MH+).

Step 3

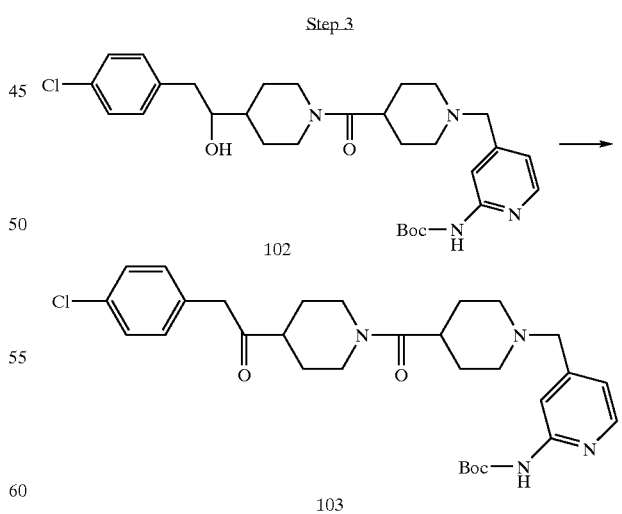

To a stirred solution of 0.34 g (2.7 mmol) of oxalyl chloride in 3 mL of anhyrous $CH_2Cl_2$ at −70° C. was added 0.44 g (5.7 mmol) of anhyrous methylsulfoxide in 2 mL of $CH_2Cl_2$. After being stirred at −70° C. for 10 minutes, the reaction mixture was added 1.2 g (2.15 mmol) of 102 in 10 mL of $CH_2Cl_2$. The stirred mixture was kept at −70° C. for 0.5 h, mixed with 1.8 mL (13 mmol) of triethylamine, and then allowed to warm up to ambient temperature by itself. The mixture was diluted with water and extracted with CH$_2$Cl$_2$. Organic extracts were washed with brine, dried over anhydrous MgSO$_4$ and concentrated to produce 1.18 g of 103 as a glass. LCMS m/z 555 (MH+).

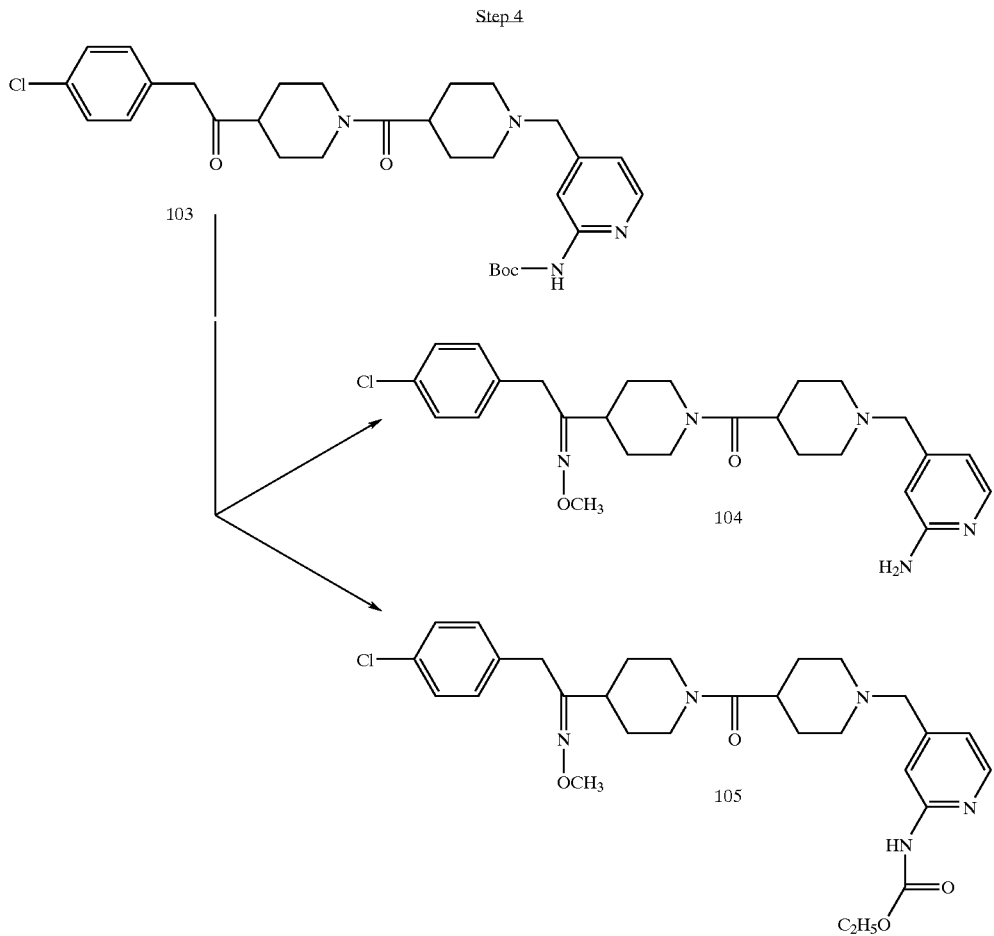

A solution of 0.8 g (1.44 mmol) of 103 and 0.6 g (7.2 mmol) of methoxylamine hydrochloride in 40 mL of ethanol and 40 mL of pyridine was heated under reflux for 18 h. The mixture was concentrated and the residue was taken up in ethyl acetate/ether and washed with water. The organic solution was dried over anhydrous MgSO$_4$ and concentrated to 0.65 g of viscous reidue which was dissolved in 8 mL of trifluoroacetic acid and 8 mL of CH$_2$Cl$_2$ and stirred at ambient temperature for 18 h. The solution was concentrated and the residue was basified with 1N NaHCO$_3$ and extracted with ethyl acetate. Organic extracts were washed with brine, dried over anhydrous MgSO$_4$ and concentrated to a gummy residue. Purification of this residue by flash chromatography with 5–8% of 7N NH$_3$-MeOH in CH$_2$Cl$_2$ produced 0.151 g of 104 as a gum, LCMS m/z 484 (MH+) and 0.146 g of 105 as a glass, LCMS m/z 556 (mH+).

Mixing a solution of 0.056 g of the free base of 104 in ethyl acetate with a solution of 0.04 g of maleic acid in ethyl acetate produced a precipitate which was isolated by filtration to give 0.06 g of a dimaleate salt of 104 (mp 155–160° C).

EXAMPLE 23

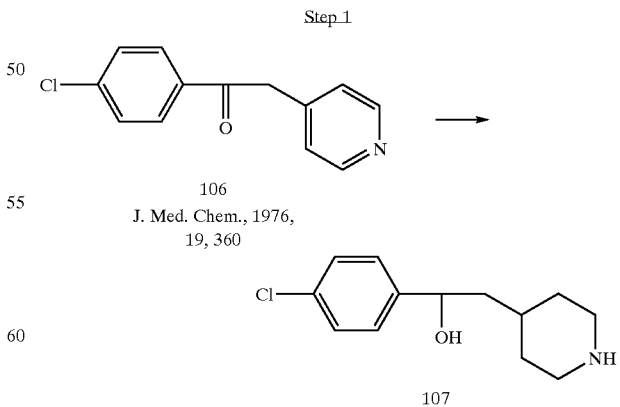

2.4 g (10. mmol) of 106 were reduced in the similar manner as that described in Example 22, step 1 to give 1.5 g of 107 as a semi-solid. LCMS m/z 240 (MH+).

Step 2
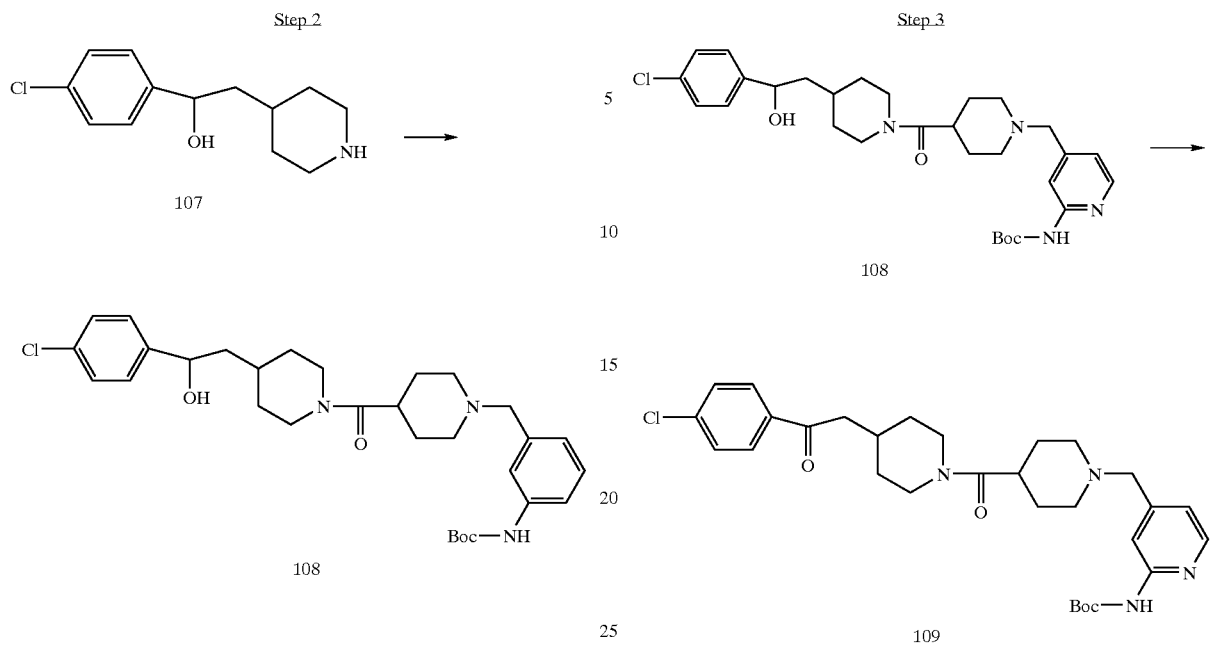
1.5 g (6.31 mmol) of 107 were coupled with 3 in the similar manner as that described in Example 22, step 2 to give 3 g of 108 as a solid (mp 104–106° C.). LCMS m/z 557 (MH+).
1.17 g (2.1 mmol) of 108 were oxidized in the similar manner as that described in Example 22, step 3 to give 0.7 g of 109 as a glass. LCMS m/z 557 (MH+).
Step 4
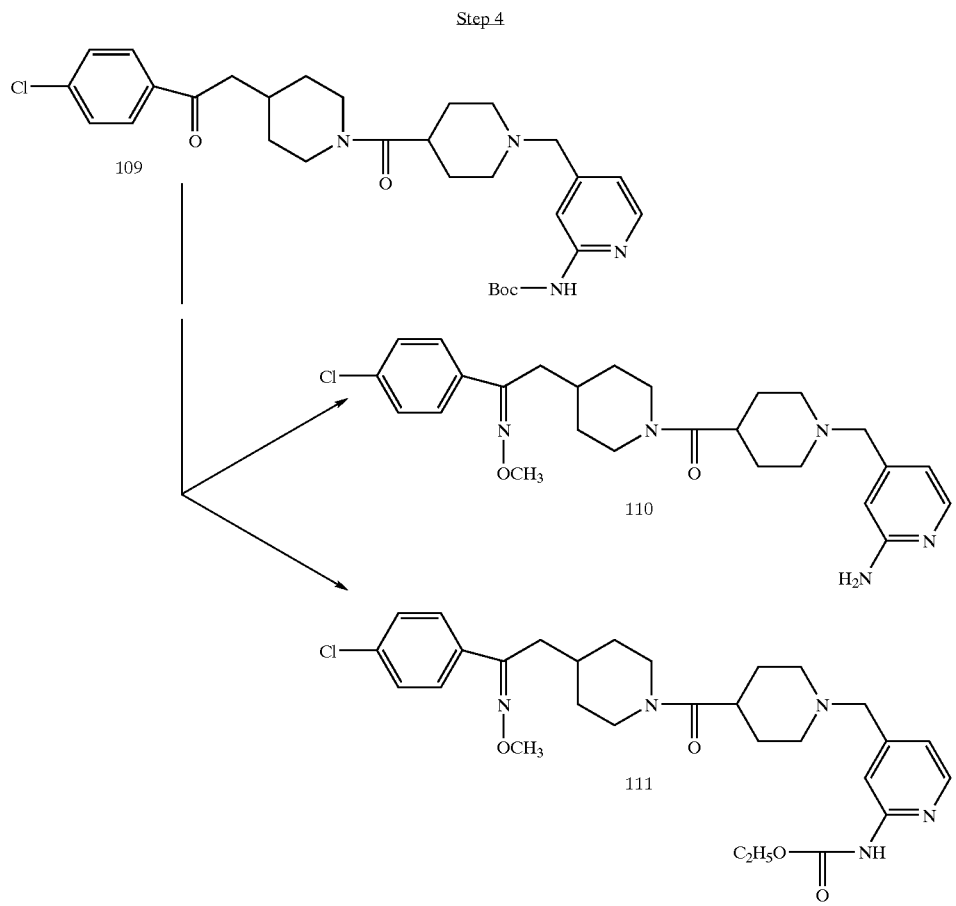

0.32 g (0.58 mmol) of 109 were reacted with 0.6 g (7.2 mmol) of methoxylamine hydrochloride in the same manner as that described in Example 22, step 4 to provide 0.065 g of 110 as a gum, LCMS m/z 484 (MH+) and 0.12 g of 111 as a glass, LCMS m/z 556 (MH+).

EXAMPLE 24

Step 1

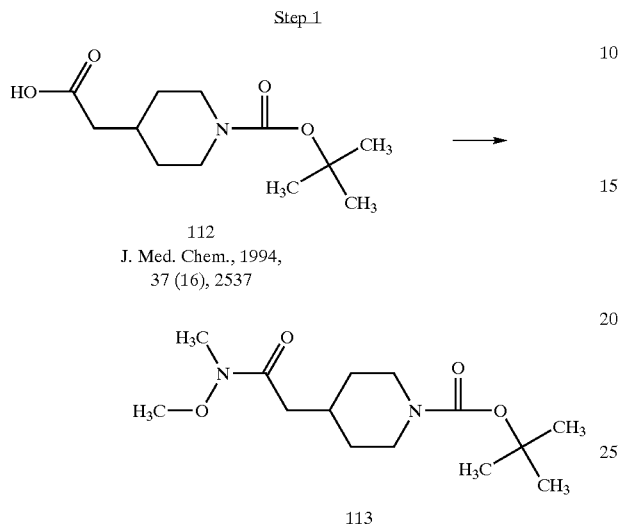

112
J. Med. Chem., 1994,
37 (16), 2537

113

A mixture of 18 g (74 mmol) of 112, 7.2 g (74 mmol) of N,O-dimethylhyroxylamine hydrochloride, 19.4 g (15 mmol) of N,N-diisopropylethylamine, 1.1 g (8 mmol) of HOBt and 14.2 g (74 mmol) of DEC in 80 mL of anhydrous DMF was stirred at ambient temperature for 18 h. The mixture was diluted with water and extracted with ethyl acetate. Organic extracts were washed with 1% $NaHCO_3$ and brine, dried over anhydrous $MgSO_4$ and concentrated to give 15.5 g of 113 as an oil. LCMS m/z 287 (MH+).

Step 2

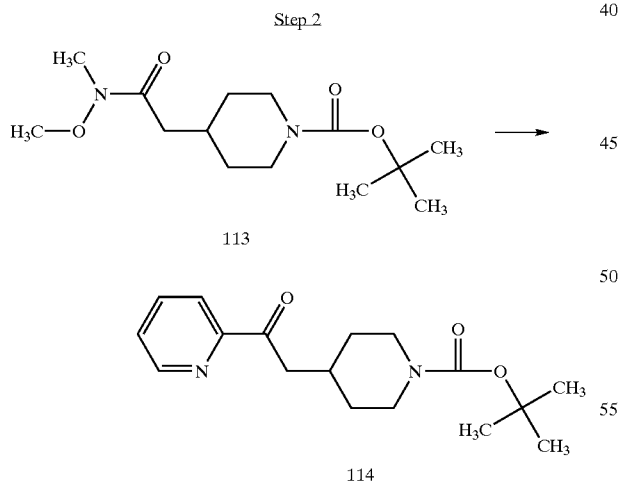

113

114

To a stirred solution of 2.9 g (18 mmol) of 2-bromopyridine in 30 mL of anhydrous THF at −78° C. was added 7.5 mL of 2.5M solution of n-BuLi in hexane dropwise for 0.5 h. After being stirred at −78° C. for 1 h, the reaction mixture was added a solution of 5.1 g (17.8 mmol) of 113 in 15 mL of THF. The mixture was allowed to stir at ambient temperature for 48 h, mixed with saturated aquous $NH_4Cl$ and extracted with ether. Organic extracts were washed with brine, dried over anhydrous $MgSO_4$ and concentrated to produce 5.7 g of 114 as an oil. LCMS m/z 305 (MH+).

Step 3

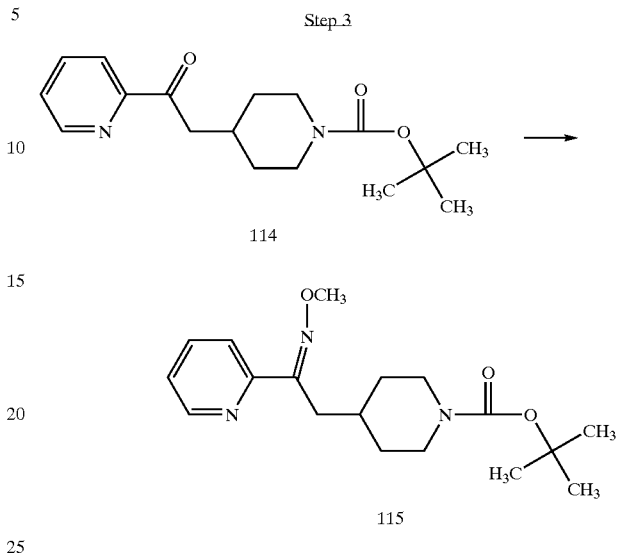

114

115

A solution of 3.15 g (10.4 mmol) of 114 and 3.47 g (41.6 mmol) of methoxylamine hydrochloride in 30 mL of ethanol and 30 mL of pyridine was heated under reflux for 18 h. The mixture was concentrated and the residue was taken up in ether and washed with water. The organic solution was dried over anhydrous $MgSO_4$ and concentrated to give 2.5 g of 115 as an oil. LCMS m/z 334 (MH+).

Step 4

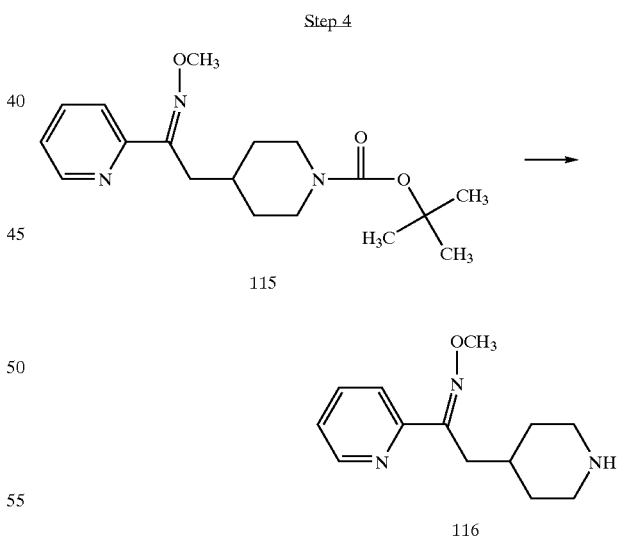

115

116

A solution of 2.4 g (7.2 mmol) of 22 in 20 mL of $CH_2Cl_2$ and 20 mL of trifluoroacetic acid was stirred at ambient temperature for 1 h. The solution was concentrated. The residue was basified with saturated aqeous $NaHCO_3$ and extracted with $CH_2Cl_2$. Organic extracts were washed with brine, dried over anhydrous $MgSO_4$ and concentrated to give 1.41 g of 23 as a glass. LCMS m/z 234 (MH+).

Step 5

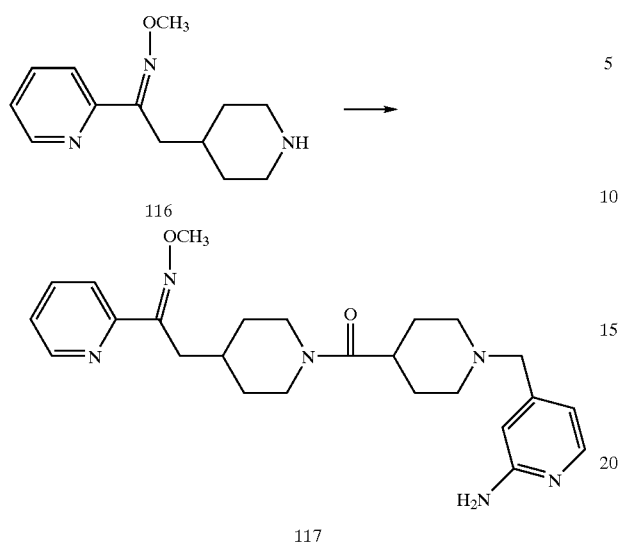

A mixture of 0.466 g (2 mmol) of 116, 0.517 g (2.2 mmol) of 5A, 0.276 g (2 mmol) of HOBt and 0.46 g (2.4 mmol) of DEC in 20 mL of anhydrous DMF was stirred at ambient temperature for 18 h. The mixture was concentrated by evaporation under reduced pressure at bath temperature of 25–45° C. and the residue was chromatographed with 4% (7N $NH_3/CH_3OH$) in $CH_2Cl_2$ to produce 0.48 g of syrup which was dissolved in 15 mL of EtAc-EtOH (3:1 v) and mixed with a solution of 0.26 g of maleic acid in 10 mL of EtAc-EtOH (1:1). The resuting precipitate was filtered to produce 0.35 g of the maleate salt of 117 (mp 160–163° C.). LCMS m/z 451 (MH+).

EXAMPLE 25

Step 1

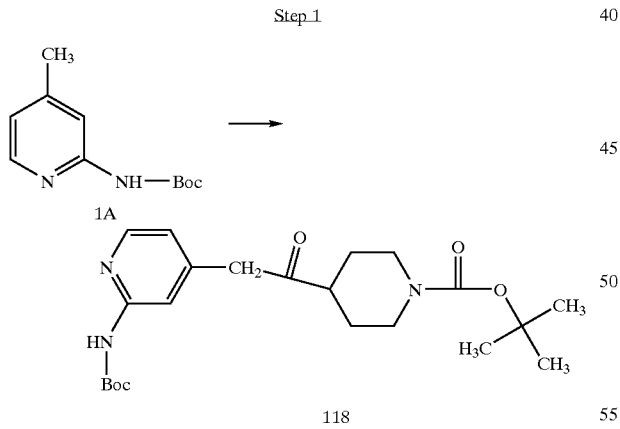

To a stirred solution of 4.16 g (20 mmol) of 1A in 80 mL of anhydrous THF at −78° C. was added dropwise 17 mL of 2.5M solution of n-BuLi in hexane for 25 minutes. After being stirred from −78° C. to room temperature for 1 h, the reaction mixture was added a solution of 6 g (22 mmol) of 26 in 100 mL of anhydrous THF and kept at room temperature for 18 h. The mixture was mixed with saturated aqeous $NH_4Cl$ and extracted with EtAc. Organic extracts were washed with brine, dried over anhydrous $MgSO_4$ and concentrated to produce 6.1 g of 118 (mp 146–149° C.). LCMS m/z 420 (MH+).

Step 2

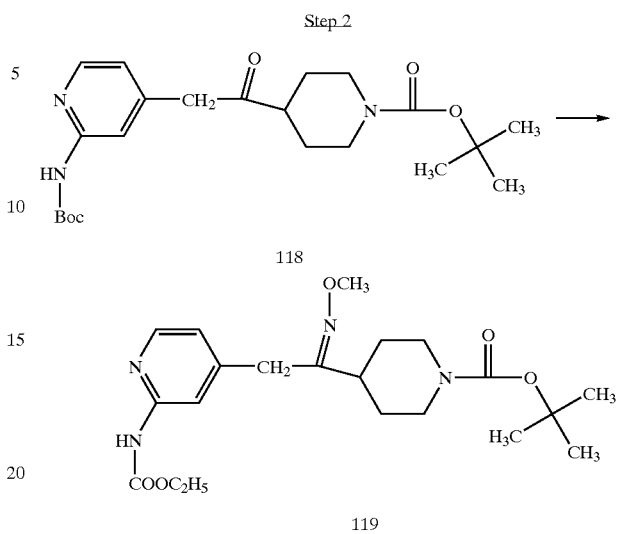

A solution of 3.71 g (8.8 mmol) of 118 and 3.7 g (44 mmol) of methoxylamine hydrochloride in 40 mL of pyridine and 40 mL of ethanol was heated under reflux for 2 days. The mixture was concentrated and the residue was taken up in $CH_2Cl_2$ and washed with saturated aqeous NaCl. Organic solution was dried over anhydrous $MgSO_4$ and concentrated to give 2.6 g of 119 as a glass. LCMS m/z 421 (MH+).

Step 3

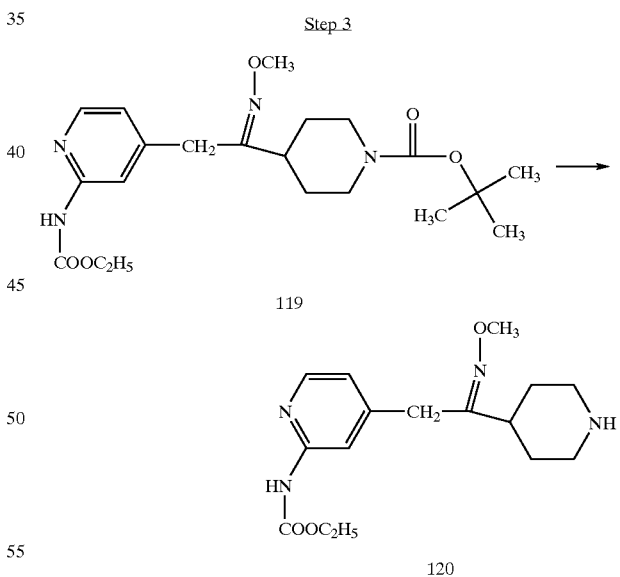

A solution of 0.9 g (2.14 mmol) of 119 in 10 mL of $CH_2Cl_2$ and 10 mL of trifluoroacetic acid was stirred at ambient temperature for 2 h. The solution was concentrated. The residue was taken up in $CH_2Cl_2$, washed with saturated $NaHCO_3$ and brine, dried over anhdrous $MgSO_4$ and concentrated to a solid residue which was triturated with $CH_3CN$ and filtered to produce 0.29 g of 120 (mp 200–205° C.). LCMS m/z 321 (MH+).

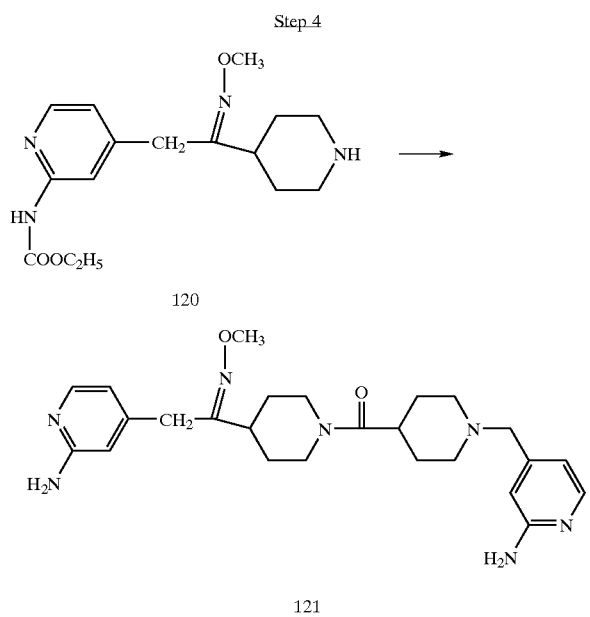

0.1 g (0.31 mmol) of 120 and 0.83 g (0.35) of 5A were coupled in the same manner as that described in Example 24, step 5 to produce 0.12 g of the maleate salt of 121 (mp 170–173° C.). LCMS m/z 538 (MH+).

EXAMPLE 26

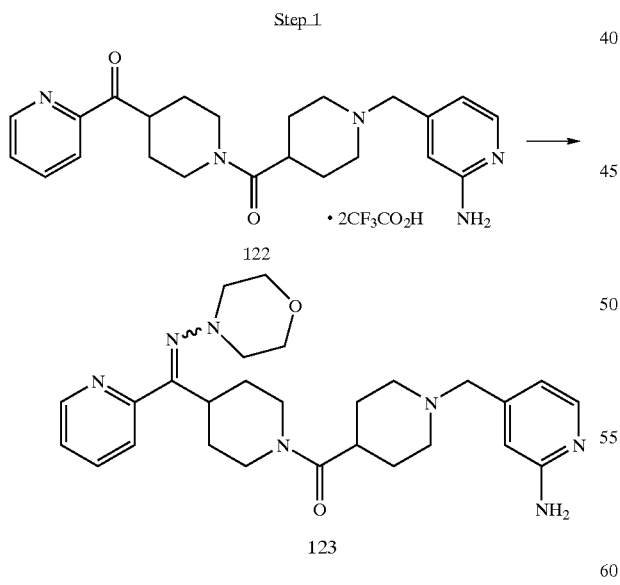

In a similar manner to that described in Example 6, step 7, 122 (0.26 g, 0.41 mmol) was converted to 123 (0.08 g, 40%).

EXAMPLE 27

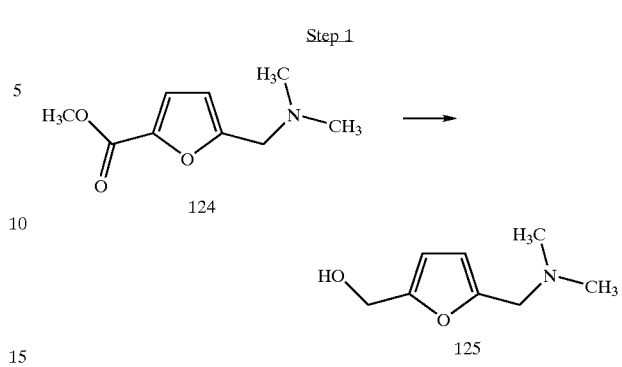

To a suspension of LAH (0.83 g, 22 mmol) in ether (20 mL) at 0° C. was added 124 (3.2 g, 17.5 mmol) in THF (15 mL) dropwise. The reaction was stirred at 0° C. for 1.5 h, and quenched by the addition of water (0.8 mL), 20% aqueous NaOH (0.8 mL), and water (2.4 mL). The mixture was stirred for 15 min and filtered and the filter cake washed with $CH_2CL_2$. The filtrate was concentrated to give an oil which was dissolved in ether (30 mL) and washed with brine and dried ($MgSO_4$). Filtration and concentration in vacuo gave 125 (2.5 g) which was used without further purification.

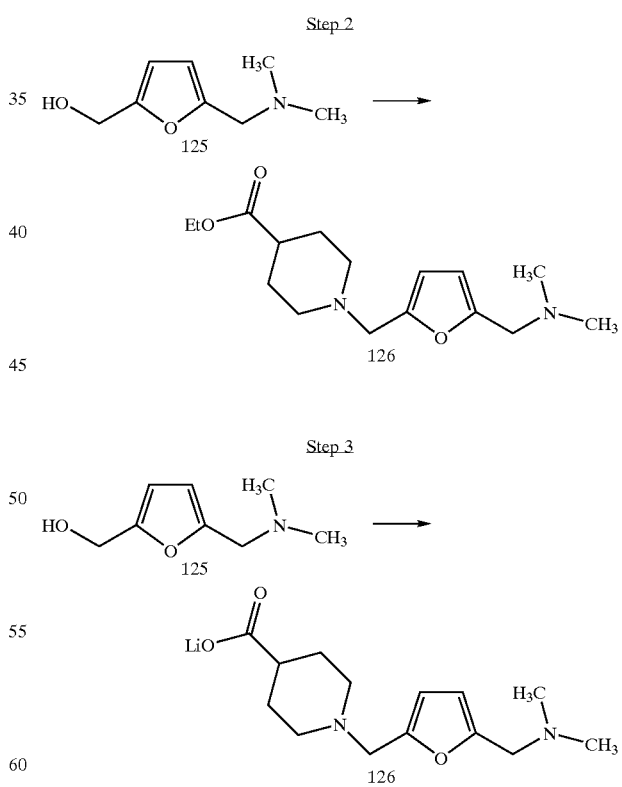

In a similar manner to that described in Example 22, step 3 and Example 1, steps 4, 5, and 6, 125 was converted to 126.

Step 4

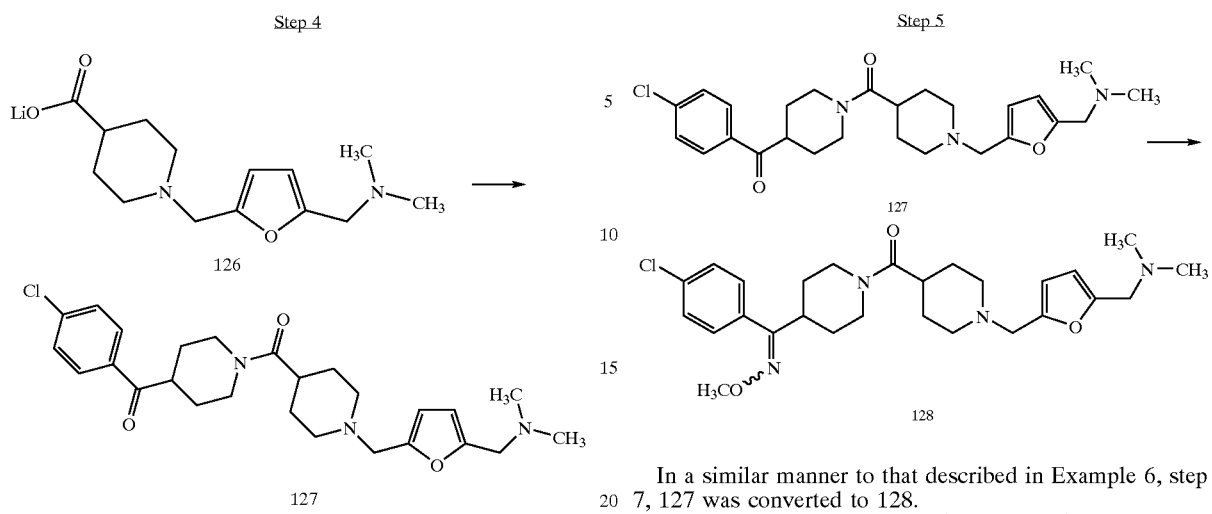

In a similar manner to that described in Example 6, step 5, 126 was converted to 127.

Step 5

In a similar manner to that described in Example 6, step 7, 127 was converted to 128.

The compounds in Table 1 (first column) are prepared from the compounds in the last column of Table 1 by following essentially the same procedures as in the examples described above. In Table 1 "Cmpd. No." stands for "Compound Number".

TABLE 1

| Cmpd. No. | STRUCTURE | Mass Spec. [M+H]+ | Starting Material |
|---|---|---|---|
| 200 | 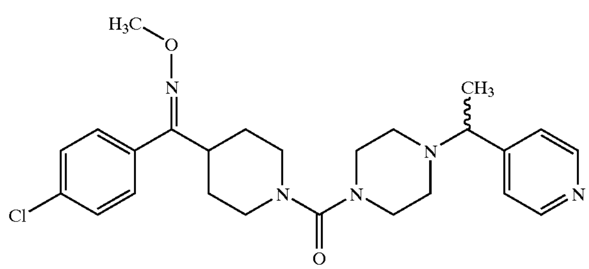 | 470.1 | |
| 201 | 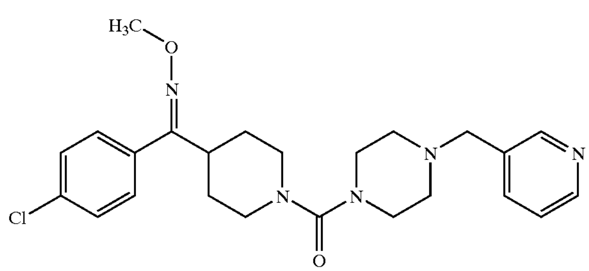 | 456.1 | |
| 202 | 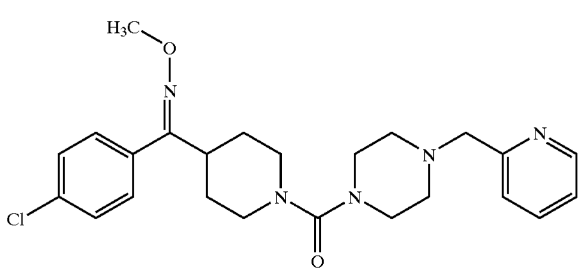 | 456.1 | |

TABLE 1-continued

| Cmpd. No. | STRUCTURE | Mass Spec. [M+H]+ | Starting Material |
|---|---|---|---|
| 203 | 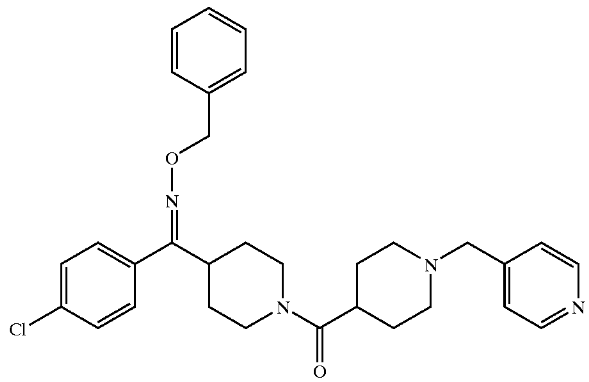 | 531.1 | |
| 204 | 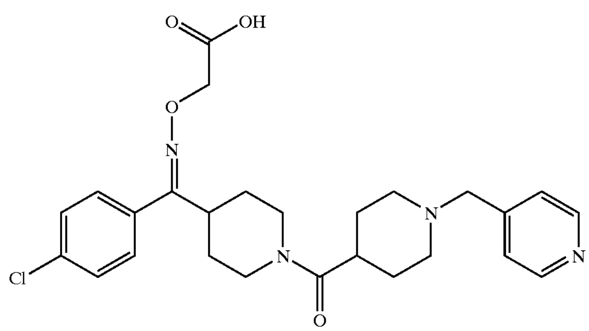 | 499.1 | |
| 205 | 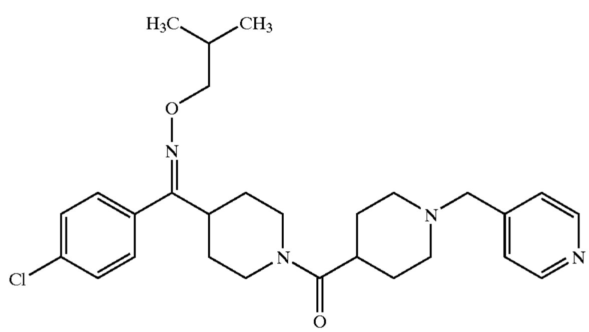 | 497.1 | |
| 206 | 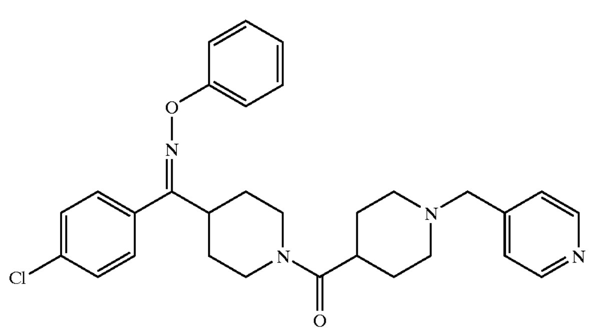 | 517.1 | |

TABLE 1-continued
| Cmpd. No. | STRUCTURE | Mass Spec. [M+H]+ | Starting Material |
|---|---|---|---|
| 207 | 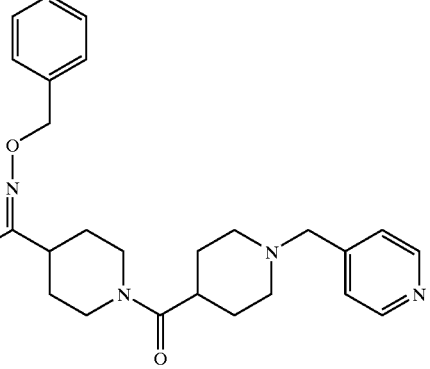 | 549.1 | 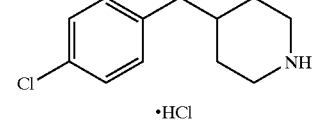 |
| 208 | 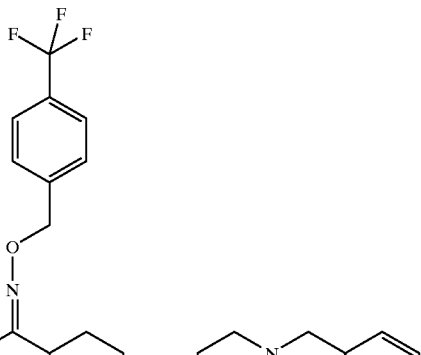 | 599.1 | 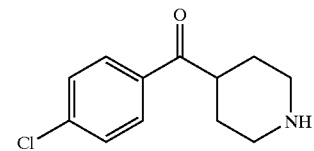 |
| 209 | 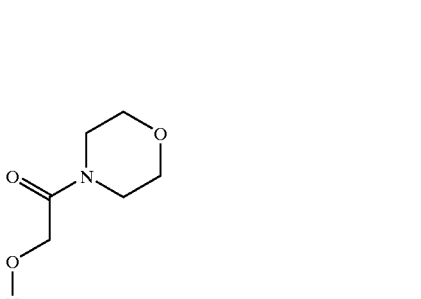 | 568.1 |  |

TABLE 1-continued

| Cmpd. No. | STRUCTURE | Mass Spec. [M+H]+ | Starting Material |
|---|---|---|---|
| 210 | 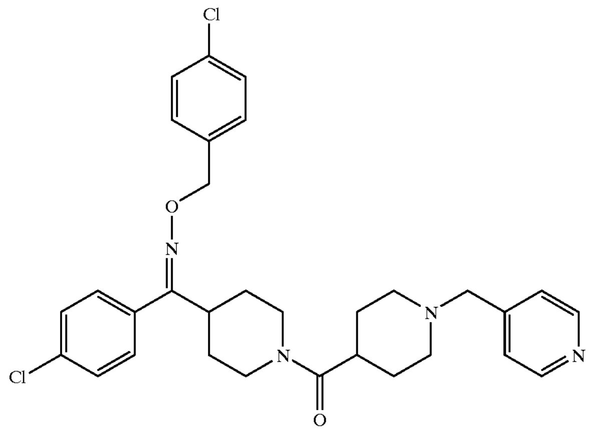 | 565.1 | |
| 211 | 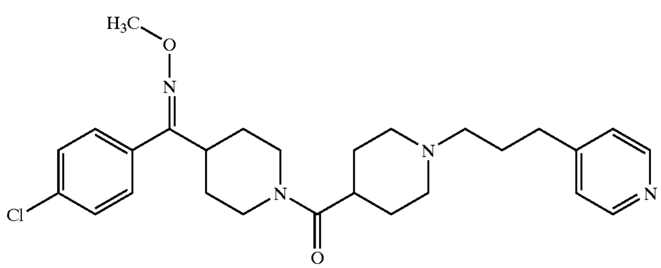 | 483 | |
| 212 | 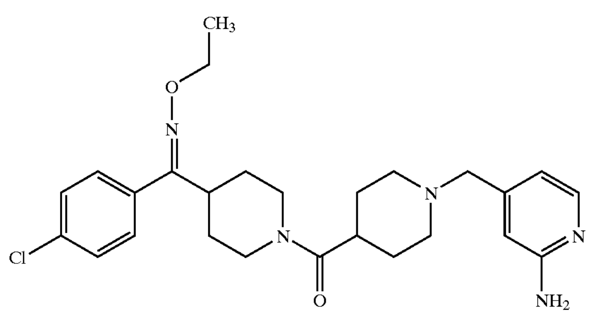 | 484.1 | |
| 213 | 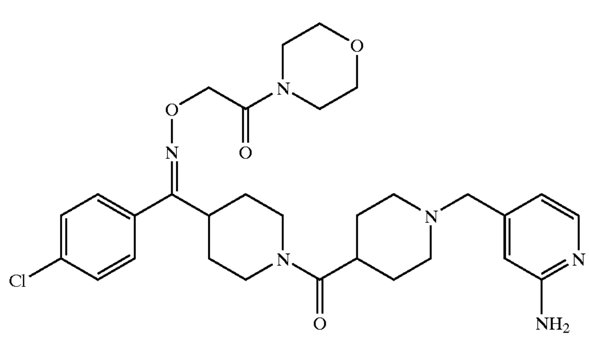 | 583.1 | |

TABLE 1-continued

| Cmpd. No. | STRUCTURE | Mass Spec. [M+H]+ | Starting Material |
|---|---|---|---|
| 214 | 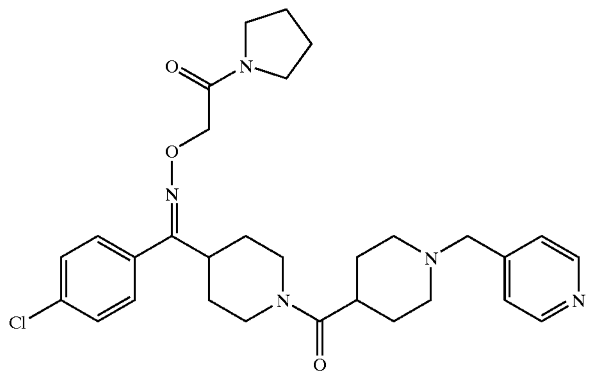 | 552.1 | |
| 215 | 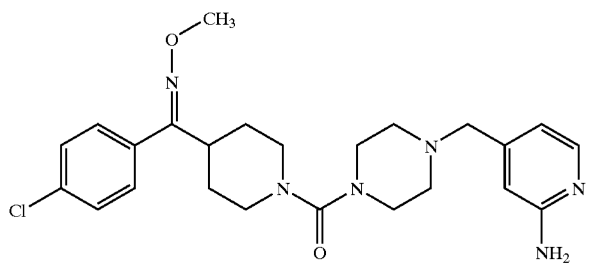 | 471 | |
| 216 | 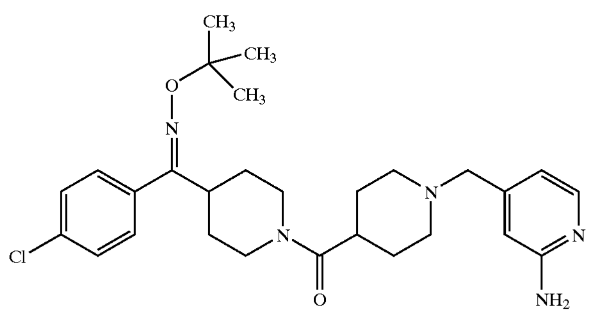 | 512 | |
| 217 | 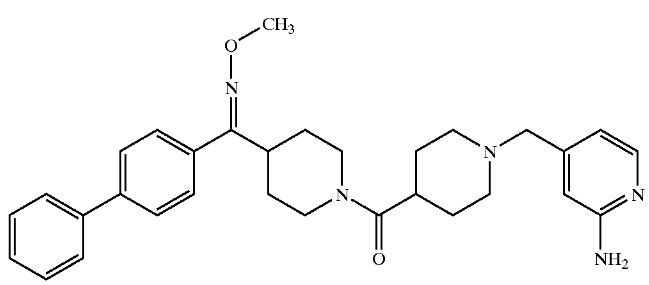 | 512 | |
| 218 | 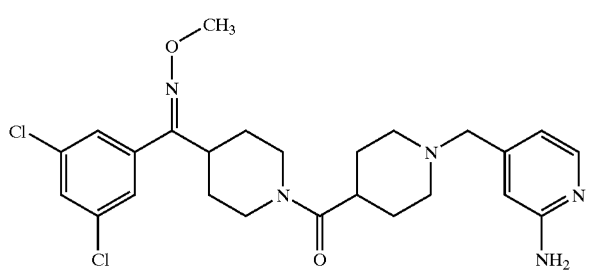 | 504 | |

TABLE 1-continued

| Cmpd. No. | STRUCTURE | Mass Spec. [M+H]+ | Starting Material |
|---|---|---|---|
| 219 | (structure) | 454 | 2-fluorobenzonitrile |
| 220 | (structure) | 470 | 2-chlorobenzonitrile |
| 221 | (structure) | 456 | (4-chlorophenyl)(piperidin-4-yl)methanone·HCl |
| 222 | (structure) | 456 | (4-chlorophenyl)(piperidin-4-yl)methanone·HCl |
| 223 | (structure) | 495 | 3,5-dimethoxybenzonitrile |
| 224 | (structure) | 470 | (4-chlorophenyl)(piperidin-4-yl)methanone·HCl |

TABLE 1-continued

| Cmpd. No. | STRUCTURE | Mass Spec. [M+H]+ | Starting Material |
|---|---|---|---|
| 225 | 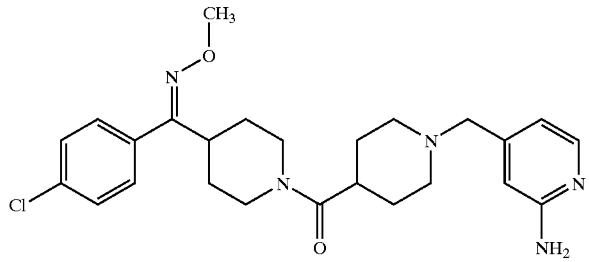 | 470 | |
| 226 | 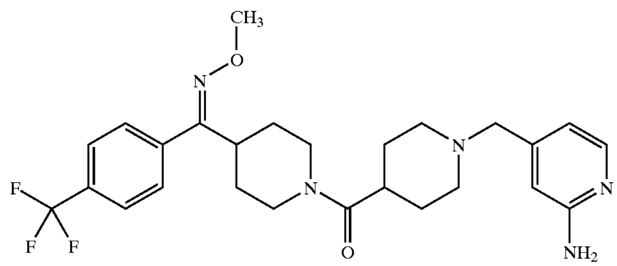 | 504 | |
| 227 | 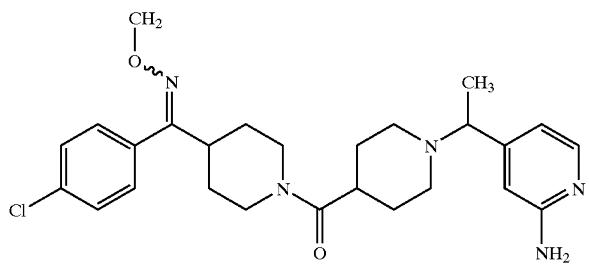 | 484 | |
| 228 | 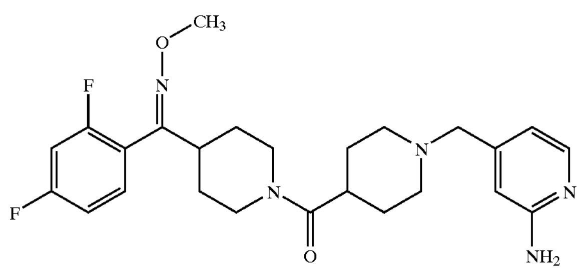 | 472 | |
| 229 | 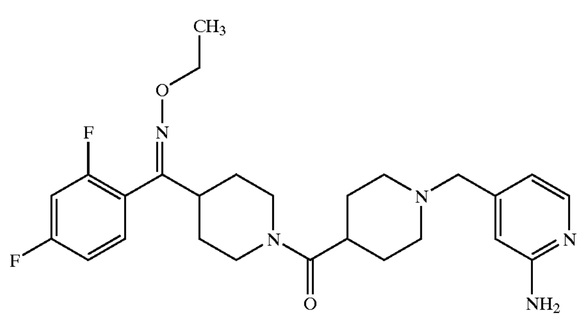 | 486 | |

TABLE 1-continued

| Cmpd. No. | STRUCTURE | Mass Spec. [M+H]+ | Starting Material |
|---|---|---|---|
| 230 | 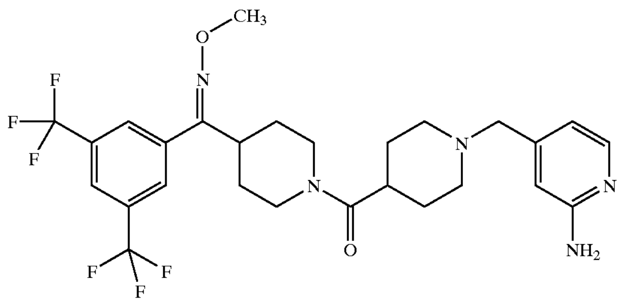 | 572 | |
| 231 | 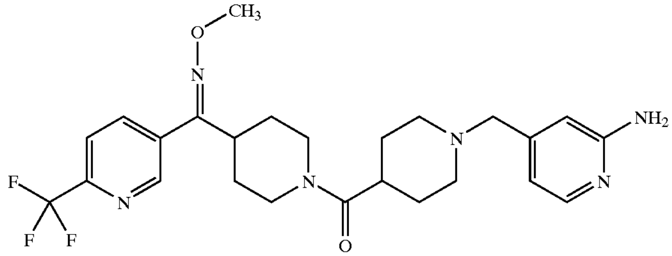 | 505 | |
| 232 | 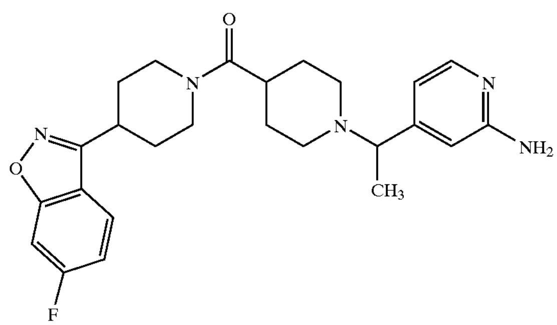 | 452 | |
| 233 | 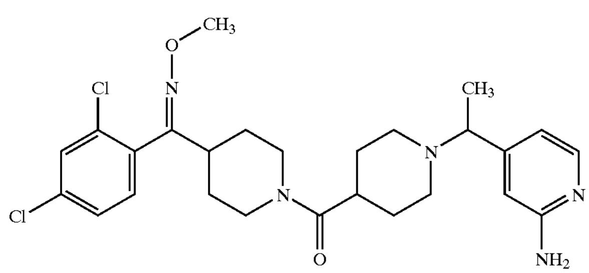 | 518 | |
| 234 | 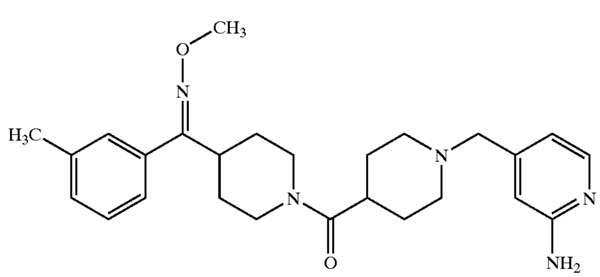 | 450 | |

TABLE 1-continued

| Cmpd. No. | STRUCTURE | Mass Spec. [M+H]+ | Starting Material |
|---|---|---|---|
| 235 | 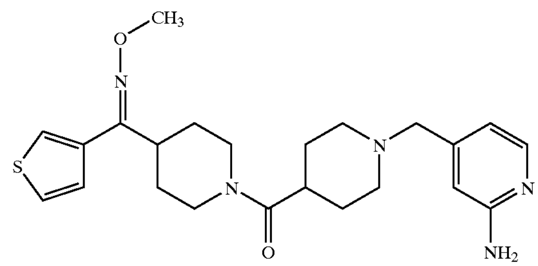 | 442 | |
| 236 | 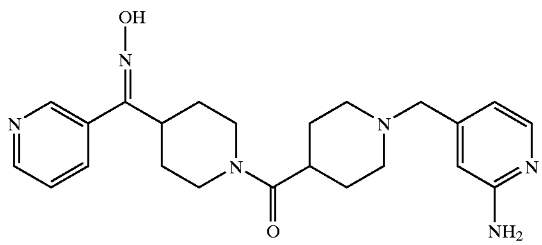 | 423 | |
| 237 | 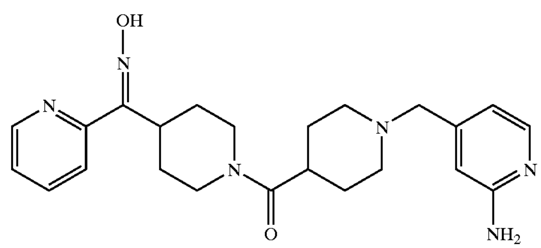 | 423 | |
| 238 | 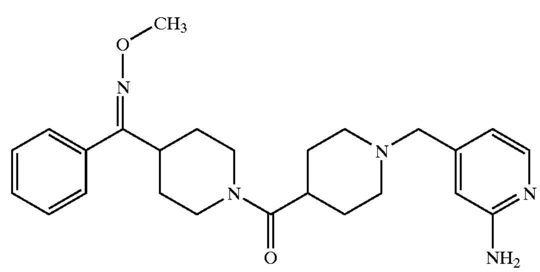 | 436 | |
| 239 | 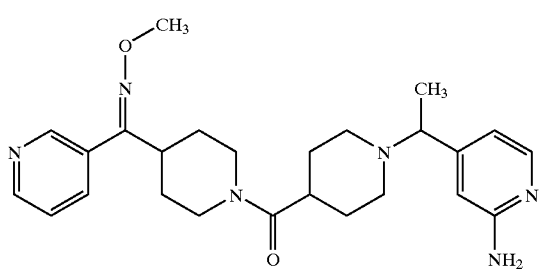 | 451 | |
| 240 | 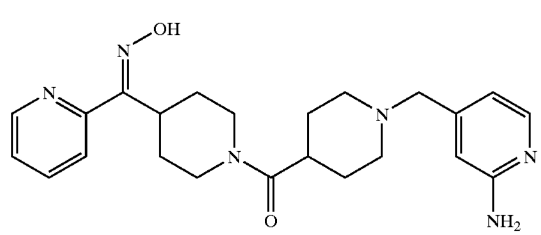 | 423 | |

TABLE 1-continued

| Cmpd. No. | STRUCTURE | Mass Spec. [M+H]+ | Starting Material |
|---|---|---|---|
| 241 | 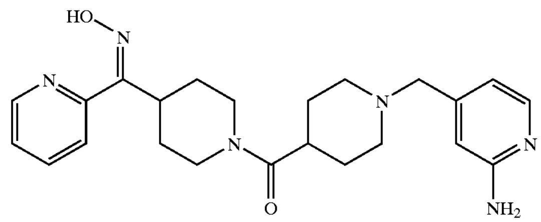 | 423 | |
| 244 | 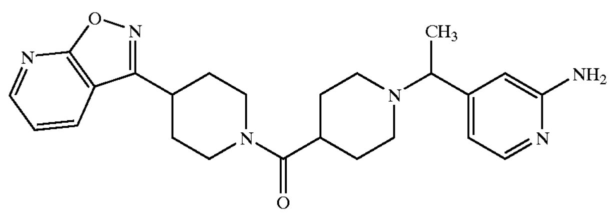 | 435 | |
| 245 | 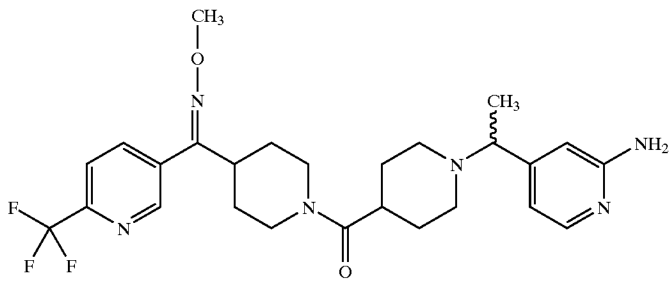 | 519 | |
| 246 | 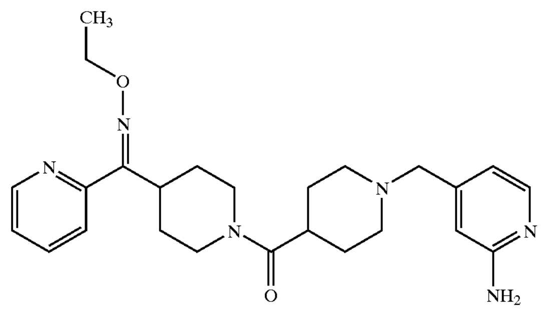 | 451 | |
| 247 | 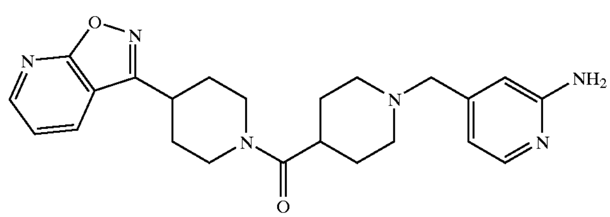 | 421 | |
| 248 | 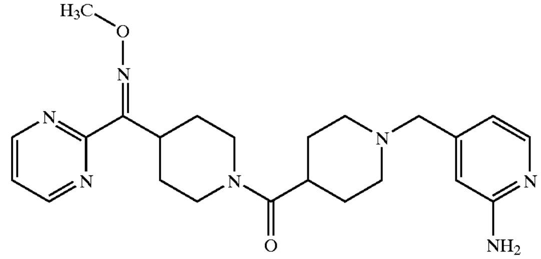 | 438 | |

TABLE 1-continued

| Cmpd. No. | STRUCTURE | Mass Spec. [M+H]+ | Starting Material |
|---|---|---|---|
| 249 | 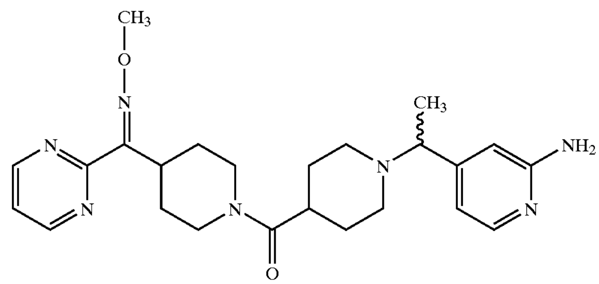 | 452 | |
| 250 | 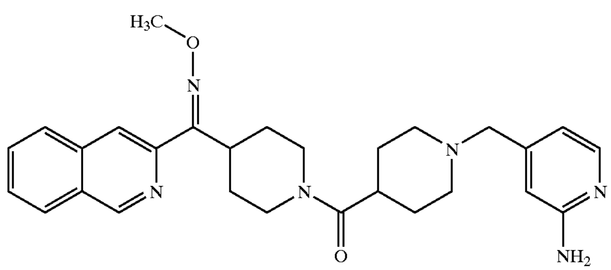 | 487 | |
| 251 | 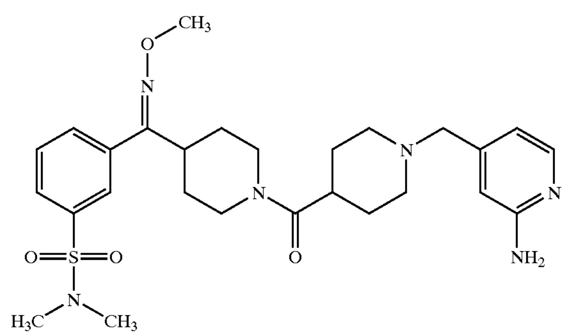 | 543 | |
| 252 | 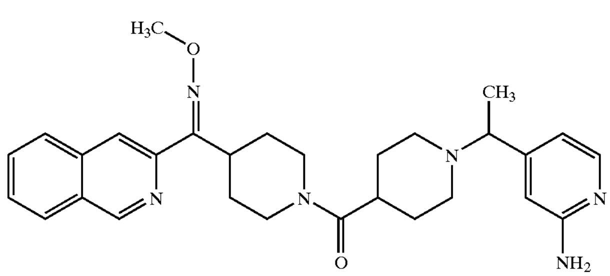 | 501 | |
| 253 | 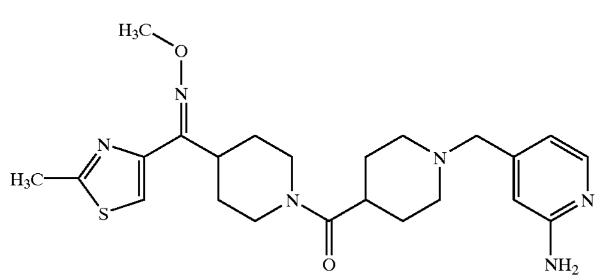 | 457 | |

TABLE 1-continued

| Cmpd. No. | STRUCTURE | Mass Spec. [M+H]+ | Starting Material |
|---|---|---|---|
| 254 | 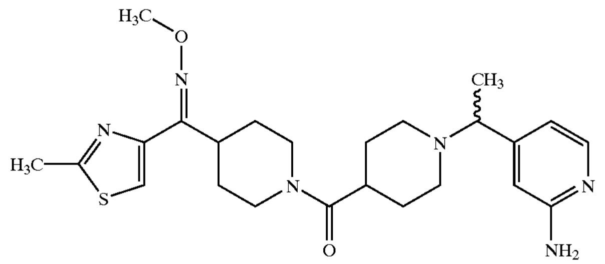 | 471 | 2-methyl-thiazole-4-carbonitrile |
| 255 | 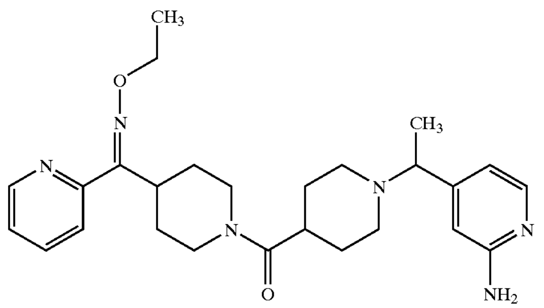 | 465 | 2-cyanopyridine |
| 256 | 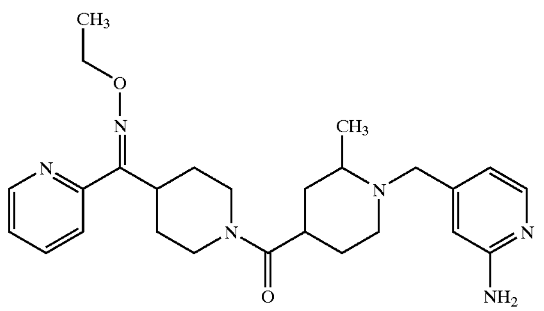 | 465 | 2-cyanopyridine |
| 257 | 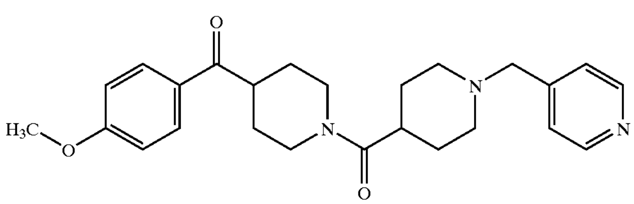 | 422 | 4-methoxybenzaldehyde |
| 258 | 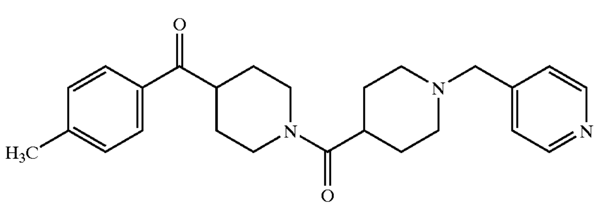 | 406 | 4-methylbenzaldehyde |
| 259 | 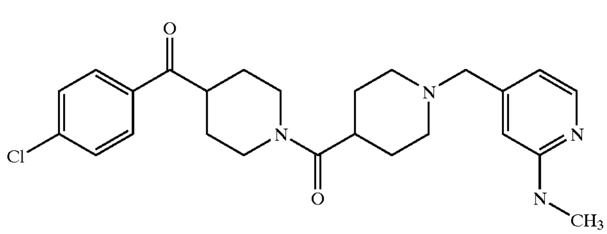 | 455 | (4-chlorophenyl)(piperidin-4-yl)methanone · HCl |

TABLE 1-continued

| Cmpd. No. | STRUCTURE | Mass Spec. [M+H]+ | Starting Material |
|---|---|---|---|
| 260 | 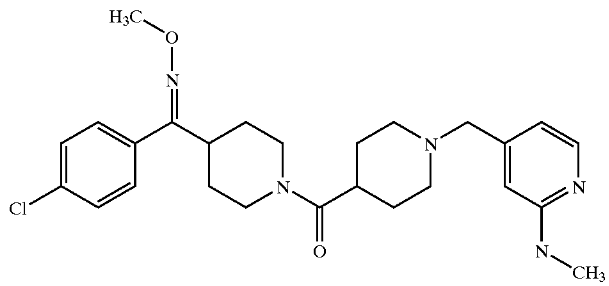 | 484 | |
| 261 | 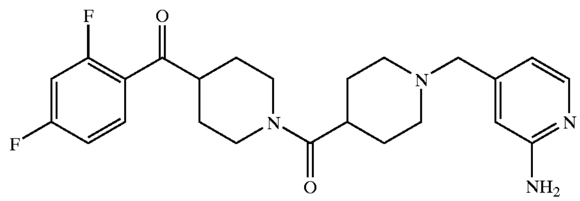 | 443 | |
| 262 | 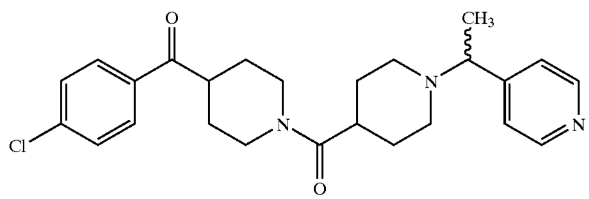 | 440 | |
| 263 | 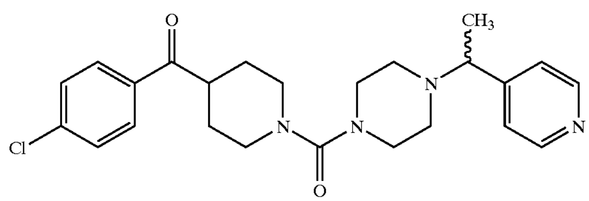 | 441 | |
| 264 | 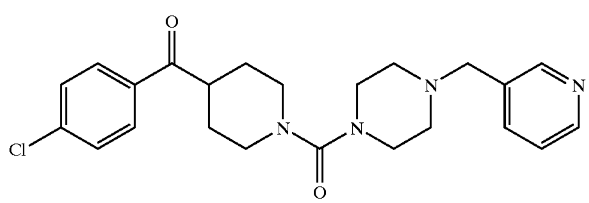 | 427 | |
| 265 | 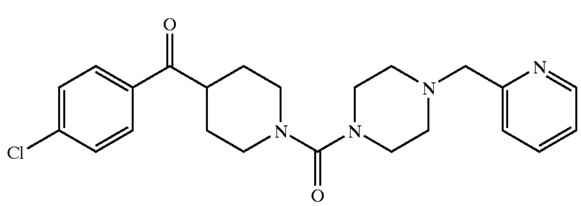 | 427 | |

TABLE 1-continued

| Cmpd. No. | STRUCTURE | Mass Spec. [M+H]+ | Starting Material |
|---|---|---|---|
| 266 | 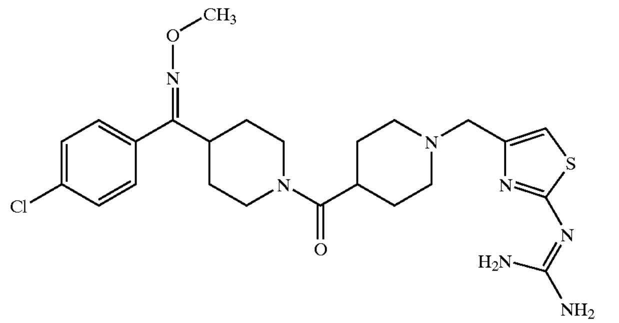 | 518 | |
| 267 | 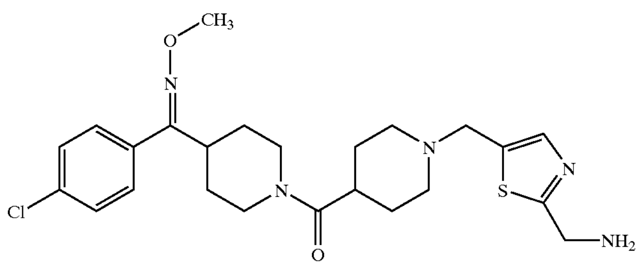 | 490 | |
| 268 | 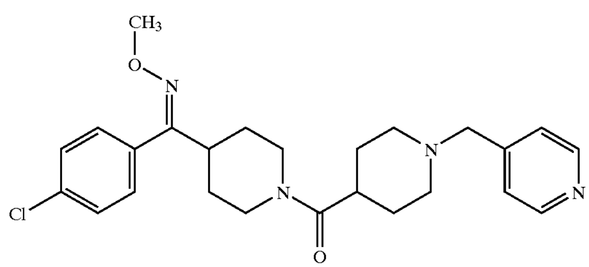 | 455 | |
| 269 | 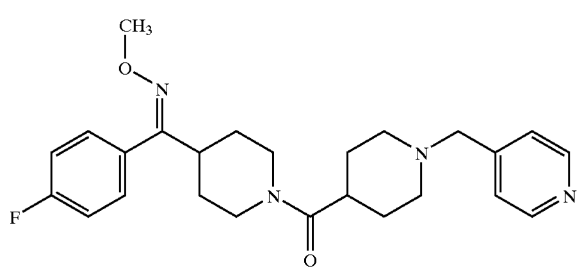 | 439 | |
| 270 | 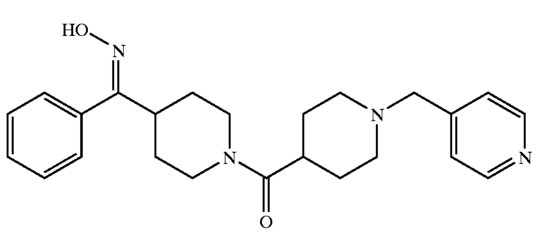 | 407 | |

TABLE 1-continued

| Cmpd. No. | STRUCTURE | Mass Spec. [M+H]+ | Starting Material |
|---|---|---|---|
| 271 | 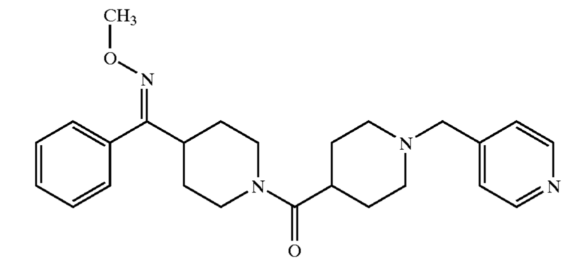 | 421 | |
| 272 | 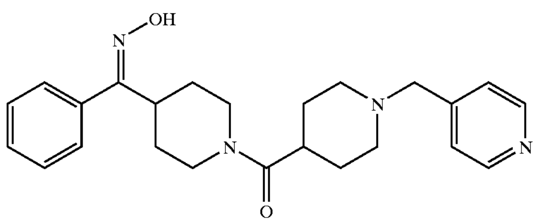 | 407 | |
| 273 | 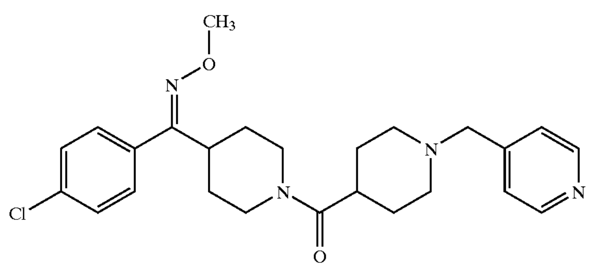 | 455 | |
| 275 | 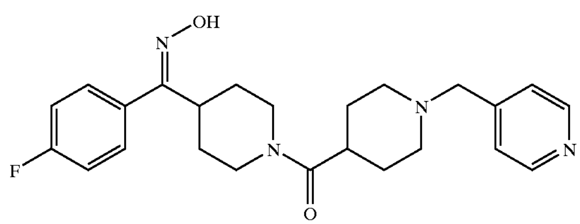 | 425 | |
| 278 | 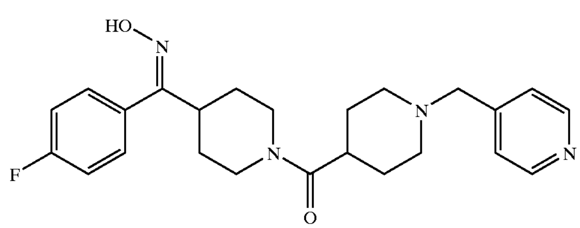 | 425 | |
| 279 | 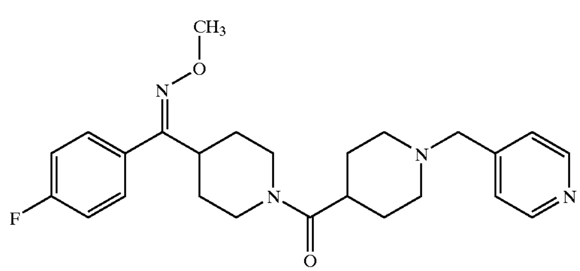 | 439 | |

TABLE 1-continued

| Cmpd. No. | STRUCTURE | Mass Spec. [M+H]+ | Starting Material |
|---|---|---|---|
| 280 | 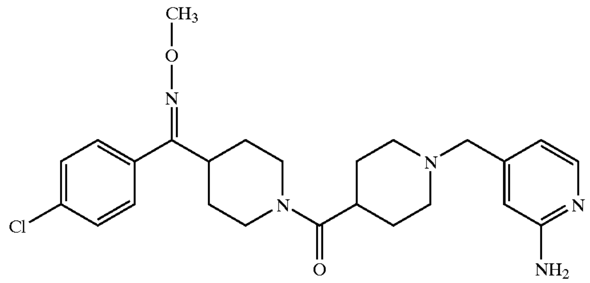 | 470 | |
| 281 | 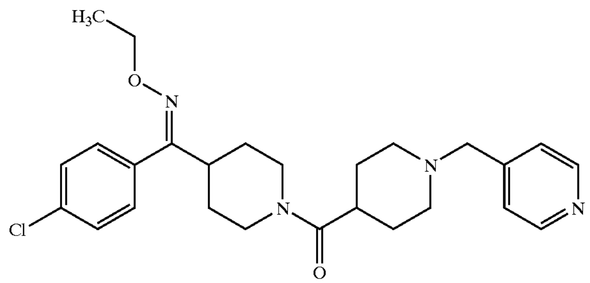 | 469 | |
| 282 | 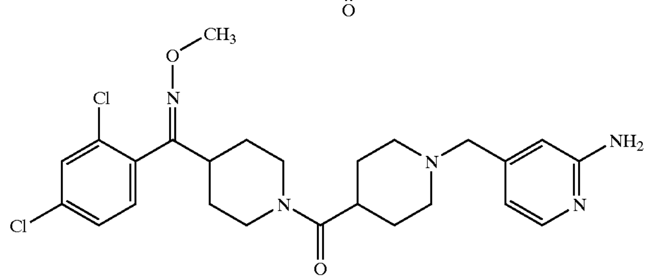 | 504 | |

The isomers 246A and 253A, below, can be separated from 246 and 253, respectively, above, by techniques well known to those skilled in the art.

246A

253A

EXAMPLE 28

Step 1

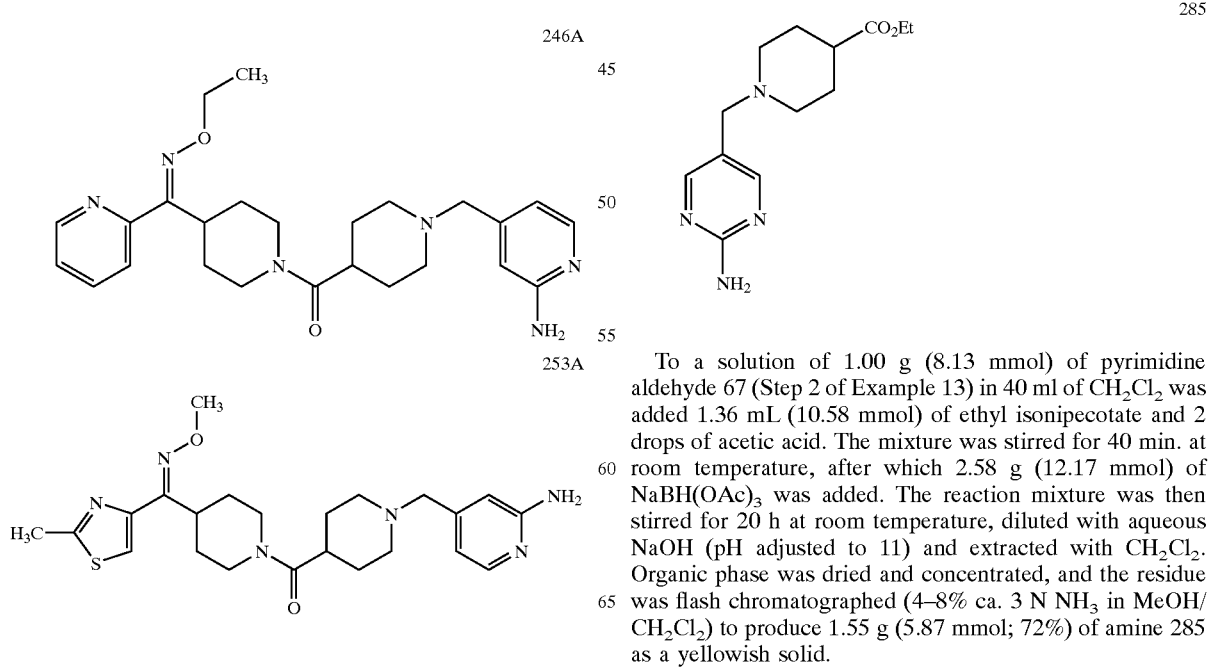

To a solution of 1.00 g (8.13 mmol) of pyrimidine aldehyde 67 (Step 2 of Example 13) in 40 ml of CH$_2$Cl$_2$ was added 1.36 mL (10.58 mmol) of ethyl isonipecotate and 2 drops of acetic acid. The mixture was stirred for 40 min. at room temperature, after which 2.58 g (12.17 mmol) of NaBH(OAc)$_3$ was added. The reaction mixture was then stirred for 20 h at room temperature, diluted with aqueous NaOH (pH adjusted to 11) and extracted with CH$_2$Cl$_2$. Organic phase was dried and concentrated, and the residue was flash chromatographed (4–8% ca. 3 N NH$_3$ in MeOH/CH$_2$Cl$_2$) to produce 1.55 g (5.87 mmol; 72%) of amine 285 as a yellowish solid.

Step 2

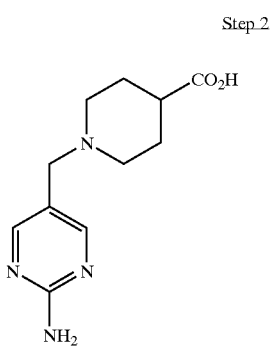

286

To a solution of 3.83 g (14.51 mmol) of ester 285 in 60 ml of 3:1:1 mixture of THF-MeOH-H$_2$O was added 1.22 g (29.02 mmol) of LiOH monohydrate. The reaction mixture was stirred at room temperature overnight, concentrated, and the residue was dried under high vacuum to produce 3.84 g of crude acid 286 lithium salt as a yellow solid. Material could be used directly or could be purified by passing through a silica gel plug eluting with ca. 3 N NH$_3$ in MeOH.

Step 3

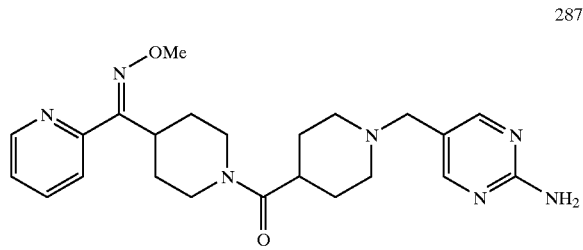

287

To a mixture of 3.32 g (14.05 mmol) of acid 286 and 4.07 g (14.05 mmol) of 4-[(E)-(methoxyimino)-2-pyridinylmethyl]piperidine dihydrochloride (see Compound 447 below) in 40 mL of DMF was added 8.94 mL (70.25 mmol) of 4-ethylmorpholine and 14.0 mL (23.52 mmol) of 50 wt. % solution of 1-propanephosphonic acid cyclic anhydride in ethyl acetate. The reaction mixture was stirred for 4.5 h at 50° C. followed by 14 h at room temperature. Concentration of the mixture was followed by exposure to high vacuum for 24 h to remove remaining DMF. The residue was partitioned between aqueous NaOH and CH$_2$Cl$_2$, organic phase was separated, dried and concentrated, and the residue was flash chromatographed (5–15% ca. 3 N NH$_3$ in MeOH/CH$_2$Cl$_2$) to produce 4.60 g (10.51 mmol; 75%) of amide 287 as a light tan foam. MS 438 (M+1).

EXAMPLE 29

Step 1

Reference: J. Heterocyclic Chem., 1966, 3, 252.

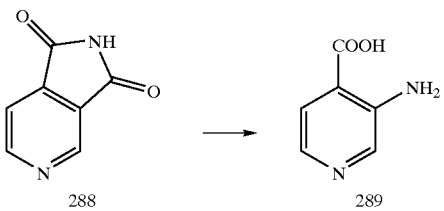

3,4 Pyridine-dicarboximide 288 (10.0 g; 67.5 mmoles) was dissolved in 162 g. of 10% aqueous NaOH and the solution was cooled to an internal temperature of 7° C. in an ice-salt bath. Bromine (3.6 ml; 70 mmoles) was added dropwise. After the addition, the solution was heated for 45 minutes at a bath temperature of 80–85° C. The yellow solution was then cooled to an internal temperature of 37° C., then 17 ml of glacial acetic acid were added dropwise to a pH of 5.5. The resulting mixture was saved overnight in a refrigerator. The solid formed was filtered and washed with 5 ml of water and 5 ml of methanol. The reaction yielded 6.35 g. of product 289 melting at 280–285° C. (decomp.).

Step 2

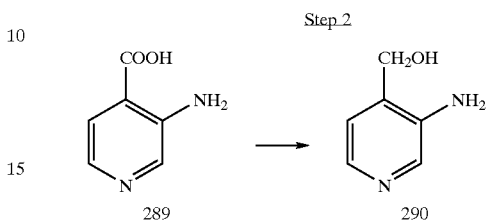

Solid Compound 289 (9.5 gr.; 69 mmoles) was carefully added in three aliquots to a slurry of lithium aluminum hydride (9.5 gr.; 250 mmoles) in 200 ml of dry tetrahydrofuran. The resulting hot mixture was stirred at room temperature for two days. After cooling in an ice bath, the reaction was quenched with very careful sequential dropwise addition of 10 ml of water, followed by 10 ml of 15% aqueous NaOH, then by 30 ml of water. The resulting solid was filtered through a pad of Celite and washed several times with THF. The oil obtained after evaporation of the solvent, solidified on standing. The reaction mixture was purified by flash chromatography on silica gel using 5% MeOH(NH$_3$)/EtOAc as eluent yielding 6.21 (72%) of Compound 290. LC-MS: m/z=125 (M+1).

Step 3

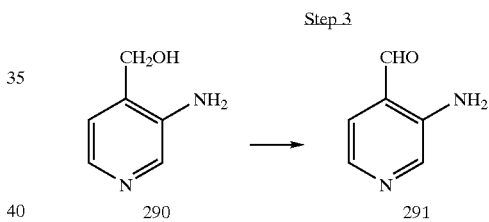

Manganese dioxide (29 gr.; 334 mmoles) was added, in one portion, at room temperature, to a suspension of 3-amino-4-hydroxymethyl pyridine 290 (5.0 gr.; 40.3 mmoles) in 500 ml of chloroform with good stirring. After two days, the solid is filtered through a pad of Celite and washed with chloroform. Removal of the solvent using reduced pressure yielded 4.2 grams (85%) of Compound 291 as a yellow solid.

Step 4

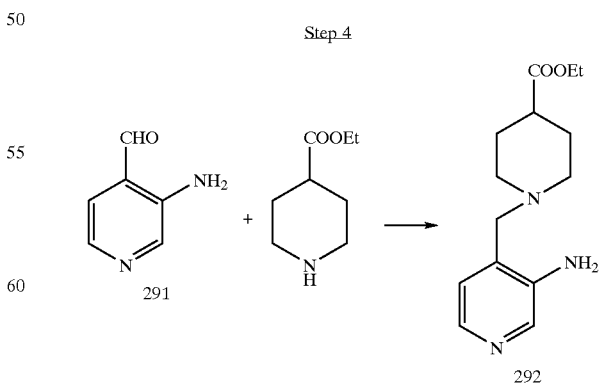

A dry dichloromethane (400 ml) solution of ethyl isonipecotate (12.5 gr.; 79.5 mmoles) and 3-amino pyridine 4-carboxyaldehyde 291 (3.33 gr.; 27.3 mmoles) was sieves were added. The mixture was stirred for an additional 90 minutes, then 20 grams (96.4 mmoles) of sodium triacetoxy borohydride was added at room temperature in one portion. After stirring for three days, the solid was filtered through a pad of Celite and washed with dichloromethane. The solution was stirred for 15 minutes with 100 ml of saturated aqueous sodium bicarbonate then separated from the aqueous layer. The organic layer was washed two more times with saturated aqueous sodium bicarbonate, then with brine and dried with anhydrous sodium sulfate. After evaporation of the solvent, the resulting oil was purified by flash chromatography on silica gel using EtOAc:Hexanes:MeOH (NH$_3$) as eluent. The procedure yielded 6.8 gr.(94%) of Compound 292. FAB-MS: m/z=264 (M+1).

Step 5

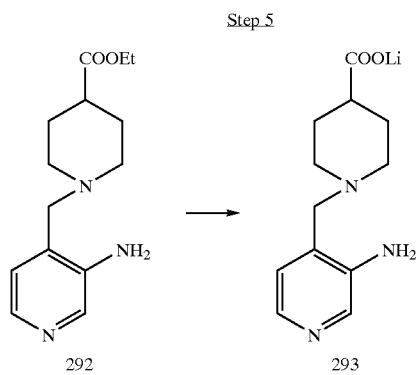

Ethyl 1-[(3-amino-4-pyridinyl)methyl]-4-piperidinecarboxylate 292 (4.75 gr.; 18.04 mmoles) was stirred for 24 hours at room temperature with 1.51 gr. (36 mmoles) of lithium hydroxide monohydrate in 75 ml of methanol. Removal of the solvent using reduced pressure yielded Compound 293 as a white solid.

Step 6

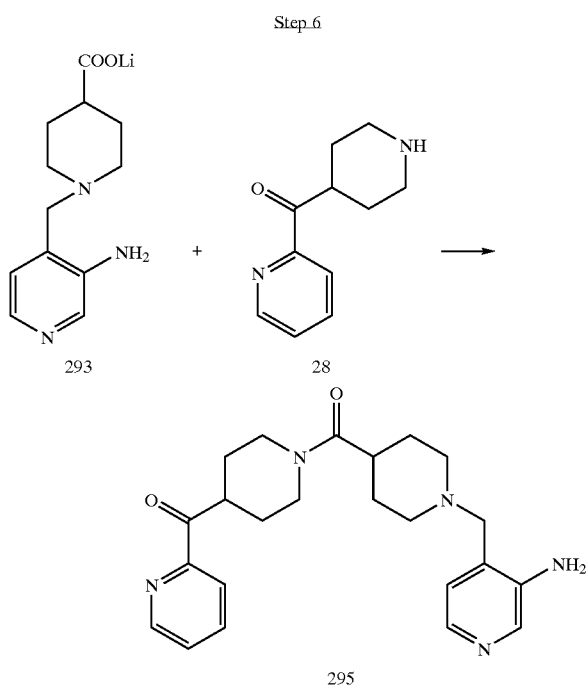

4-(2-pyridinylcarbonyl)piperidine 28 (Step 4 in Example 6) (0.3 gr.; 1.58 mmoles), lithium 1-[(3-amino-4-pyridinyl)methyl]-4-piperidinecarboxylate 293 (0.34 gr.; 1.4 mmoles), DEC (0.38 gr.; 2.0 mmoles), and HOBT (0.27 gr.; 2.0 mmoles) were stirred at room temperature in 10 ml of dry DMF for two days. The reaction was quenched with 50 ml. of 0.5 N aqueous NaOH, then the solution was extracted with dichloromethane. The combined extracts were washed with brine and dried over anhydrous sodium sulfate. The product 295 was isolated by flash chromatography on silica gel using EtOAc:Hexanes:MeOH(NH$_3$) (50:45:5) as eluent. Yields: 0.27 gr. (47%). FAB-MS: m/z=408 (M+1).

Step 7

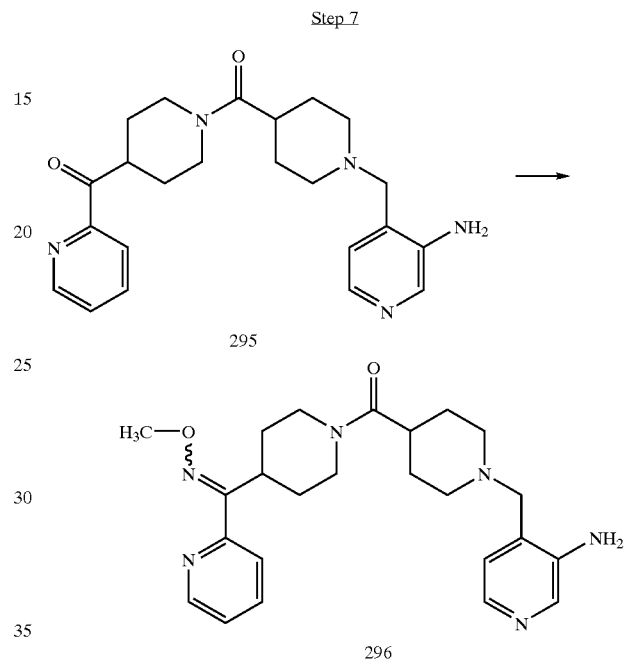

1-[[[1-[(3-amino-4-pyridinyl)methyl]-4-piperidinyl] carbonyl]-4-(2-pyridinylcarbonyl)piperdine 295 (0.196 gr.; 0.48) and methoxyamine hydrochloride (0.401 gr. 4.8; mmoles) were heated, under N$_2$, at a bath temperature of 70° C. for 24 hours in 6.0 ml of dry pyridine. After removing the pyridine using reduced pressure, the residue was treated with saturated aqueous sodium bicarbonate. The resulting mixture was extracted several times with dichloromethane. The combined extracts were washed with brine and dried over anhydrous sodium sulfate. The reaction mixture was purified by silica gel preparative thin layer chromatography. The plates were eluted with EtOAc:Hexanes:MeOH(NH$_3$) (60:35:5) and the product 296 was extracted with 10% MeOH(NH3)/EtOAc. Yields: 0.15 gr. (71%). FAB-MS: m/z=437 (M+1).

EXAMPLE 30

Step 1

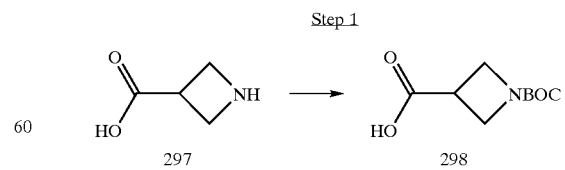

A mixture of 297 (1 g, 10 mmol) in 1:1 water-dioxane (50 mL) was treated with Et$_3$N (4 mL, 13 mmol) and BOC$_2$O (2.8 g, 13 mmol) at 4° C. and allowed to warm to 20° C. for one day. The solvent was then removed in vacuo. The residue was taken up in 1:1 water-ethyl acetate and the organic layer was discarded. The aqueous layer was acidified with 1 N aqueous HCl and extracted three times with ethyl acetate. The combined organic phases were washed with water and brine, dried (Na$_2$SO$_4$), and concentrated to give 298 as a white solid (1.8 g, 90%).

Step 2

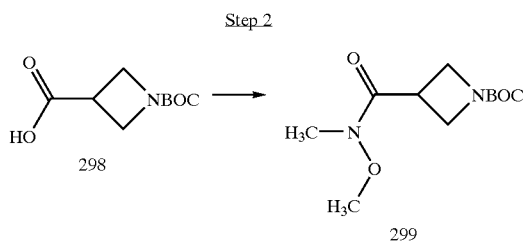

A mixture of 298 (1.8 g, 9 mmol), N,O-dimethylhydroxylamine hydrochloride (2.6 g, 27 mmol), EDCl (5 g, 27 mmol), HOBt (0.1 g, 1 mmol), and DIPEA (12.5 mL, 72 mmol) in DMF (30 mL) was stirred at 20° C. overnight. The reaction was then concentrated to half volume in vacuo, poured onto water, and extracted three times with ethyl acetate. The combined organic phases were washed with saturated aqueous NH$_4$Cl, saturated aqueous NaHCO$_3$, water and brine, dried (Na$_2$SO$_4$), and concentrated to give 299 as a clear oil (2.1 g, 98%).

Step 3

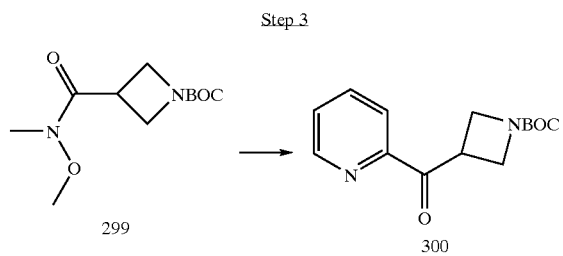

To a solution of 2-bromopyridine (1.2 mL, 12 mmol) in THF (60 mL) at −78° C. was added n-BuLi (8 mL of a 1.6 M solution in hexanes, 12 mmol) dropwise over 15 min. After stirring for an additional 30 min at −78 ° C., a solution of 299 (1 g, 4 mmol) in THF (20 mL) was slowly added. The reaction was then heated to 60° C. for 1 h. After cooling to 20° C., the reaction was diluted with ether, quenched with saturated aqueous Na$_2$SO$_4$, and dried with solid Na$_2$SO$_4$. The mixture was filtered through a plug of solid Na$_2$SO$_4$ and concentrated in vacuo. Flash column chromatography (0–20% ethyl acetate-hexanes) yielded 300 as a yellow oil (0.12 g, 11%).

Step 4

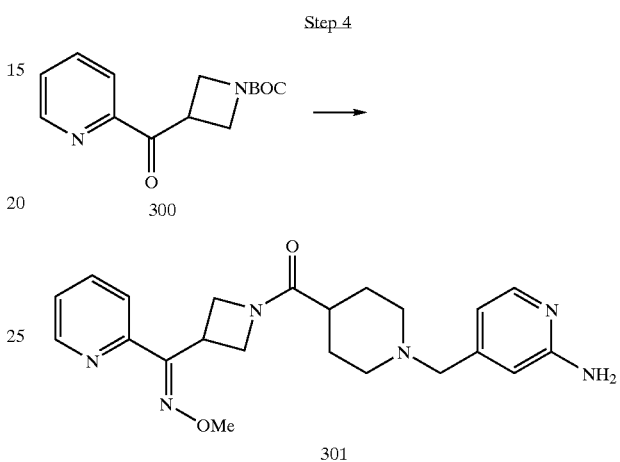

Following procedures similar to those of Steps 4 to 7 of Example 6, compound 301 was obtained. MS 409 (M+1).

Following procedures similar to those described in the examples above, the compounds in Table 2 were prepared.

TABLE 2

| Compound | STRUCTURE | MS (M + 1) |
|---|---|---|
| 302 | 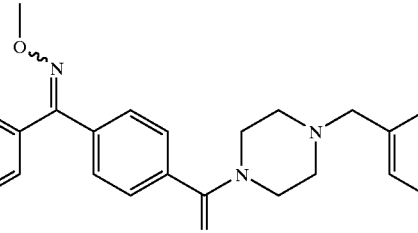 | 430 |
| 303 | 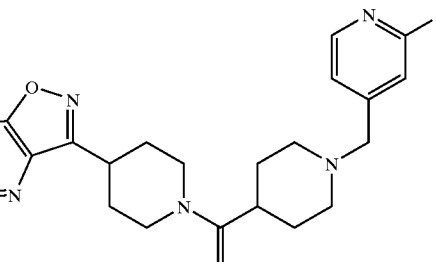 | 421 |

TABLE 2-continued

| Compound | STRUCTURE | MS (M + 1) |
|---|---|---|
| 304 | 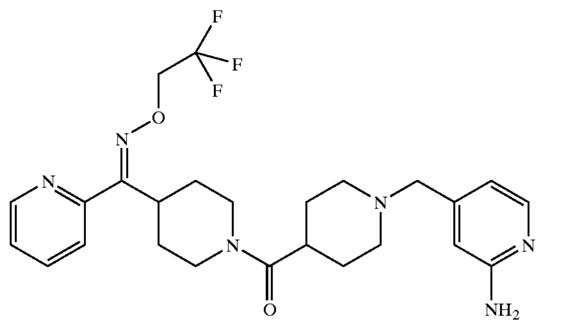 | 505 |
| 305 | 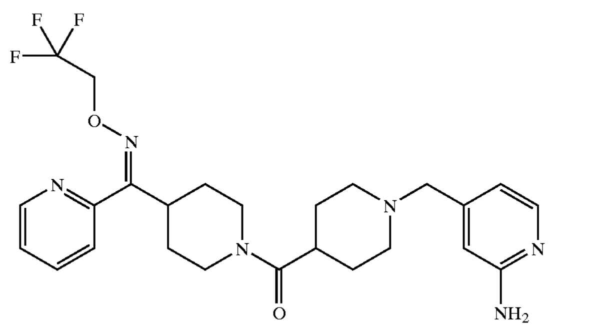 | 505 |
| 306 | 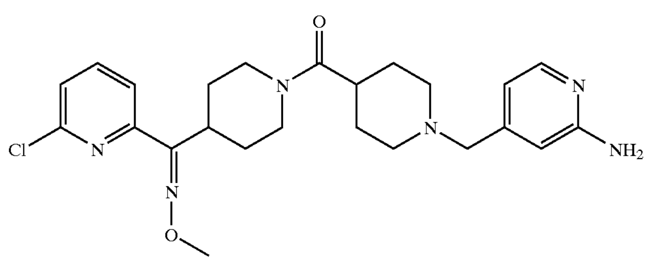 | 471 |
| 307 | 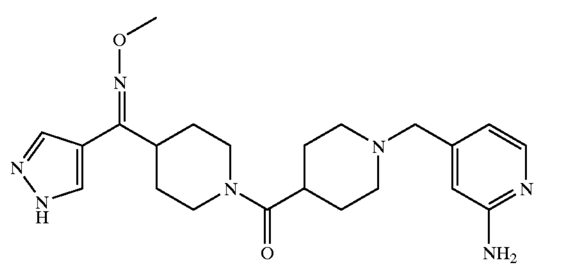 | 426 |
| 308 | 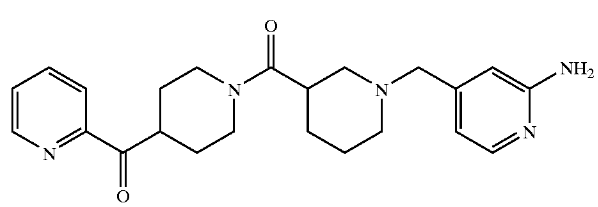 | 408 |

TABLE 2-continued

| Compound | STRUCTURE | MS (M + 1) |
|---|---|---|
| 309 | 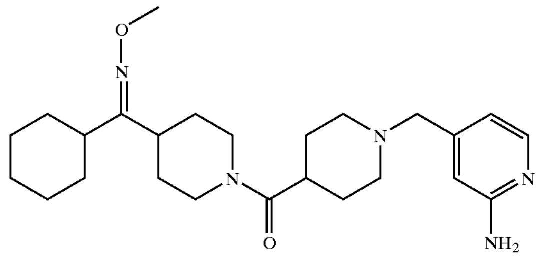 | 442 |
| 310 | 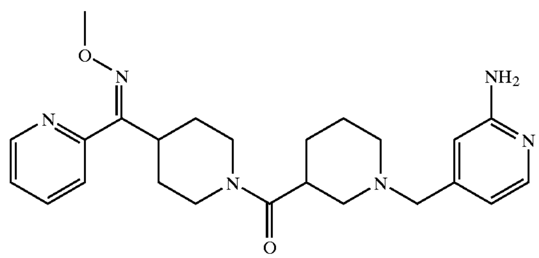 | 437 |
| 311 | 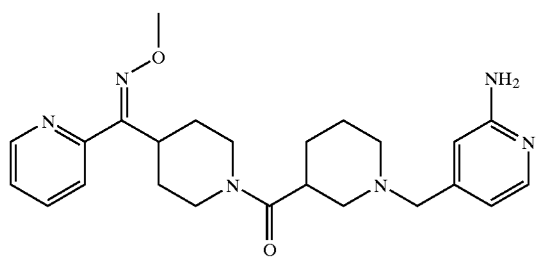 | 437 |
| 312 | 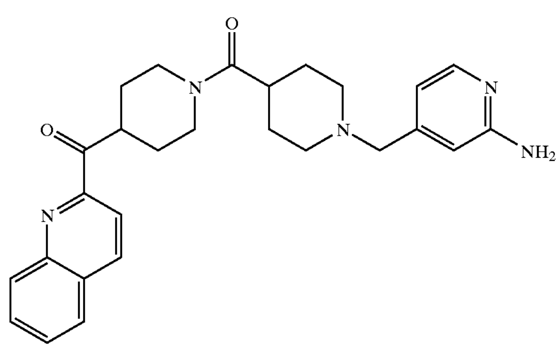 | 458 |
| 313 | 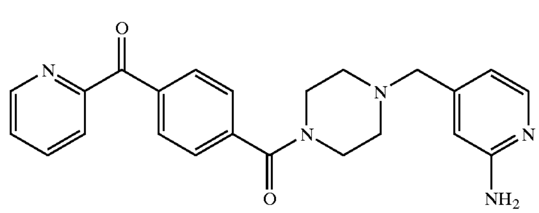 | 402 |

TABLE 2-continued

| Compound | STRUCTURE | MS (M + 1) |
|---|---|---|
| 314 | 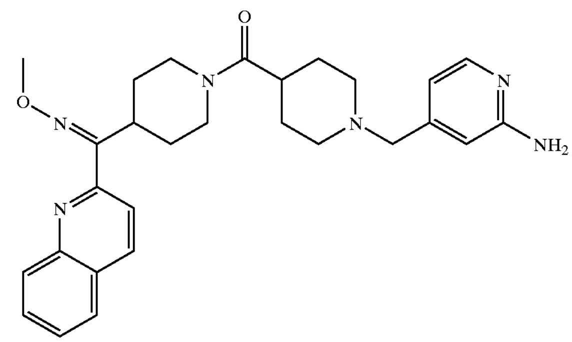 | 487 |
| 315 | 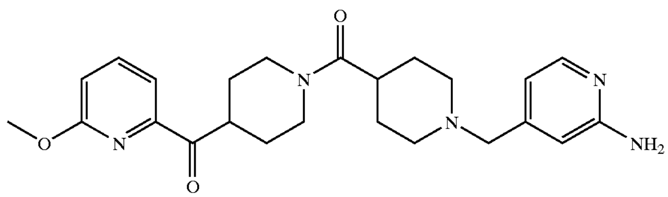 | 438 |
| 316 | 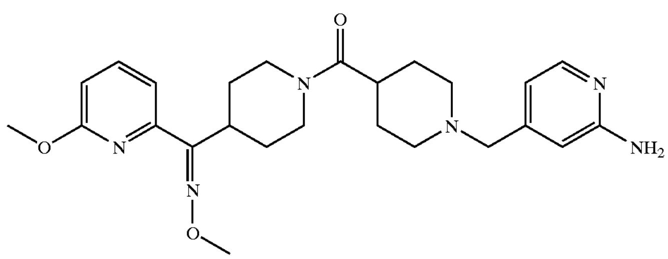 | 467 |
| 317 | 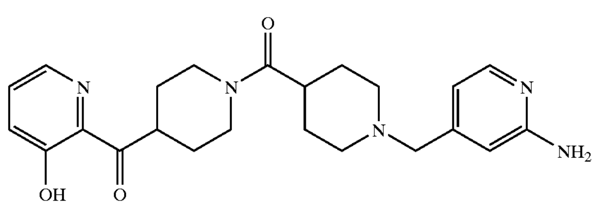 | 424 |
| 318 | 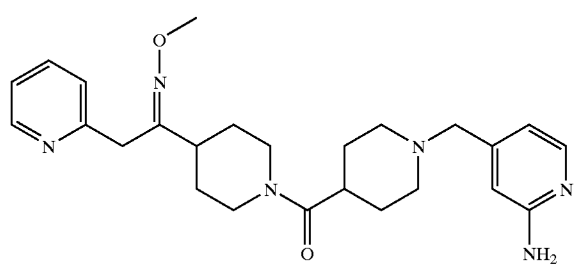 | 451 |
| 319 | 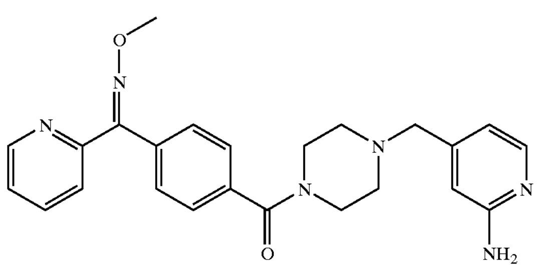 | 430 |

TABLE 2-continued
| Compound | STRUCTURE | MS (M + 1) |
|---|---|---|
| 320 | 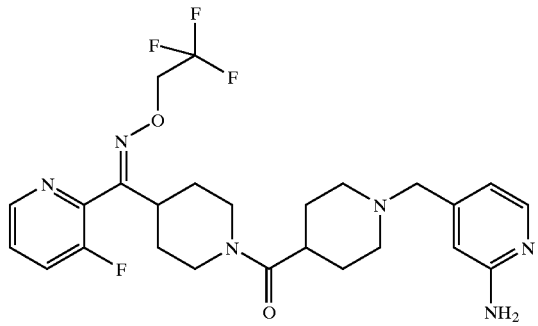 | 523 |
| 321 | 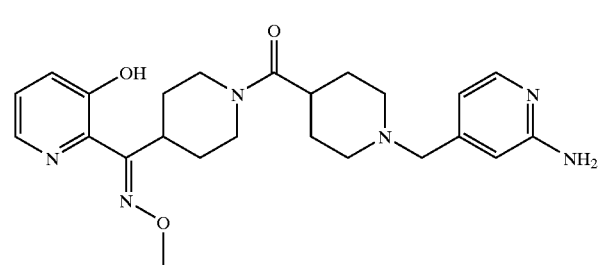 | 453 |
| 322 | 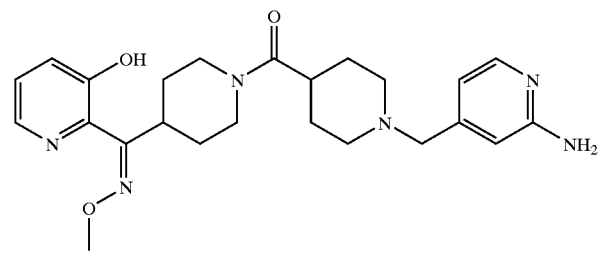 | 453 |
| 323 | 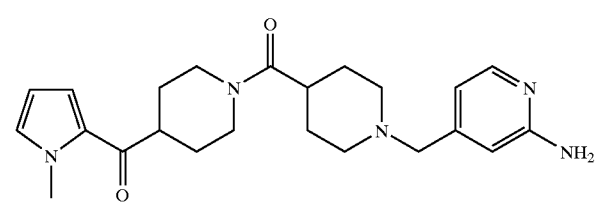 | 410 |
| 324 | 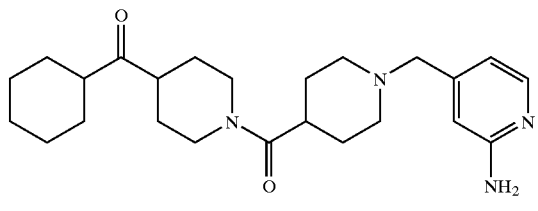 | 413 |
| 325 | 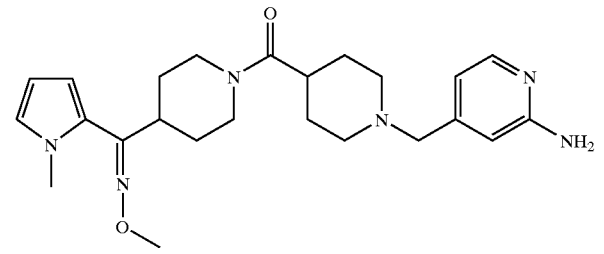 | 439 |

TABLE 2-continued

| Compound | STRUCTURE | MS (M + 1) |
|---|---|---|
| 326 | 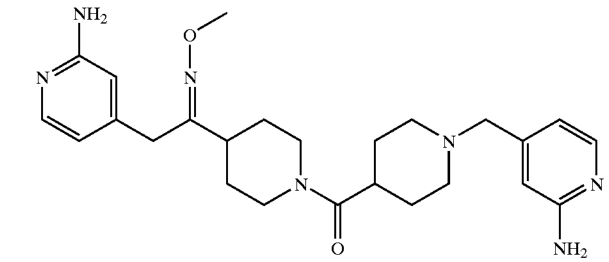 | 466 |
| 327 | 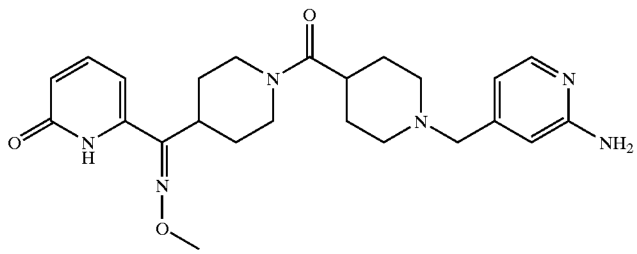 | 453 |
| 328 | 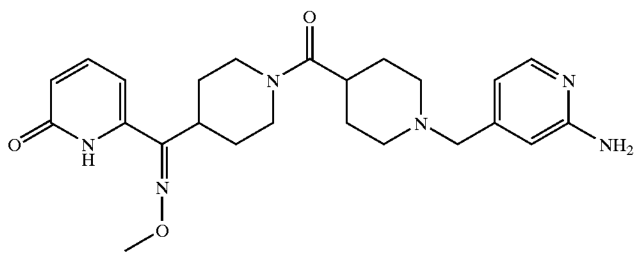 | 453 |
| 329 | 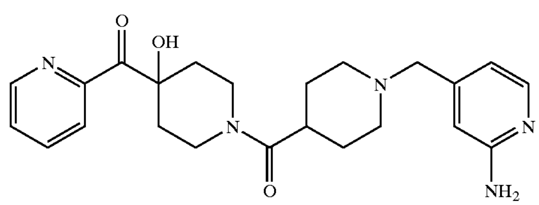 | 424 |
| 330 | 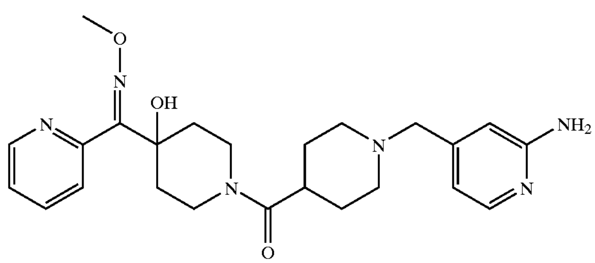 | 453 |
| 331 | 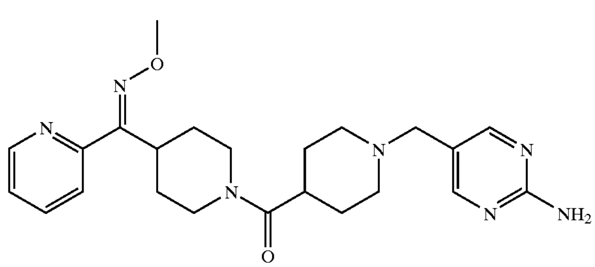 | 438 |

TABLE 2-continued

| Compound | STRUCTURE | MS (M + 1) |
|---|---|---|
| 332 | 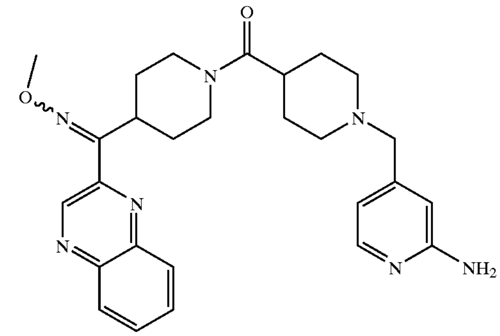 | 488 |
| 333 | 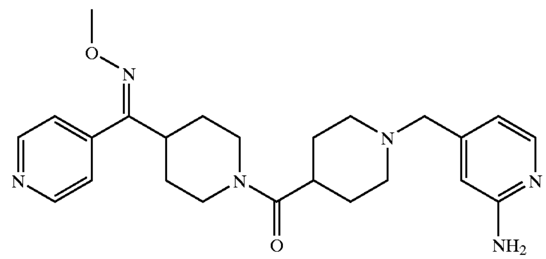 | 437 |
| 334 | 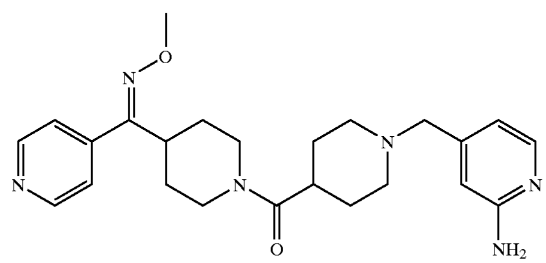 | 437 |
| 335 | 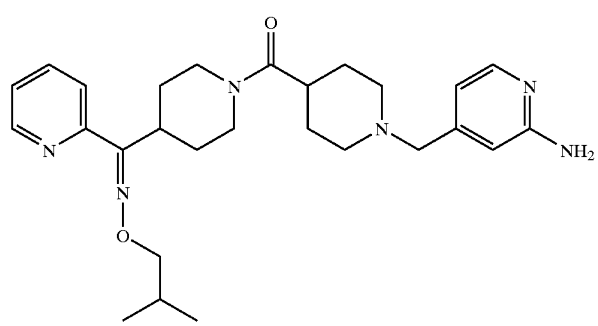 | 479 |
| 336 | 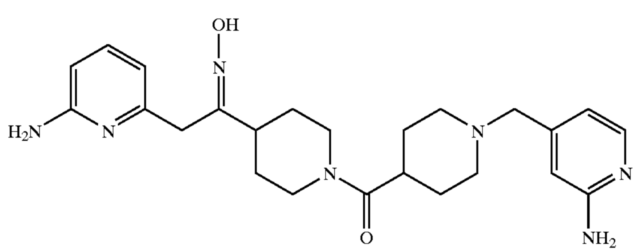 | 452 |

TABLE 2-continued

| Compound | STRUCTURE | MS (M + 1) |
|---|---|---|
| 337 | 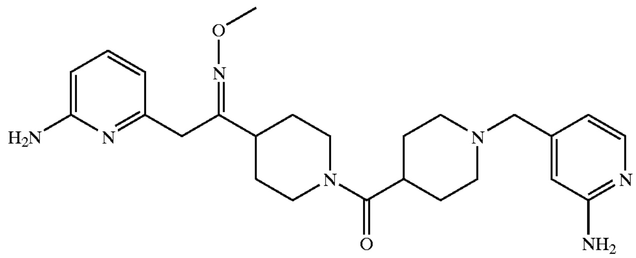 | 466 |
| 338 | 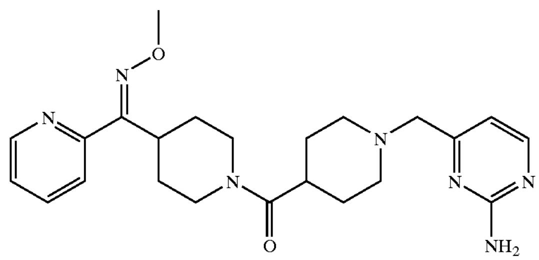 | 438 |
| 339 | 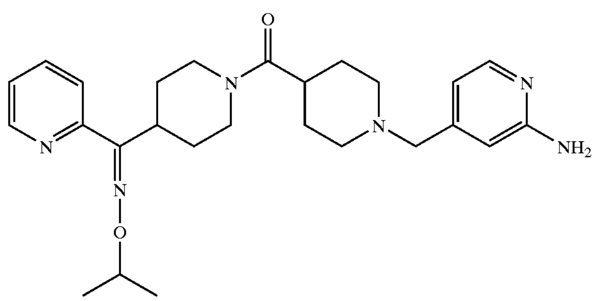 | 465 |
| 340 | 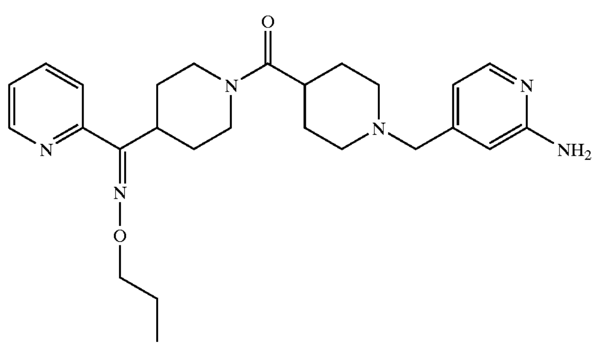 | 465 |
| 341 | 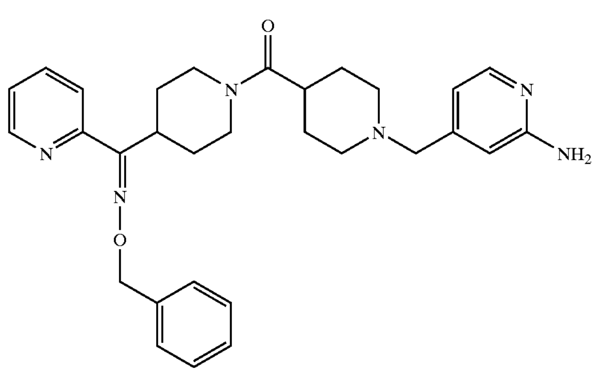 | 513 |

TABLE 2-continued
| Compound | STRUCTURE | MS (M + 1) |
|---|---|---|
| 342 | 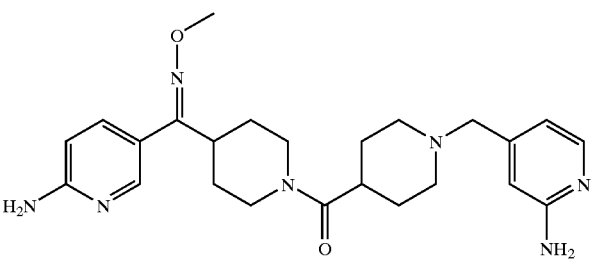 | 452 |
| 343 | 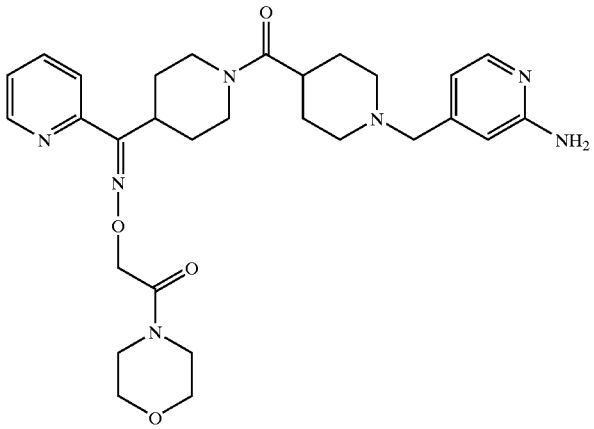 | 550 |
| 344 | 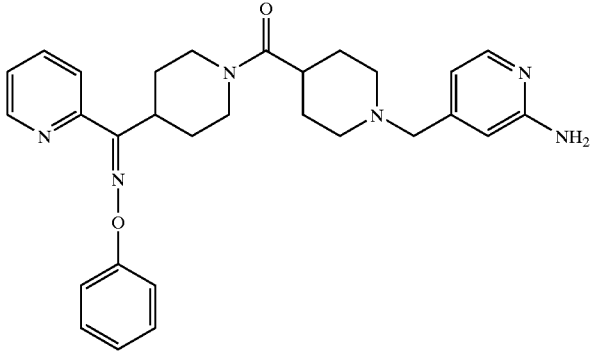 | 499 |
| 345 | 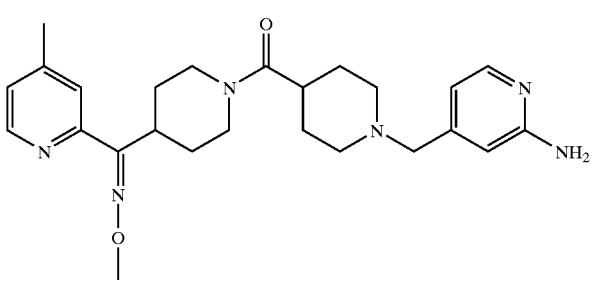 | 451 |

TABLE 2-continued

| Compound | STRUCTURE | MS (M + 1) |
|---|---|---|
| 346 | 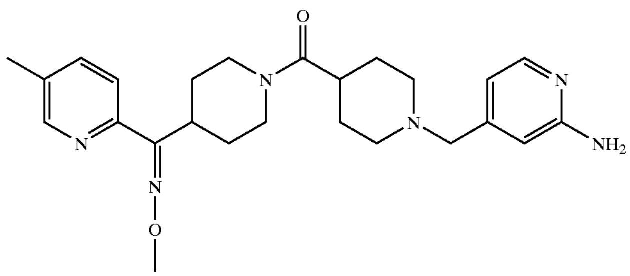 | 451 |
| 347 | 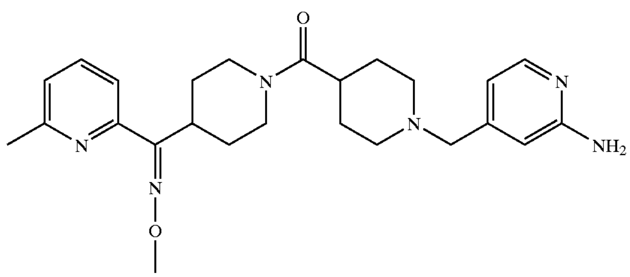 | 451 |
| 348 | 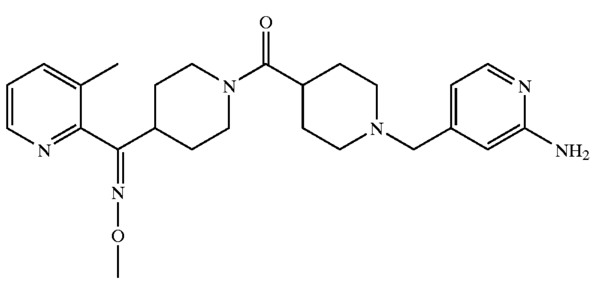 | 451 |
| 349 | 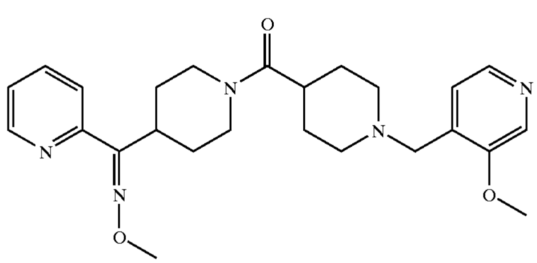 | 452 |
| 350 | 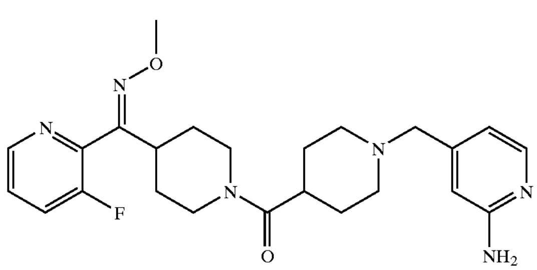 | 455 |

TABLE 2-continued

| Compound | STRUCTURE | MS (M + 1) |
|---|---|---|
| 351 | 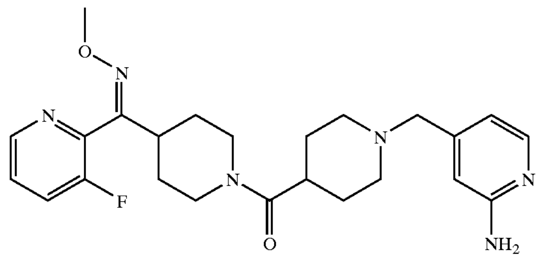 | 455 |
| 352 | 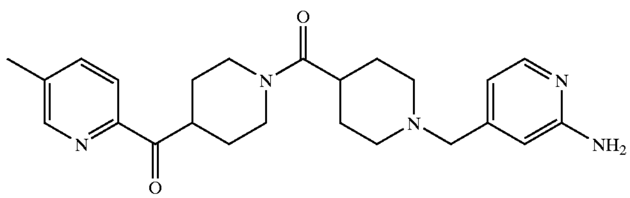 | 422 |
| 353 | 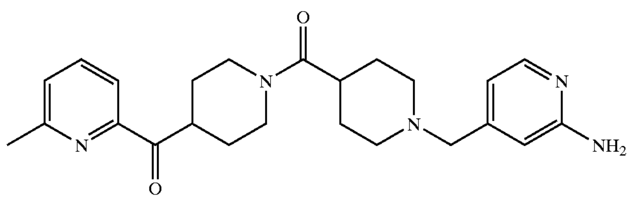 | 422 |
| 354 | 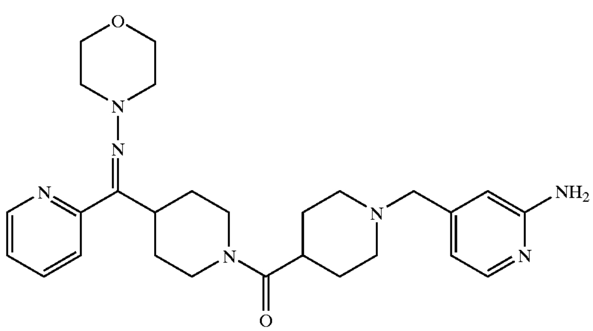 | 492 |
| 355 | 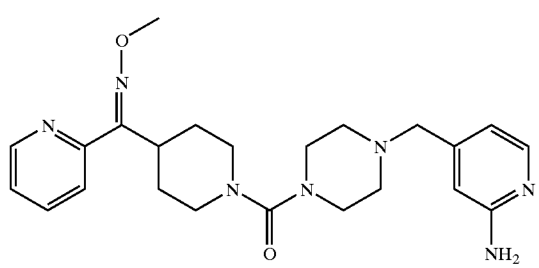 | 438 |
| 356 | 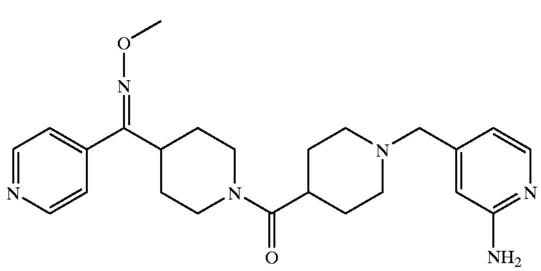 | 437 |

TABLE 2-continued
| Compound | STRUCTURE | MS (M + 1) |
|---|---|---|
| 357 | 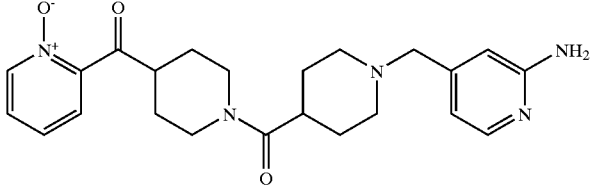 | 424 |
| 358 | 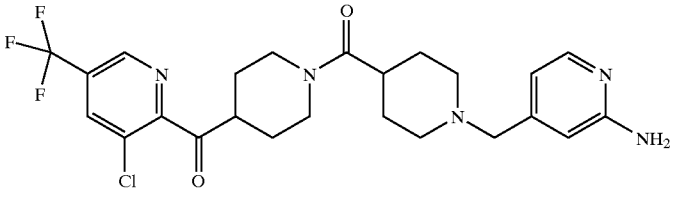 | 510 |
| 359 | 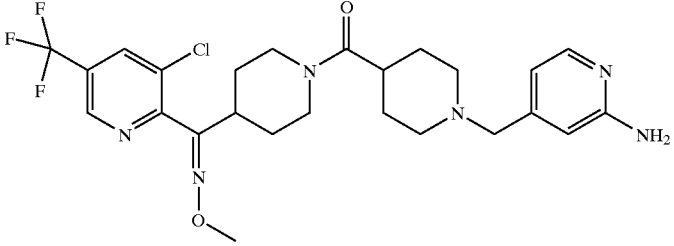 | 539 |
| 360 | 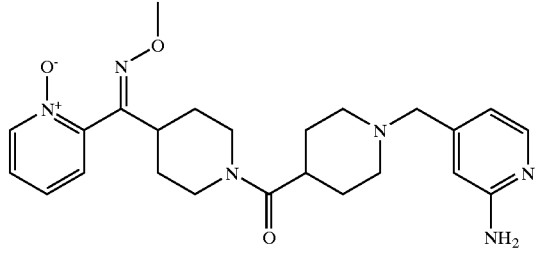 | 453 |
| 361 | 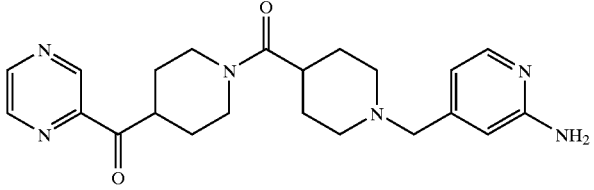 | 409 |
| 362 | 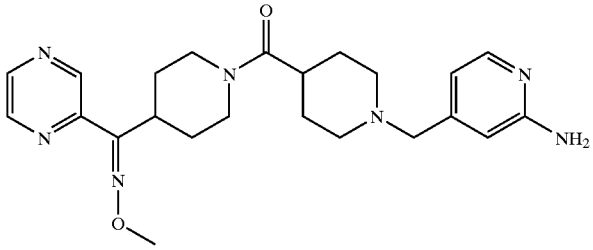 | 438 |

TABLE 2-continued

| Compound | STRUCTURE | MS (M + 1) |
|---|---|---|
| 363 | 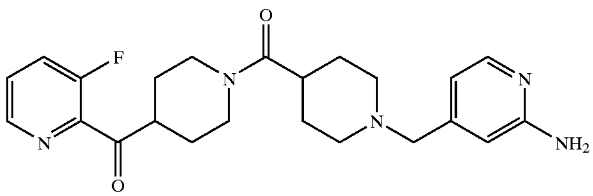 | 426 |
| 364 | 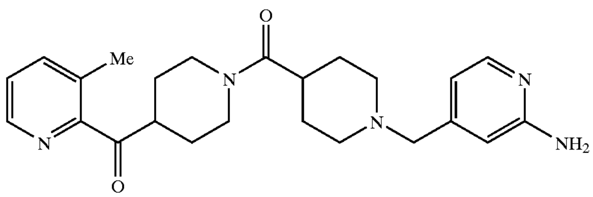 | 422 |
| 365 | 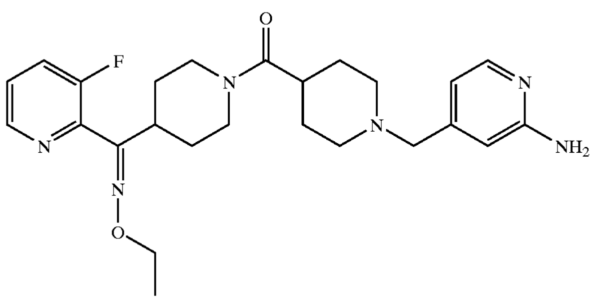 | 483 |
| 366 | 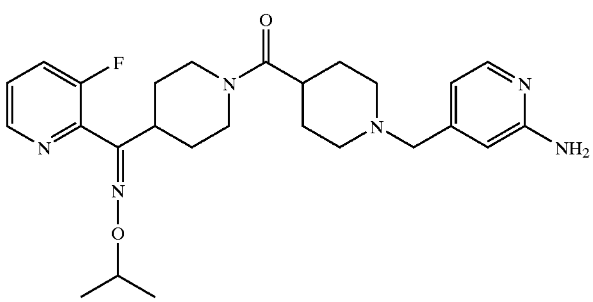 | 483 |
| 367 | 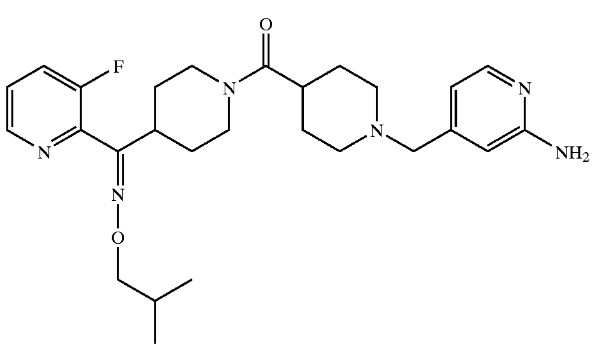 | 497 |

TABLE 2-continued

| Compound | STRUCTURE | MS (M + 1) |
|---|---|---|
| 368 | 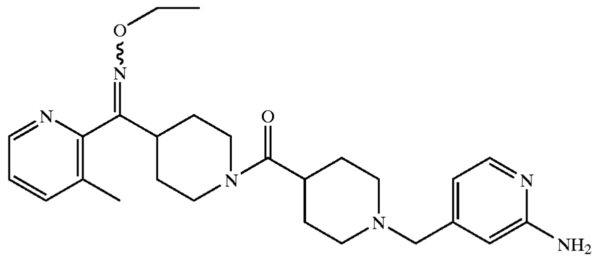 | 465 |
| 369 | 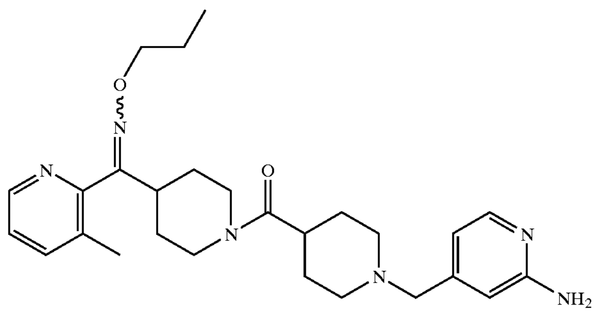 | 479 |
| 370 | 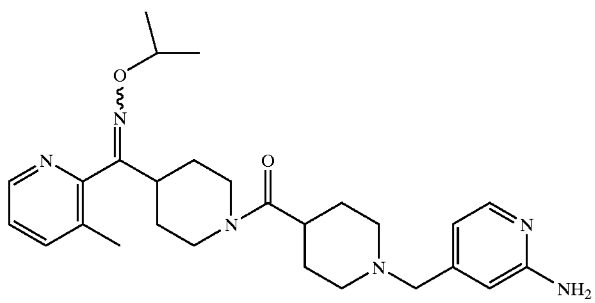 | 479 |
| 371 | 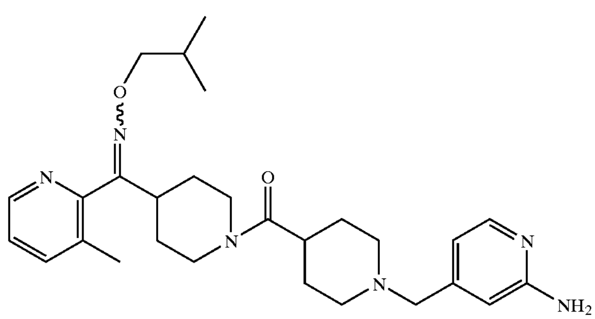 | 493 |
| 372 | 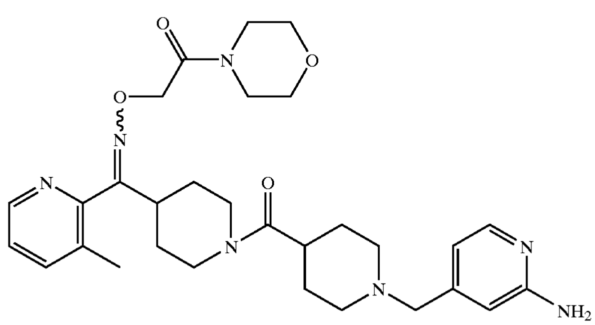 | 564 |

TABLE 2-continued

| Compound | STRUCTURE | MS (M + 1) |
|---|---|---|
| 373 | 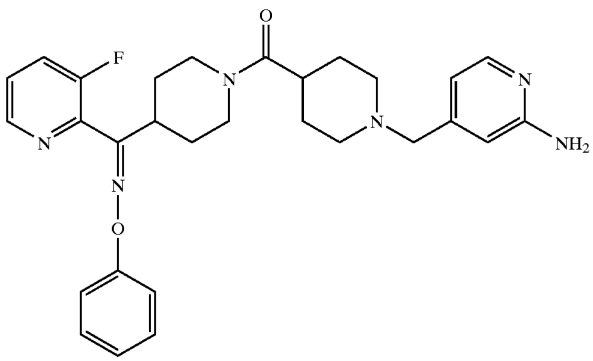 | 517 |
| 374 | 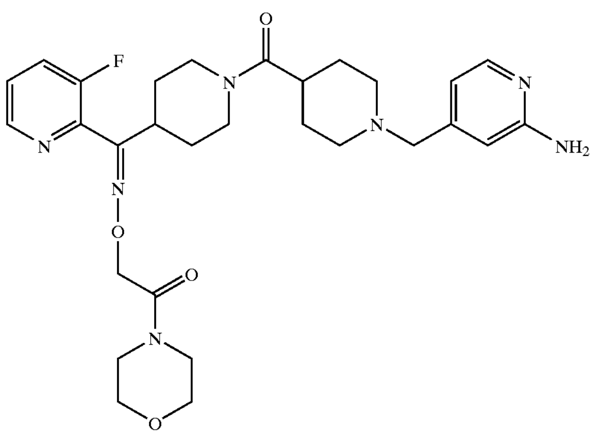 | 568 |
| 375 | 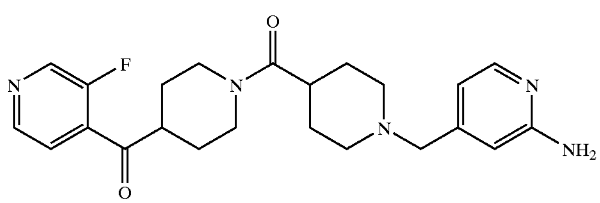 | 426 |
| 376 | 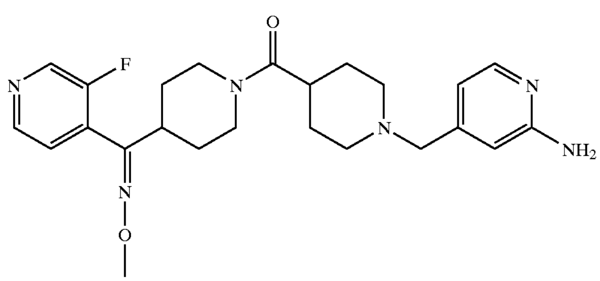 | 455 |
| 377 | 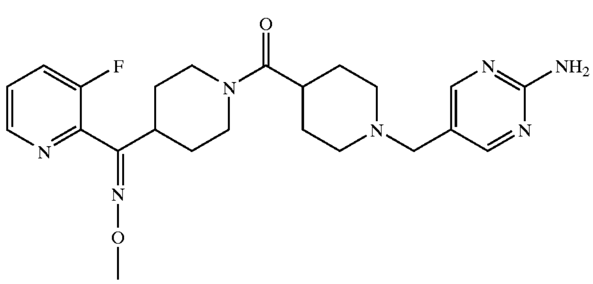 | 456 |

TABLE 2-continued

| Compound | STRUCTURE | MS (M + 1) |
|---|---|---|
| 378 | 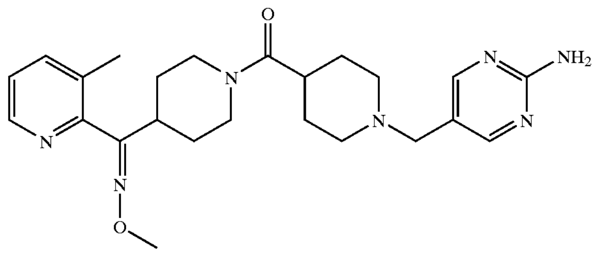 | 452 |
| 379 | 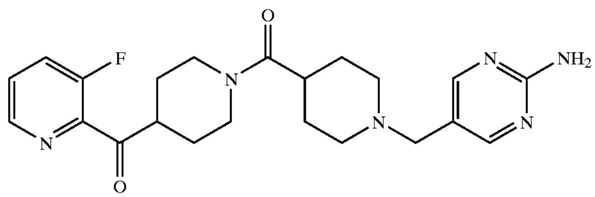 | 427 |

If one were to follow procedures similar to those described in the examples above, the compounds in the "Structure" column of Table 3 would be obtained using the starting material listed in Table 3. Each compound in Table 3 is a mixture of oxime isomers, as represented by the ∼∼∼ bond between the oxime nitrogen and the OH or OCH$_3$ moiety. In Table 3 "CMPD" stands for "Compound".

TABLE 3

| CMPD | Structure | Starting Material |
|---|---|---|
| 380 | 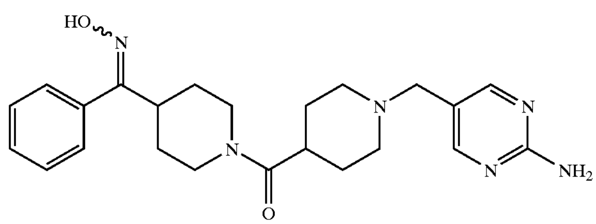 | •HCl |
| 381 | 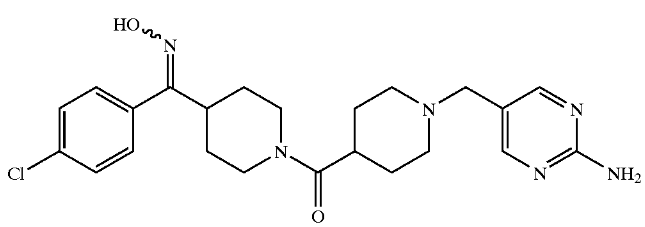 | •HCl |
| 382 | 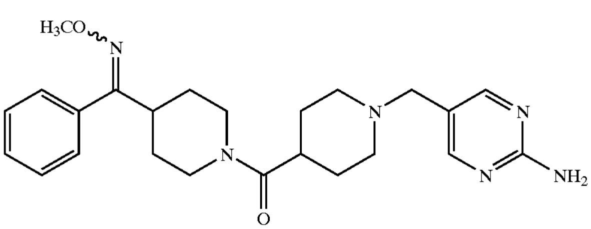 | •HCl |

TABLE 3-continued

| CMPD | Structure | Starting Material |
|---|---|---|
| 383 | 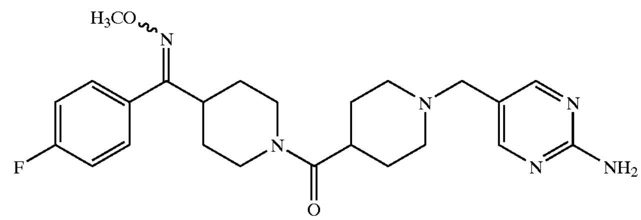 | |
| 384 | 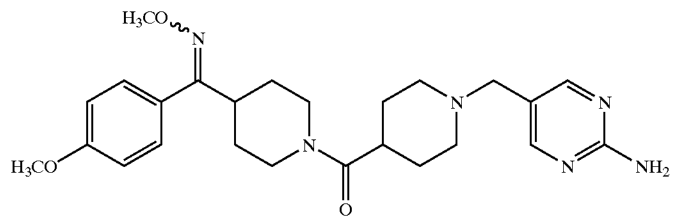 | |
| 385 | 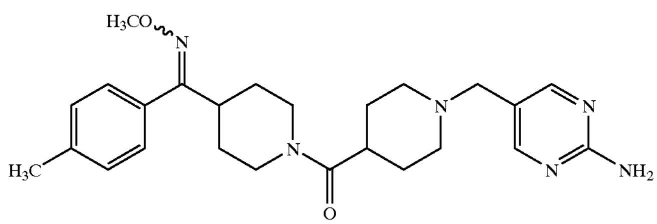 | |
| 386 | 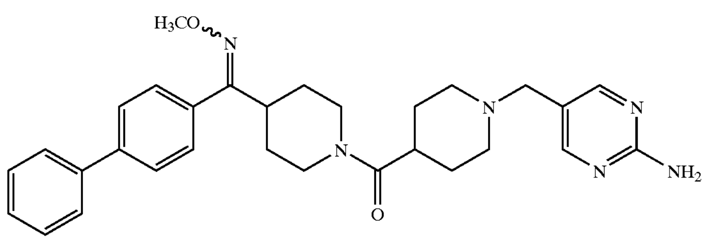 | |
| 387 | 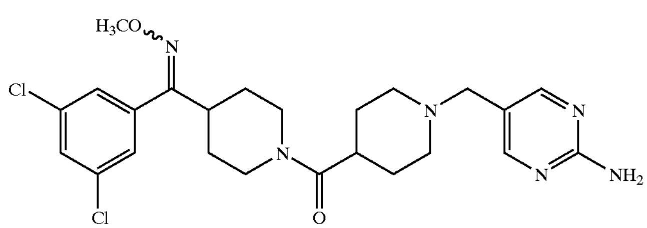 | |
| 388 | 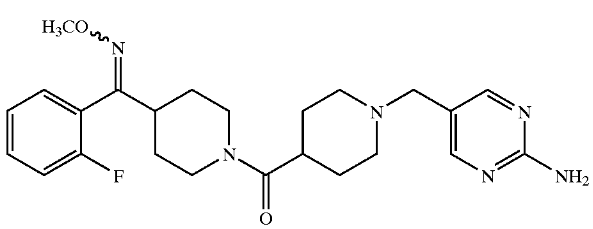 | |

US 6,720,328 B2
137                                                                         138
TABLE 3-continued
| CMPD | Structure | Starting Material |
|---|---|---|
| 389 | 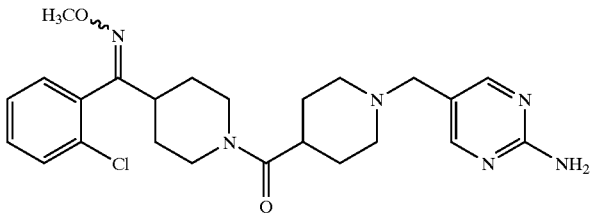 | 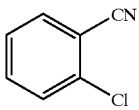 |
| 390 | 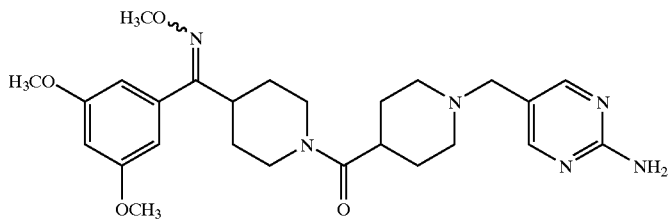 | 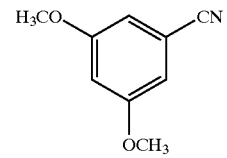 |
| 391 | 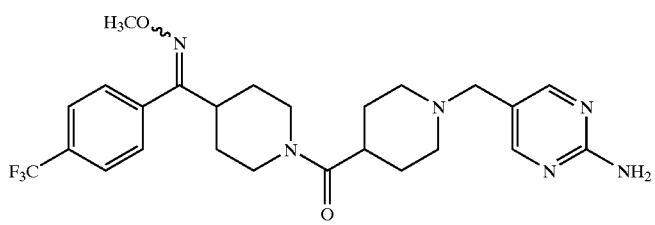 | 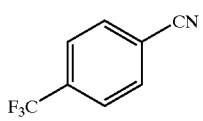 |
| 392 | 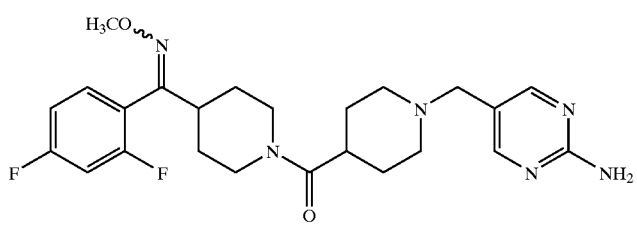 | 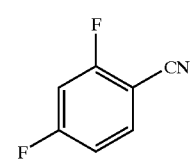 |
| 393 | 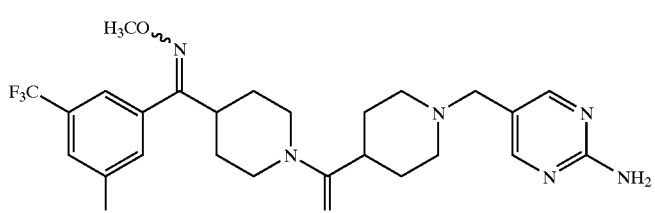 | 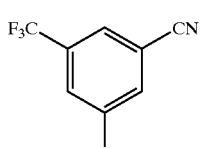 |
| 394 | 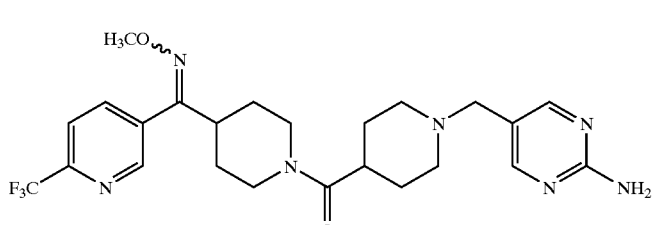 | 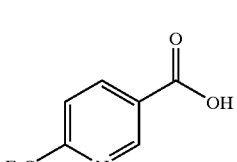 |

TABLE 3-continued
| CMPD | Structure | Starting Material |
|---|---|---|
| 395 | 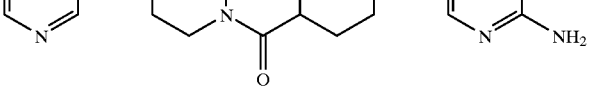 |  |
| 396 | 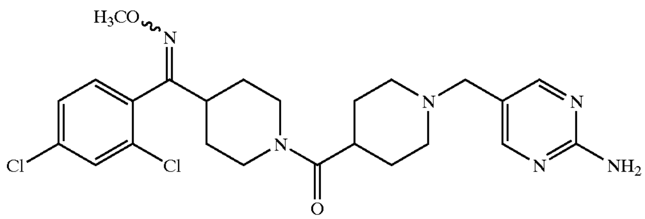 | 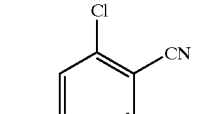 |
| 397 | 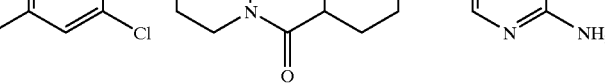 |  |
| 398 | 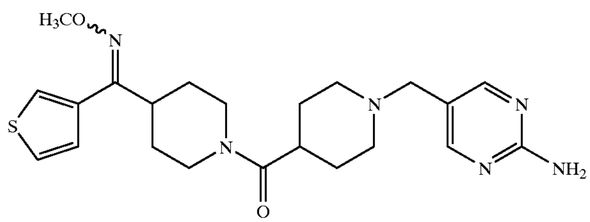 | 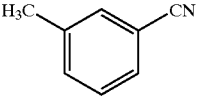 |
| 399 | 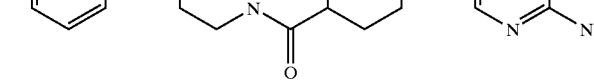 |  |
| 400 | 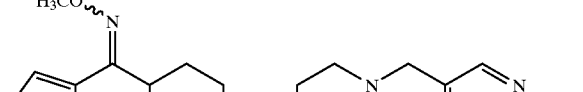 | 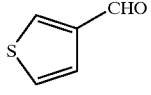 |
| 401 | 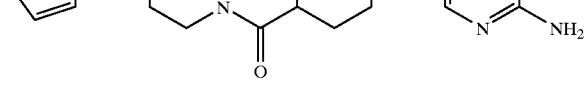 |  |

TABLE 3-continued

| CMPD | Structure | Starting Material |
|---|---|---|
| 402 | 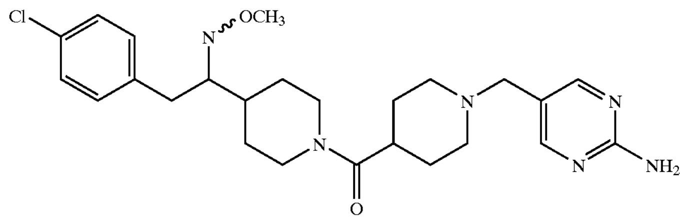 | |
| 403 | 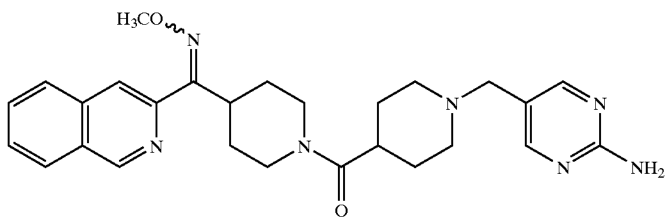 | |
| 404 | 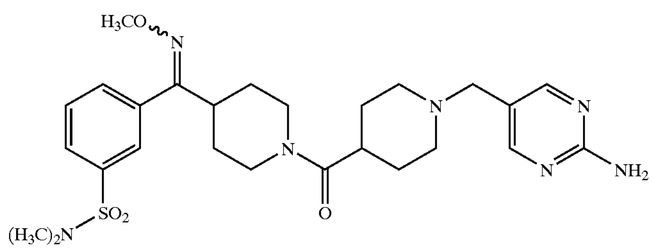 | |
| 405 | 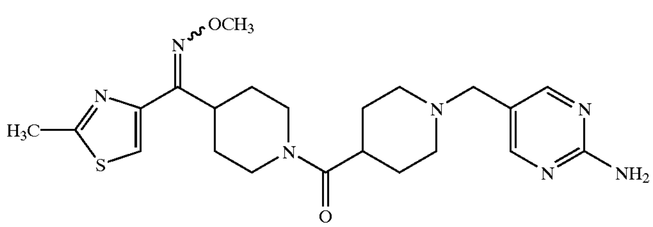 | |
| 406 | 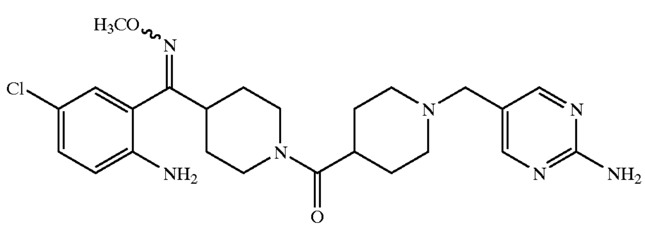 | |
| 407 | 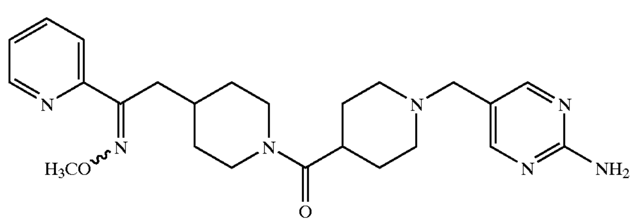 | |

TABLE 3-continued

| CMPD | Structure | Starting Material |
|---|---|---|
| 408 | 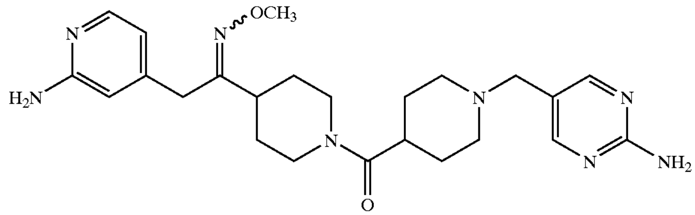 | |
| 409 | 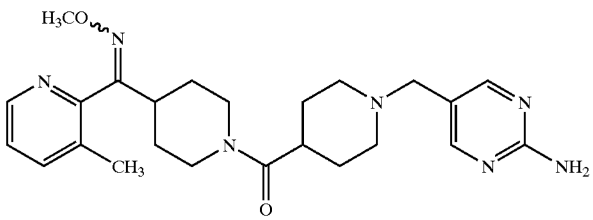 | |
| 410 | 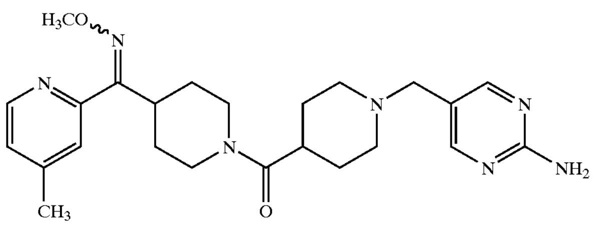 | |
| 411 | 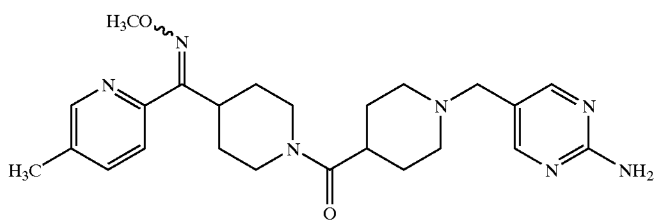 | |
| 412 | 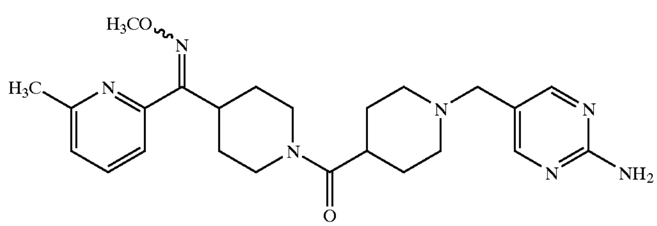 | |
| 413 | 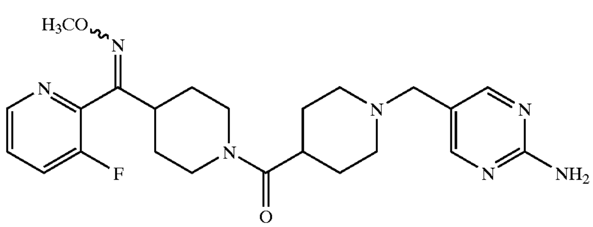 | |
| 414 | 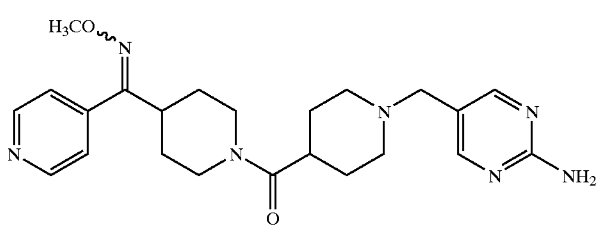 | |

TABLE 3-continued

| CMPD | Structure | Starting Material |
|---|---|---|
| 415 | 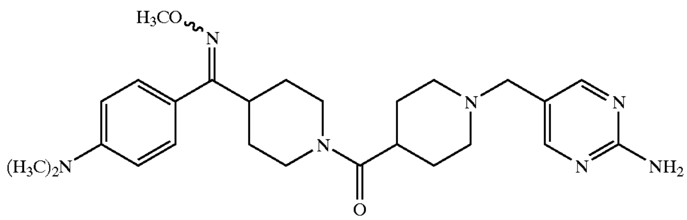 | |
| 416 | 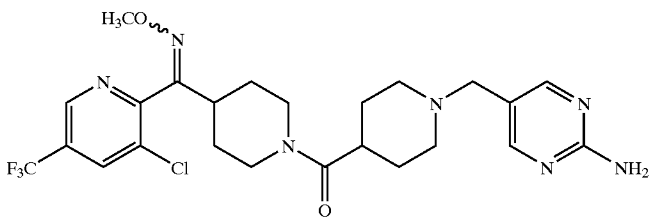 | |
| 417 | 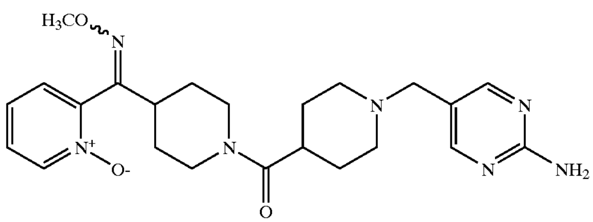 | |
| 418 | 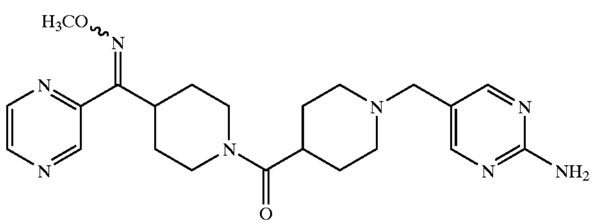 | |
| 419 | 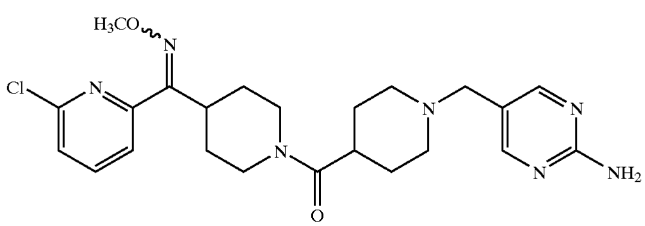 | |
| 420 | 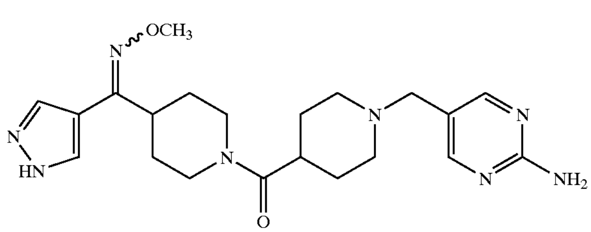 | |

TABLE 3-continued

| CMPD | Structure | Starting Material |
|---|---|---|
| 421 | 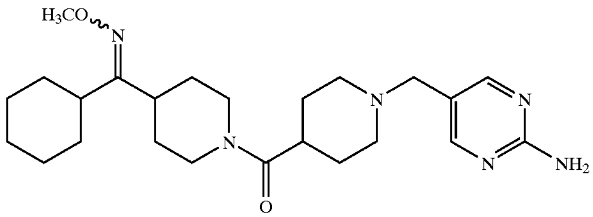 | |
| 422 | 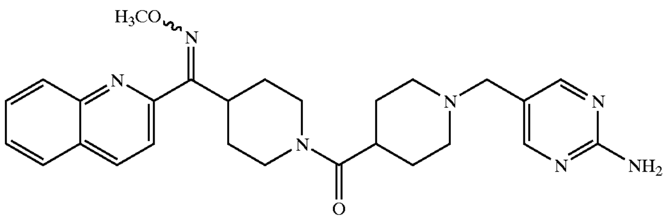 | |
| 423 | 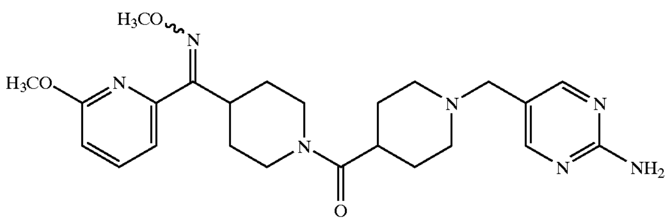 | |
| 424 | 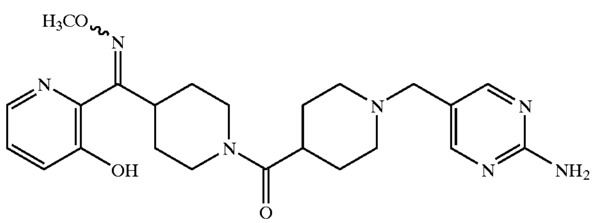 | |
| 425 | 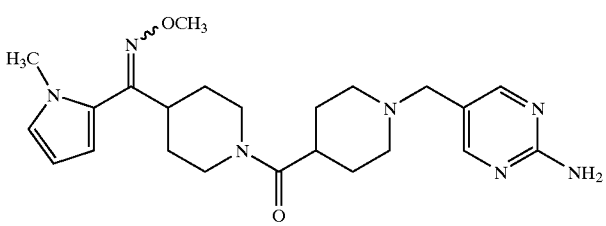 | |
| 426 | 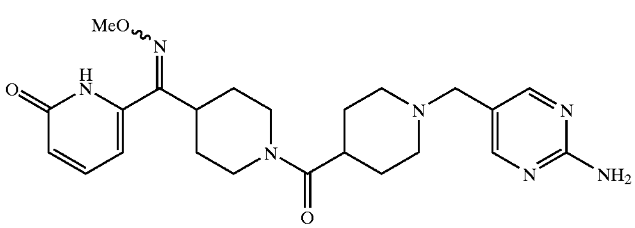 | |
| 427 | 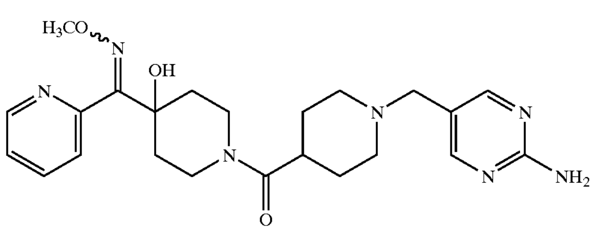 | |

TABLE 3-continued

| CMPD | Structure | Starting Material |
|---|---|---|
| 428 | 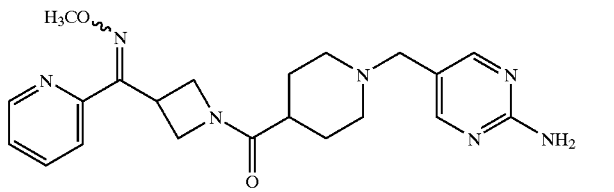 | |
| 429 | 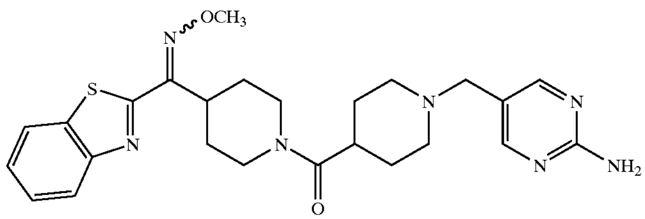 | |
| 430 | 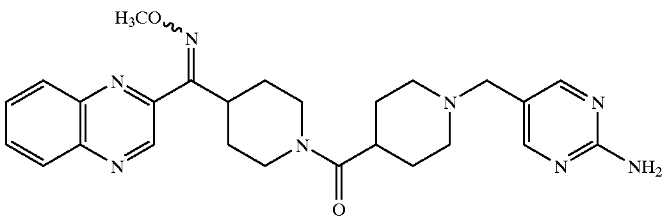 | |
| 431 | 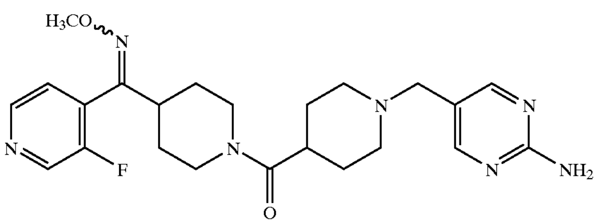 | |
| 432 | 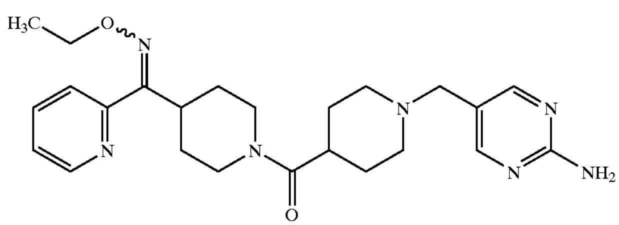 | |
| 433 | 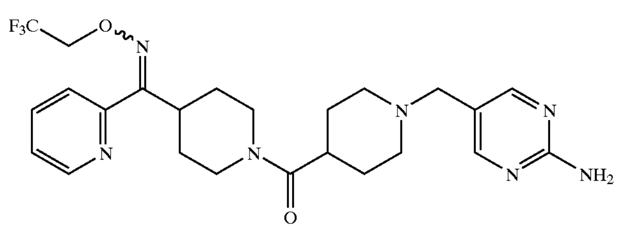 | |
| 434 | 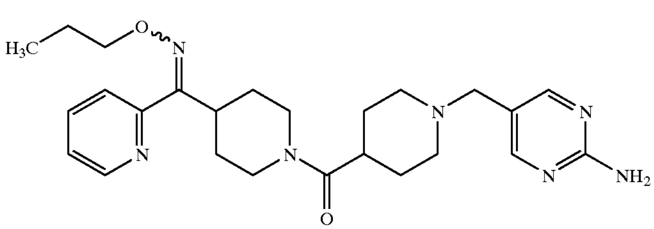 | |

TABLE 3-continued

| CMPD | Structure | Starting Material |
|---|---|---|
| 435 | (isobutyl-O-N=C(2-pyridyl)-piperidine-N-C(O)-piperidine-CH2-pyrimidine-2-NH2) | H3CO-N(CH3)-C(O)-piperidine-N-Boc |
| 436 | (benzyl-O-N=C(2-pyridyl)-piperidine-N-C(O)-piperidine-CH2-pyrimidine-2-NH2) | H3CO-N(CH3)-C(O)-piperidine-N-Boc |
| 437 | (morpholine-C(O)-CH2-O-N=C(2-pyridyl)-piperidine-N-C(O)-piperidine-CH2-pyrimidine-2-NH2) | H3CO-N(CH3)-C(O)-piperidine-N-Boc |
| 438 | (isopropyl-O-N=C(2-pyridyl)-piperidine-N-C(O)-piperidine-CH2-pyrimidine-2-NH2) | H3CO-N(CH3)-C(O)-piperidine-N-Boc |
| 439 | (phenyl-O-N=C(2-pyridyl)-piperidine-N-C(O)-piperidine-CH2-pyrimidine-2-NH2) | H3CO-N(CH3)-C(O)-piperidine-N-Boc |

EXAMPLE 31

Step 1

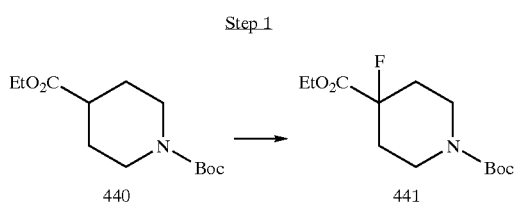

To a solution of LDA (233 mL, 2.0 M in THF/heptane/ethylbenzene, 0.466 mol) in THF (300 mL) at 0° C. was added, dropwise over 1.0 h, a solution of compound 440 (100 g, 0.389 mol) in THF (~400 mL). The red-orange solution was stirred at 0° C. for 30 min, and then transferred by cannula to a pre-cooled (0° C.) solution of N-fluorobenzenesulfonimide (153 g, 0.485 mol) in dry THF (~600 mL). The reaction mixture was stirred at 0° C. for 30 min, and then at rt for 18 h. The total solvent volume was reduced to approximately one third, and EtOAc (~1 L) was added. The solution was washed successively with water, 0.1 N aq. HCl, saturated aq. NaHCO$_3$, and brine. The organic layer was dried over MgSO$_4$, filtered, and concentrated under reduced pressure to yield a crude liquid. Separation by flash chromatography (6:1 hexanes-EtOAc) gave compound 441 (93.5 g, 87%).

Step 2

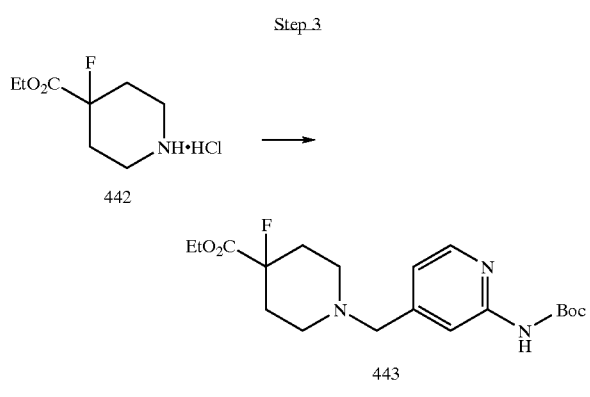

In a manner similar to that described in Example 6, Step 4, compound 441 was converted to compound 442.

Step 3

In a manner similar to that described in Example 1, Step 4, compound 442 was converted to compound 443.

Step 4

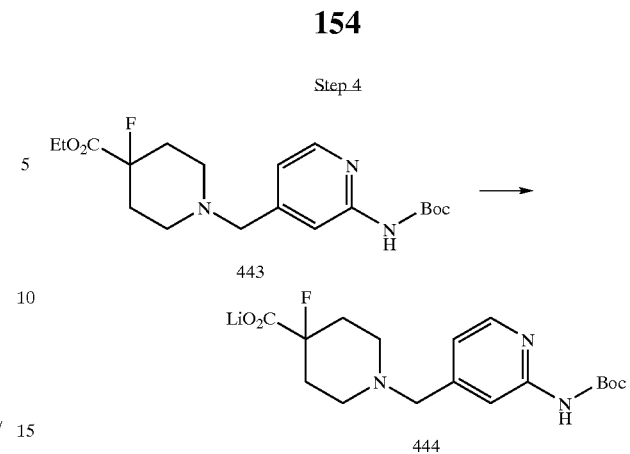

In a manner similar to that described in Example 1, Step 5, compound 443 was converted to compound 444.

Step 5

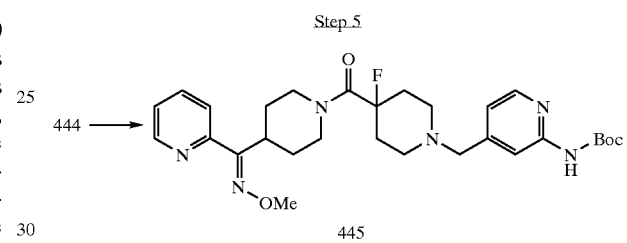

In a manner similar to that described in Example 6, Step 5, compound 5 was converted to compound 445.

Step 6

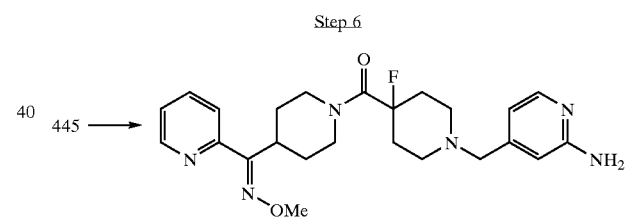

In a manner similar to that described in Example 6, Step 6, compound 445 was converted to compound 446.

In the above examples, the compound 4-[(E)-(methoxyimino)-2-pyridinylmethyl]piperidine dihydrochloride:

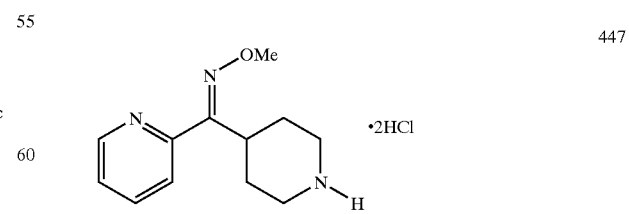

can be used to prepare the compounds of this invention, for example, see Examples 6 and 28. Preferably, Compound 447 is prepared from a compound of formula:

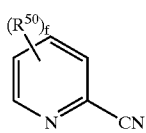

448 and from a compound of Formula 449:

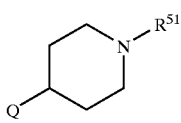

449

$R^{50}$ is an alkyl or aryl group, f is 0 to 4, $R^{51}$ is an alkyl group, and Q is a halo group, wherein said alkyl, aryl, and halo groups are as defined above.

Compound 447 can be prepared from 448 and 449 by:

(a) converting the compound of formula 449 into its Grignard form (449A):

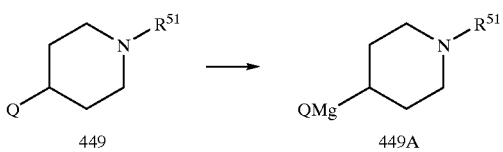

(b) reacting the compound of formula 448 with the compound of formula 449A to obtain a compound of formula 450:

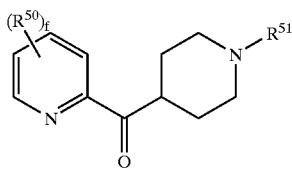

450

(c) reacting the compound of formula 450 with a suitable alkyl chloroformate of formula 451

$R^{51}$—OCOCl         451 to yield a compound of formula 452:

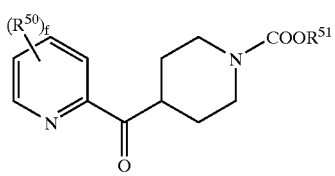

452

(d) forming the salt (formula 453):

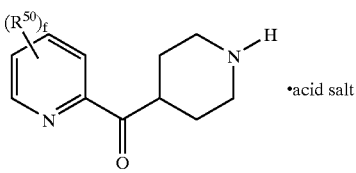

453

(e) reacting the compound of formula 453 with an alkoxyamine ($NH_2OR^{51}$) or its hydrochloride to form an oxime of formula 454:

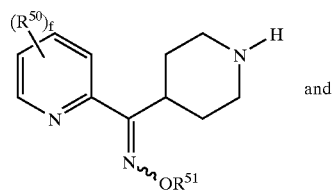 and

454

(f) isomerizing the compound of formula 454 by treatment with a strong acid and simultaneously converting to the desired acid salt of Formula 454 with an enriched E isomer, wherein the E isomer predominates over the Z-isomer by at least a 90:10 ratio. When f=0, $R^{51}$ is methyl, and the acid used for isomerization is HCl in the compound of formula 454, the final product is the compound of formula 447.

This preparation can be represented as follows:

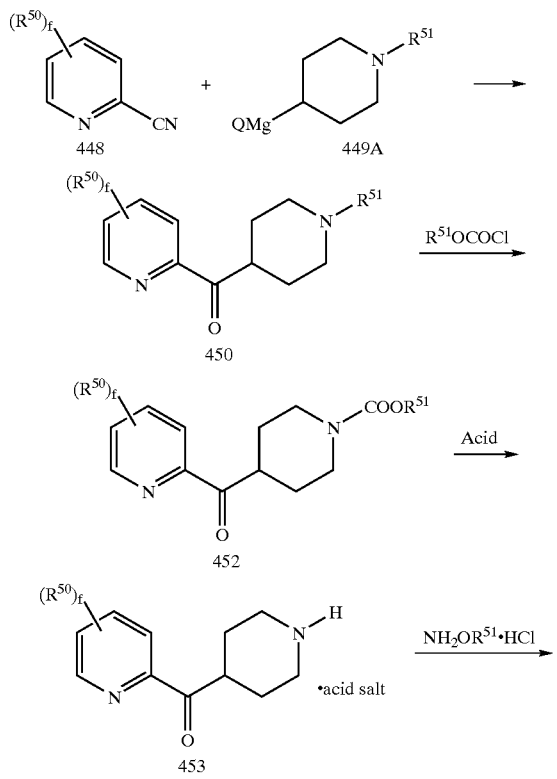

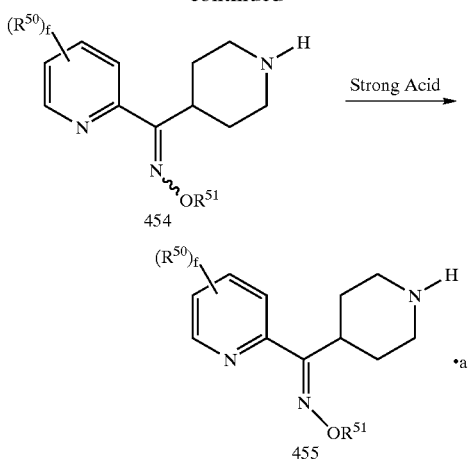

Following the above process the Compound 447 can be prepared as follows:

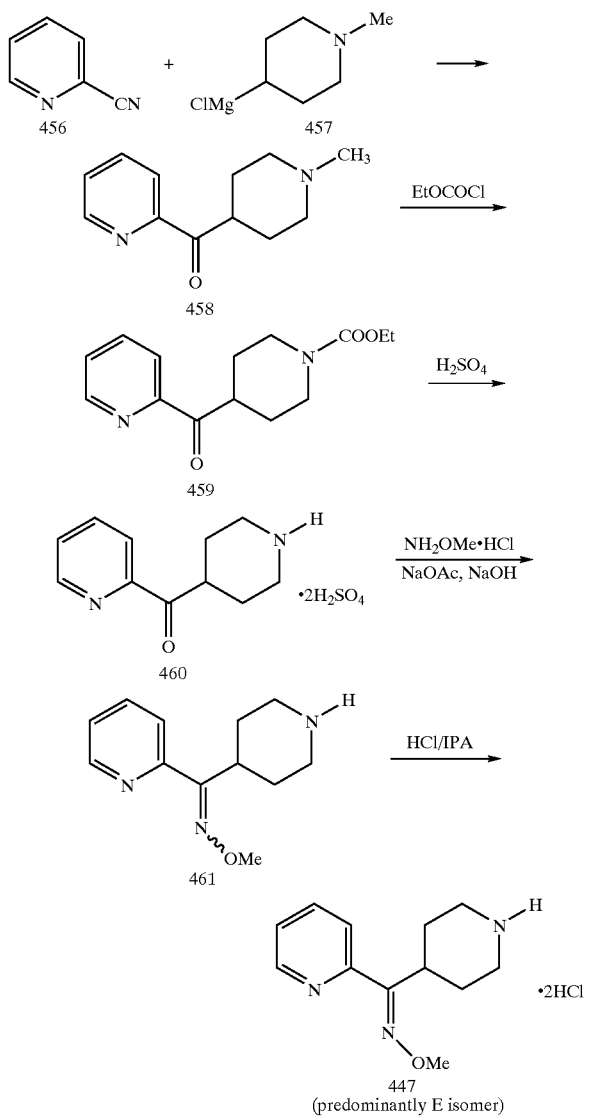

The conversion of compound 461 to 447 predominantly yields the E-isomer of compound 447 in high stereochemical purity and high yields. Isomerization of a mixture of phenyl compounds by acid catalysis is discussed by T. Zsuzsanna et al, *Hung.Magy.Km.Foly.*, 74(3) (1968), 116–119.

The above process starts with Compound 449. In step 1, a 4-halo-1-alkylpiperidine (or a 4-halo-1-arylpiperidine) is converted to its Grignard analog (449A) by reacting with magnesium. The reaction is performed generally at temperatures of about −10° C. to reflux. Generally a hydrocarbon solvent such as, for example, toluene, xylene, chlorobenzene, dichlorobenzene and the like, or mixture of hydrocarbons listed above with an ether, such as, for example, a $C_5$–$C_{12}$ alkyl ether, 1,2-dimethoxyethane, 1,2-diethoxyethane, diglyme, 1,4-dioxane, tetrahydrofuran and the like are suitable for this reaction. The solution is cooled to around −10° C. to about 10° C. and then reacted with a suitable 2-cyanopyridine (448), for about 10–120 minutes. Examples of suitable 2-cyanopyridines are 2-cyanopyridine, 4-methyl-2-cyanopyridine, 4-ethyl-2-cyanopyridine, 4-phenyl-2-cyanopyridine, and the like. Preferred are 2-cyanopyridine and 4-methyl-2-cyanopyridine. The Grignard compound is used generally in about 1–4 molar equivalents with respect to the compound of formula 448, preferably in about 1–3 molar equivalents and typically in about 1.5–2.5 molar equivalents. The product of formula 450 may be isolated by procedures well known in the art, such as, for example, treatment with an acid (e.g. HCl), preferably in a suitable solvent (e.g., tetrahydrofuran or ethyl acetate).

The product of Formula 450 may then be reacted with an alkyl chloroformate in the next step. Suitable alkyl chloroformates are, for example, methyl chloroformate, ethyl chloroformate, propyl chloroformate, and the like, with the preferred being methyl chloroformate or ethyl chloroformate. Generally a hydrocarbon solvent such as, for example, toluene, xylene, chlorobenzene, dichlorobenzene and the like, or mixture of a hydrocarbons listed above with an ether such as, for example, a $C_5$–$C_{12}$ alkyl ether, 1,2-dimethoxyethane, 1,2-diethoxyethane, diglyme, 1,4-dioxane, tetrahydrofuran and the like is suitable for this reaction. The reaction is generally performed at about 25–100° C., preferably about 40–90° C. and typically about 50–80° C., for about 1–5 hours. After the reaction, generally the generated acid is washed off and the product of formula 452 may be isolated by organic solvent extraction.

The compound of Formula 452 may then be converted into its acid salt by treatment with an acid such as, for example, sulfuric acid, hydrochloric acid, trifluoroacetic acid and the like, generally in a solvent at temperatures between ambient and reflux of the solvent. Suitable solvents include hydrocarbons such as, for example, toluene, xylene, chlorobenzene, dichlorobenzene and the like. There being two nitrogen atoms in the compound of Formula 452, the salt generally has 2 moles of acid to a mole of compound 452.

The compound of formula 453 may then be converted to an alkyloxime of formula 454 by reacting it with an alkoxyamine (or its hydrochloride), usually in aqueous solution form. Suitable alkoxyamines are, for example, methoxyamine, ethoxyamine and the like. Methoxyamine is preferred. The alkoxyamine (or its hydrochloride) is employed generally in about 1 to about 4 molar equivalents, preferably in about 1 to about 3 molar equivalents, and typically in about 1 to about 2 molar equivalents. Generally, the reaction is catalyzed by a weak acid such as, for example, acetic acid, formic acid and the like, or mixtures thereof. A cosolvent such as, for example, methanol, ethanol, isopropanol, n-butanol and the like, or mixtures thereof may be added. The product of formula 454, after work-up, is a mixture of the Z- and the E-isomers, whose ratio may be analyzed for its stereochemical make-up, using techniques well known in the art such as, for example, HPLC.

Treating the compound of formula 454 with a strong acid under the reaction conditions described below isomerizes the mixture of the Z and the E-isomers into predominantly the E-isomer. Generally, the compound of formula 454 may be dissolved in a solvent such as, for example, ethanol, methanol, isopropanol, n-butanol and the like, ether such as methyl tert-butyl ether, tetrahydrofuran and the like, hydrocarbon such as, for example, heptane, hexane, toluene and the like, nitrile such as, for example, acetonitrile, benzonitrile and the like, or mixtures of such solvents. The dissolved compound is then treated with a strong acid such as, for example, HCl, HBr, $H_2SO_4$ and the like, at temperatures in the range of 20 to 100° C. for about 1–20 hours. The acid is employed generally in about 1 to about 8 molar equivalents, preferably in about 1 to about 6 molar equivalents, and typically in about 2 to about 4 molar equivalents. Work-up typically forms predominantly the acid salt of the E-isomer of the compound of formula 454, which is in fact the compound of formula 447 when $R^{51}$=methyl, n=0 and the acid salt is HCl in 454.

The products of the various steps in the process described above may be isolated and purified by conventional techniques such as, for example, filtration, recrystallization, solvent extraction, distillation, precipitation, sublimation and the like, as is well known to those skilled in the art. The products may be analyzed and/or checked for purity by conventional methods such as, for example, thin layer chromatography, NMR, HPLC, melting point, mass spectral analysis, elemental analysis and the like, well known to those skilled in the art.

$H_3$-Receptor Binding Assay

The source of the $H_3$ receptors in this experiment was guinea pig brain. The animals weighed 400–600 g. The brain tissue was homogenized with a solution of 50 mM Tris, pH 7.5. The final concentration of tissue in the homogenization buffer was 10% w/v. The homogenates were centrifuged at 1,000×g for 10 min. in order to remove clumps of tissue and debris. The resulting supernatants were then centrifuged at 50,000×g for 20 min. in order to sediment the membranes, which were next washed three times in homogenization buffer (50,000×g for 20 min. each). The membranes were frozen and stored at −70° C. until needed.

All compounds to be tested were dissolved in DMSO and then diluted into the binding buffer (50 mM Tris, pH 7.5) such that the final concentration was 2 µg/ml with 0.1% DMSO. Membranes were then added (400 µg of protein) to the reaction tubes. The reaction was started by the addition of 3 nM [$^3$H]R-α-methyl histamine (8.8 Ci/mmol) or 3 nM [$^3$H]N$^\alpha$-methyl histamine (80 Ci/mmol) and continued under incubation at 30° C. for 30 min. Bound ligand was separated from unbound ligand by filtration, and the amount of radioactive ligand bound to the membranes was quantitated by liquid scintillation spectrometry. All incubations were performed in duplicate and the standard error was always less than 10%. Compounds that inhibited more than 70% of the specific binding of radioactive ligand to the receptor were serially diluted to determine a $K_i$ (nM).

Compounds 23, 30, 31, 32, 33, 44, 45, 49, 50, 53, 54, 55, 56, 57A, 59, 75, 76, 83, 88, 92, 99, 104, 110, 117, 128, 200, 201, 203–215, 217–241, 244–246, 246A, 247–253, 253A, 254–273, 275, 278, 280–282, 287, 296, 301–310, and 312–379 had a $K_i$ within the range of about 0.25 to about 370 nM.

Preferred Compounds 23, 30, 31, 32, 33, 50, 53, 54, 55, 56, 57A, 59, 92, 212, 215, 218, 219, 220, 224, 225, 226, 227, 229, 233, 235, 237, 238, 246, 246A, 247, 248, 251, 253, 253A, 268–273, 275, 278–281, 287, 296, 301, 304–307, 309, 312, 314–318, 320–356, and 358–376 had a $K_i$ within the range of about 0.25 to about 33 nM.

Most preferred Compounds 30, 31, 32, 33, 54, 55, 56, 56A, 225, 237, 246A, 253A, 273, 280, 287, 296, 301, 304–307, 309, 312, 314–318, 320–348, 350–356, 359–372, and 374–376 had a $K_i$ within the range of about 0.25 to about 16 nM.

More preferred compound 32 had a $K_i$ of 0.83 nM.

More preferred compounds 54, 55, 253A, 287, 320 had a $K_i$ within the range of about 1.05 to about 9.75 nM.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 150 mg, preferably from about 1 mg to about 75 mg, more preferably from about 1 mg to about 50 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 75 mg/day, in two to four divided doses.

The methods of this invention described above using a compound of Formula I also include the use of one or more compounds of Formula I, and the methods of this invention described above using a compound of Formula I in combination with an $H_1$ receptor antagonist also include the use of one or more compounds of Formula I in combination with one or more $H_1$ receptor antagonists.

While the present has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

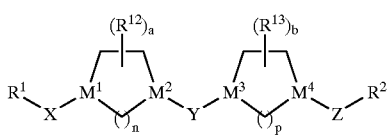
(I)

or a pharmaceutically acceptable salt or solvate thereof, wherein:
  (1) $R^1$ is selected from:
    (a) aryl;
    (b) heteroaryl;
    (c) heterocycloalkyl
    (d) alkyl;
    (e) cycloalkyl; or
    (f) alkylaryl;
  wherein said $R^1$ groups are optionally substituted with 1 to 4 substituents independently selected from:
    (1) halogen;
    (2) hydroxyl;
    (3) lower alkoxy;
    (4) —$CF_3$;
    (5) $CF_3O$—;
    (6) —$NR^4R^5$;
    (7) phenyl;
    (8) —$NO_2$;
    (9) —$CO_2R^4$;
    (10) —$CON(R^4)_2$ wherein each $R^4$ is the same or different;
    (11) —$S(O)_mN(R^{20})_2$ wherein each $R^{20}$ is the same or different H or alkyl group;
    (12) —CN; or
    (13) alkyl; or
  (2) $R^1$ and X taken together form a group selected from:

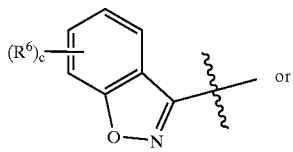
or
II

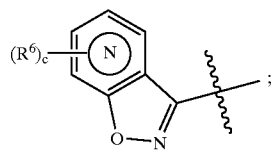
III wherein Ⓝ represents a nitrogen atom located at one of the 4 non-fused positions of the ring;

(3) X is selected from: =C(O), =C($NOR^3$), =C($NNR^4R^5$),

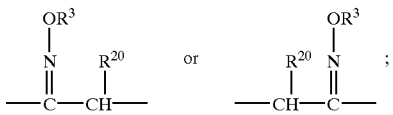

(4) $M^1$ is carbon;
  (5) $M^2$ is N;
  (6) one of $M^3$ and $M^4$ is C and the other is N;
  (7) Y is selected from: is —$CH_2$—, =C(O), =C($NOR^{20}$) (wherein $R^{20}$ is as defined above), or =C(S);
  (8) Z is a $C_1$–$C_6$ alkyl group;
  (9) $R^2$ is a five or six-membered heteroaryl ring, said six-membered heteroaryl ring comprising 1 or 2 nitrogen atoms with the remaining ring atoms being carbon, and said five-membered heteroaryl ring containing 1 or 2 heteroatoms selected from: nitrogen, oxygen, or sulfur with the remaining ring atoms being carbon; said five or six membered heteroaryl rings being optionally substituted with 1 to 3 substituents independently selected from: halogen, hydroxyl, lower alkyl, lower alkoxy, —$CF_3$, $CF_3O$—, —$NR^4R^5$, phenyl, —$NO_2$, —$CO_2R^4$, —$CON(R^4)_2$ wherein each $R^4$ is the same or different, —$CH_2NR^4R^5$, —$(N)C(NR^4R^5)_2$, or —CN;
  (10) $R^3$ is selected from:
    (a) hydrogen;
    (b) $C_1$–$C_6$ alkyl;
    (c) aryl;
    (d) heteroaryl;
    (e) heterocycloalkyl;
    (f) arylalkyl;
    (g) —$(CH_2)_e$—$C(O)N(R^4)_2$ wherein each $R^4$ is the same or different,
    (h) —$(CH_2)_e$—$C(O)OR^4$;
    (i) —$(CH_2)_e$—$C(O)R^{30}$ wherein $R^{30}$ is a heterocycloalkyl group, or

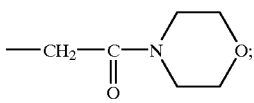

(j) —$CF_3$; or
    (k) —$CH_2CF_3$;
  wherein said aryl, heteroaryl, heterocycloalkyl, and the aryl portion of said arylalkyl are optionally substituted with 1 to 3 substituents selected from: halogen, —OH, —$OCF_3$, —$CF_3$, —CN, —$N(R^{45})_2$, —$CO_2R^{45}$, or —$C(O)N(R^{45})_2$, wherein each $R^{45}$ is independently selected from: H, alkyl, alkylaryl, or alkylaryl wherein said aryl moiety is substituted with 1 to 3 substituents independently selected from —$CF_3$, —OH, halogen, alkyl, —$NO_2$, or —CN;

(11) $R^4$ is selected from: hydrogen, $C_1$–$C_6$ alkyl, aryl, alkylaryl, said aryl and alkylaryl groups being optionally substituted with 1 to 3 substituents selected from: halogen, —$CF_3$, —$OCF_3$, —OH, —$N(R^{45})_2$, —$CO_2R^{45}$, —$C(O)N(R^{45})_2$, or —CN; wherein $R^{45}$ is as defined above;

(12) $R^5$ is selected from: hydrogen, $C_1$–$C_6$ alkyl, —$C(O)R^4$, —$C(O)_2R^4$, or —$C(O)N(R^4)_2$ wherein each $R^4$ is independently selected, and $R^4$ is as defined above;

(13) or $R^4$ and $R^5$ taken together with the nitrogen atom to which they are bound forms a five or six membered heterocycloalkyl ring;

(14) $R^6$ is selected from: alkyl, aryl, alkylaryl, halogen, hydroxyl, lower alkoxy, —$CF_3$, $CF_3O$—, —$NR^4R^5$, —$NO_2$, —$CO_2R^4$, —$CON(R^4)_2$ wherein each $R^4$ is the same or different, or —CN;

(15) $R^{12}$ is selected from: alkyl, hydroxyl, alkoxy, or fluoro;

(16) $R^{13}$ is selected from: alkyl, hydroxyl, alkoxy, or fluoro;

(17) a is 0 to 2;

(18) b is 0 to 2;

(19) c is 0 to 2;

(20) e is 0 to 5;

(21) m is 1 or 2;

(22) n is 2, and

(23) p is 2.

2. The compound of claim 1 wherein $R^1$ is selected from:

(A) aryl;

(B) substituted aryl, wherein the substituents on said substitued aryl are selected from: (1) halo; or (2) alkyl; or (3) substituted alkyl;

(C) heteroaryl;

(D) substituted heteroaryl; or (E) when $R^1$ is taken together with X, then the moiety is

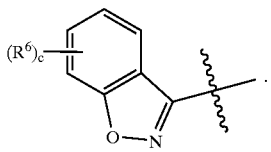

II

3. The compound of claim 2 wherein $R^1$ is selected from:

(A) phenyl;

(B) substituted phenyl wherein the substituents on said substitued phenyl are selected from: (1) halo; (2) alkyl; (3) alkyl substituted with halo;

(C) heteroaryl selected from: pyridyl, thienyl, pyrimidinyl, thiazolyl or pyridyl N-Oxide;

(D) alkyl substituted thiazolyl; or (E) when $R^1$ is taken together with X, then the moiety is

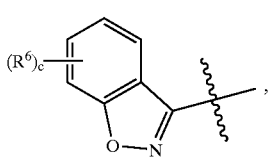

II wherein c is 0 or 1, and when c is 1 then $R^6$ is halo.

4. The compound of claim 3 wherein $R^1$ is selected from:

(A) phenyl;

(B) substituted phenyl, wherein the substituents on said substitued phenyl are independently selected from: chloro, fluoro or trifluoromethyl;

(C) heteroaryl selected from:

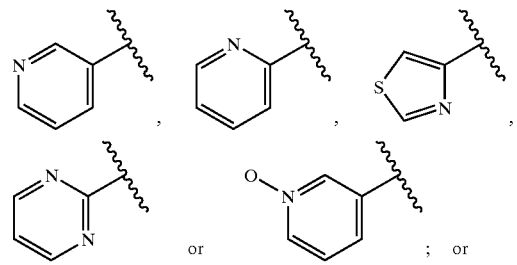

(D) substituted heteroaryl of the formula:

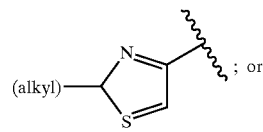

(E) when $R^1$ is taken together with X, then the moiety is

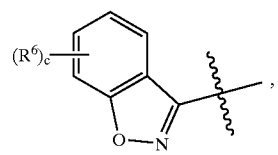

II wherein c is 0 or 1, and when c is 1 then $R^6$ is fluoro.

5. The compound of claim 1 wherein $R^1$ is selected from:

(A) phenyl;

(B) substituted phenyl, wherein the substituents on said substitued phenyl are independently selected from: chloro, fluoro or trifluoromethyl;

(C) pyridyl; or (D) substituted heteroaryl of the formula:

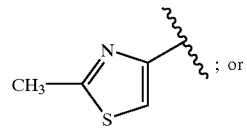

(E) when $R^1$ is taken together with X, then the moiety is

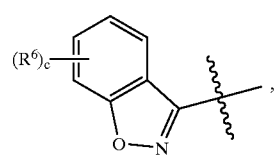

II wherein c is 0 or 1, and when c is 1 then $R^6$ is fluoro.

6. The compound of claim 5 wherein $R^1$ is pyridyl.

7. The compound of claim 6 wherein $R^1$ is

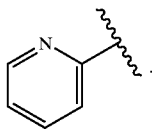.

8. The compound of claim 1 wherein X is =C(NOR$^3$), and $R^3$ is selected from H or alkyl.
9. The compound of claim 8 wherein $R^3$ is selected from H, methyl or ethyl.
10. The compound of claim 9 wherein $R^3$ is methyl.
11. The compound of claim 1 wherein $M^3$ is carbon, and $M^4$ is nitrogen.
12. The compound of claim 1 wherein:
n is 2;
a is 0 or 1;
b is 0 or 1;
c is 0 or 1, and when c is 1 then $R^6$ is halo;
e is 1 to 5; and
p is 2.
13. The compound of claim 1 wherein Y is =C(O).
14. The compound of claim 1 wherein Z is $C_1$ to $C_3$ alkyl.
15. The compound of claim 1 wherein Z is

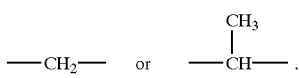.

16. The compound of claim 1 wherein $R^2$ is a six membered heteroaryl ring.
17. The compound of claim 16 wherein $R^2$ is selected from pyridyl, pyridyl substituted with —NR$^4$R$^5$, pyrimidinyl, or pyrimidinyl substituted with —NR$^4$R$^5$.
18. The compound of claim 17 wherein $R^2$ is pyridyl substituted with —NH$_2$, or pyrimidinyl substituted with —NH$_2$.
19. The compound of claim 18 wherein $R^2$ is

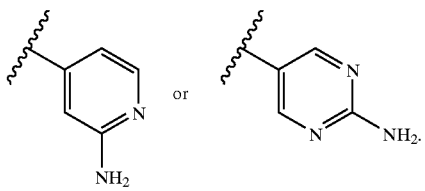.

20. The compound of claim 1 wherein $R^4$ is H or lower alkyl; $R^5$ is H, $C_1$ to $C_6$alkyl, or —C(O)R$^4$; $R^{12}$ is alkyl, hydroxy or fluoro; and $R^{13}$ is alkyl, hydroxy or fluoro.
21. The compound of claim 20 wherein $R^4$ is H or methyl; $R^5$ is H or methyl; $R^{12}$ is hydroxy or fluoro; and $R^{13}$ is hydroxy or fluoro.
22. The compound of claim 1 wherein:
(1) $R^1$ is selected from:
(A) aryl;
(B) substituted aryl, wherein the substituents on said substitued aryl are selected from: (1) halo; or (2) alkyl; or (3) substituted alkyl;
(C) heteroaryl; or
(D) substituted heteroaryl; or
(E) when $R^1$ is taken together with X, then the moiety is

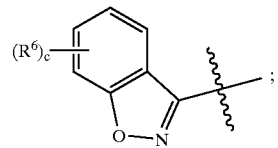

(2) X is =C(NOR$^3$);
(3) $R^3$ is selected from H or alkyl;
(4) $M^2$ is nitrogen;
(5) Y is =C(O);
(6) $M^3$ and $M^4$ are selected such that: (1) one is carbon and the other is nitrogen;
(7) Z is $C_1$ to $C_3$ alkyl; and
(8) $R^2$ is a six membered heteroaryl ring.
23. The compound of claim 22 wherein:
(1) $R^1$ is selected from:
(A) phenyl;
(B) substituted phenyl wherein the substituents on said substitued phenyl are selected from: (1) halo; (2) alkyl; (3) alkyl substituted with halo;
(C) heteroaryl selected from: pyridyl, thienyl, pyrimidinyl, thiazolyl or pyridyl N-Oxide; or
(D) alkyl substituted thiazolyl; or
(E) when $R^1$ is taken together with X, then the moiety is

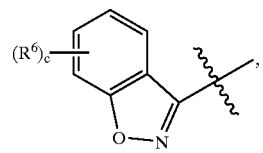

wherein c is 0 or 1, and when c is 1 then $R^6$ is halo;
(2) $R^3$ is selected from H, methyl or ethyl;
(3) n is 2,
(4) a is 0 or 1,
(5) b is 0 or 1,
(6) c is 0 or 1 and when c is 1 then $R^6$ is halo,
(7) e is 1 to 5,
(8) p is 2,
(9) $R^4$ is H or lower alkyl,
(10) $R^5$ is H, $C_1$ to $C_6$alkyl, or —C(O)R$^4$;
(11) $R^{12}$ is alkyl, hydroxy or fluoro, and
(12) $R^{13}$ is alkyl, hydroxy or fluoro.
24. The compound of claim 23 wherein $R^2$ is $R^1$ is 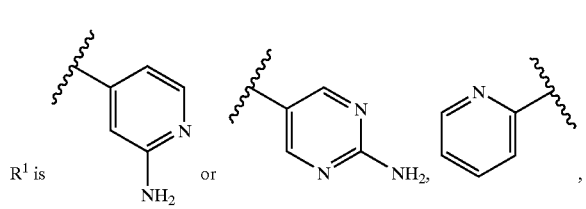, $M^2$ is nitrogen, $M^3$ is carbon, and $M^4$ is nitrogen.
25. The compound of claim 1 selected from the group consisting of

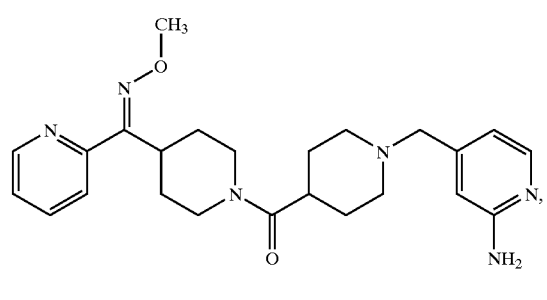
(32)
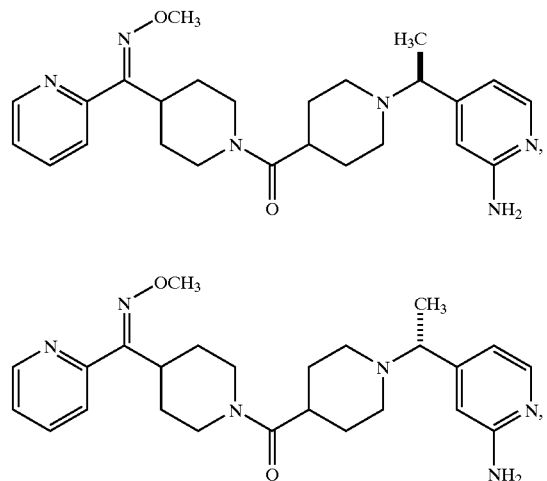
54
55
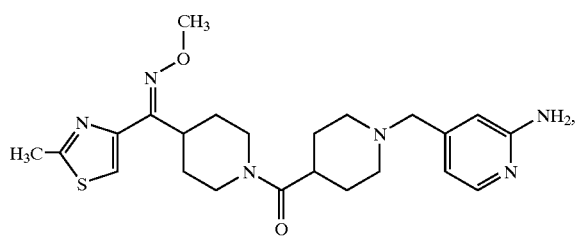
253A
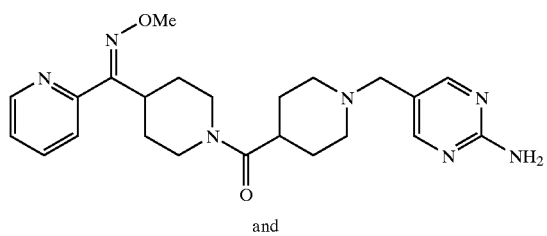
and
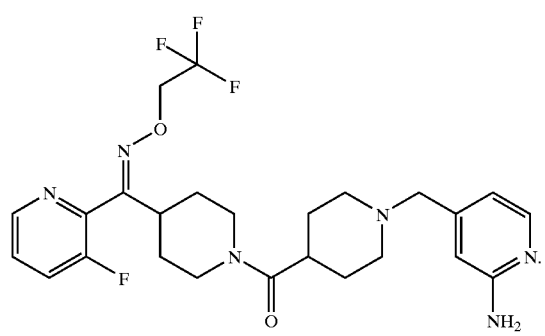
26. The compound of claim 1 having the formula:
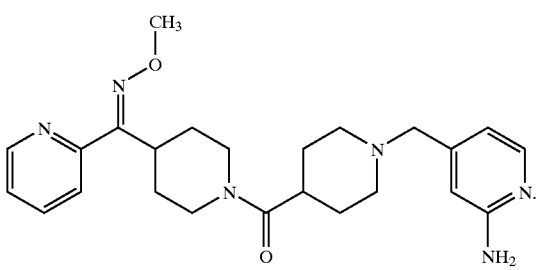
(32)
27. The compound of claim 1 having the formula:
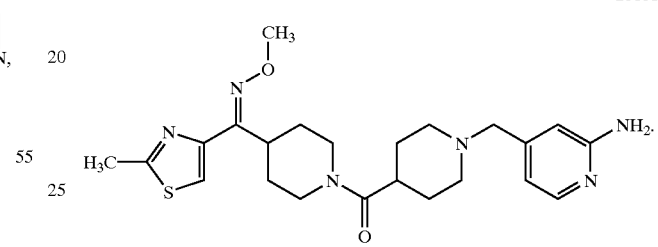
253A
28. The compound of claim 1 having the formula:
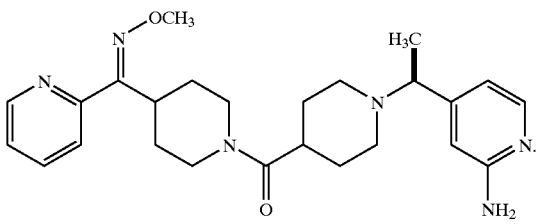
54
29. The compound of claim 1 having the formula:
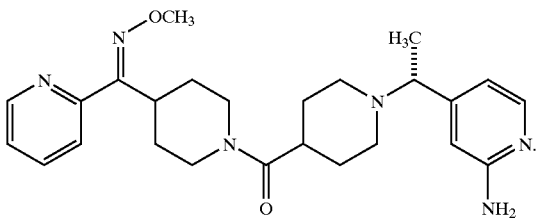
55
30. The compound of claim 1 having the formula:
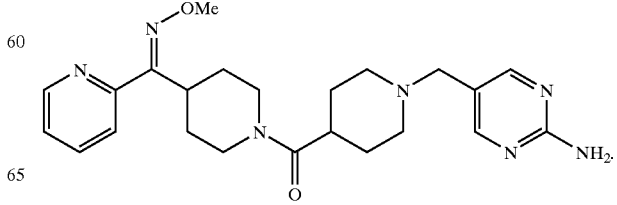
287

31. The compound of claim 1 having the formula:

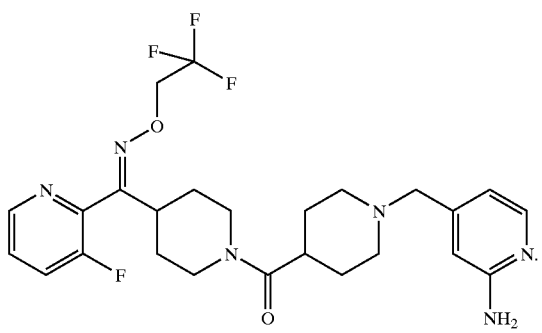

32. The compound of claim 1 having the formula:

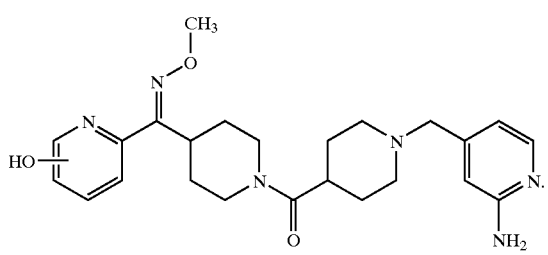
(32A)

33. The compound of claim 1 having the formula:

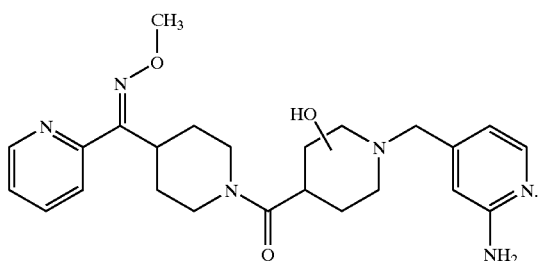
(32B)

34. A pharmaceutical composition comprising an effective amount of a compound of claim 1 and a pharmaceutically effective carrier.

35. A method of treating: allergy, allergy-induced airway responses, congestion, obesity, hypersomnia, narcolepsy, schizophrenia, and migraine comprising administering to a patient in need of such treatment an effective amount of a compound of claim 1.

36. The method of claim 35 wherein allergy-induced airway responses are treated.

37. The method of claim 35 wherein allergy or nasal congestion is treated.

38. A pharmaceutical composition comprising an effective amount of a compound of claim 1 and a pharmaceutically effective carrier, wherein said compound of claim 1 is selected from:

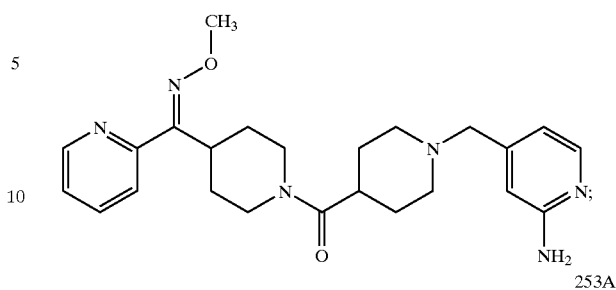
(32)

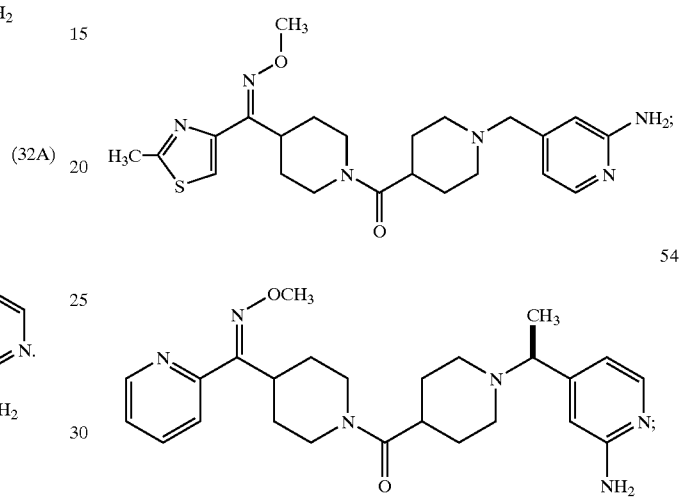

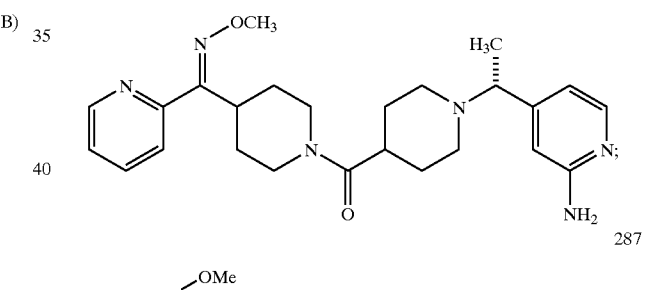

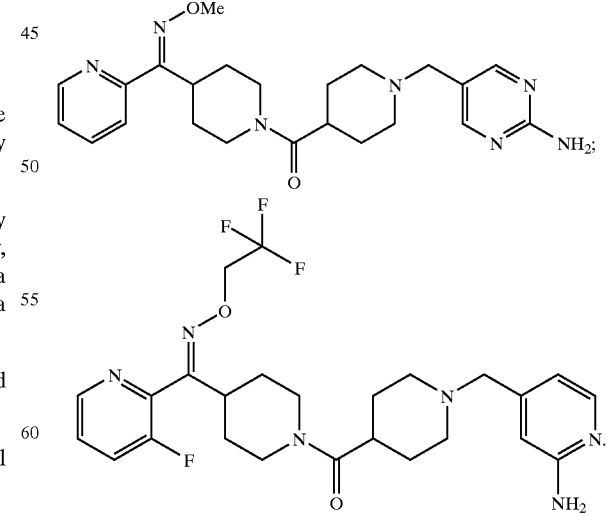

39. A method of treating: allergy, allergy-induced airway responses, congestion, obesity, hypersomnia, narcolepsy, schizophrenia, and migraine comprising administering to a patient in need of such treatment an effective amount of a compound of claim 1, wherein said compound of claim 1 is selected from:
40. The method of claim 39 wherein allergy-induced airway responses are treated.
41. The method of claim 39 wherein allergy or nasal congestion is treated.
42. A compound of claim 1 selected from the group consisting of
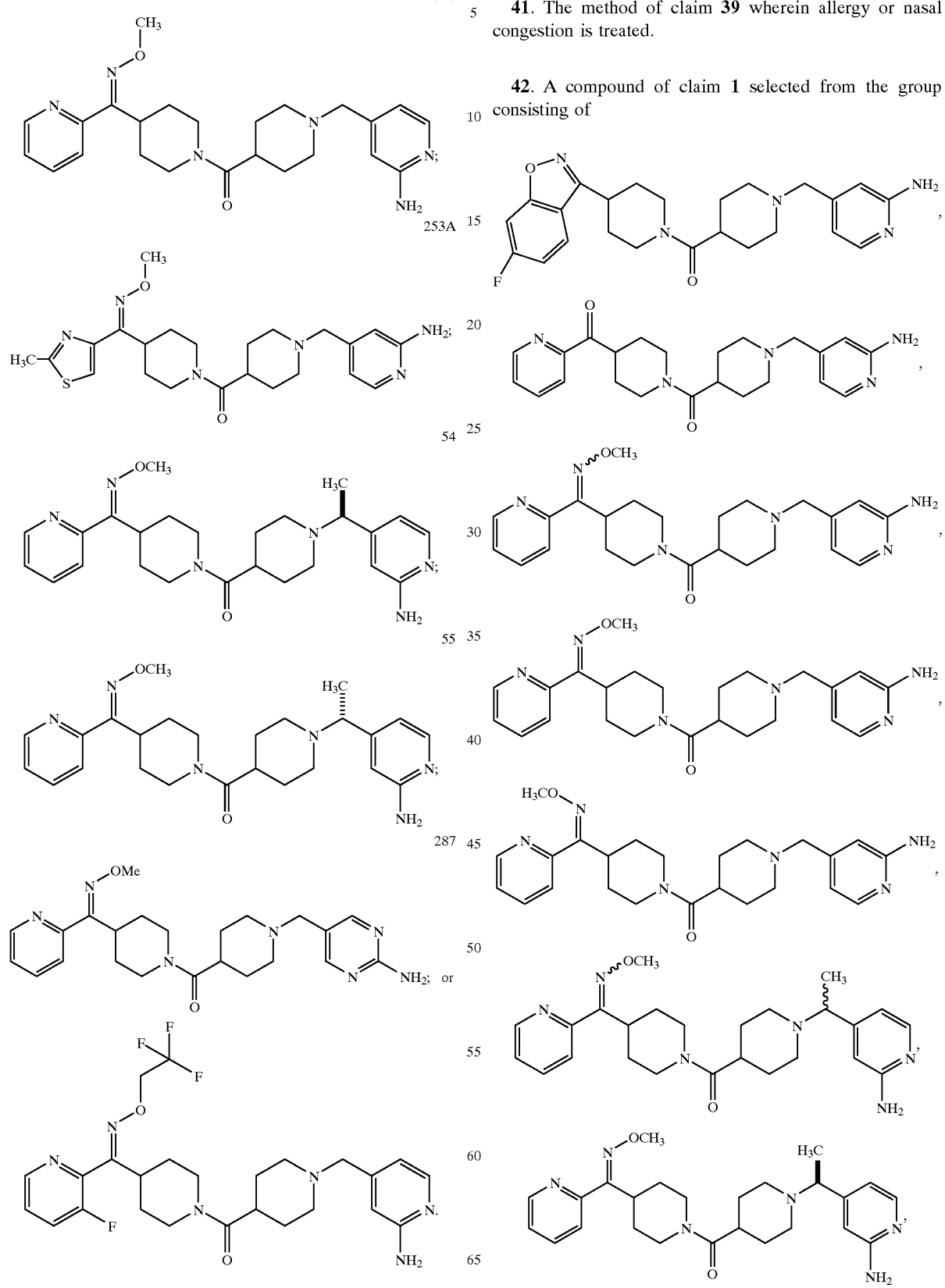

173
-continued
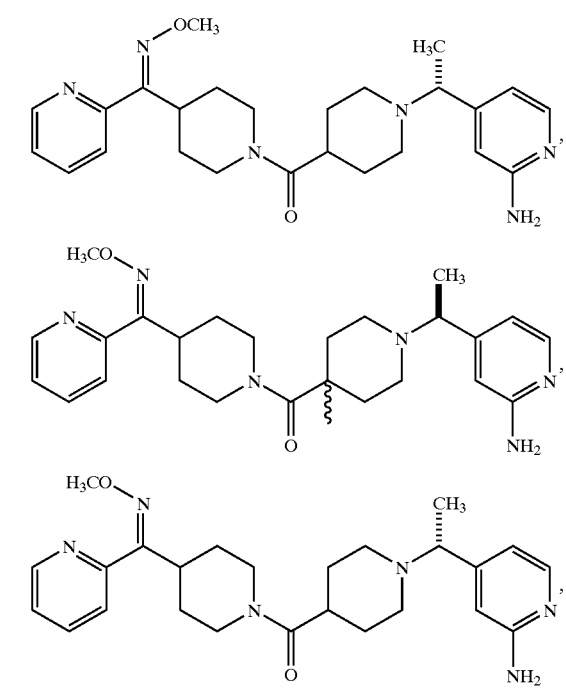
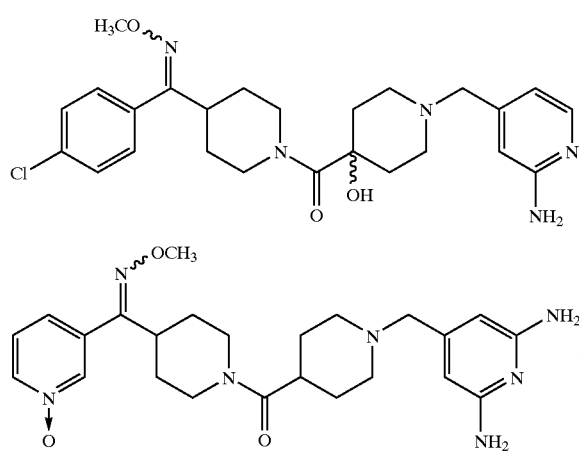
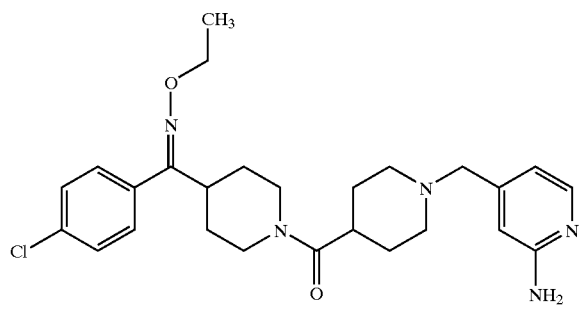
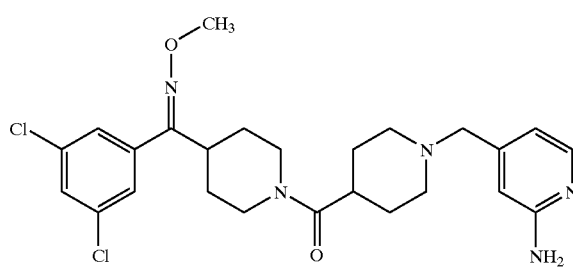
174
-continued
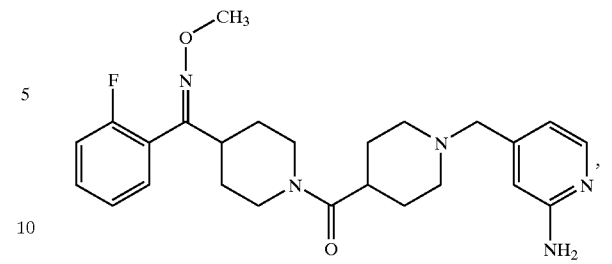
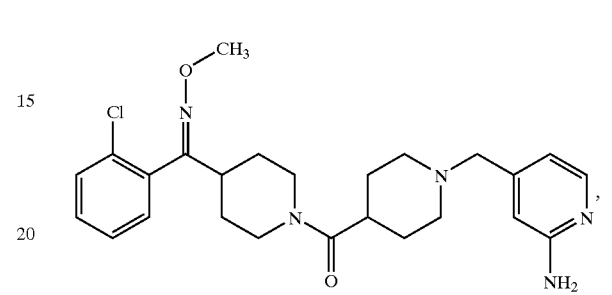
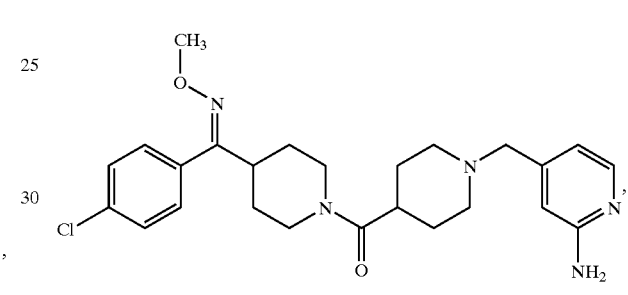
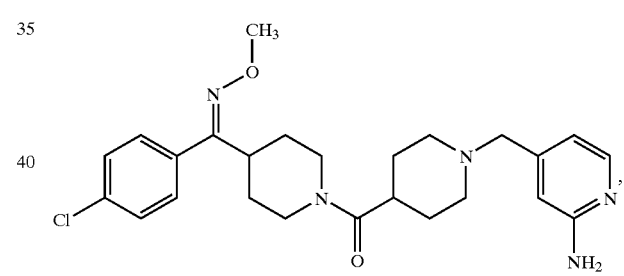
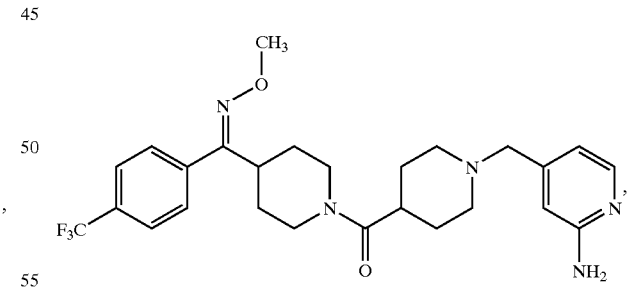
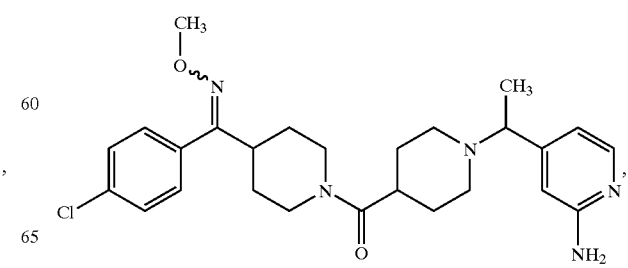

175
-continued
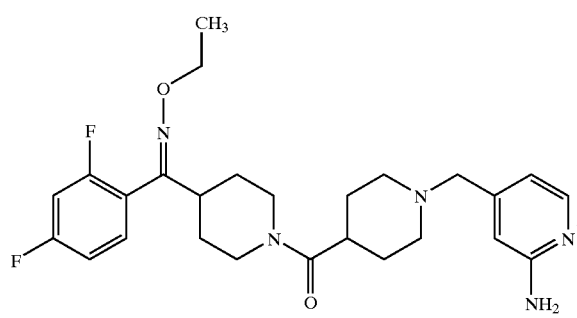
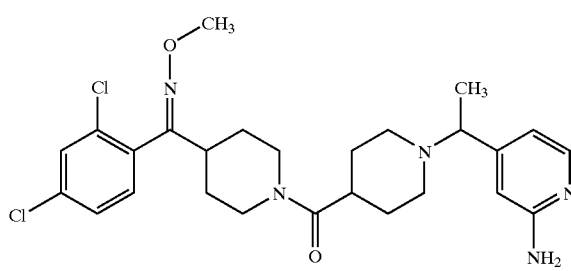
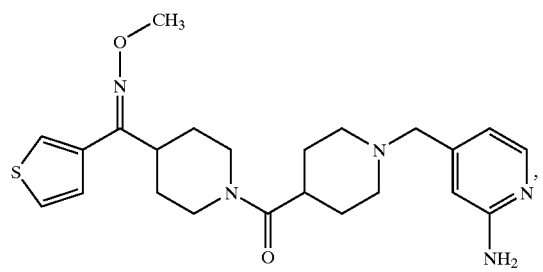
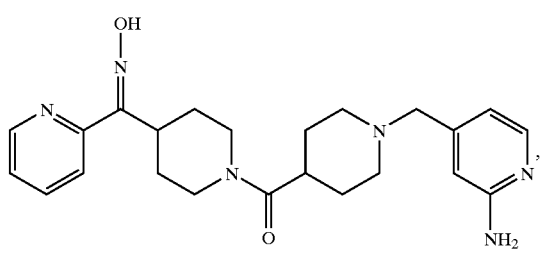
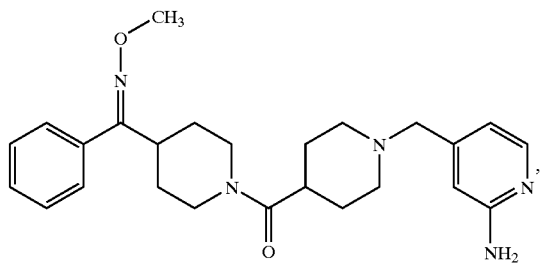
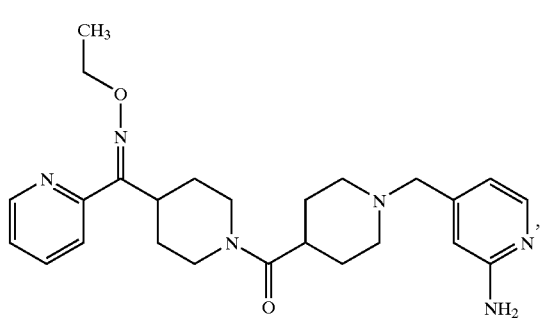
176
-continued
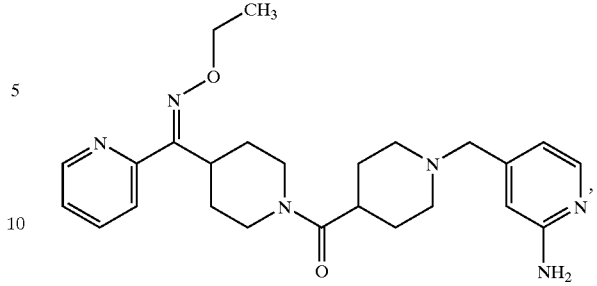
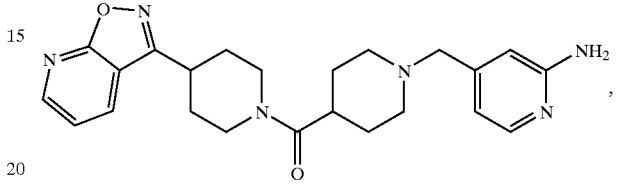
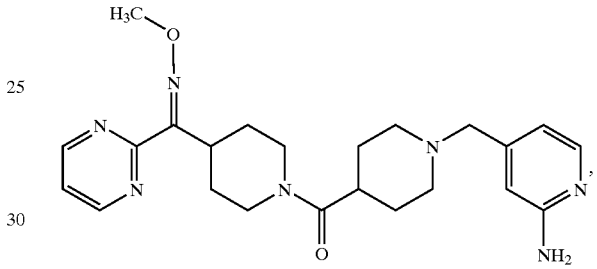
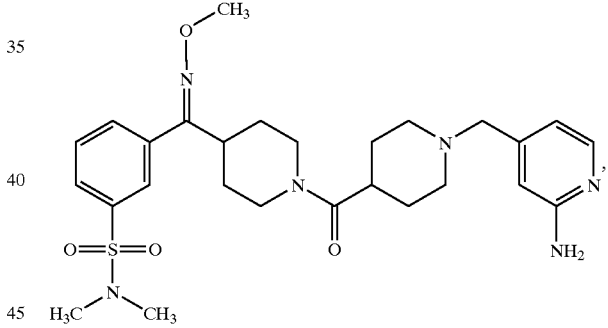
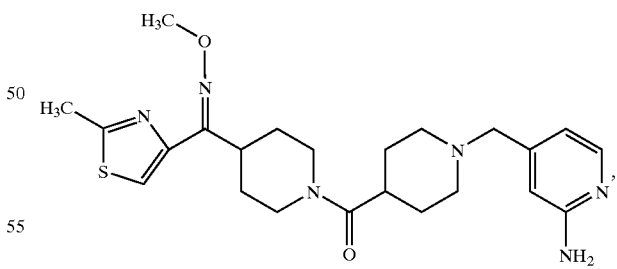
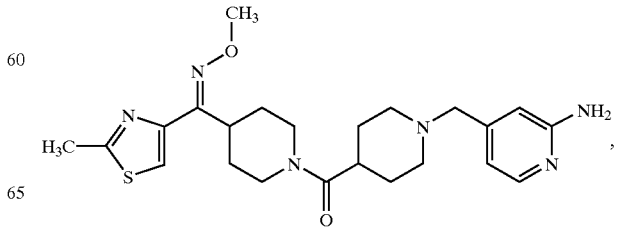

177
-continued
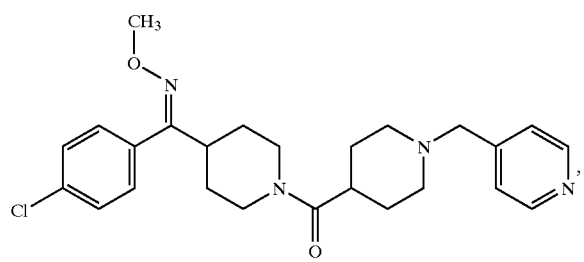
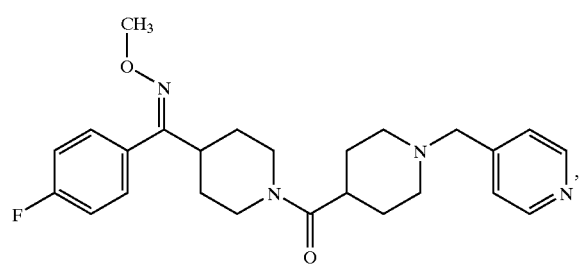
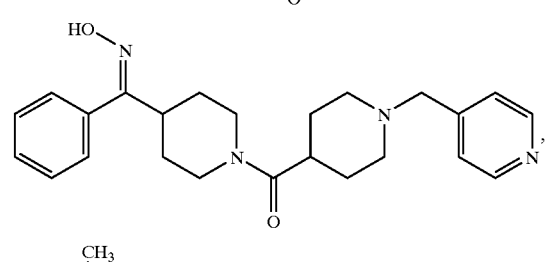
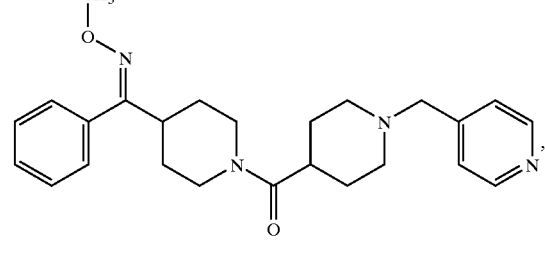
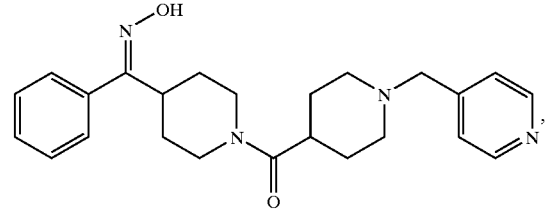
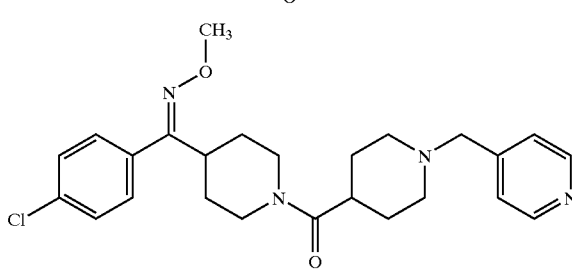
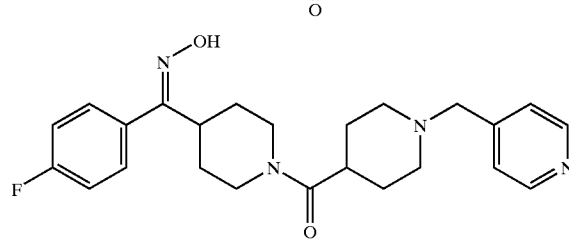
178
-continued
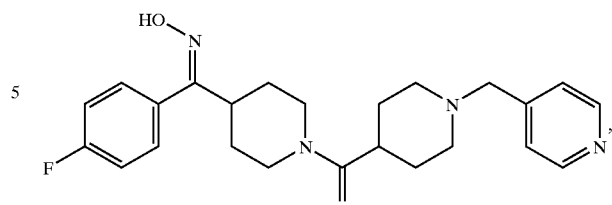
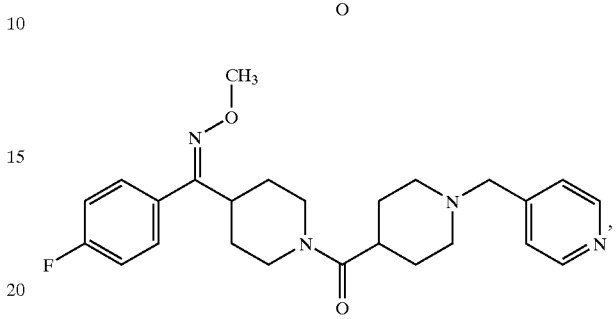
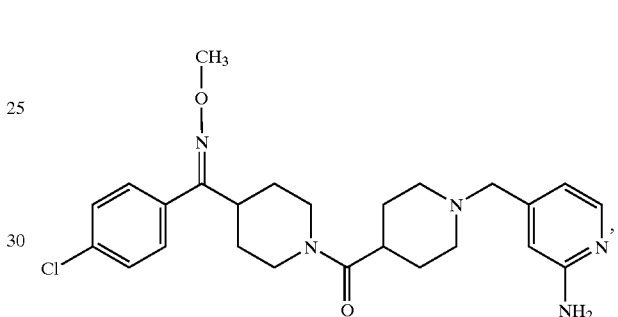
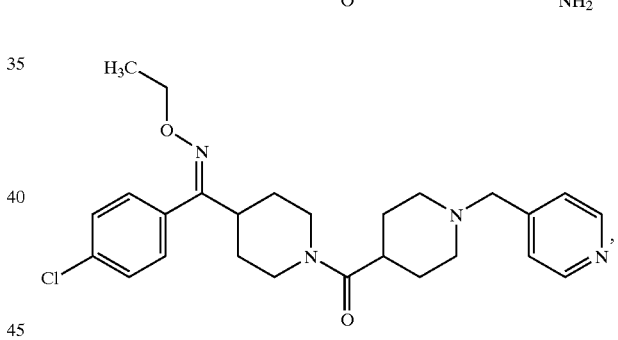
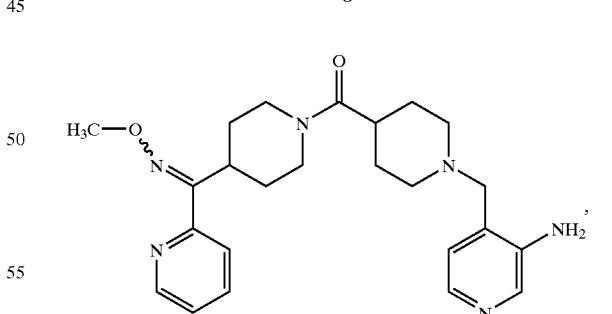
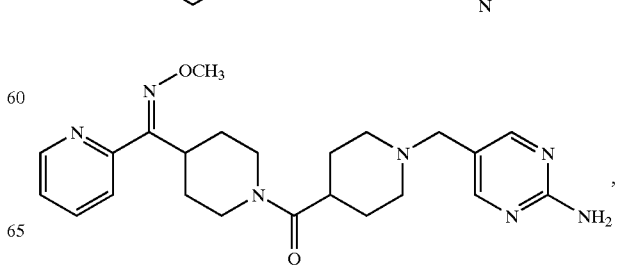

179
-continued
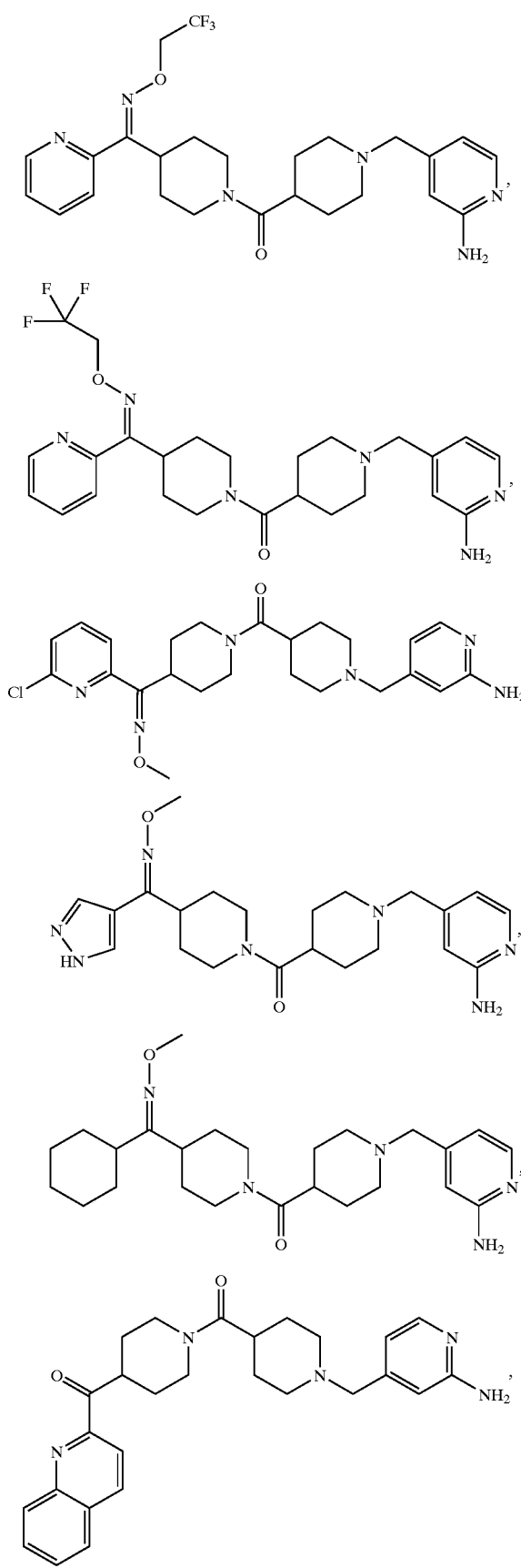
180
-continued
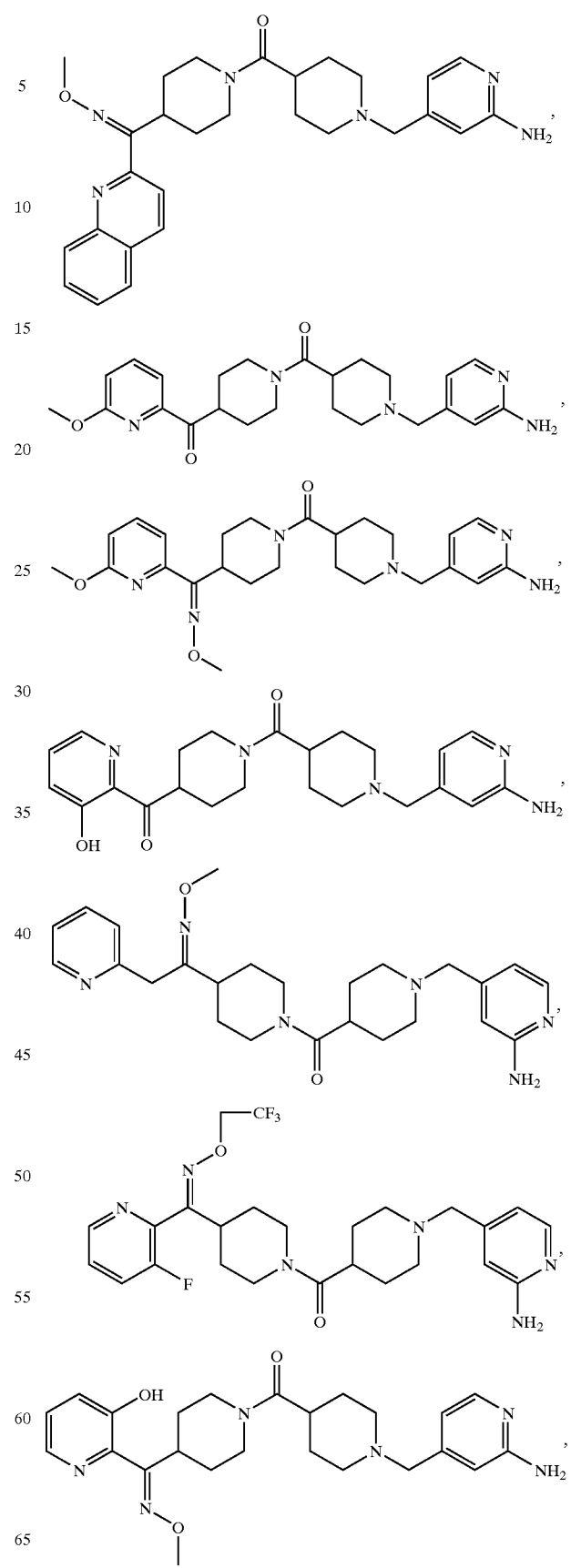

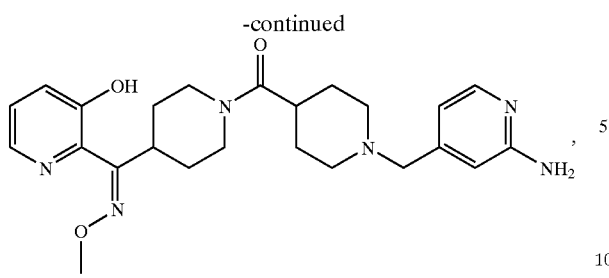
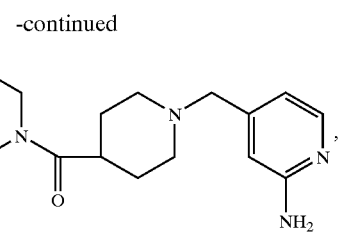
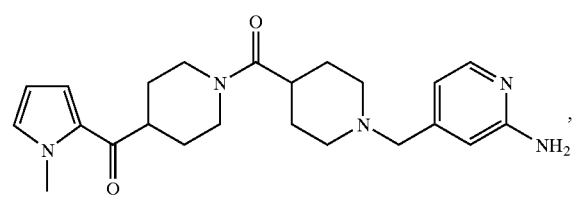
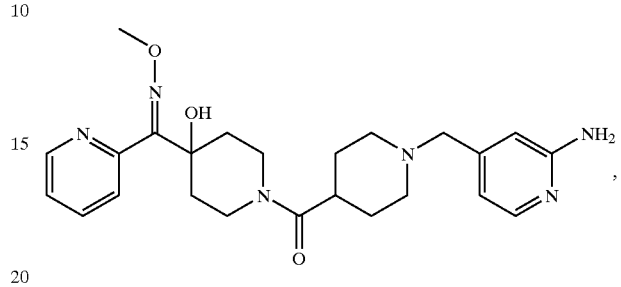
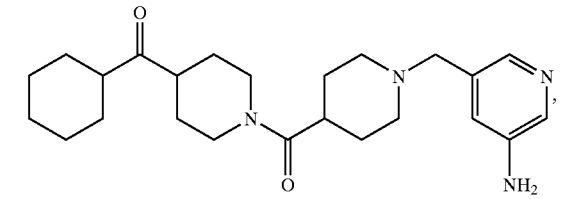
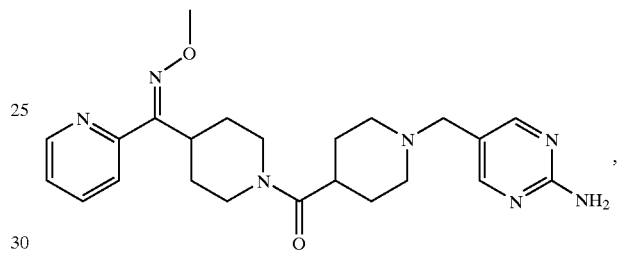
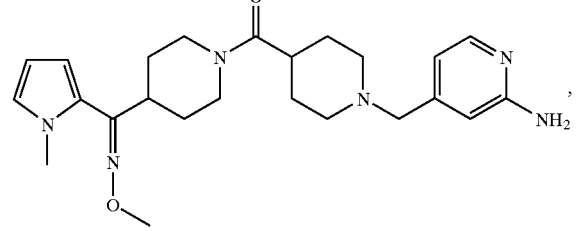
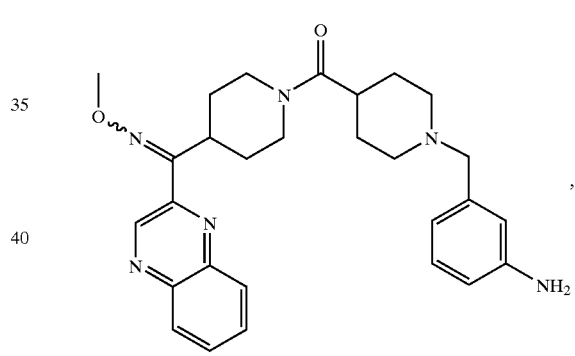
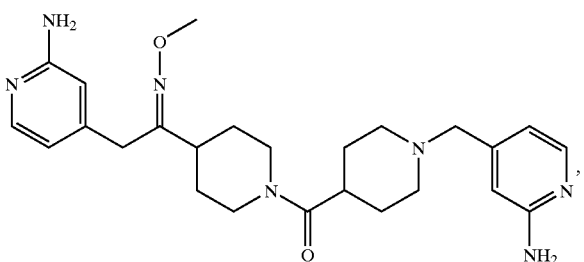
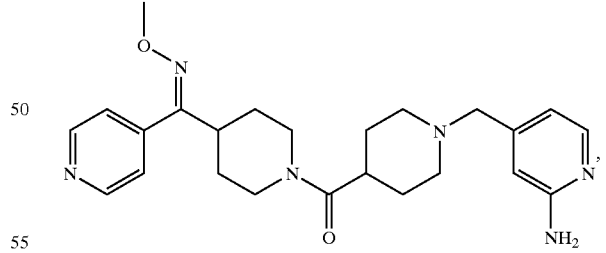
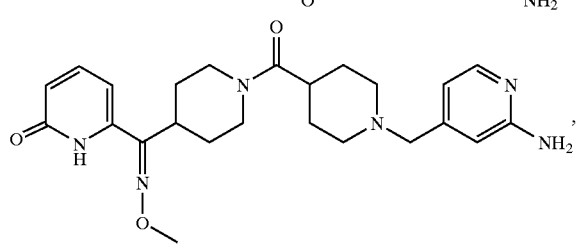
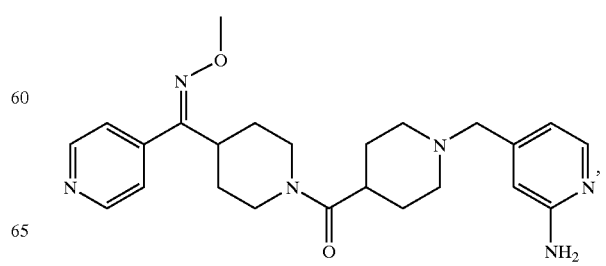
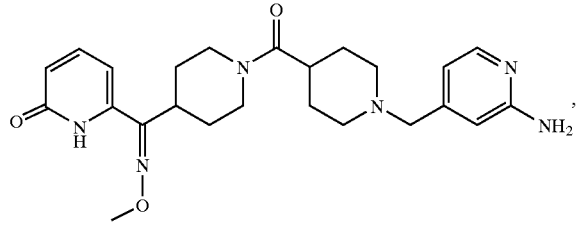

-continued
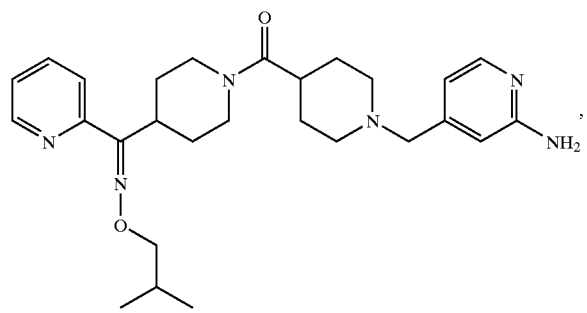
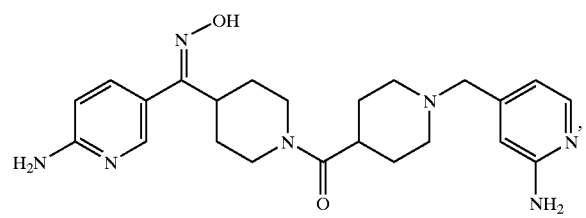
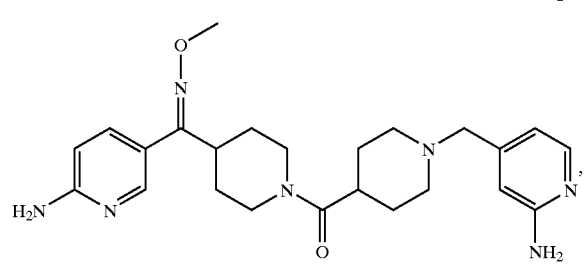
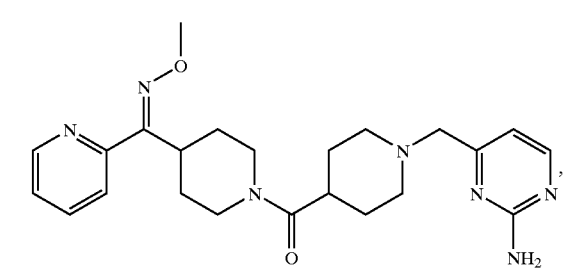
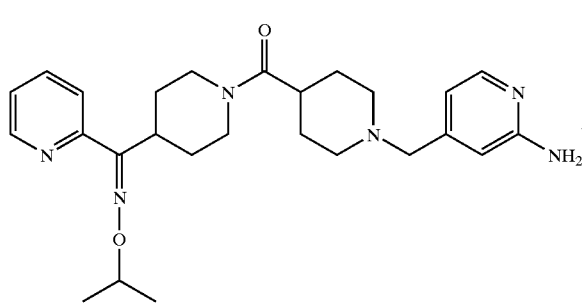
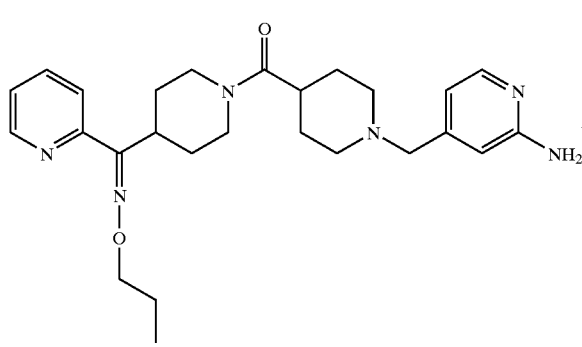
-continued
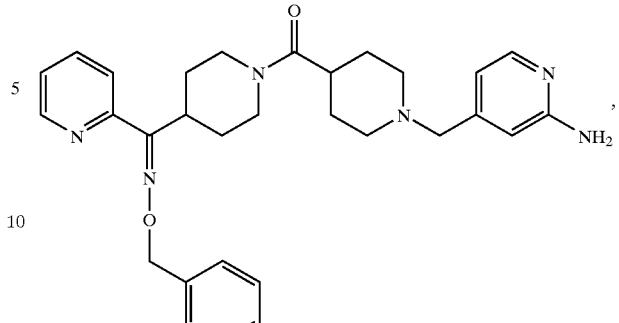
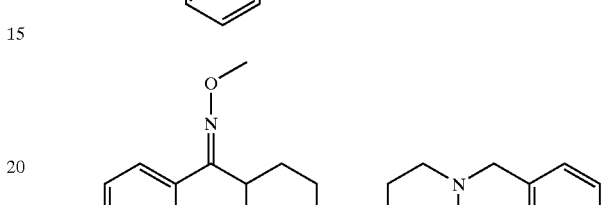
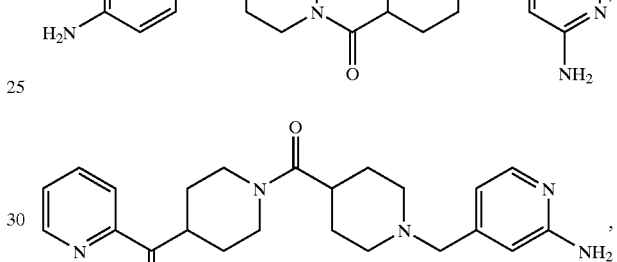
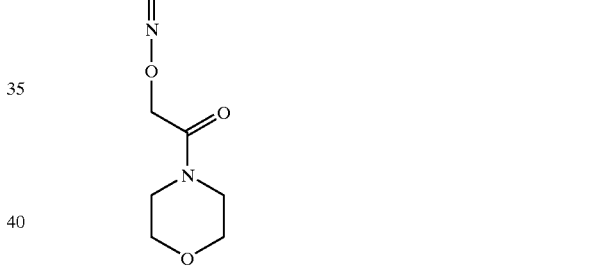
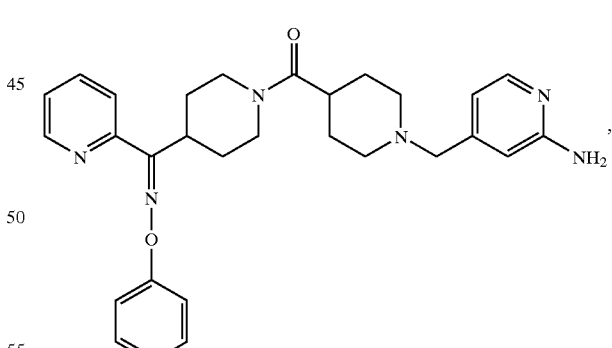
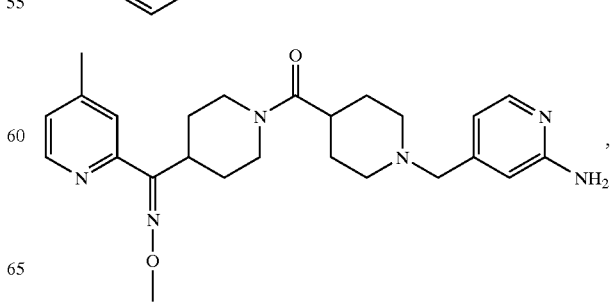

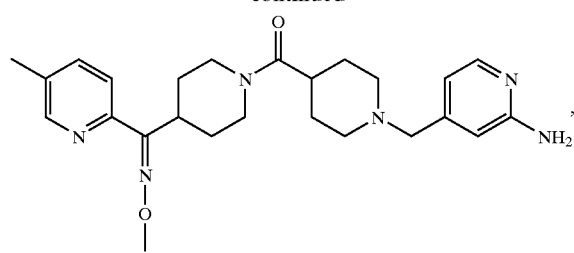
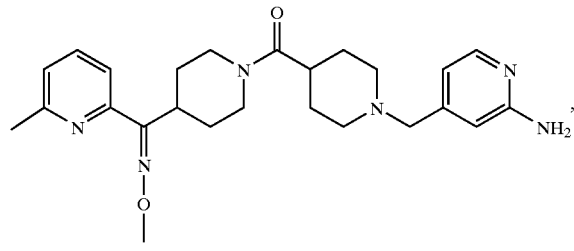
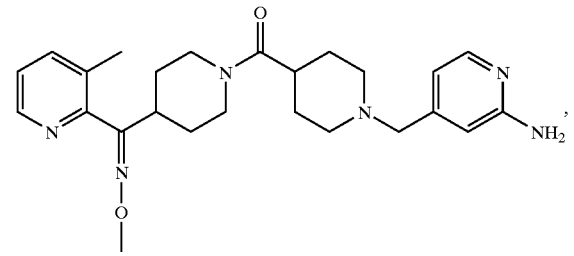
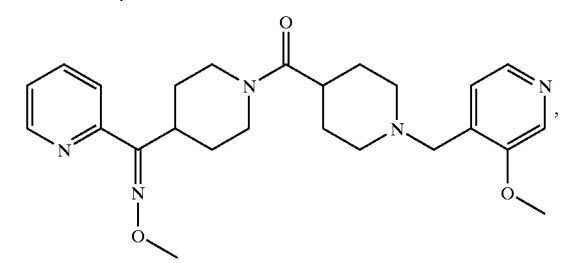
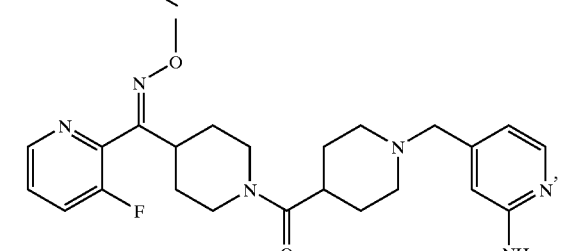
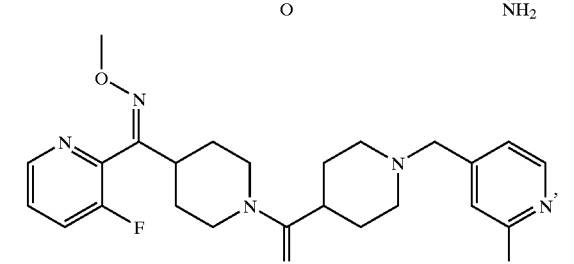
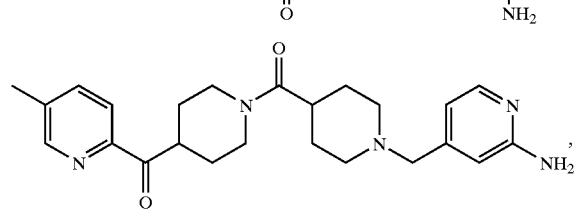
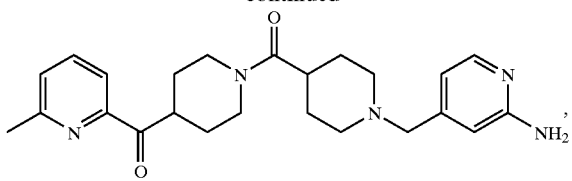
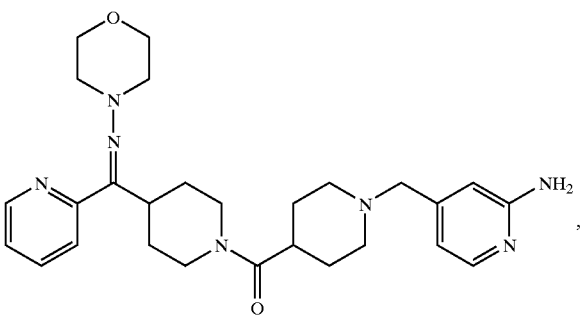
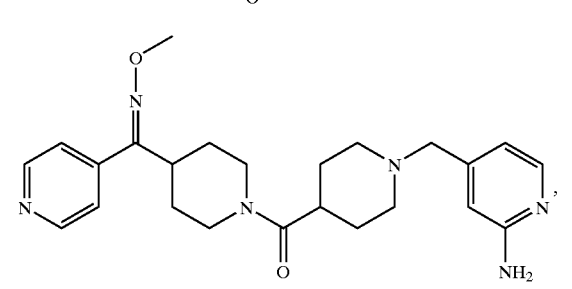
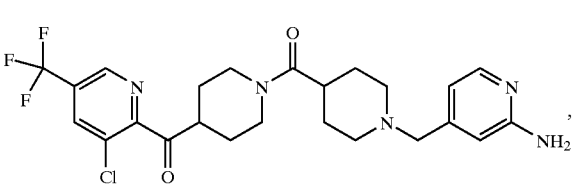
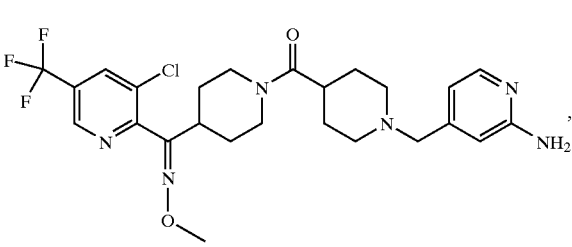
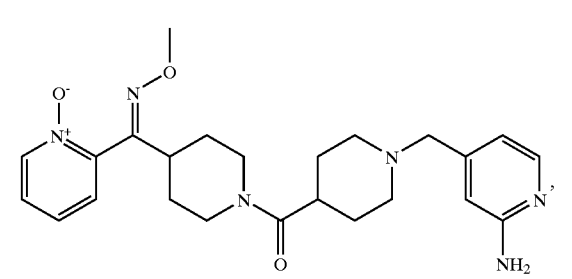
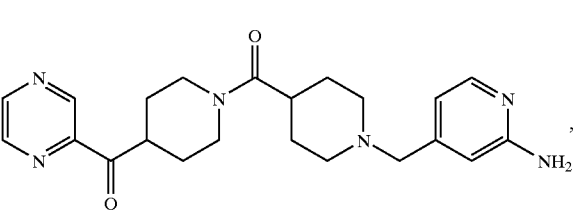

-continued
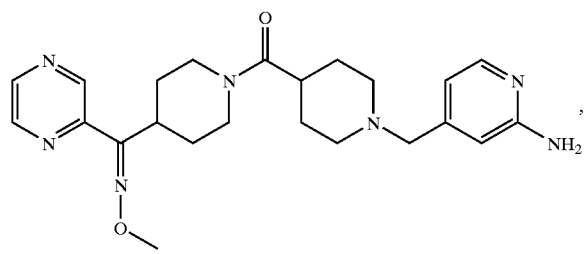
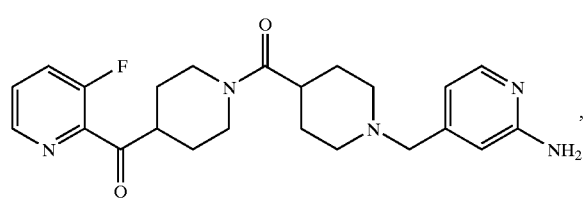
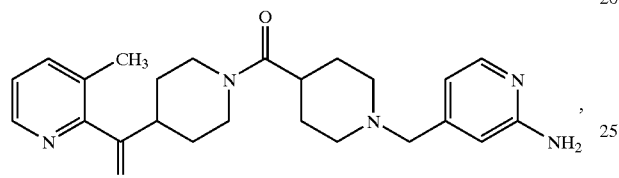
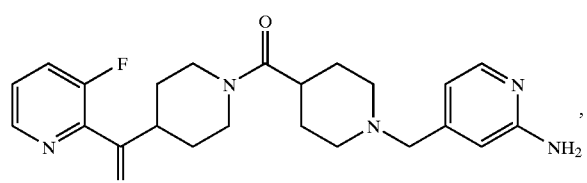
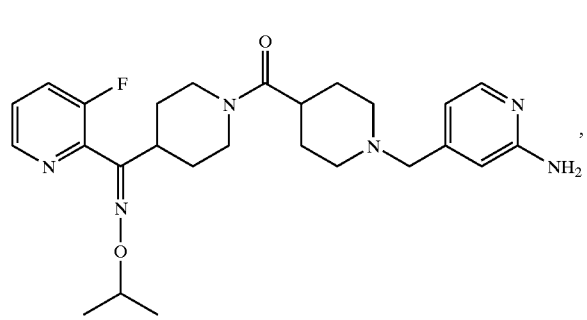
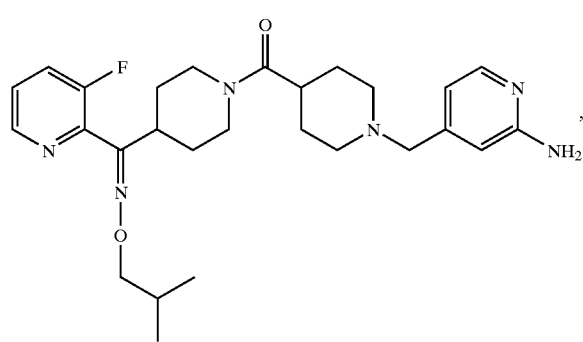
-continued
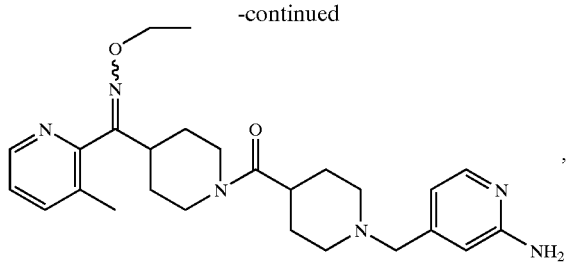
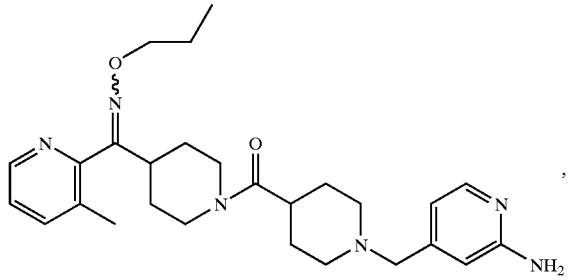
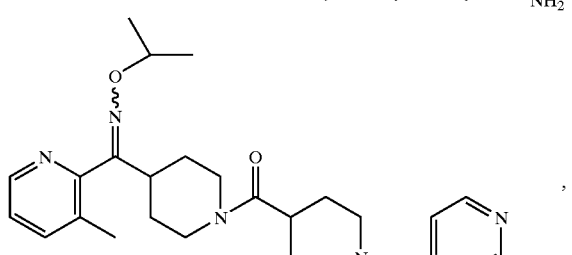
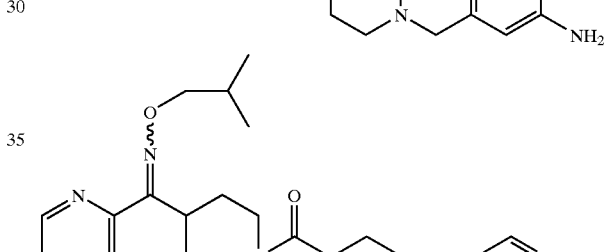
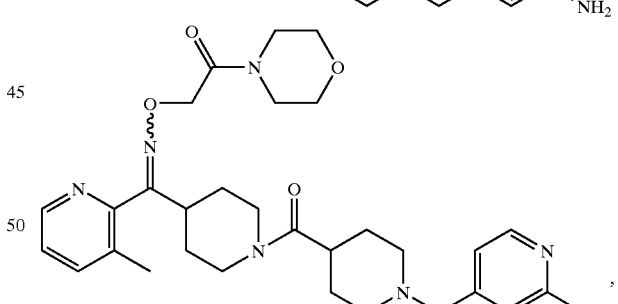
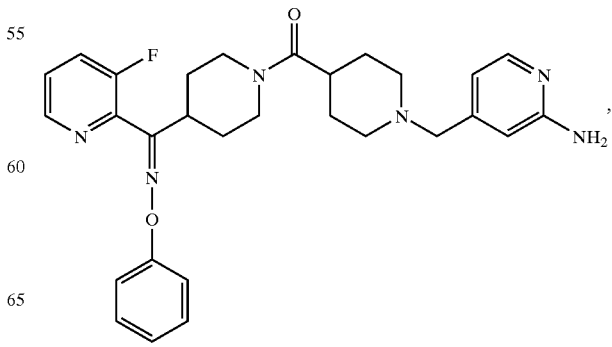

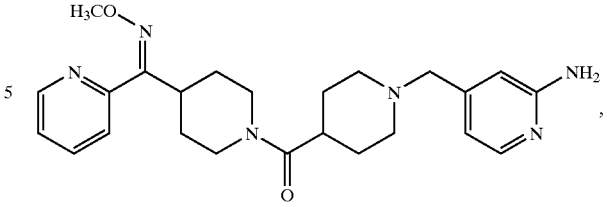
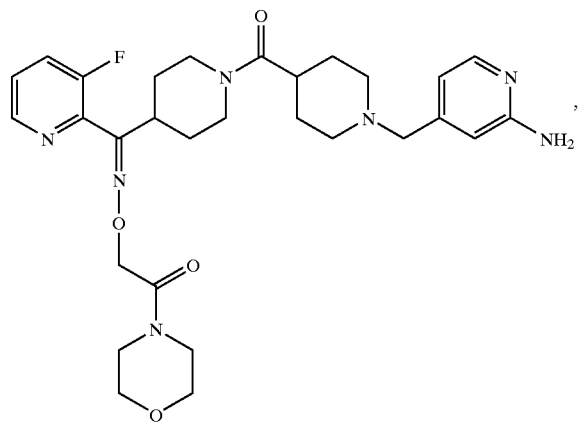
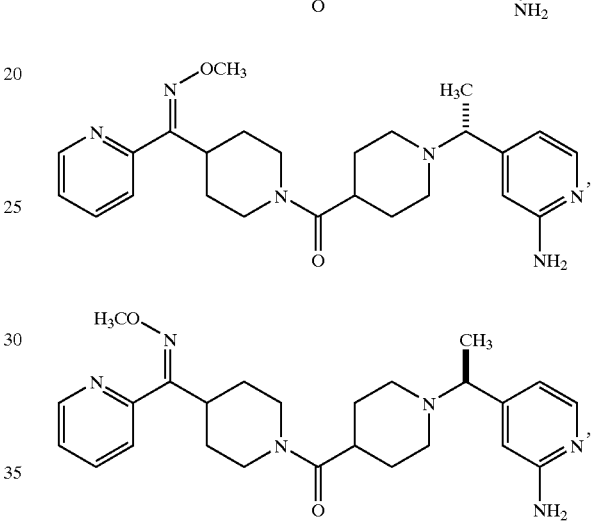
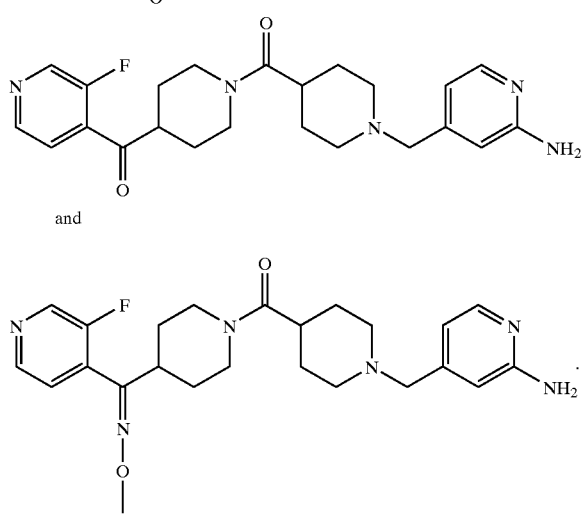
43. A compound of claim 1 selected from the group consisting of
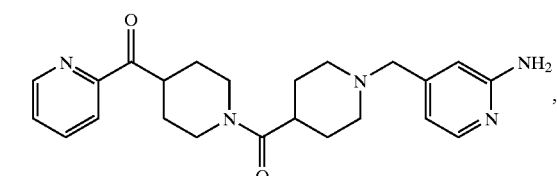
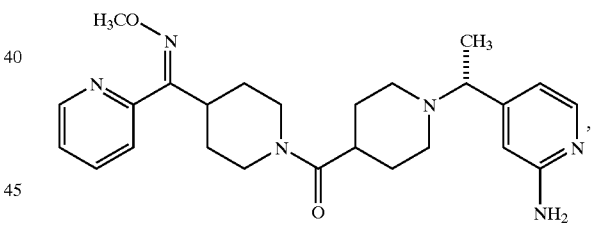
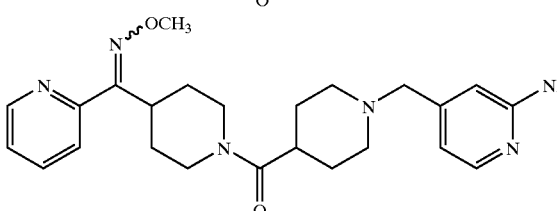
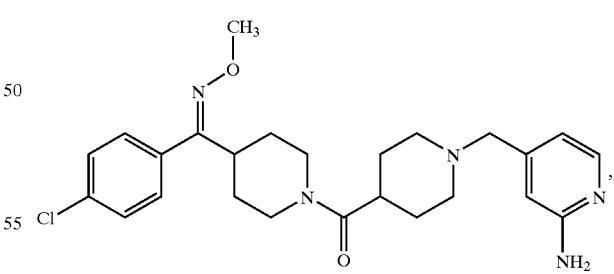
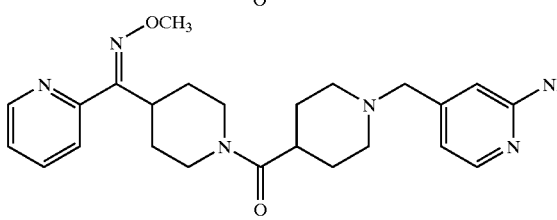
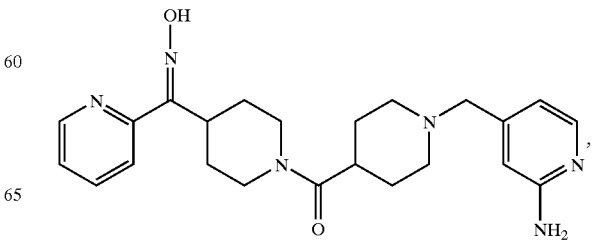

191
-continued
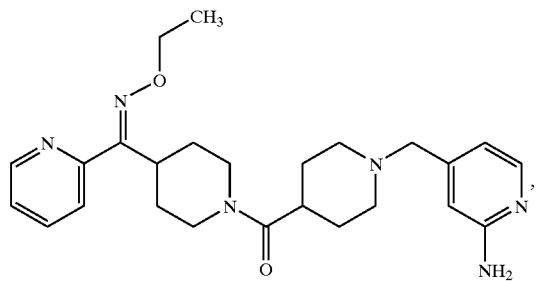
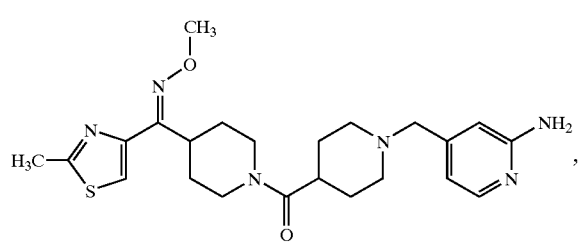
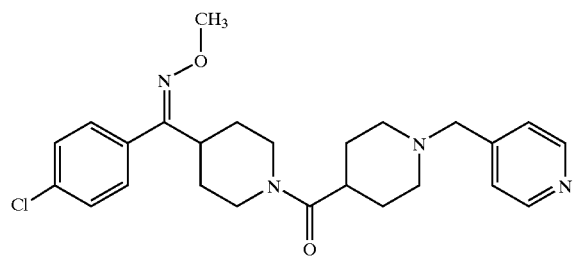
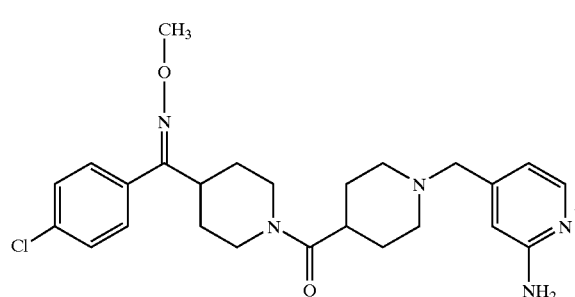
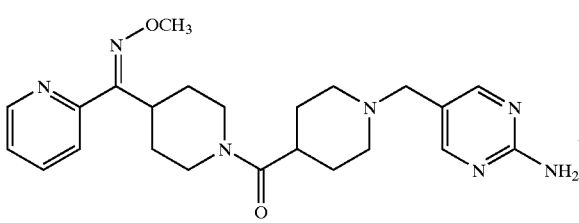
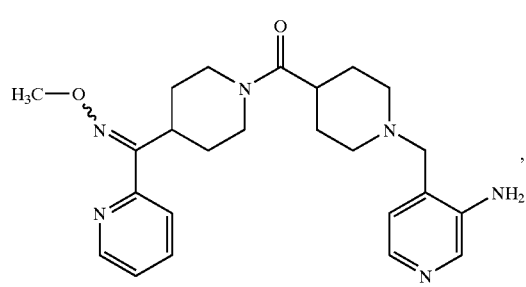
192
-continued
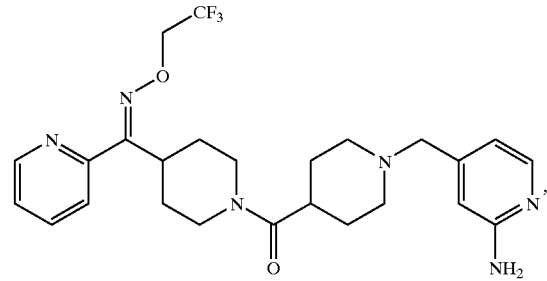
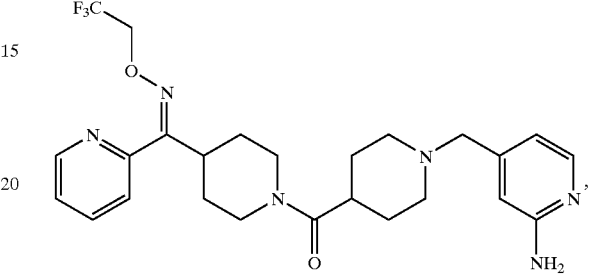
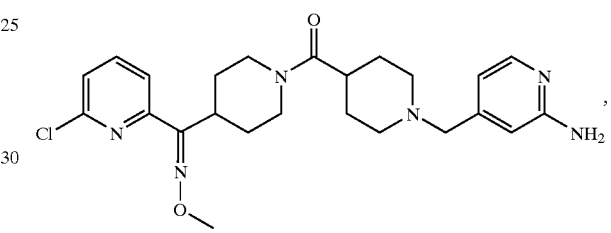
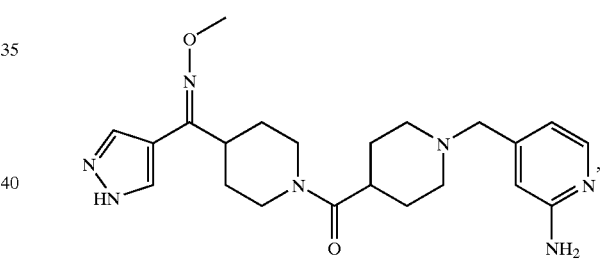
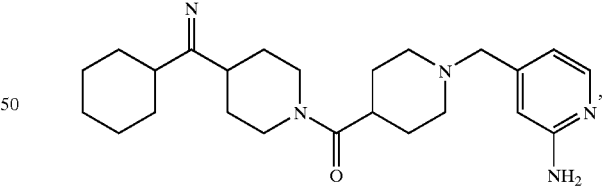
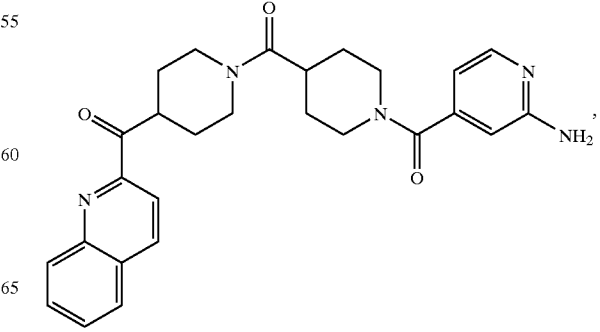

-continued
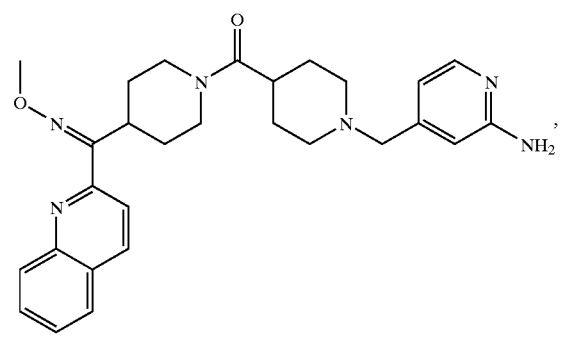
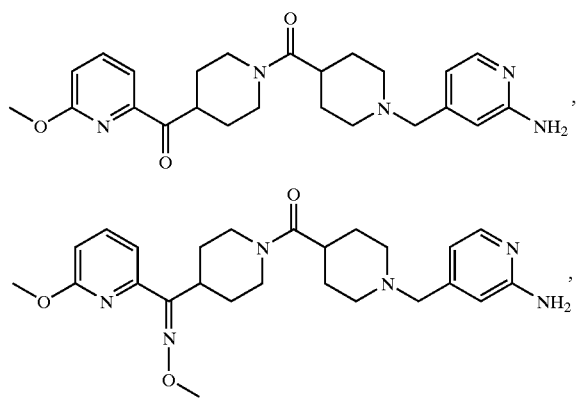
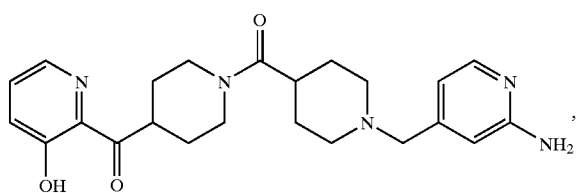
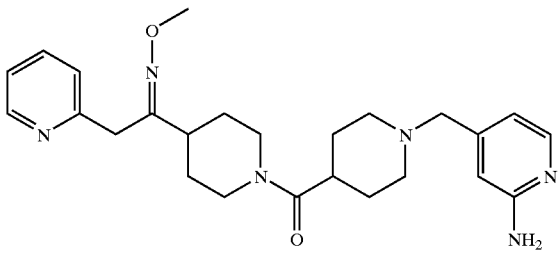
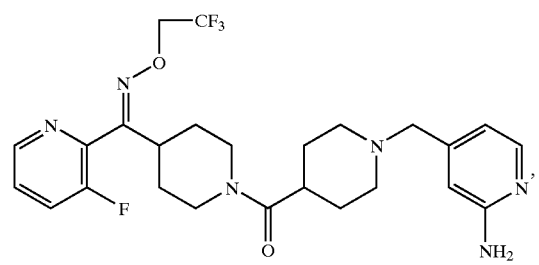
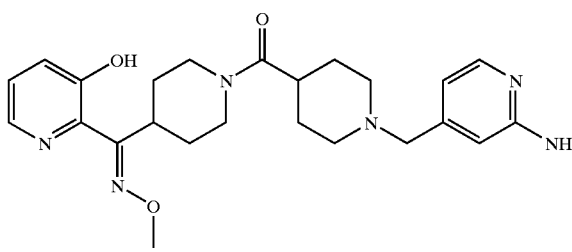
-continued
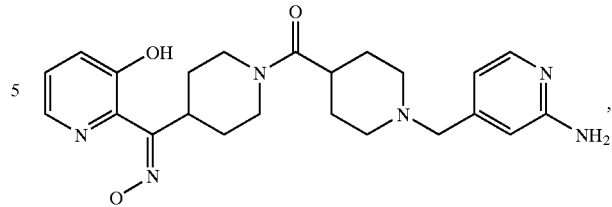
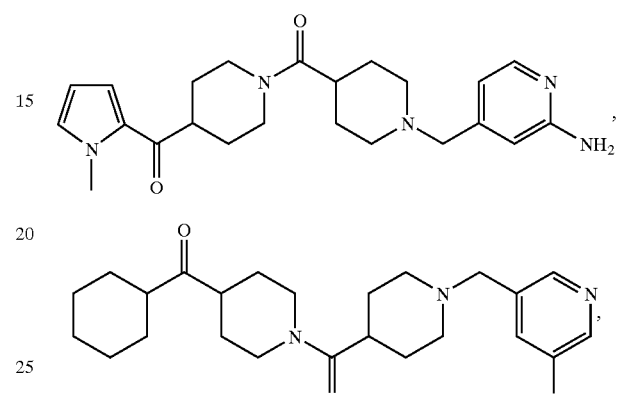
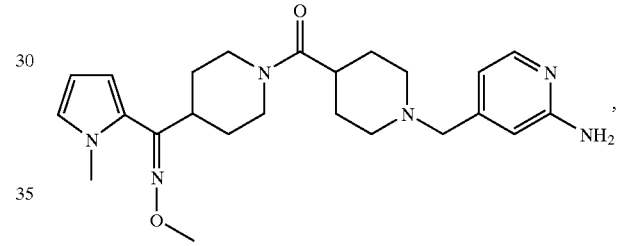
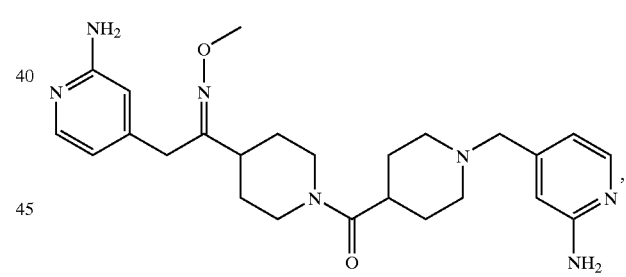
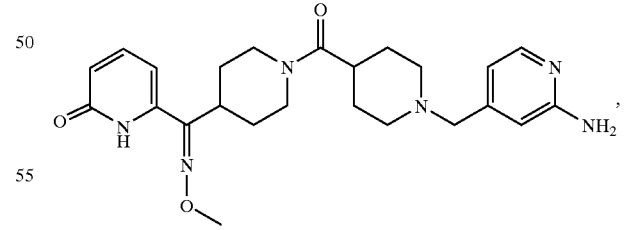
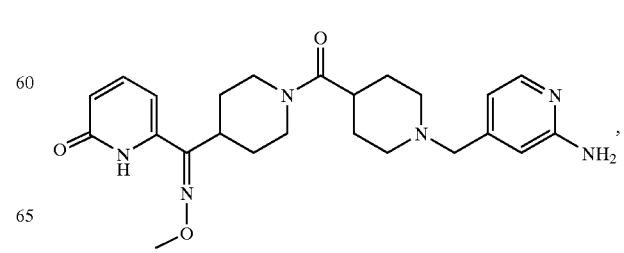

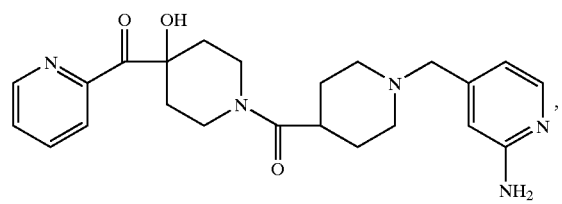
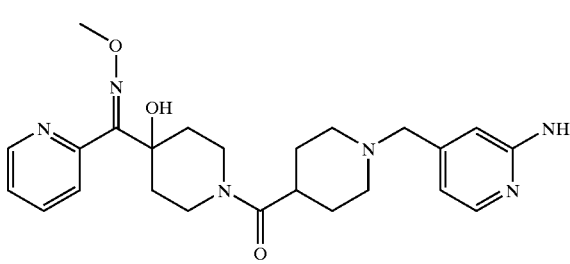
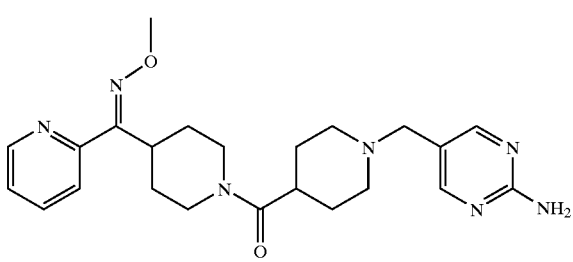
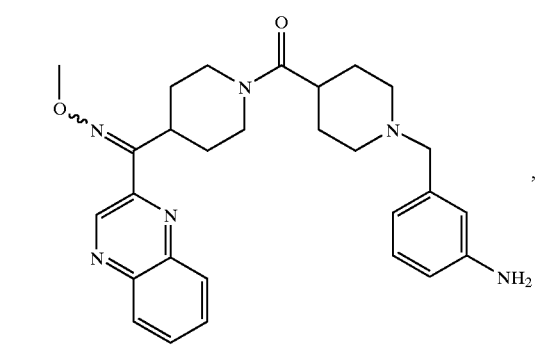
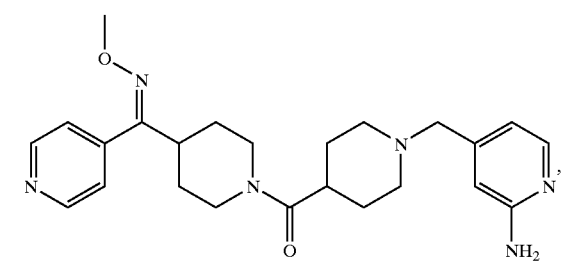
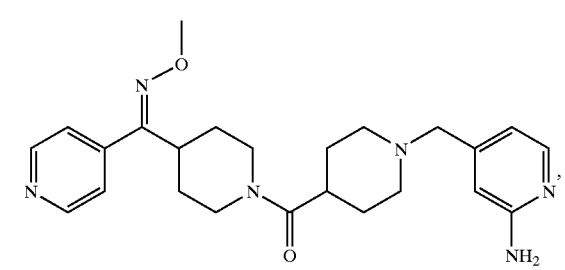
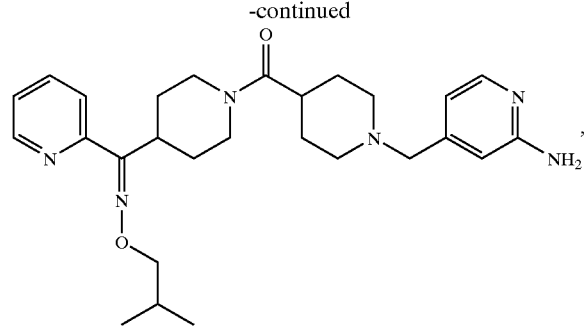
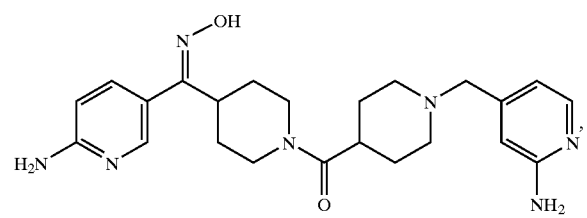
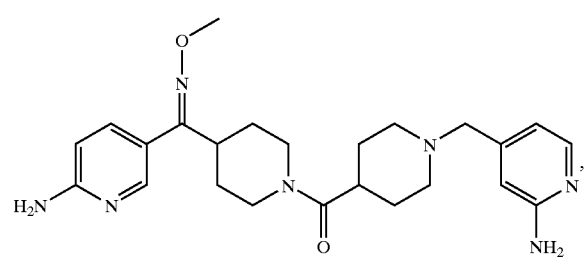
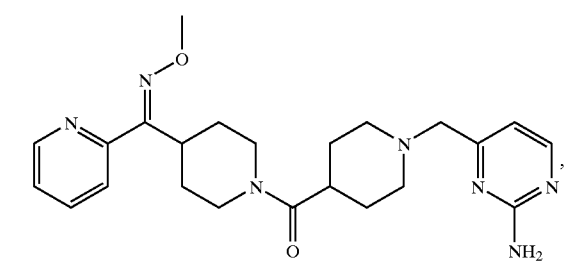
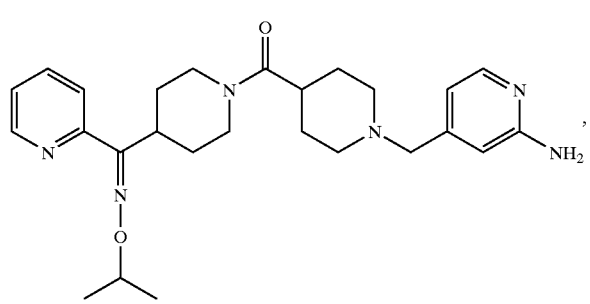
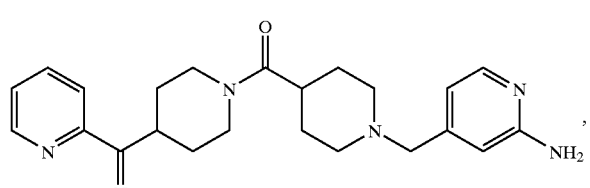

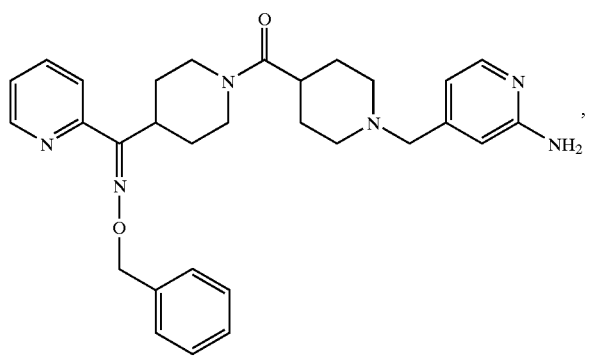
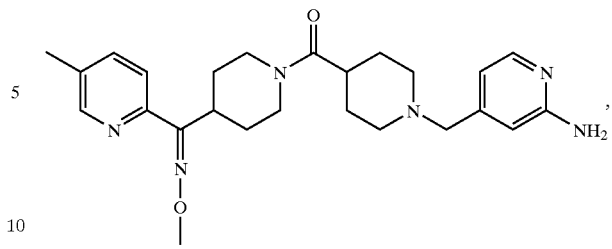
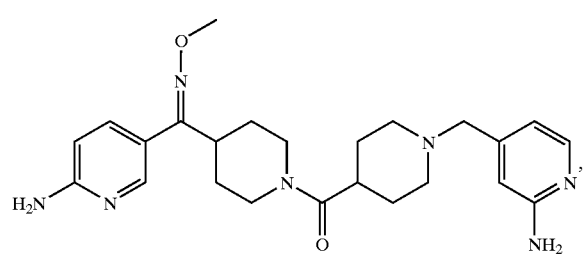
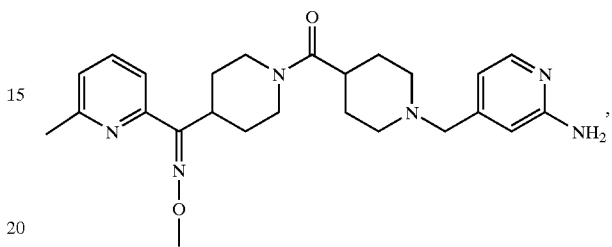
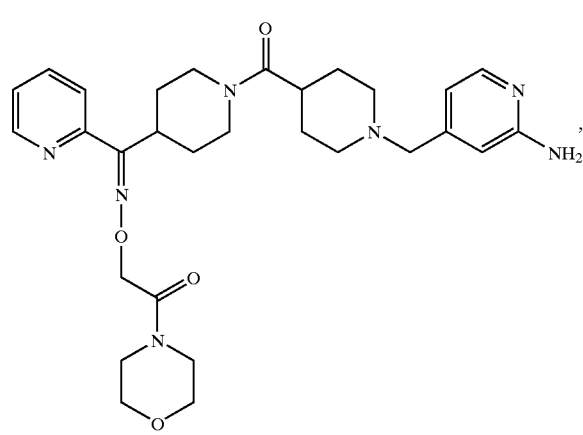
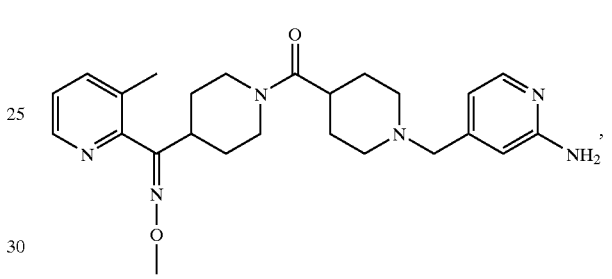
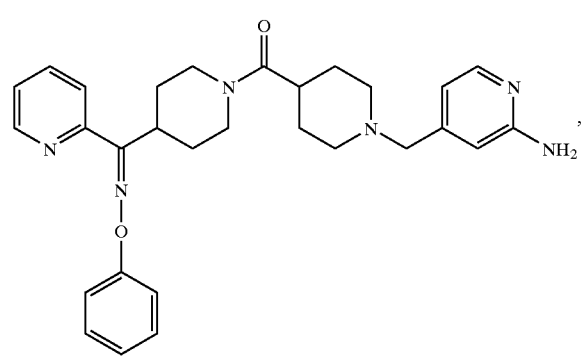
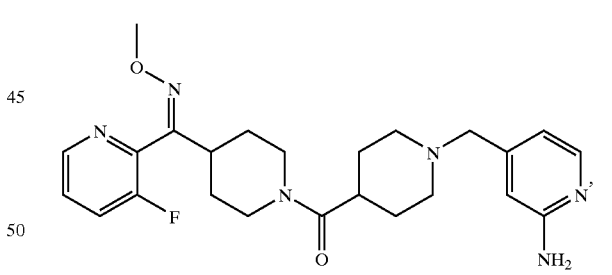
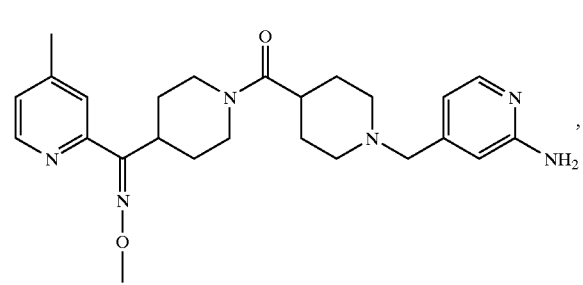
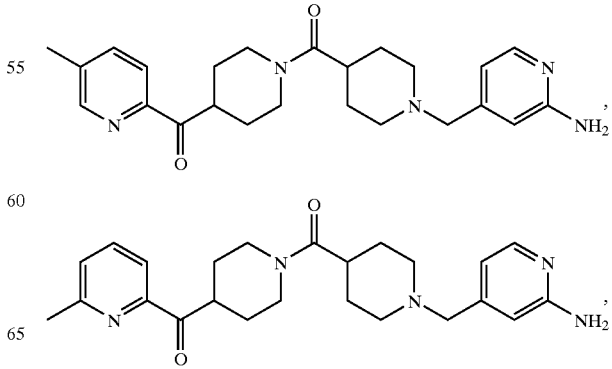

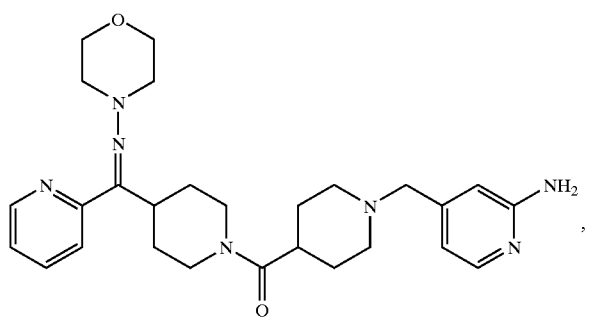,
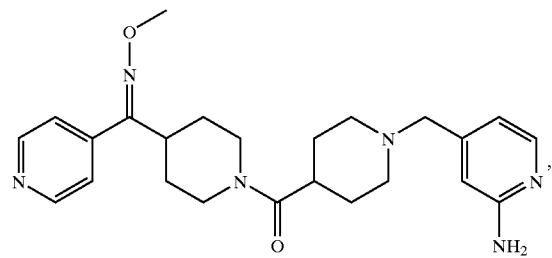,
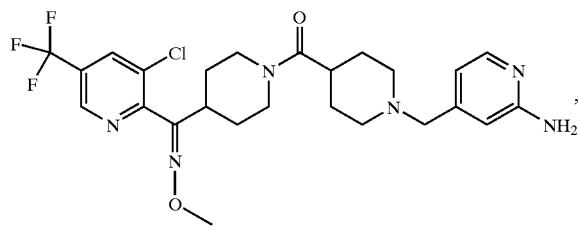,
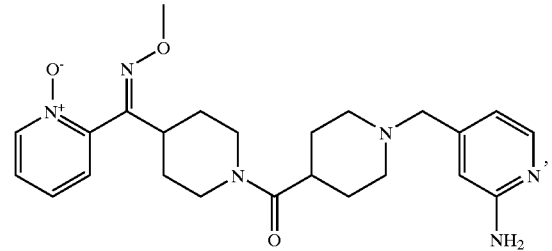,
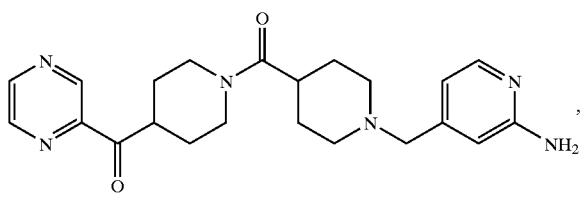,
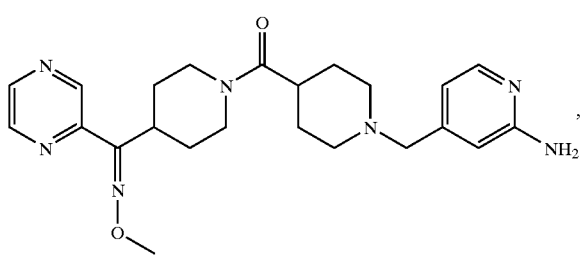,
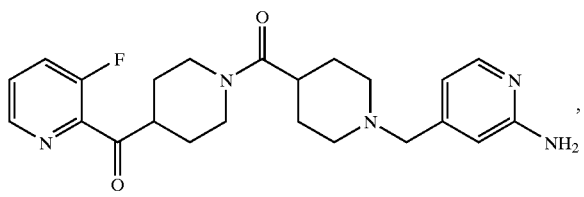,
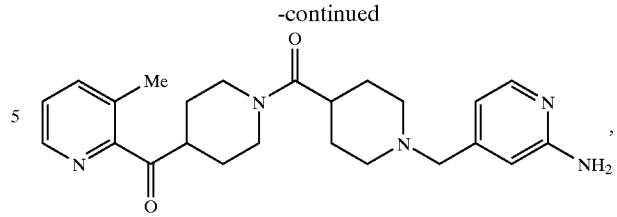,
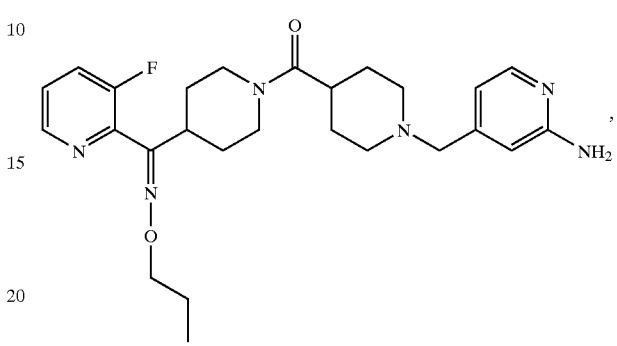,
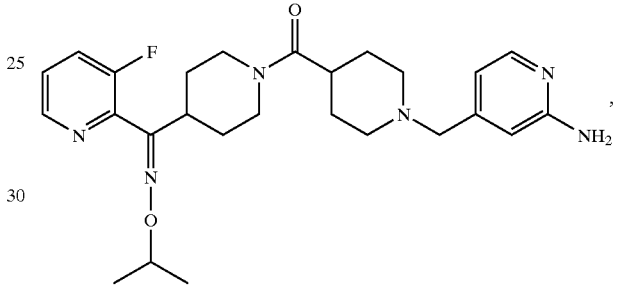,
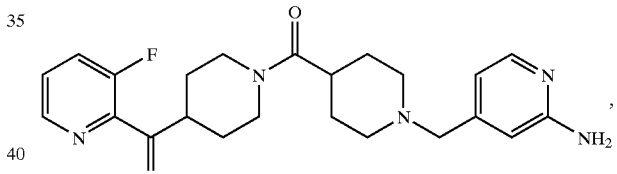,
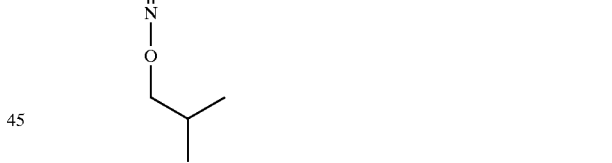,
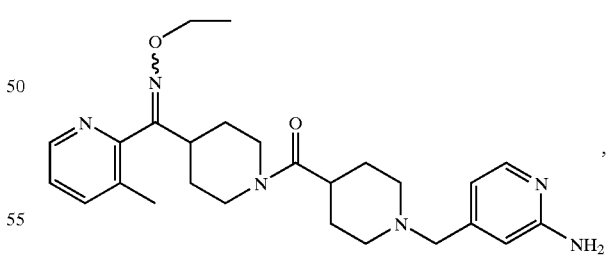,
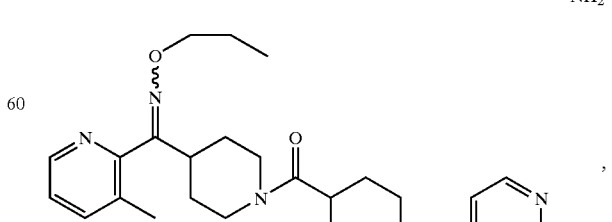,

201
-continued
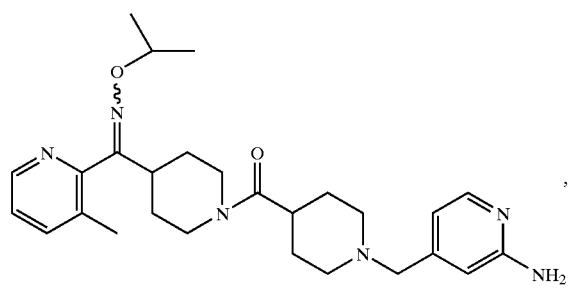
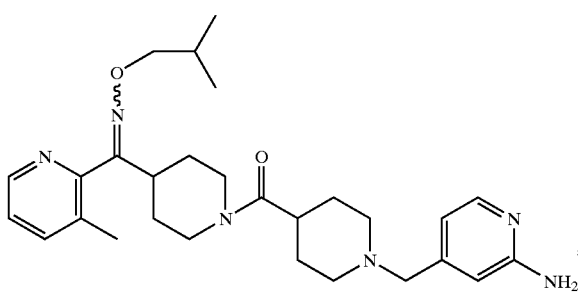
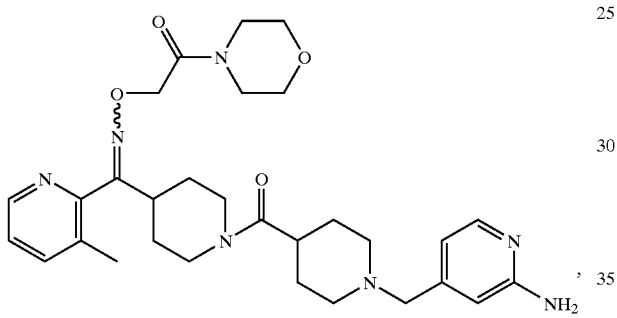
202
-continued
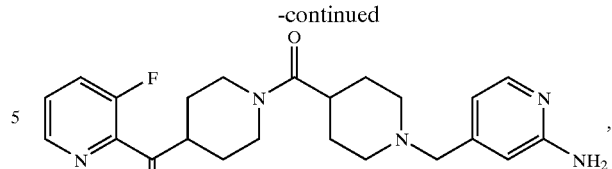
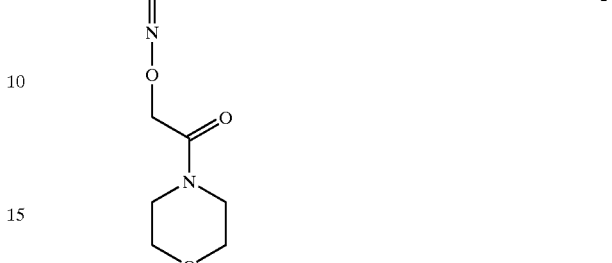
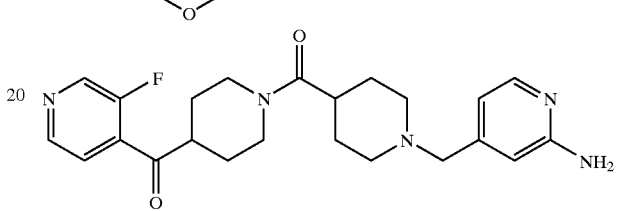
and
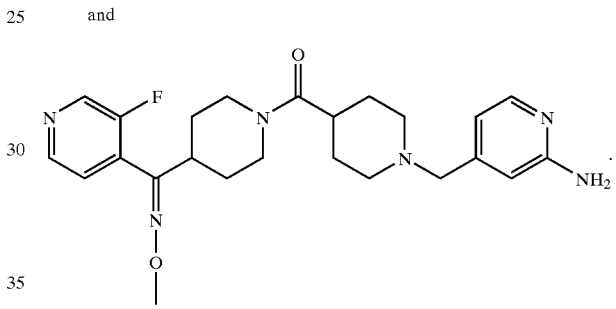
* * * * *

UNITED STATES PATENT AND TRADEMARK OFFICE
CERTIFICATE OF CORRECTION

PATENT NO. : 6,720,328 B2
DATED : April 13, 2004
INVENTOR(S) : Robert G. Aslanian et al.

It is certified that error appears in the above-identified patent and that said Letters Patent is hereby corrected as shown below:

Column 161,
Line 46, change "-CE$_3$" to -- -CF$_3$ --.

Column 166,
Lines 55-64, delete " 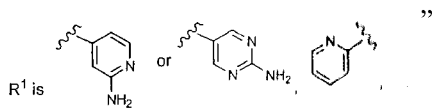 "

$R^1$ is 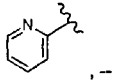

and insert

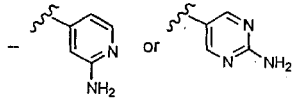

$R^1$ is 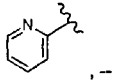 , --

Signed and Sealed this

Tenth Day of August, 2004

JON W. DUDAS
*Acting Director of the United States Patent and Trademark Office*